United States Patent
Tate et al.

(10) Patent No.: US 9,056,164 B2
(45) Date of Patent: Jun. 16, 2015

(54) RADIOPHARMACEUTICAL ADMINISTRATION METHODS, FLUID DELIVERY SYSTEMS AND COMPONENTS THEREOF

(75) Inventors: Leon J. Tate, Cranberry Township, PA (US); James H. Shigeno, Pittsburgh, PA (US); Jared E. Neff, New Kensington, PA (US); Scott R. Griffith, Murrysville, PA (US); Joseph E. Bisegna, Cheswick, PA (US); Paul J. Miller, Pittsburgh, PA (US); Scott Yanke, Dousman, WI (US)

(73) Assignee: Bayer Medical Care Inc., Indianola, PA (US)

( * ) Notice: Subject to any disclaimer, the term of this patent is extended or adjusted under 35 U.S.C. 154(b) by 2220 days.

(21) Appl. No.: 11/981,429

(22) Filed: Oct. 31, 2007

(65) Prior Publication Data

US 2008/0177126 A1 Jul. 24, 2008

Related U.S. Application Data

(60) Provisional application No. 60/979,541, filed on Oct. 12, 2007, provisional application No. 60/878,304, filed on Jan. 1, 2007.

(51) Int. Cl.
*A61M 5/00* (2006.01)
*A61M 25/00* (2006.01)
*A61M 5/172* (2006.01)
*G06F 19/00* (2011.01)

(52) U.S. Cl.
CPC ............... *A61M 5/172* (2013.01); *A61M 5/007* (2013.01); *G06F 19/3468* (2013.01)

(58) Field of Classification Search
USPC ............... 604/7–9, 19, 80–81, 99, 257, 284
See application file for complete search history.

(56) References Cited

U.S. PATENT DOCUMENTS 2,584,397 A * 2/1952 Pitman ............................ 141/59
3,760,806 A * 9/1973 Leeper ........................ 604/892.1
(Continued)

FOREIGN PATENT DOCUMENTS

EP 0379177 7/1994
EP 0486283 4/1998
(Continued)

OTHER PUBLICATIONS

LabVIEW Software, National Instruments website (www.ni.com/labview).
(Continued)

*Primary Examiner* — Quynh-Nhu H Vu
(74) *Attorney, Agent, or Firm* — Joseph L. Kent; David Schramm; James R. Stevenson

(57) ABSTRACT

A fluid path set for a fluid delivery system includes a tube coil that is designed to optimally position one or more volumes of a pharmaceutical within an ionization chamber to measure and prepare a pharmaceutical dose for administration to a patient. The fluid path set includes a medical fluid component having a first tubing section for connection to a source of a medical fluid, a pharmaceutical component having a second tubing section for connection to a source of a pharmaceutical, and a coil assembly which includes the tube coil. The tube coil may be maintained in a desired dimensional geometry by means of a core structure around which the tube coil is positioned.

17 Claims, 87 Drawing Sheets

(56) References Cited

U.S. PATENT DOCUMENTS

| | | | |
|---|---|---|---|
| 4,307,713 A | 12/1981 | Galkin et al. | |
| 4,562,829 A | 1/1986 | Bergner | |
| 4,697,622 A * | 10/1987 | Swift et al. | 141/1 |
| 4,857,728 A | 8/1989 | Smith, Jr. | |
| 4,968,305 A | 11/1990 | Takahashi et al. | |
| 4,994,012 A | 2/1991 | Nakayama et al. | |
| 5,017,191 A | 5/1991 | Yamada et al. | |
| 5,039,863 A | 8/1991 | Matsuno et al. | |
| 5,112,327 A | 5/1992 | Iinuma et al. | |
| 5,207,642 A * | 5/1993 | Orkin et al. | 604/65 |
| 5,254,094 A | 10/1993 | Starkey et al. | |
| 5,274,239 A | 12/1993 | Lane et al. | |
| 5,288,285 A | 2/1994 | Carter | |
| 5,334,179 A * | 8/1994 | Poli et al. | 604/403 |
| 5,489,931 A | 2/1996 | Shibata et al. | |
| 5,494,036 A | 2/1996 | Uber, III et al. | |
| 5,514,071 A | 5/1996 | Sielaff, Jr. et al. | |
| 5,569,181 A | 10/1996 | Heilman et al. | |
| 5,611,785 A | 3/1997 | Mito et al. | |
| 5,656,035 A * | 8/1997 | Avoy | 604/191 |
| 5,739,508 A | 4/1998 | Uber, III | |
| 5,806,519 A | 9/1998 | Evans, III et al. | |
| 5,820,614 A | 10/1998 | Erskine et al. | |
| 5,840,026 A | 11/1998 | Uber, III et al. | |
| 5,843,037 A | 12/1998 | Uber, III | |
| 5,865,766 A * | 2/1999 | Bonsall et al. | 600/578 |
| 5,897,530 A * | 4/1999 | Jackson | 604/132 |
| 5,911,252 A | 6/1999 | Cassel | |
| 5,927,351 A | 7/1999 | Zhu et al. | |
| 5,928,194 A | 7/1999 | Maget | |
| 6,074,359 A * | 6/2000 | Keshaviah et al. | 604/29 |
| 6,339,718 B1 | 1/2002 | Zatezalo et al. | |
| 6,397,098 B1 | 5/2002 | Uber, III et al. | |
| 6,482,170 B1 * | 11/2002 | Andersen | 604/27 |
| 6,521,184 B1 * | 2/2003 | Edgson et al. | 422/82.02 |
| 6,632,189 B1 * | 10/2003 | Fallen et al. | 604/4.01 |
| 6,712,786 B2 * | 3/2004 | Azzolini | 604/80 |
| 6,767,319 B2 * | 7/2004 | Reilly et al. | 600/5 |
| 6,870,175 B2 | 3/2005 | Dell et al. | |
| 6,948,522 B2 * | 9/2005 | Newbrough et al. | 137/550 |
| 7,086,431 B2 * | 8/2006 | D'Antonio et al. | 141/330 |
| 7,094,216 B2 | 8/2006 | Trombley, III et al. | |
| 7,151,267 B2 | 12/2006 | Lemer | |
| 7,552,746 B2 * | 6/2009 | Shin et al. | 137/587 |
| 7,734,331 B2 * | 6/2010 | Dhawale et al. | 600/431 |
| 8,475,404 B2 * | 7/2013 | Foshee et al. | 604/82 |
| 2003/0004463 A1 | 1/2003 | Reilly et al. | |
| 2003/0036674 A1 | 2/2003 | Bouton | |
| 2003/0036713 A1 | 2/2003 | Bouton et al. | |
| 2003/0175196 A1 | 9/2003 | Blackwell et al. | |
| 2003/0216609 A1 | 11/2003 | Dell et al. | |
| 2004/0015038 A1 | 1/2004 | Lemer | |
| 2004/0073189 A1 * | 4/2004 | Wyatt et al. | 604/411 |
| 2004/0092905 A1 * | 5/2004 | Azzolini | 604/412 |
| 2004/0162515 A1 * | 8/2004 | Chornenky et al. | 604/19 |
| 2004/0260143 A1 | 12/2004 | Reilly et al. | |
| 2004/0260242 A1 * | 12/2004 | Hughes et al. | 604/140 |
| 2005/0029465 A1 | 2/2005 | Lemer | |
| 2005/0033238 A1 * | 2/2005 | Cope et al. | 604/167.01 |
| 2005/0203329 A1 | 9/2005 | Muto et al. | |
| 2005/0277833 A1 | 12/2005 | Williams, Jr. | |
| 2006/0089604 A1 * | 4/2006 | Guerrero | 604/247 |
| 2006/0100578 A1 | 5/2006 | Lieberman | |
| 2006/0106345 A1 | 5/2006 | Flaker et al. | |
| 2006/0195045 A1 | 8/2006 | Gable et al. | |
| 2007/0060898 A1 * | 3/2007 | Shaughnessy et al. | 604/284 |
| 2007/0088252 A1 * | 4/2007 | Pestotnik et al. | 604/82 |
| 2009/0131862 A1 * | 5/2009 | Buck et al. | 604/67 |
| 2010/0030181 A1 * | 2/2010 | Helle et al. | 604/411 |

FOREIGN PATENT DOCUMENTS

| | | |
|---|---|---|
| EP | 1616587 | 1/2006 |
| FR | 2867294 | 9/2005 |
| JP | 05264789 | 10/1993 |
| JP | 06312009 | 11/1994 |
| JP | 06345133 | 12/1994 |
| JP | 08011907 | 1/1996 |
| JP | 2000167053 | 6/2000 |
| JP | 2000350783 | 12/2000 |
| JP | 2002306609 | 10/2002 |
| JP | 2002341040 | 11/2002 |
| JP | 2003098259 | 4/2003 |
| JP | 2004290455 | 10/2004 |
| JP | 2004353875 | 12/2004 |
| JP | 2005040197 | 2/2005 |
| JP | 2006003223 | 1/2006 |
| JP | 2006015055 | 1/2006 |
| JP | 2006325826 | 12/2006 |
| JP | 2006325827 | 12/2006 |
| JP | 2006017660 | 5/2008 |
| WO | 03010557 | 2/2003 |
| WO | 03029841 | 4/2003 |
| WO | 2004004787 | 1/2004 |
| WO | 2004091688 | 10/2004 |
| WO | 2005020274 | 3/2005 |
| WO | 2005118031 | 12/2005 |
| WO | 2006007750 | 1/2006 |
| WO | 2006051855 | 5/2006 |

OTHER PUBLICATIONS

MEDRAD Stellant Injector, MEDRAD Inc. website (http://web2.medrad.com/products/ct/stellant.html).

Pulse Spray Injector, AngioDynamics Incorporated website (www.angiodynamics.com/products/pulsespray_injector.asp).

MEDRAD Mark V Injector, MEDRAD Inc. website (http://web2.medrad.com/products/cv/mark-v-provis.html).

Capitail Pyrimid Glove Box, Guyline Limited website (www.guyline.com.hk).

MEDRAD Continuum Infusion System, MEDRAD Inc. website (http://web2.medrad.com/products/mr/continuum.html).

MEDRAD Spectris Solaris Injector, MEDRAD Inc. website (http://web2.medrad.com/products/mr/spectris-solaris.html).

Pegasus Infusion Pump, Instechlabs website (www.instechlabs.com/Pumps/pegasus/index.php).

Australian Government, [radioisotopes] their role in society today, Ansto.

International Search Report from counterpart application PCT/US07/88028 filed Dec. 20, 2007.

* cited by examiner

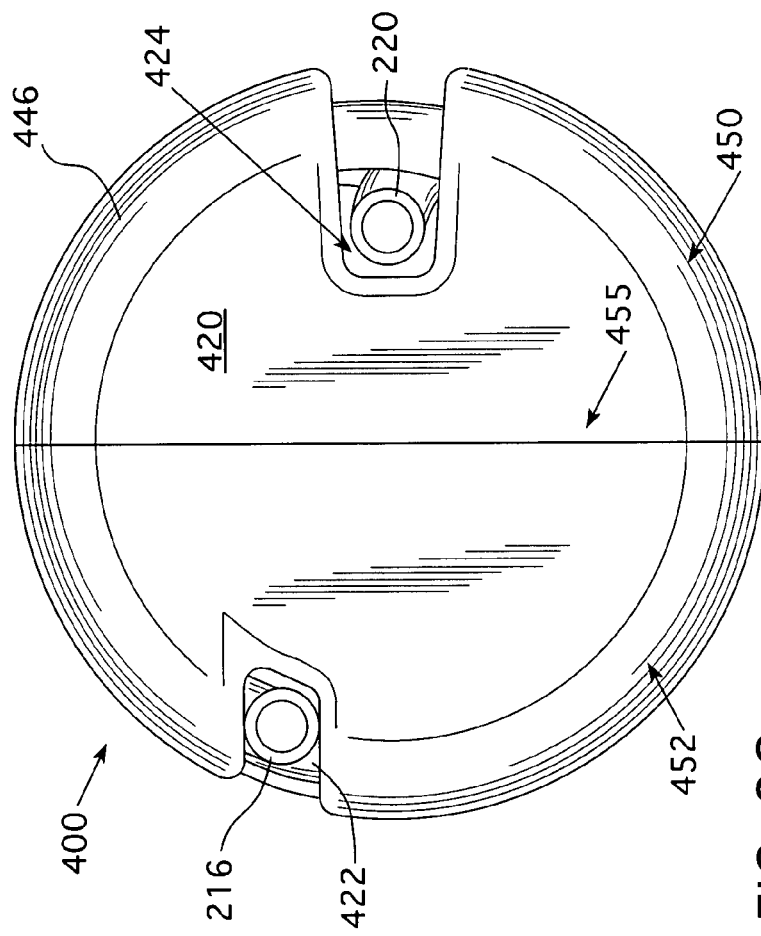
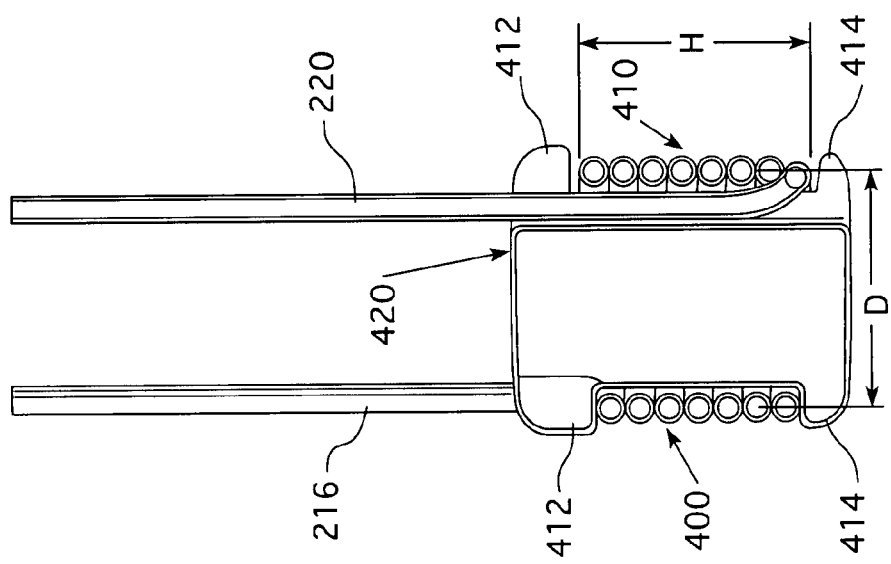
FIG. 3C
FIG. 3B

System Preparation

FDG Assay Information

Lot Number 1072 — 1070
000043218765

Date 1074 — 1074a Activity 1080
Today — [grid] — 700.0 mCi

Time 1076 — 1076a Volume 1082
7:15 AM — AM/PM — 30.0 ml

Clear All — 1078

Cancel 1084 — OK 1086

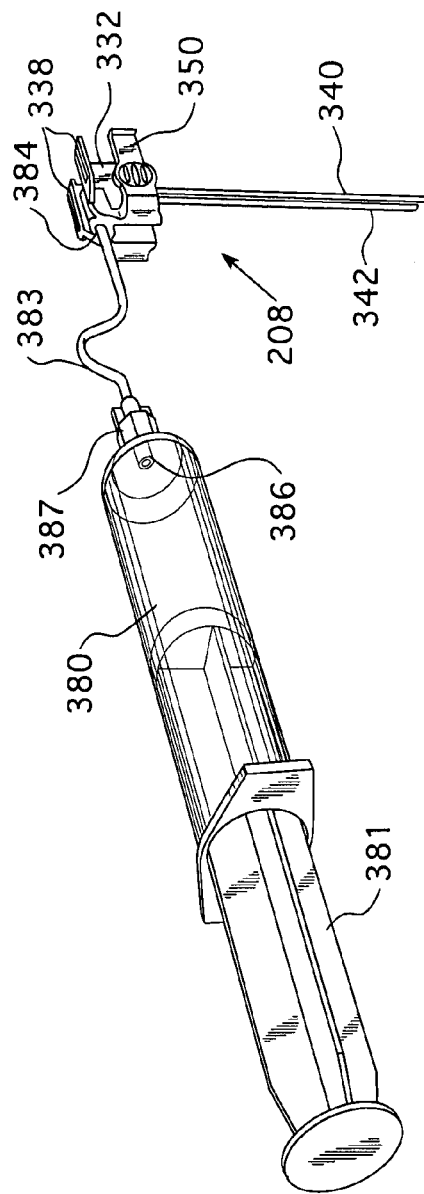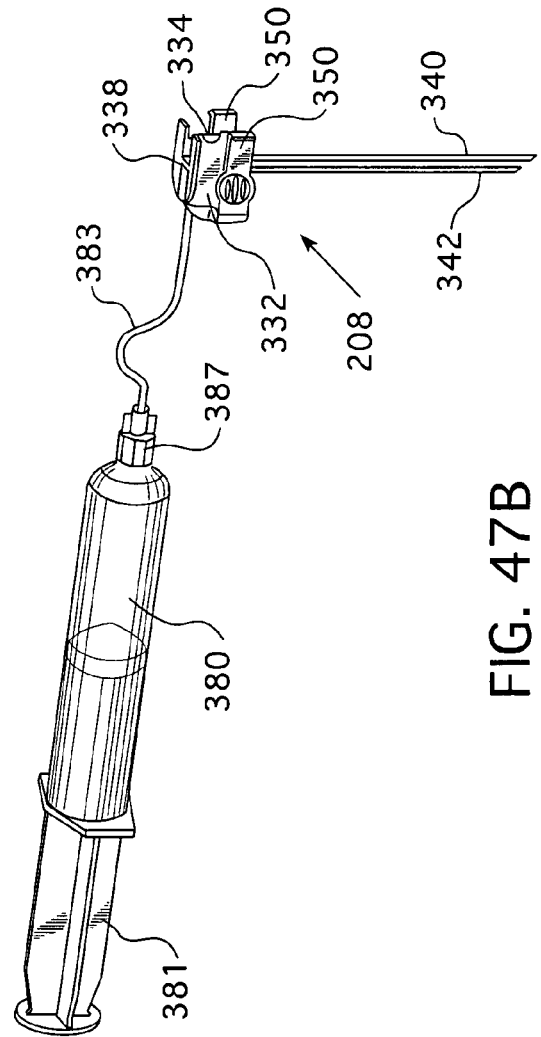
FIG. 47A
FIG. 47B

RADIOPHARMACEUTICAL ADMINISTRATION METHODS, FLUID DELIVERY SYSTEMS AND COMPONENTS THEREOF

CROSS-REFERENCE TO RELATED APPLICATIONS

This application claims the benefit of U.S. Provisional Patent Application Ser. No. 60/979,541, filed on Oct. 12, 2007, and U.S. Provisional Patent Application Ser. No. 60/878,304, filed on Jan. 1, 2007, the disclosures of which are incorporated herein by reference.

BACKGROUND OF THE INVENTION

The present invention relates to methods, systems and components thereof for delivering pharmaceutical substances to patients for imaging procedures and, more particularly, for delivering radiopharmaceuticals to patients for positron emission tomography (PET) or single-photon emission computerized tomography (SPECT) procedures.

PET and SPECT are noninvasive, three-dimensional, imaging procedures that provide information regarding physiological and biochemical processes in patients. PET and SPECT images of, for example, the brain or another organ, are produced by injecting the patient with a dose of a radiopharmaceutical (using, for example, fluid delivery systems such as those disclosed in U.S. Pat. No. 6,767,319, JP Publication Nos. 2000-350783 and 2002-306609 and PCT Publication Nos. WO 2004/091688, WO 2006/007750 and 2004/004787, the disclosures of which are incorporated herein by reference) and then creating an image based on the radiation emitted by the radiopharmaceutical. The radiopharmaceutical generally includes a radioactive substance, such as a radioisotope, that can be absorbed by certain cells in the brain or other organs, concentrating it there.

Radioisotopes, especially those with short half-lives, can be relatively safely administered to patients in the form of a labeled substrate, ligand, drug, antibody, neurotransmitter or other compound or molecule that is normally processed or used by the body (for example, glucose). The radioisotope acts as a tracer of specific physiological or biological processes. For example, fluorodeoxyglucose (FDG) is a normal molecule of glucose, the basic energy fuel of cells, to which is attached a radioisotope or radioactive fluor (i.e., F-18). The F-18 radioisotope is produced in a cyclotron equipped with a unit to synthesize the FDG molecule.

Cells (for example, in the brain) that are more active in a given period of time after an injection of FDG will absorb more FDG because they have a higher metabolism and require more energy. The F-18 radioisotope in the FDG molecule experiences a radioactive decay, emitting a positron. When a positron collides with an electron, annihilation occurs, liberating a burst of energy in the form of two beams of gamma rays in opposite directions. The PET scanner detects the emitted gamma rays to compile a three dimensional image.

To allow for cell uptake of the radiopharmaceutical, the patient typically rests for a period of time (45-90 minutes for FDG) after the radiopharmaceutical is injected. After sufficient time for cell uptake has elapsed, the patient is typically placed on a movable bed that slides into the PET (or SPECT or other suitable) scanner. The PET scanner includes several rings of radiation detectors. Each detector emits a brief pulse of light every time it is struck with a gamma ray coming from the radioisotope within the patient's body. The pulse of light is amplified, by for example a photomultiplier, and the information is sent to the computer for forming images of the patient.

To minimize the radiation dose to patients, radiopharmaceuticals containing radioisotopes, such as Flourine-18, Technetium-99, Carbon-11, Copper-64, Gallium-67, Iodine-123, Nitrogen-13, Oxygen-15, Rubidium-82, Thallium-201, Chromium-51, Iodine-131, Iodine-151, Iridium-192, Phosphorus-32, Samarium-153, and Yttrium-90, having relatively short half-lives are typically used for PET and SPECT imaging procedures and other radio-therapies. F-18, for example, has a half-life of 109.7 minutes.

Because of its short half-life, the radioactivity level of the radioisotope will quickly decrease after it is manufactured in a cyclotron or a reactor. Consequently, the elapsed time (and corresponding decrease in radioactivity level of the radioisotope) after synthesis of the radiopharmaceutical must be factored into calculating the volume of radiopharmaceutical required to be injected into the patient to deliver the desired radioactivity dose. If the time delay after synthesis is long in relation to the radioisotope's half-life or if the calculated volume of radiopharmaceutical to be injected into the patient is insufficient to deliver the desired radioactivity dose, the delivered radioactivity dose may be too low to provide diagnostic-quality images, resulting in wasted time and effort and exposing the patient and medical personnel to unnecessary radiation.

Further, long-term radiation exposure to technologists and other personnel working in the scanner room can pose a significant health risk. Although the half-life of the radiopharmaceutical is rather short and the applied dosages are considered an acceptable risk to the patient, under current procedures administering personnel are exposed each time they work with the radiopharmaceuticals and other contaminated materials, such as tubing and syringes, used to inject the radiopharmaceuticals into patients. Constant and repeated exposure over an extended period of time can be harmful.

A number of techniques are used to reduce radiation exposure to medical personnel, including minimizing the time of exposure of personnel, maintaining distance between personnel and the source of radiation and shielding personnel from the source of radiation. In general, the radiopharmaceuticals are typically delivered to a nuclear medicine hospital suite or other medical facility from a radiopharmaceutical synthesis facility (within or outside the hospital or medical facility) equipped with a cyclotron in, for example, a lead-shielded container (often called a "PIG"). Often, the radiopharmaceutical is manually drawn from such containers into a shielded syringe. See, for example, U.S. Pat. No. 5,927,351, disclosing a drawing station for handling radiopharmaceuticals for use in syringes. Remote injection mechanisms can also be used to maintain distance between the operator and the radiopharmaceutical. See, for example, U.S. Pat. No. 5,514,071, disclosing an apparatus for remotely administering radioactive material from a lead encapsulated syringe. Nevertheless, these current procedures and systems still result in unnecessary and repeated exposure of technicians and other medical personnel to radiation.

It has long been recognized as very desirable to develop devices, systems, components and methods for calculating and delivering accurate and effective doses of radiopharmaceuticals to patients, while reducing the exposure of administering or other medical personnel to such hazardous pharmaceuticals.

SUMMARY OF THE INVENTION

The present invention broadly contemplates and provides devices, systems, components and methods for accurately calculating or delivering effective doses of pharmaceuticals to patients.

In a first aspect, the invention provides a fluid path set including a tube coil that is designed to optimally position one or more volumes of a pharmaceutical within an ionization chamber to optimally measure and prepare a pharmaceutical dose for administration to a patient. The tube coil may be maintained in a desired dimensional geometry by means of a core structure around which the tube coil is positioned or coiled.

The fluid path set includes a medical fluid component comprising a first tubing section for connection to a source of a medical fluid, a pharmaceutical component comprising a second tubing section for connection to a source of a pharmaceutical, a coil assembly component comprising a tube coil having a height of approximately 1.53 inches, a diameter of approximately 1.95 inches and a volume capacity of approximately 12.5 ml, and a connector comprising a first port for connecting the first tubing section of the medical fluid component, a second port for connecting the second tubing section of the pharmaceutical component and a third port for connecting the tube coil of the coil assembly component.

In a second aspect, the present invention provides a vial access system for inserting a cannula into a pharmaceutical container, such as a vial. The vial access system includes structures that shields the operator from exposure to hazardous pharmaceuticals, such as radiopharmaceuticals, and is designed with an inclined bottom surface to tilt the pharmaceutical container from the horizontal and thereby allow the cannula to optimally extract the pharmaceutical from the container.

The vial access system includes a base portion comprising a substantially horizontal lower surface and a sloped upper surface adapted to support a vial comprising a bottom wall and a substantially cylindrical wall connected thereto. The sloped upper surface is adapted to ensure that a residual volume of fluid in the vial gathers in an area defined at least partially by a portion of the junction between the bottom wall and the cylindrical wall of the vial.

In a third aspect, the present invention provides a vented cannula for insertion into a pharmaceutical container, such as a vial. The vented cannula may be used in the vial access system of the present invention or may be fluidly connected to a shielded syringe to provide an alternate fluid delivery system.

The vented cannula includes a main hub comprising two opposed lateral sides and defining a fluid port and a vent, a fluid draw needle in connection with the fluid port and adapted to be placed within the container, a vent needle in connection with the vent and adapted to be placed within the container; and two resilient arms connected to the opposed lateral sides of the main hub. Each of the two arms includes a top edge and a hook member formed thereon and extending outwardly therefrom.

In a fourth aspect, the present invention provides a fluid delivery system having a retractable shielded cover to shield operators of the system from the fluid path components and the pharmaceutical contained therein. In another aspect, the fluid path components and the pharmaceutical may be disposed in a slidable drawer that may be removed from the shielded system to allow access thereto.

The fluid delivery system includes a housing having an upper surface defining a plurality of recessed portions for accommodating one or more components of a fluid path set, a cover movably connected to the housing and a locking mechanism associated with the cover. The cover is adapted to move between a first position that exposes the upper surface and a second position that overlies the upper surface, and the locking mechanism is adapted to lock the cover in the second position.

In another aspect, the fluid delivery system includes a syringe comprising a body defining a discharge outlet and a plunger movably disposed within the body, a connector comprising a valve member and defining first, second and third ports, a first tubing segment connected between the discharge outlet of the syringe and the first port of the connector, a cannula defining a fluid port, a second tubing segment connected between the fluid port of the cannula and the second port of the connector, a third tubing segment comprising a first end connected to the third port of the connector and a second end comprising a second connector, and a per-patient tubing set comprising a first end that is adapted to be connected to the second connector on the second end of the third tubing segment and a patient end that is adapted to be connected to venous access device in a patient.

In a fifth aspect, the present invention provides a method of priming the fluid path components of the fluid delivery system to remove air therefrom and to prepare the system to administer a pharmaceutical dose to a patient.

A method of priming at least a portion of a fluid path set in a fluid delivery system includes: (1) placing a tubing section of the fluid path set in fluid connection with a source of a radiopharmaceutical; (2) placing a portion of the tubing section within a dose calibrator of the fluid delivery system; (3) pumping a volume of the radiopharmaceutical through the tubing section; (4) monitoring the dose calibrator to determine if a measured activity level is substantially equal to or above a predetermined activity level; and (5) if the measured activity level is substantially equal to or above the predetermined activity level, then concluding that the tubing section of the fluid path set has been primed.

In a sixth aspect, the present invention provides a carrying system for connecting to and transporting a vial shield (containing a pharmaceutical vial). The carrying system may be used to transport the vial shield to and place the vial shield within the fluid delivery system of the present invention. In another aspect, the carrying system may be used to position the vial shield within the vial access device of the present invention.

The vial shield carrying system includes a collar unit adapted to removably engage a flange on the vial shield and a handle unit adapted to engage the collar unit. The collar unit defines two elongated slots formed in a top surface thereof, each of the slots including a pin disposed therein and extending between two opposing walls thereof. The handle unit includes a handle connected to a U-shaped cross piece that defines two, downwardly extending arms having hook members formed therein. The open ends of the hook members are formed on opposite ends of the arms and are adapted to engage the pins in the slots of the collar unit through rotation of the handle.

In a seventh aspect, the present invention provides a system and a method for calibrating a radiopharmaceutical delivery system in which the difference between the expected (based on decay from the initial activity) and measured activities of two radioisotopes are used to calculate an estimated error in the measured activity of a third radioisotope. In response to a difference between the expected and measured activity of the first or the second radioisotope, the gain of the ionization chamber is adjusted to eliminate or reduce the error for that radioisotope. When the estimated error of the third radioisotope falls within an acceptable range, the activity of the third radioisotope is measured to check that the actual error between the expected and measured activity of the third radioisotope is substantially similar to the estimated error.

Preferably, the energy levels of the first, second and third radioisotopes are less than, greater than, and relatively close to, respectively, the energy level of the radioisotope to be delivered by the system to the patient. In addition, the operator may take consecutive measurements of the first and second radioisotopes (i.e., in an iterative fashion) and adjust the gain of the ionization chamber in response thereto, before measuring the activity of the third radioisotope and comparing it against the estimated error of the third radioisotope.

A method of calibrating includes (1) measuring an activity level of a first radioisotope in an ionization chamber of the fluid delivery system, the first radioisotope having an energy level less than that of the radioisotope to be delivered to the patient; (2) comparing the measured activity level of the first radioisotope to an expected activity level of the first radioisotope; (3) adjusting the gain of the ionization chamber to compensate for the difference, if any, between the measured activity and the expected activity of the first radioisotope; (4) measuring an activity level of a second radioisotope in the ionization chamber of the fluid delivery system, the second radioisotope having an energy level similar to or greater than that of the radioisotope to be delivered to the patient; (5) comparing the measured activity level of the second radioisotope to an expected activity level of the second radioisotope; (6) adjusting the gain of the ionization chamber to compensate for the difference, if any, between the measured activity and the expected activity of the second radioisotope; and (7) calculating an estimated error in a measured activity of a third radioisotope based on the differences, if any, between the measured activity and the expected activity of the first radioisotope and the measured activity and the expected activity of the second radioisotope.

Broadly contemplated herein are improvements in radiopharmaceutical administration methods and systems. These inventions include, but are not limited to, the configuration and layout of a fluid path set for use in a fluid delivery system, arrangements for piercing and drawing fluid from a radiopharmaceutical container (such as a vial), arrangements for optimizing the positioning of a tube coil within an ionization chamber, a handle/carrying system for transporting vial shields or "pigs" that keeps an operator's hand and fingers at a safe distance from a vial access cap, and a vial access system that ensures an optimal draw of fluid from a radiopharmaceutical container.

The novel features which are considered characteristic of the present invention are set forth herebelow. The invention itself, however, both as to its construction and its method of operation, together with additional objects and advantages thereof, will be best understood from the following description of the specific embodiments when read in connection with the accompanying drawings.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification.

FIG. 3B is a partial cross-sectional view of FIG. 3A.

FIG. 3C is a plan view (in partial cross-section) taken along line 3C-3C of FIG. 3A.

FIGS. 8, 9, 10, 11, 12A, 12B, 13, 14, 15, 16A, 16B, 17, 18, 19, 20, 21 and 22 are various depictions of a graphical user interface for use in system preparation tasks.

FIG. 47A is a perspective view of the vented cannula shown in FIGS. 6C and 6G-6J being utilized as part of a first alternate fluid delivery system.

FIG. 47B is another perspective view showing the first alternate fluid delivery system of FIG. 47A.

DETAILED DESCRIPTION OF THE PREFERRED EMBODIMENTS

Figure 1A:
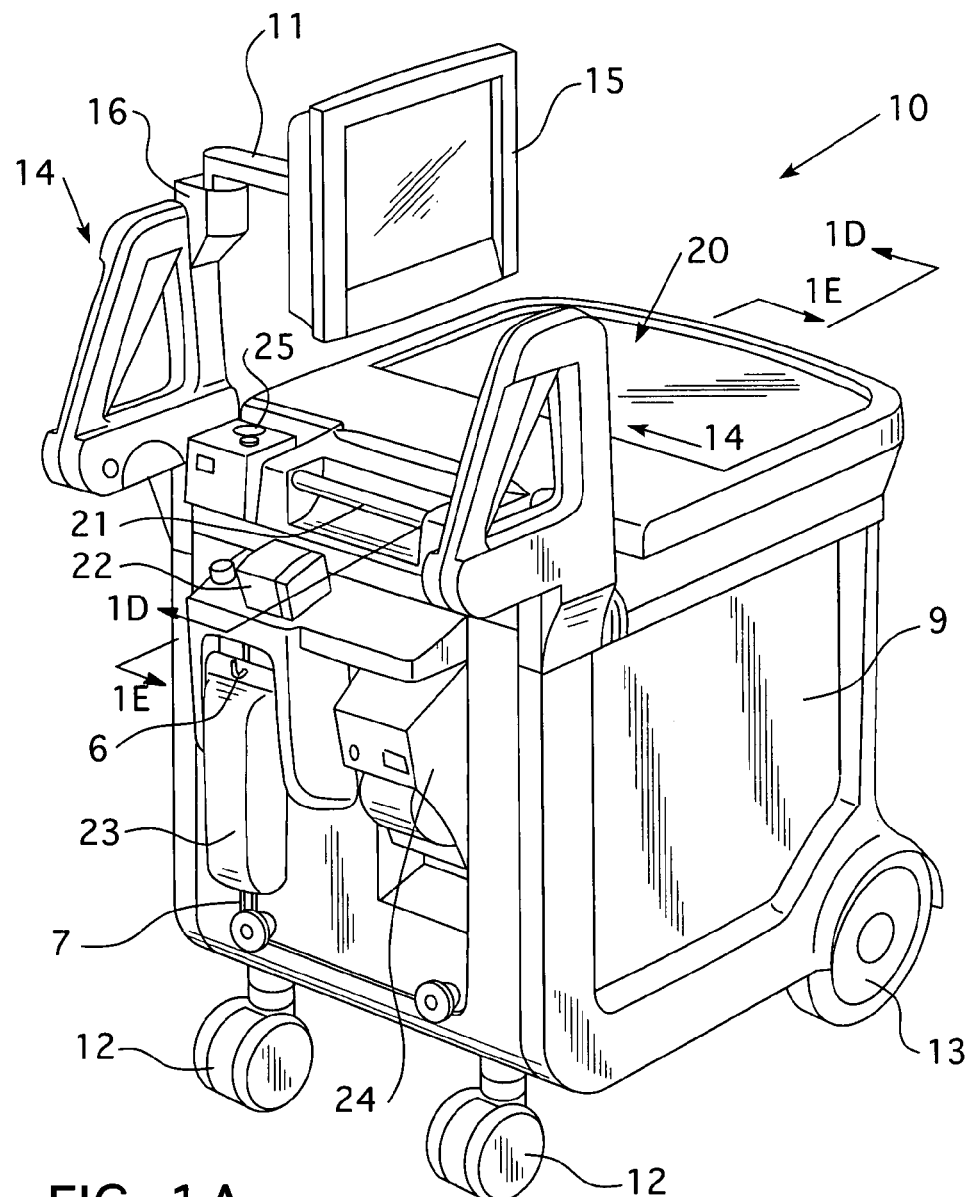
FIG. 1A is a perspective view of a fluid delivery system of the present invention.

As used herein, the term "pharmaceutical" refers to any substance or drug to be injected or otherwise delivered into the body (either human or animal) in a medical procedure and includes, but is not limited to, substances used in imaging procedures (for example, contrast media) and therapeutic substances. A number of such pharmaceutical substances pose a danger to both the patient and the personnel administering the substance if not handled and/or injected properly. Examples of hazardous pharmaceuticals include, but are not limited to, radiopharmaceuticals, biological pharmaceuticals, chemotherapeutic pharmaceuticals and gene therapeutic pharmaceuticals.

Turning now to the drawings, FIGS. 1A-1E show a preferred embodiment of the administration, injector or fluid delivery system 10 of the present invention. The fluid delivery 10 is preferably a cart-like apparatus 9 having wheels 13 and/or casters 12 for allowing the system to be movable. One or more of the wheels 13 may be lockable to prevent the system 10 from moving once it is in position. The system 10 also preferably includes one or more handles 14 for allowing an operator to move or position the system 10. Alternately, the fluid delivery system 10 may be a stand-alone or fixed-position apparatus.

The fluid delivery system 10 includes a display or graphical user interface (GUI) 15 for programming and operating the system 10. The GUI display 15 is preferably attached to one of the handles 14 (as shown) of the system 10. The display 15 may be a color display and incorporate touch-screen capability, as known in the art, for ease of use. The display 15 may be fixed, but is preferably pivotally connected to the fluid delivery system 10 (as shown), by means of a movable arm 11 that is pivotally connected to a joint 16. Further, the display 15 may be tilted or swiveled with respect to the arm 11 to allow for optimal positioning of the display 15 by an operator.

The fluid delivery system 10 preferably includes a retractable lid or cover 20 having a primary handle including a latch release 1 (see FIGS. 1D and 1E) and a secondary handle 21. The lid 20 preferably covers an upper surface 103 that defines a number of recessed portions, such as wells and troughs, into which a vial or container (see 902 in FIG. 4C) of a pharmaceutical or a radiopharmaceutical (discussed in more detail below) and various components of a multi-patient fluid path set (hereinafter MPDS; discussed in more detail below) may be positioned during an injection procedure. A locking mechanism, such as a combination or a key lock (not shown), may be used to lock the lid 20 in a closed position to, for example, prevent use or access of the system 10 by unauthorized personnel. In another embodiment, the locking mechanism may be a software-implemented lock, such as a password-protected access point, that is accessible through the display 15 and is adapted to lock the cover in a closed position and/or to prevent unauthorized personnel from accessing or operating the system 10.

The lid 20 is slidable or retractable (by, for example, using primary handle and latch release 1) with respect to the cart 9 to allow for insertion and removal of the vial or container 902 and MPDS from the fluid delivery system 10. The lid 20, upper surface 103 and various other portions of the cart 9 preferably include suitable radioactive shielding (such as lead) for minimizing potential radiation exposure from the radiopharmaceutical to the operator. In this manner, the radiopharmaceutical vial 902 and the components of the MPDS can lie below the plane of surface 103, whereupon the surface 103 or one or more portions thereof can be covered by the lid 20 during use to limit radiation exposure to the operator or other medical personnel. Further, instead of a retractable lid 20, surface 103 itself could be disposed on a portion of the injector apparatus 10 (e.g., a drawer-type mechanism) that slidably displaces with respect to a remainder of the injector apparatus 10.

Figure 1B:
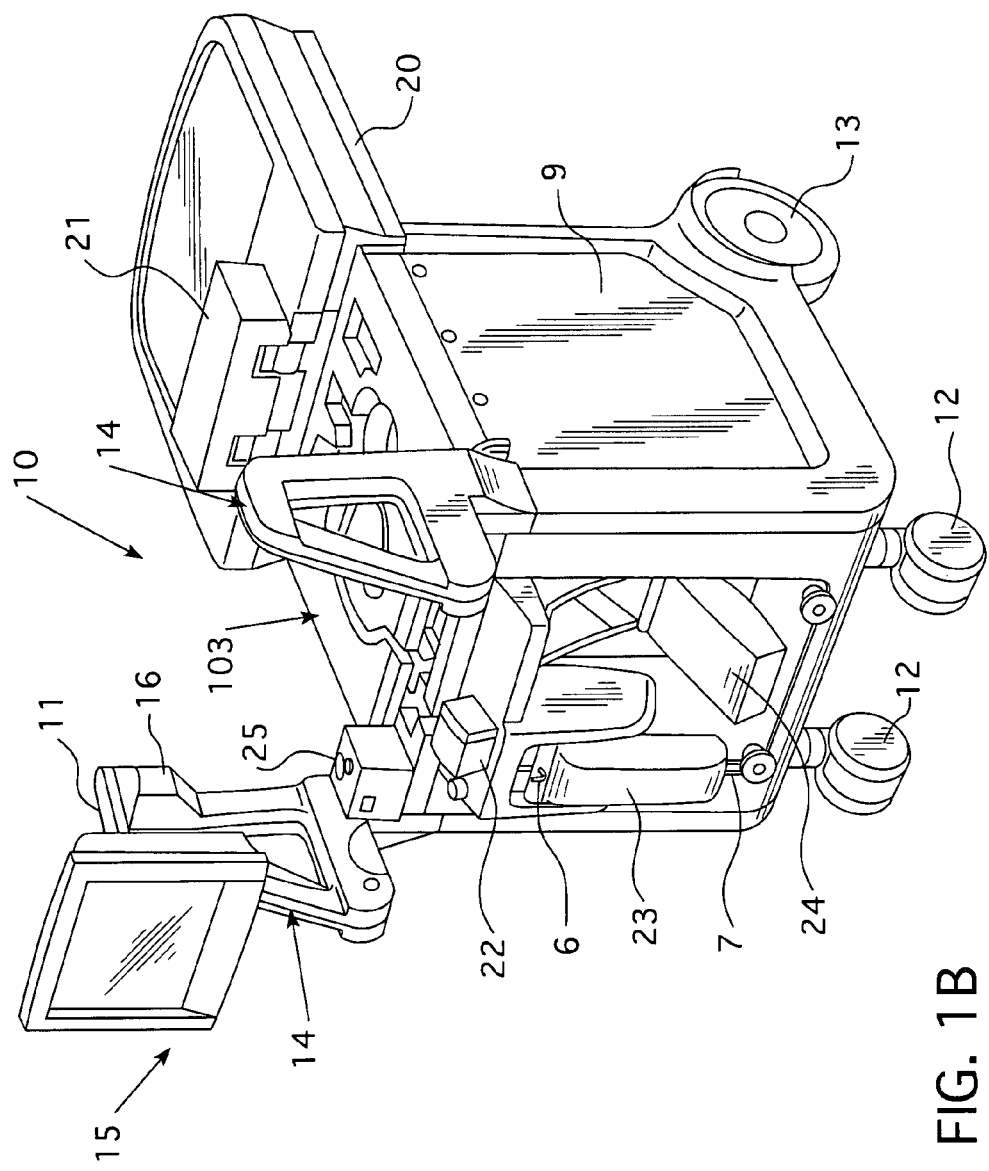
FIG. 1B is another perspective view of the fluid delivery system of FIG. 1A with the shielded cover thereof in a retracted position.
Figure 1C:
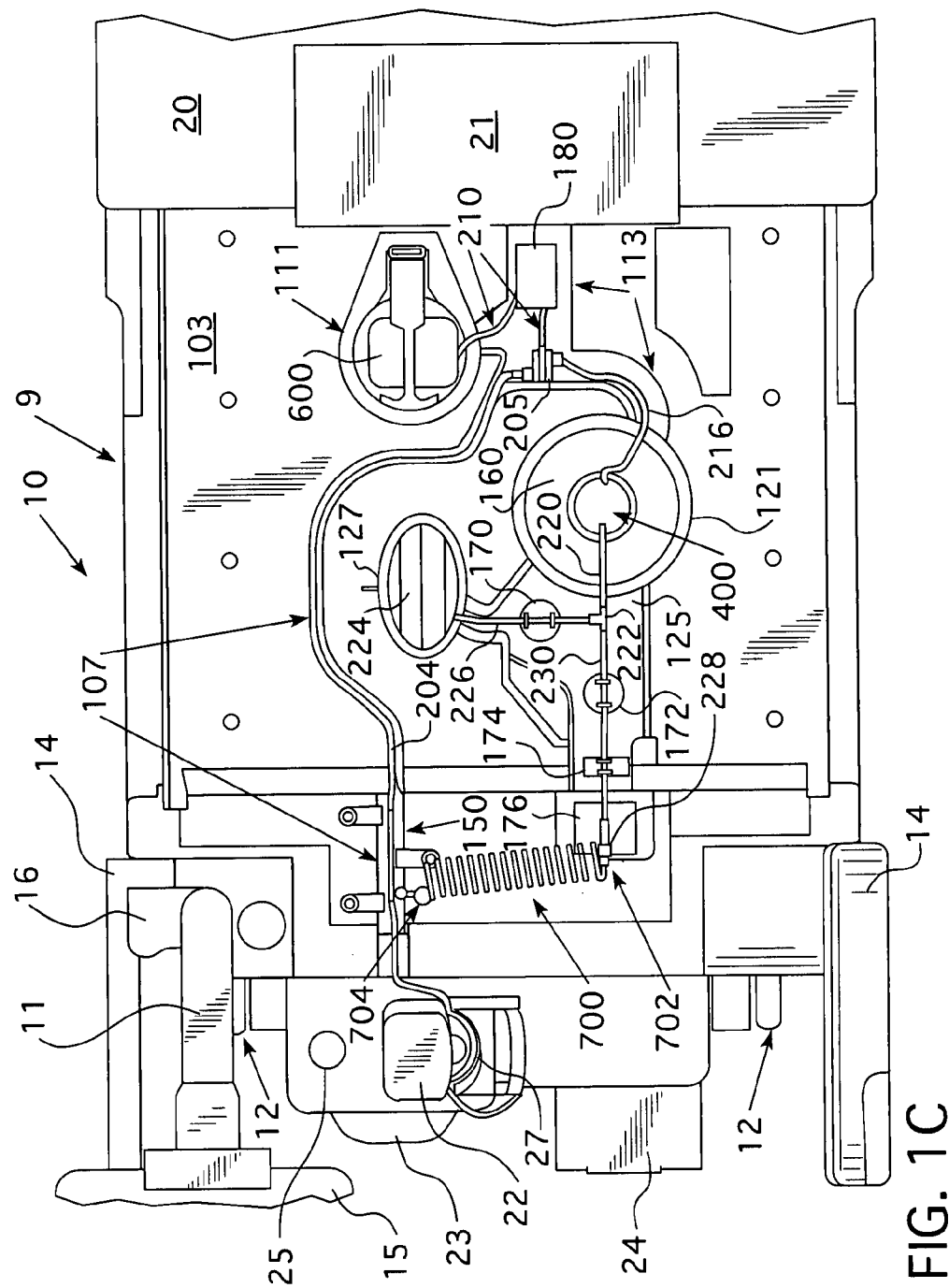
FIG. 1C is a top plan view of the fluid delivery system shown in FIGS. 1A and 1B with various fluid path components positioned therein.
Figure 1D:
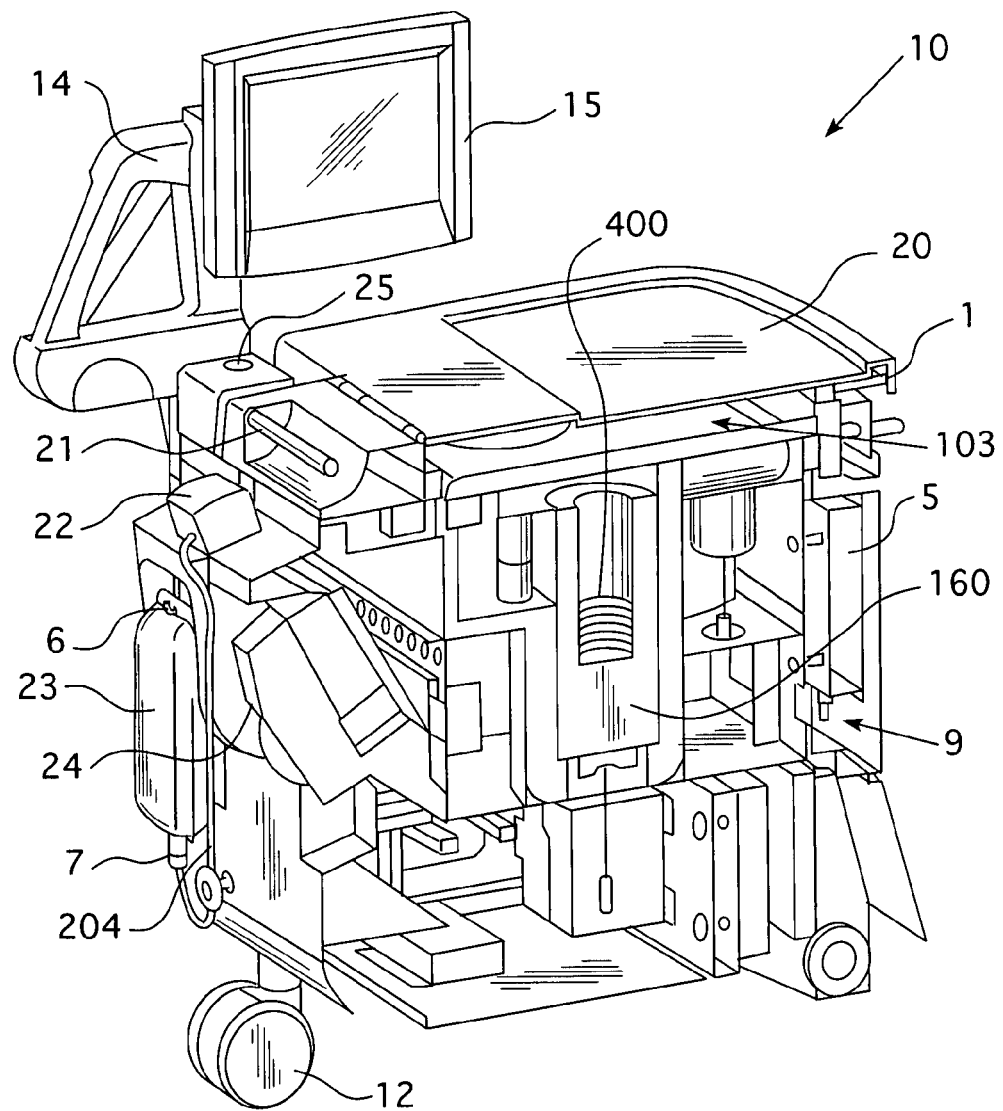
FIG. 1D is a cross-sectional view taken along line 1D-1D of FIG. 1A.
Figure 1E:
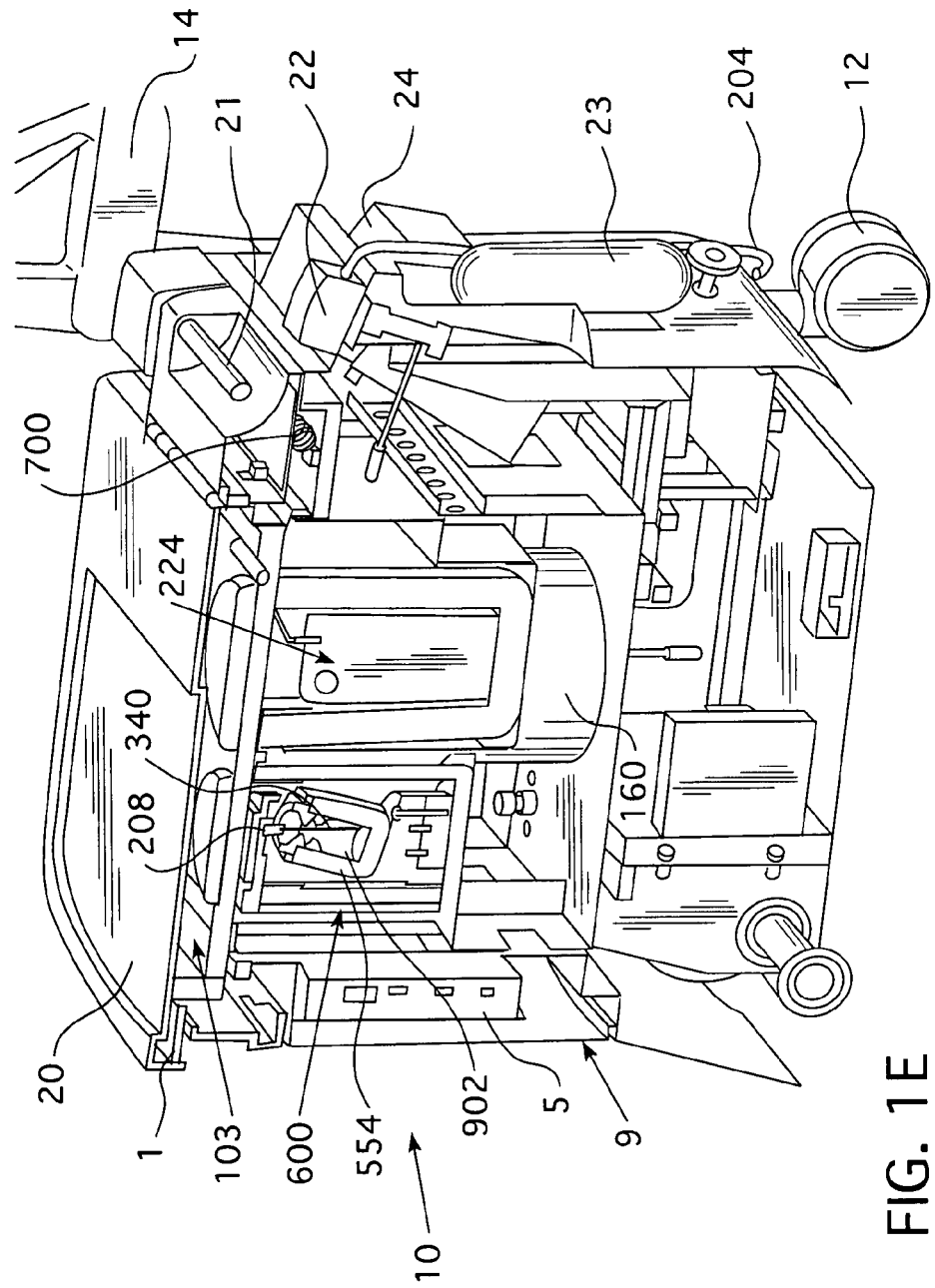
FIG. 1E is a cross-sectional view taken along line 1E-1E of FIG. 1A.

As further shown in FIGS. 1A, 1B and 1D, the fluid delivery system 10 includes a pumping mechanism, such as a peristaltic pump 22, a removable/replaceable source of medical fluid 23 (such as saline), a printer 24 and an interrupt button 25. The peristaltic pump 22 is shown in a closed position in FIG. 1A, but may be opened (see FIGS. 1B, 1C and 2B) to receive a length of tubing 27 (see FIGS. 1C and 2) in fluid connection with the source of medical fluid 23 to inject the fluid into a patient (discussed in more detail below). While a peristaltic pump 22 is currently preferred, any suitable type of pumping mechanism, such as a piston-driven syringe pump, gear pump, rotary pump or in-line pump, may be used.

The printer 24 may be used to generate records of the injection and/or imaging procedures performed on patients, for inclusion in patients' medical records or for billing or inventory purposes. The printer 24 may be pivotally connected to the system 10 (see FIG. 1B) to allow an operator to load paper or labels into the printer 24.

The interrupt button 25 allows an operator to quickly and easily pause or abort an injection procedure in the event of, for example, patient discomfort or an emergency, without having to resort to the GUI display 15 (which also can be manipulated to pause or abort an injection procedure). The interrupt button 25 may be connected to LEDs and/or a printed circuit board to provide visual and/or auditory alarms when the interrupt button 25 has been activated.

Turning to FIGS. 1C-1E, 2A and 2B, additional features and components of the fluid delivery system 10, including the upper surface 103, the MPDS 200, a vial access device 600 and a single-patient fluid path set 700 (hereinafter SPDS), will be discussed.

As shown in FIG. 1C, the upper surface 103 generally defines wells and recesses or troughs into which various components of the MPDS are situated. Specifically, a first recess or trough 107 accommodates a first tubing section 204 of the MPDS 200 and a tubing holder 150 for holding the tubing section 204 and preventing it from getting kinked or tangled with, for example, the SPDS 700. The first tubing section 204 may also include the tubing length 27 that is placed within the peristaltic pump 22 and is in fluid connection with the medical fluid source 23.

Figure 3A:
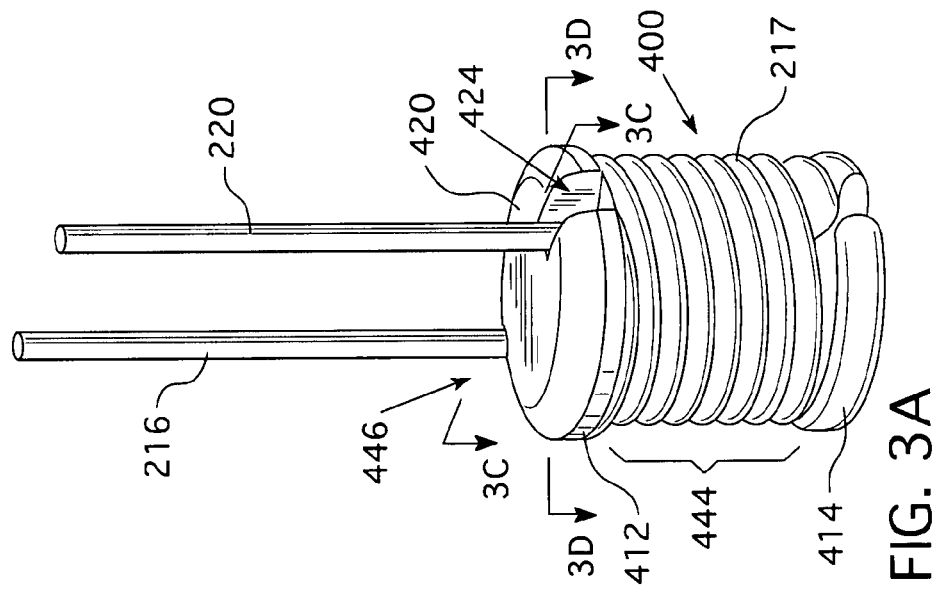
FIG. 3A is an elevational view of a preferred embodiment of a coil assembly of the present invention.

The first trough 107 leads into a second recess or trough 113 that accommodates a second pumping mechanism 180, such as a peristaltic pump, and a T-connector 205 (preferably including check valves 214, 215) of the MPDS 200. As shown in FIG. 1C, the second trough 113 also leads to a first well 111 that accommodates a vial access device 600 and a radiopharmaceutical vial or container 902 disposed in a vial shield or PIG 554 (discussed in more detail below) and to a second well 121 that accommodates a dose calibrator or ionization chamber 160 for the fluid delivery system 10. As shown in FIGS. 1D and 3F, the ionization chamber 160 preferably accommodates a coil assembly 400 of the MPDS 200 (discussed in more detail below).

A third recess or trough 125 extends from the second well 121 to a third well 127 and further along the surface 103 of the fluid delivery system 10. The trough 125 accommodates a T-connector 222 of the MPDS 200, two pinch valves 170, 172, an air detector 174 and a mount or retainer 176 for holding the connector end 228 of the MPDS 200. The pinch valves are preferably powered and controlled by the fluid delivery system 10, but alternately could be manually-operated. In another alternate embodiment, the pinch valves 170, 172 and the T-connector 222 of the MPDS 200 may be replaced with a manual or automated 3-way stopcock.

The third well 127 accommodates a waste receptacle or bag 224 for receiving medical fluid and/or pharmaceutical that is discarded during, for example, a priming procedure (discussed in more detail below) to prepare the system 10 for an injection procedure.

As shown in FIG. 1C, the SPDS 700 includes a length of tubing (preferably coiled, as shown) having a first end 702 that is attachable to the connector end 228 of the MPDS 200 and a patient end 704 having a luer connector that is attachable to, for example, a catheter (not shown) placed in a venous structure of a patient. As discussed in more detail below, the MPDS 200 may be used for multiple patients but the SPDS 700 is intended to be used on a per-patient basis and discarded after use with a single patient to prevent, for example, cross-contamination between patients.

As can be appreciated after reviewing FIG. 1A-1E, the secondary handle 21 of lid 20 overlies the tubing holder 150 and the mount 176 when the lid 20 and handle 21 are closed to cover the MPDS 200. The secondary handle 21 may be flipped open (from the closed position shown in FIG. 1A) without retracting the cover 20 to allow an operator to connect the SPDS 700 to the MPDS 200 (as discussed in more detail below). As best shown in FIG. 1C, the SPDS 700 may be placed under the secondary handle 21 when it is closed.

The fluid delivery system 10 further includes a system controller 5 (see FIGS. 1D and 1E) in communication with the various components thereof, including the GUI 15, the pumps 22, 180, the dose calibrator or ionization chamber 160, the stop button 25, the air detector 176, the printer 24 and the motors 30, 31 (see FIG. 3F) for pinch valves 170, 172, respectively, for controlling the operation of the system 10. The system controller 5 is preferably a single-board computer, including a CPU having a main memory.

As can be appreciated, the wells and troughs formed in the upper surface 103 can be sized, configured or arranged as suitable for the length, design or configuration of the MPDS 200 or other components thereof, including the radiopharmaceutical vial 902, vial shield 554, vial access device 600, ionization chamber 160, waste receptacle 224, etc.

It should be understood that FIG. 1C in no way is intended to convey dimensions or relative dimensions of the aforementioned recessed portions or MPDS components; instead, FIG. 1C conveys general positional relationships of such recessed portions with respect to one another.

It should further be understood and appreciated that the recessed portions shown and described with respect to FIG. 1C are preferably encased throughout with suitable radioactive shielding to further minimize exposure to an operator.

Figure 2A:
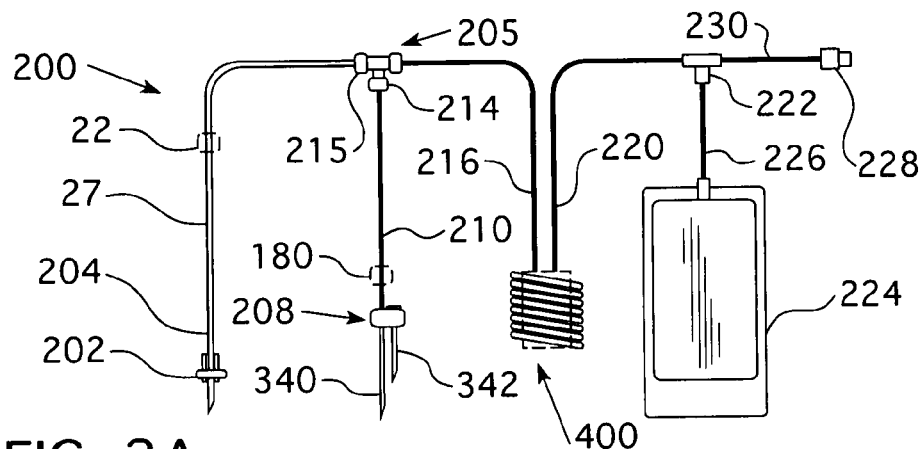
FIG. 2A is a schematic illustration of the multi-patient fluid path set and components thereof of the present invention.
Figure 2B:
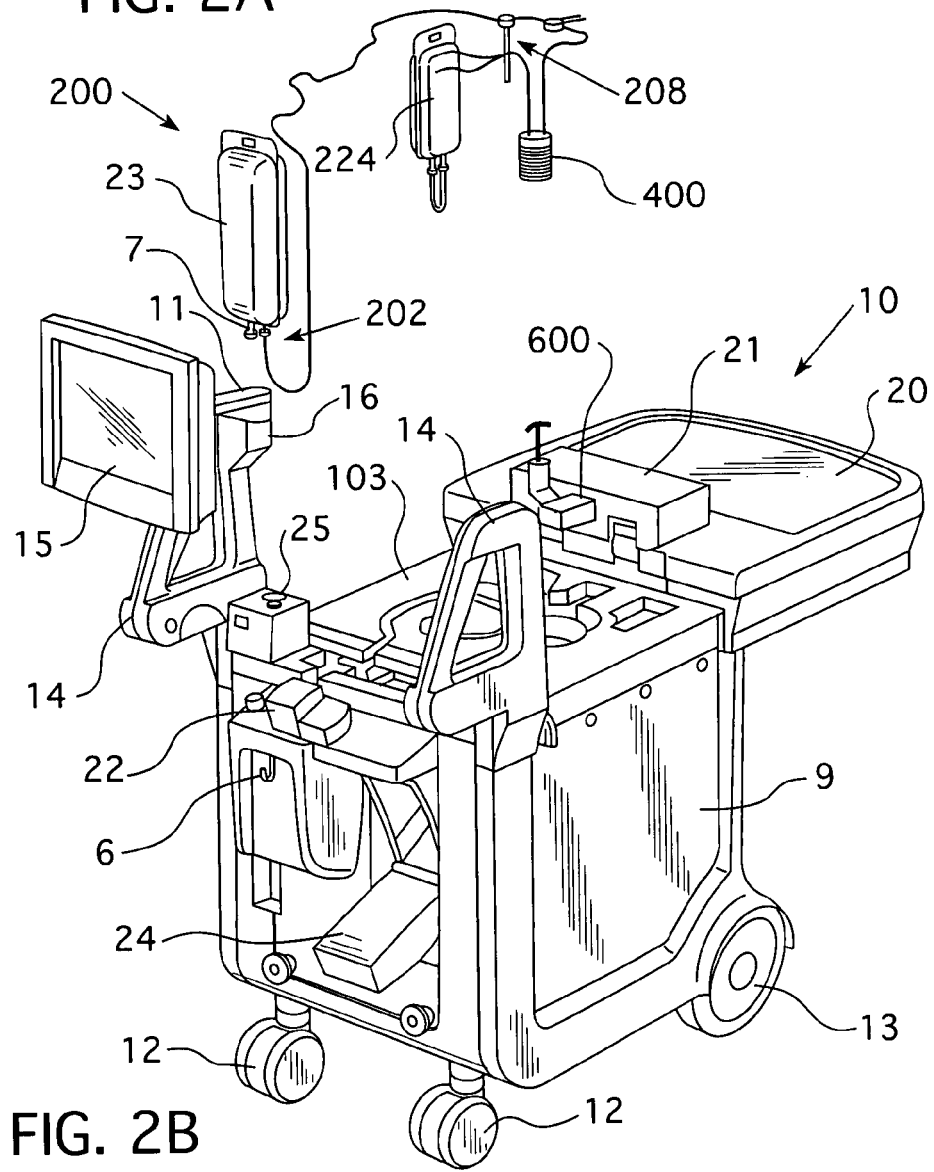
FIG. 2B is an exploded view showing the multi-patient fluid path set shown in FIG. 2A connected to a fluid source and disposed above the fluid delivery system shown in FIGS. 1A-1E.

Turning now to FIGS. 2A and 2B, a preferred embodiment of the MPDS 200 and components thereof will be discussed. In addition, specific details of the coil assembly 400 employed in the MPDS 200 are shown and described with respect to FIGS. 3A-3F and FIG. 1D.

By way of a general overview, the MPDS 200 in accordance with at least one presently preferred embodiment of the present invention allows for FDG (or other radiopharmaceutical) to be drawn from a bulk radiopharmaceutical vial 902 and placed into a coil assembly 400 that allows an ionization chamber 160 to measure the amount of activity in the coil assembly 400. Once the system prepares a dose having the desired activity level, the fluid delivery system 10 will deliver the FDG dose to the patient (through the SPDS 700).

Generally, the MPDS 200 can be considered in terms of four components: (1) a medical fluid or saline component; (2) an FDG or pharmaceutical component; (3) a coil assembly component; and (4) a waste component. The saline component preferably draws saline out of a bulk source 23 (e.g., via peristaltic pump 22). This is then used to prime the MPDS (i.e., remove air therefrom), position FDG in the coil assembly 400 in the ionization chamber 160, and then deliver the dose to the patient.

The FDG component preferably serves to draw FDG out of a bulk radiopharmaceutical vial 902 (e.g., via peristaltic pump 180) and place the same into the fluid path to the ionization chamber 160.

The coil assembly component preferably is employed to position the radiopharmaceutical to allow its radioactivity level to be optimally measured by the ionization chamber 160. Through the arrangement of the coil assembly 400 (as discussed in more detail below), the radiopharmaceutical can be optimally oriented and located within the "linear region" of the ionization chamber 160 to more accurately measure its activity level and prepare an optimal dose for injection into a patient.

The waste component preferably holds the saline fluid and/or radiopharmaceutical that are discarded during the prime and dose preparation procedures, which are conducted to prepare the fluid path and the pharmaceutical dose for injection into a patient.

FIG. 2A schematically illustrates the MPDS 200 in accordance with a preferred embodiment of the present invention. The MPDS shown in FIG. 2A may preferably be pre-connected as shown and may originally be stored in a sterile packet or container for use in an injector apparatus, such as fluid delivery system 10, when desired. For a non-restrictive and illustrative appreciation of a manner in which MPDS 200 can be incorporated in an injector apparatus, simultaneous reference may be made to FIGS. 1A-1E and 2B (and the discussion thereof hereinabove).

Primary components of MPDS 200 include, as shown, a spike 202 for connecting the MPDS to the medical fluid or saline source 23, a vented cannula 208 for connecting with a source of FDG or other radiopharmaceutical, a coil assembly 400, a T-connector 205 with check valves 214, 215 for fluidly connecting the saline source 23, the radiopharmaceutical source and the coil assembly 400, a waste bag 224, a connector end 228, and a T-connector 222 for fluidly connecting the coil assembly 400, the waste bag 224 and the connector end 228.

In general, MPDS 200 and fluid delivery system 10 are configured for priming (i.e., purging air from) the MPDS 200, delivering pharmaceutical (e.g., FDG) to a patient, and providing a saline flush, while minimizing or eliminating exposure of administering or operating personnel to the detrimental effects of the pharmaceutical and minimizing or eliminating creation of contaminated waste. Moreover, MPDS 200 and other elements of the present invention also facilitate safe delivery of the pharmaceutical to multiple destinations (for example, dose delivery to a series of patients).

A T-connector 205 and check valves 214, 215 preferably accommodate a first tubing section 204 that is in fluid connection with spike 202 and a second tubing section 210 in fluid connection with cannula 208. The check valves 214, 215 may be integrally formed with the T-connector 205 or may be separate components, or they could be combined into a single dual check valve. The check valves 214, 215 prevent saline from being pumped by peristaltic pump 22 into second tubing section 210 and the pharmaceutical from being pumped by peristaltic pump 180 into the first tubing section 204.

A third tubing section 216 thence preferably leads to coil assembly 400 (including tube coil 444), and a fourth tubing section 220 preferably leads from the coil assembly 400 to the T-connector 222. As described below, in a preferred embodiment the tube coil 444 is formed from a tubing section 217 that has dimensions different from those of the third tubing section 216 and the fourth tubing section 220. In an alternate embodiment, the third tubing section 216, the tube coil 444 and the fourth tubing section 220 are formed from the same length of tubing.

A fifth tubing section 226 leads from the T-connector 222 to the waste receptacle 224 and a sixth tubing section 230 leads from the T-connector 222 to the connector end 228. As shown above in FIG. 1C, the connector end 228 mates with the first end 702 of the SPDS 700 for delivery of a pharmaceutical to a patient.

In a preferred embodiment, the connector end 228 is a swabable luer valve (Part No. 245204024 provided by Halkey-Roberts Corporation of St. Petersburg, Fla.) that is biased to close or seal off the connector end 228 of the MPDS 200 when the SPDS 700 is not connected thereto. The swabable luer valve prevents the MPDS 200 from being contaminated and allows an operator to swab or clean (by, for example, an alcohol wipe) the connector end 228 prior to connecting an SPDS 700 thereto. Alternately, however, the connector end 228 may be a standard luer connector as known in the art.

As schematically shown in FIG. 2A, the tubing length 27 of the first tubing section 204 can be placed within pump 22 (indicated by dotted lines) to pump saline or other medical fluid from source 23 and a portion of the second tubing section 210 can be placed within pump 180 (indicated by dotted lines) to pump a radiopharmaceutical from a radiopharmaceutical source.

Absolute and relative dimensions of the components shown in FIG. 2A, including tubing, may be chosen to best suit the applications at hand. Preferably, the first tubing section 204 is approximately 56.75 inches in length, has an outer diameter (OD) of approximately 0.188 inches and an inner diameter (ID) of approximately 0.062 inches and has a 45 durometer, the third tubing section 216 is approximately 5 inches in length, has an OD of approximately 0.163 inches and an ID of approximately 0.062 inches and has a 60 durometer, the fourth tubing section 220 is approximately 12 inches in length, has an OD of approximately 0.163 inches and an ID of approximately 0.062 inches and has a 60 durometer, and the fifth tubing section 226 and the sixth tubing section 230 are each approximately 5 inches in length, have an OD of approximately 0.163 inches and an ID of approximately 0.062 inches and have a 60 durometer. The second tubing section 210 is approximately 8.75 inches in length and is formed of microbore tubing having an OD of about 0.094 inches and an ID of about 0.032 inches and a 45 durometer. The tubing in tube coil 444 preferably is approximately 41 inches in length, has an OD of about 0.218 inches and an ID of about 0.156 inches and an 80 durometer.

Preferably, the microbore tubing of second tubing section 210 is formed of, for example, silicone, C-Flex, or silicone-like PVC material. Essentially, the use of microbore tubing in second tubing section 210 improves volume accuracy and thereby improves measured activity accuracy (i.e., of pharmaceutical delivered to the patient) and reduces radiopharmaceutical waste.

By way of tubing material for the other tubing sections 204, 216, 220, 226, 230 and tube coil 444, essentially any suitable polymeric material, including standard PVC or pump tubing, may be employed.

Figure 2C:
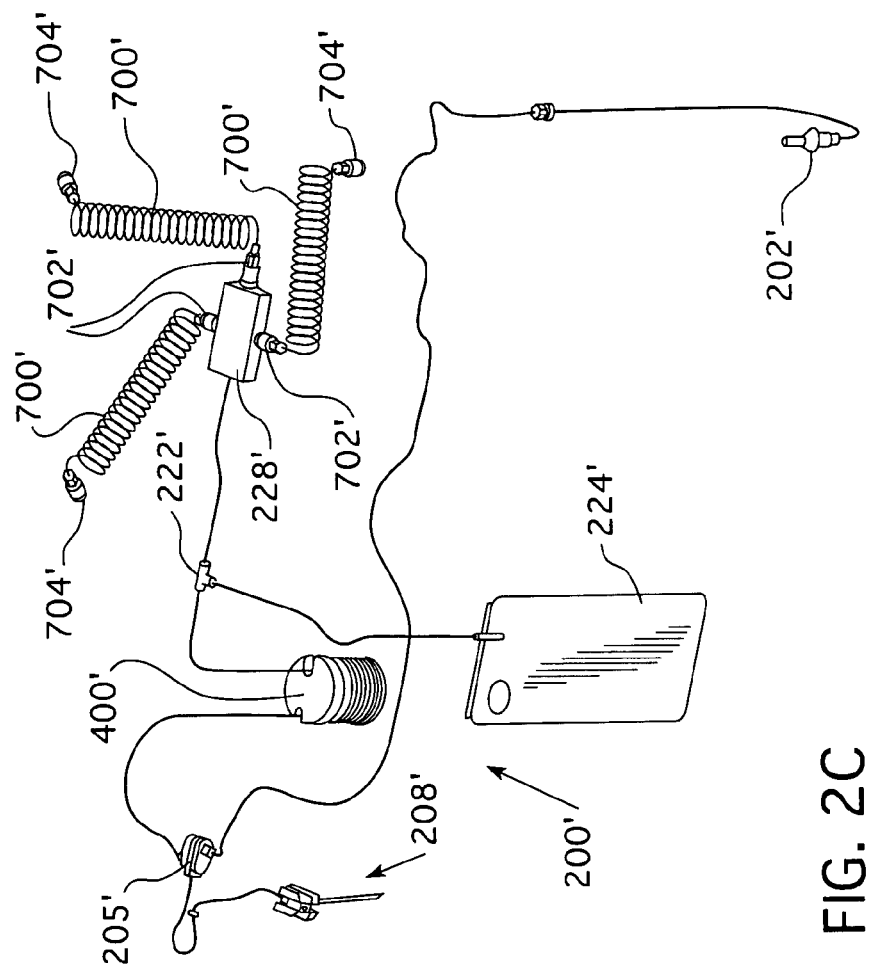
FIG. 2C is a perspective view of an alternate embodiment of the multi-patient fluid path set of the present invention.

In an alternate embodiment of the MPDS 200' shown in FIG. 2C, a conventional manifold 228' or stopcock may be substituted for the connector end 228 of the MPDS 200 (all other components of the MPDS 200' may be identical or similar to those shown in FIG. 2A and are denoted in FIG. 2C by prime notations). As shown in FIG. 2C, the manifold 228' includes three outlet ports (preferably including swabable valves) to which respective first ends 702' of the SPDSs 700' are connected. By connecting the respective patient ends 704 of the SPDSs 700' to, for example, catheters placed in patients, pharmaceutical doses can be delivered sequentially or concurrently to three separate patients. While the manifold 228' shown in FIG. 2C includes three ports for connection to three SPDSs 700', two, four, five or any suitable number of ports may be included in manifold 228' for connection with a like number of SPDSs 700'.

Referring again to FIGS. 1A-2B, the placement of the MPDS 200 in the fluid delivery system 10 and the connection of the SPDS will now be discussed. To set up the system 10 at, for example, the beginning of the day, the operator lifts the secondary handle 21, grasps the primary handle and latch release 1 and retracts the lid 20 to reveal the upper surface 103 of the system 10. If a used MPDS 200 is present in the system 10, the operator will remove and discard it.

A new MPDS 200 may be removed from its (typically sterile) packaging and placed in the system 10 as shown in FIG. 1C. This includes placing the waste receptacle 224 into well 127, placing coil assembly 400 into ionization chamber 160, placing second tubing section 210 into operative connection with pump 180, placing the tubing length 27 of the first tubing section 204 into operative connection with pump 22 and tubing holder 150, placing vented cannula 208 into fluid connection with radiopharmaceutical source or vial 902 located in well 111, placing fifth tubing section 226 in operative connection with pinch valve 170, and placing sixth tubing section 230 in operative connection with pinch valve 172, air detector 174 and mount 176. A saline source 23 may be hung on hook 6 (see FIGS. 1A, 1B and 2B) or otherwise mounted on fluid delivery system 10, and spike 202 is inserted into port 7 (see FIGS. 1A, 1B and 2B) of source 23 to fluidly connect the MPDS 200 to the source 23. Of course, this installation procedure does not need to completed in the order described above, but may be completed in any suitable order consistent with the description or drawings hereof.

After the MPDS 200 is installed and preferably primed (as discussed below), the first end 702 of the SPDS 700 is connected to the connector end 228 of the MPDS 200 and the SPDS 700 is preferably primed to provide a wet connection at the patient end 704 of the SPDS 700, which is then connected to a catheter (not shown) located in a patient. The SPDS 700 is preferably a coiled tubing formed of standard PVC, approximately 60 inches in length and having an OD of approximately 0.100 inches and an ID of approximately 0.060 inches and a 90 durometer.

As shown in FIGS. 2A and 2B, the MPDS 200 includes a coil assembly 400. In the broadest sense, coil assembly 400 may include a section of tubing (including portions of third and fourth tubing sections 216, 220) that is simply gathered (in a coiled or an uncoiled, amorphous fashion) and placed inside ionization chamber 160.

As shown in FIGS. 3A-3F, however, a preferred embodiment of coil assembly 400 includes a (preferably thermoformed) core element or structure 446 that is preferably configured for allowing a tubing section 217 to be wrapped thereupon and to assume the coiled tube section indicated at 444. As such, the coiled tube section or tube coil 444 is preferably formed on the core element 446 to facilitate optimal positioning of the tube coil 444 within the ionization chamber 160.

To facilitate positioning of the tube coil 444, the core element 446 preferably includes a tube channel 410 defined by shoulders 412, 414 (see FIG. 3B) that retain tube coil 444 therebetween to hold the tube coil 444 in position and to prevent tube kinking. Further, the upper surface 420 of core element 446 defines an inlet channel or groove 422 and an outlet channel or groove 424 to accommodate third tubing section 216 and fourth tubing section 220, respectively.

In an alternate embodiment, the core element 446 could include a coiled tube channel (not shown) formed therealong to further guide and retain the tubing segments or turns that form tube coil 444 between shoulders 412, 414.

The core element 446 preferably is self-centering when inserted into the sleeve 162 of the ionization chamber 160 of the fluid delivery system 10 to thereby facilitate optimal performance (see FIG. 3F). This may be achieved either through structural features of the coil assembly 400, the structure of core element 446 itself, or a combination thereof when used with the sleeve 162 of the ionization chamber 160.

Figure 3D:
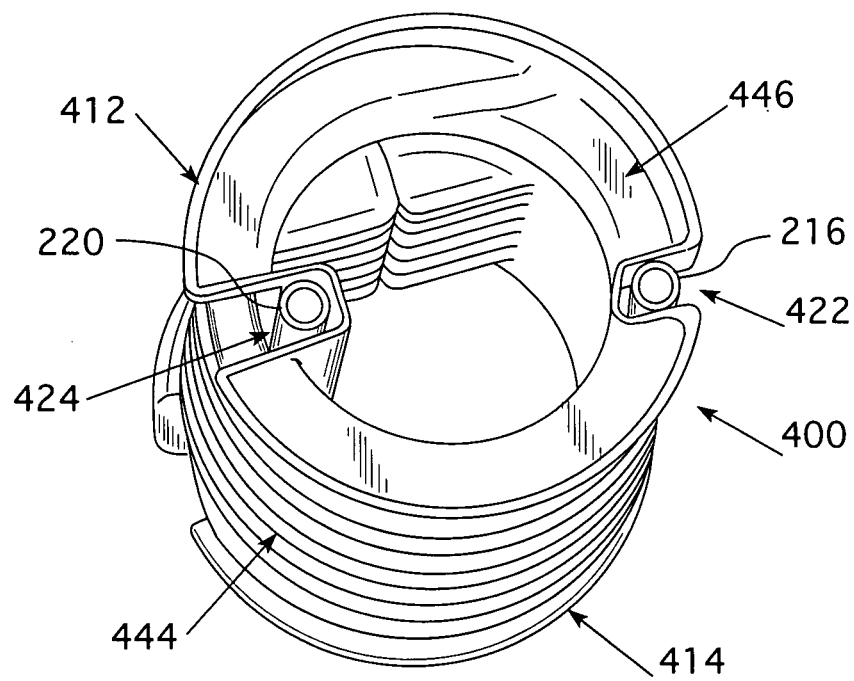
FIG. 3D is a cross-sectional view taken along line 3D-3D of FIG. 3A.
Figure 3E:
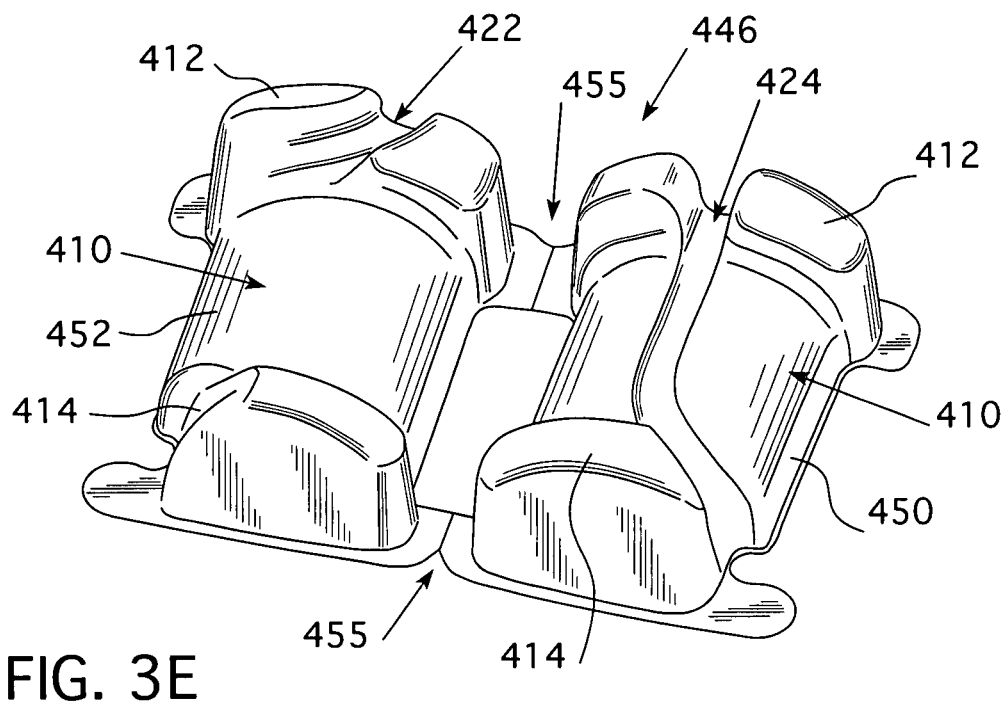
FIG. 3E is a perspective view of the core element of the coil assembly shown in FIG. 3A.
Figure 3F:
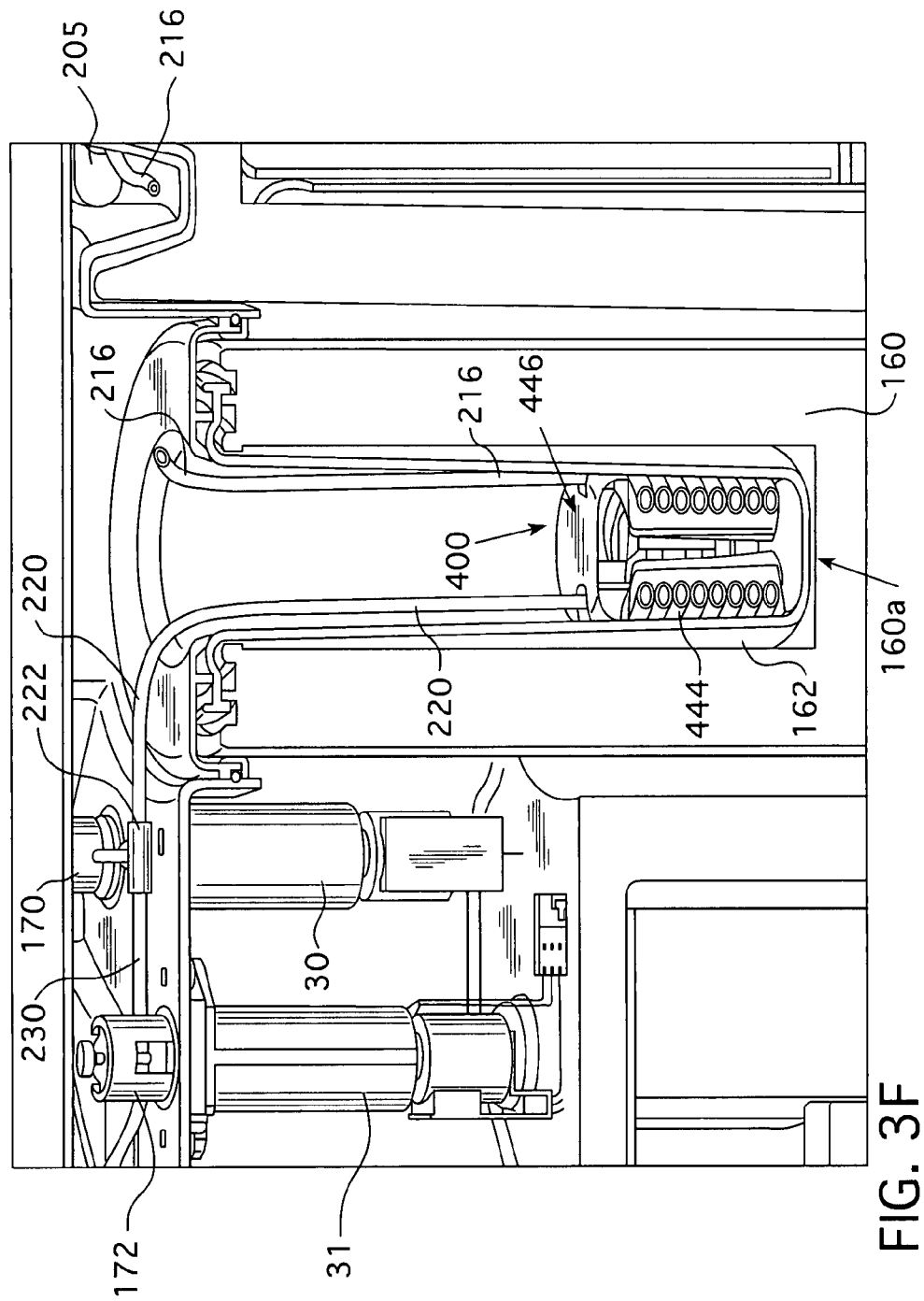
FIG. 3F is an enlarged view of FIG. 1D showing the coil assembly in the ionization chamber of the fluid delivery system.

As best shown in FIG. 3E, the core element 446 is preferably formed by folding two elements (450, 452) together along an integral hinge 455. Suitable form-locking mechanisms can be molded onto the core element 446 to facilitate clasping of the elements 450, 452 together.

FIGS. 1C, 1D and 3F show coil assembly 400 positioned concentrically in the sleeve 162 of the ionization chamber 160. The core element 446 and the tube coil 444 are sized and dimensioned so that the coil assembly 400 is optimally positioned within the "linear region" of the ionization chamber 160 so that the ionization chamber 160 can accurately determine the activity level of one or more volumes of radiopharmaceutical that is located within the tube coil 444. The "linear region" of an ionization chamber is the region in which activity level measurements are repeatable and predictable. For the preferred ionization chamber (Model IK-102 Short Ionization Chamber provided by Veenstra Instruments) used in system 10, the "linear region" is located within a window of 5 mm to 65 mm measured from the base or bottom wall 160a of the ionization chamber 160 (see FIG. 3F).

In a preferred embodiment, the tube coil 444 is comprised of approximately 7 turns (see FIGS. 3A and 3B) formed from a length of tubing that is approximately 41.0 inches. As shown in FIG. 3B, the height H of the tube coil 444 is approximately 1.53 inches and the diameter D of the tube coil 444 is approximately 1.95 inches. The tube coil 444 is preferably formed from a tube having an OD of 0.218 inches and an ID of 0.156 inches. Further, based on the length and ID of the tubing, the tube coil 444 preferably has a volume capacity of approximately 12.5 ml.

As discussed heretofore, a source, container or vial 902 (see FIG. 4C) of a pharmaceutical or radiopharmaceutical is placed into the fluid delivery system 10 (e.g., in well 111 formed in upper surface 103) to prepare and perform an injection procedure. A radiopharmaceutical container or vial 902 is typically placed in a conventional vial shield or PIG 554 for transport by personnel.

Figure 4A:
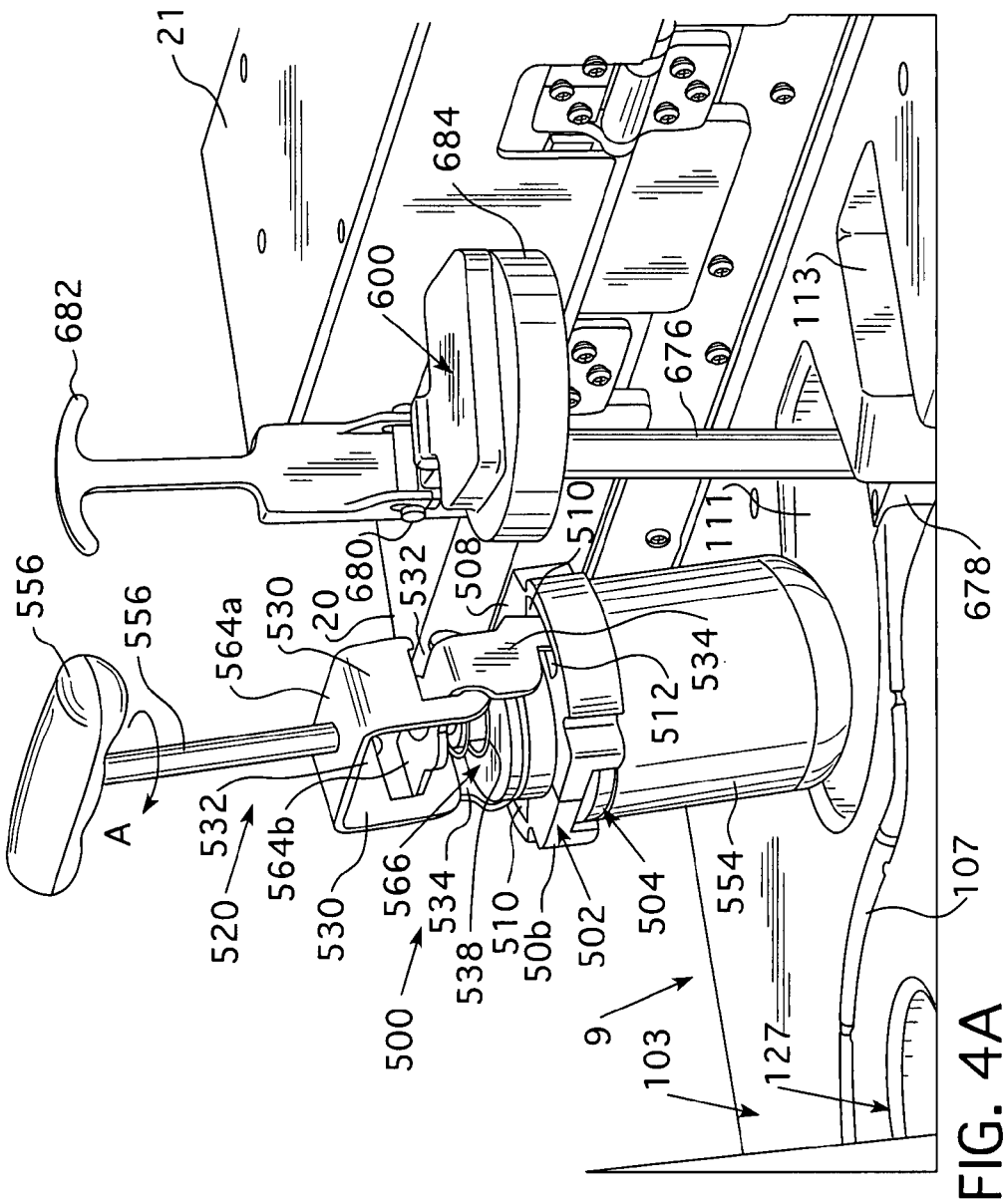
FIG. 4A is an elevational view of preferred embodiments of a vial shield carrying system and a vial access system of the present invention.
Figure 4B:
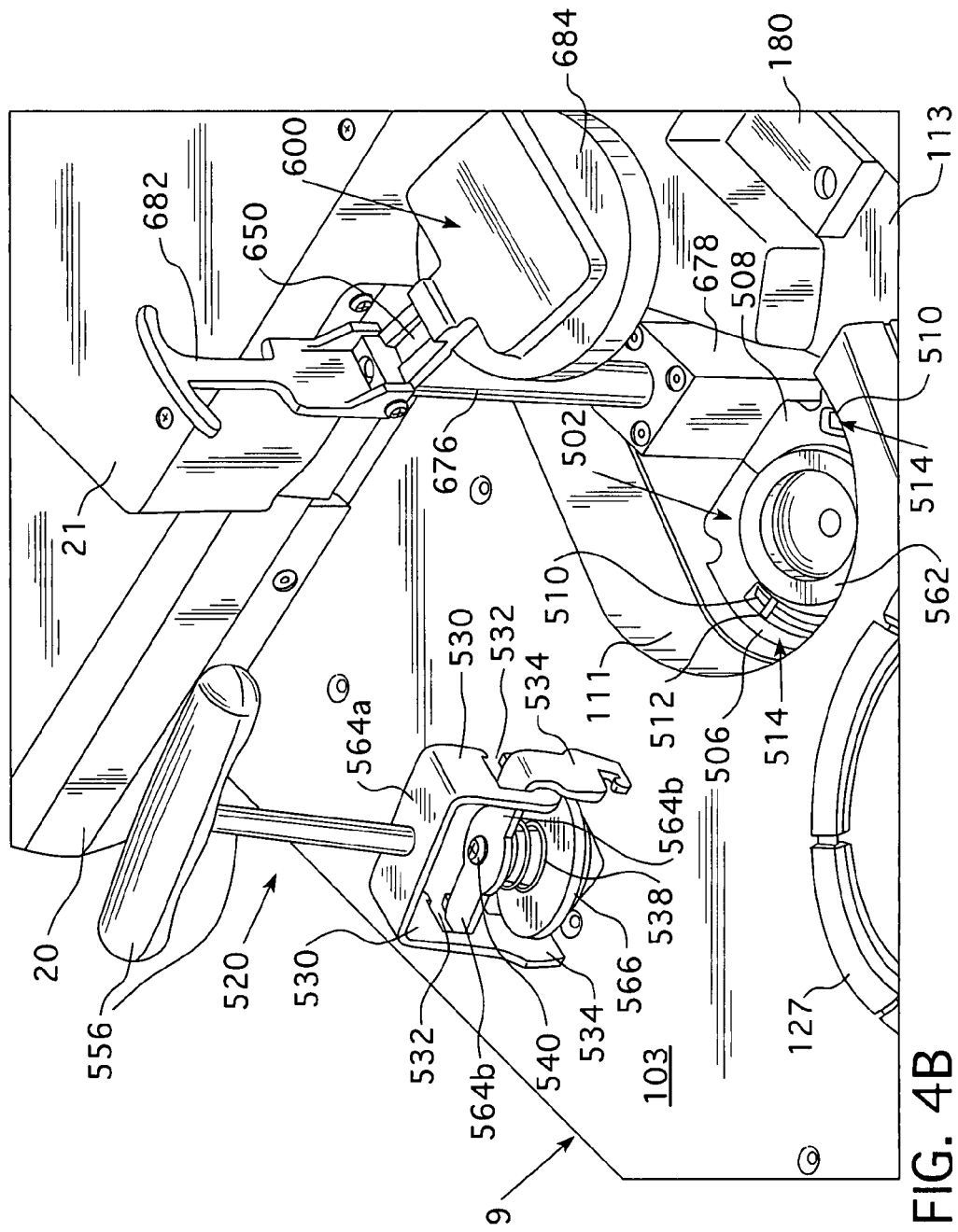
FIG. 4B is a perspective view showing the vial shield, the vial shield carrying system and the vial access system of FIG. 4A.
Figure 4C:
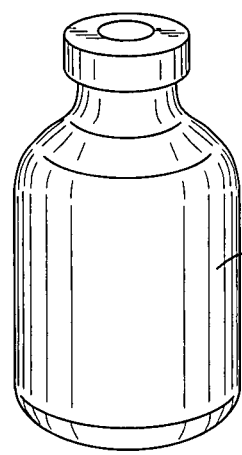
FIG. 4C is an elevational view of a pharmaceutical vial that may be used in the fluid delivery system of the present invention.

Turning now to FIGS. 4A and 4B, preferred embodiments of a vial shield carrying device or system 500 and a vial access system 600 of the present invention are shown. Vial access system 600 is removably disposed within well 111 of fluid delivery system 10 and operates to hold vial shield 554 and to access the contents of the vial 902 contained therein. (Vial access system 600 will be described in more detail below with reference to FIGS. 6A-6J.

As best shown in FIG. 4A, the vial shield 544 (containing a radiopharmaceutical vial 902) includes a flange 504 formed along a top end thereof and a removable septum cap 562 that is securely and removably engaged with the vial shield 544 (e.g., via threading) to allow insertion and removal of the vial 902 therefrom.

As shown in FIGS. 4A and 4B, the carrying system 500 includes a collar unit 502 that removably engages the flange 504 formed on the vial shield 554. The collar 502 may be formed in two pieces 506, 508 that are pivotally connected together (e.g., at one end thereof) to allow the collar 502 to engage and disengage the flange 504.

The collar 502 includes two elongated slots 510 formed in a top surface therein. As best shown in FIG. 4B, the slots 510 each include a pin 512 disposed therein and extending between two opposing walls 514 thereof.

The carrying system 500 further includes a handle unit 520 that engages with the collar unit 502 and the septum cap 562 to allow the vial shield 554 (and vial 902) to be carried and installed in the fluid delivery system 10. The handle unit 520 includes a handle 556 that is rigidly connected to a generally U-shaped cross piece 564a. The cross-piece 564a defines two, downwardly extending arms 530 having slots 532 formed thereon.

The slots 523 each form a slight hook on the ends thereof and are adapted to engage and retain a second cross piece 564b that supports a plunger 566 having a generally frustoconical shape that mates with a generally frustoconical recess of the septum cap 562 (see FIG. 4B).

The second cross piece 564b is also generally U-shaped and defines two downwardly extending arms 534 having hooks 536 formed therein. The open ends of the hooks 536 are formed on opposite ends of the arms 534 and are adapted to accept and retain the pins 512 in slots 510 of collar 502. The slots 510 are sized to provide sufficient clearance for the arms 534 to be inserted thereinto (in a downward direction) and for the hooks 536 to engage pins 512 (through rotation of handle 556).

The plunger 566 is connected to the second cross piece 564b by means of a connector (such as a screw 540) and a spring 538. The plunger 566 is biased by spring 538 to ensure a tight fit between the plunger 566 and the septum cap 562.

To engage and carry the vial shield 554, the collar 502 is connected to the flange 504 of the vial shield 554 as described above. The handle unit 520 is then moved into proximity to the vial shield 554 (by an operator grasping the handle 556 and moving the unit 520 into position) and the arms 534 are lowered into the slots 510 of the collar 502. At substantially the same time, the plunger 566 is engaged with the septum cap 562, with the spring 538 insuring a tight fit between the two. The operator then turns the handle unit 520 in a clockwise direction (see Arrow A in FIG. 4A) to seat the pins 512 in slots 510 into the hooks 536 of arms 534.

The operator then lifts the combined vial shield 554 and vial carrying system 500 (by moving the handle unit 520 in an upward direction) and transports it to, for example, the fluid delivery system 10. The operator then lowers the vial shield 554 into the vial access system 600 disposed in well 111 (see FIG. 4A) and rotates the handle unit 520 in a counter-clockwise direction to disengage the hooks 536 from the pins 512. The operator then lifts the handle 556 in an upward direction to remove the arms 534 from the slots 510 and the plunger 566 from the septum cap 562, thereby leaving the vial shield 554 (with septum cap 562 and collar 502) in vial access device 600 in well 111 (see FIG. 4B).

In a preferred embodiment, the plunger 566 includes radioactive shielding (such as lead) to shield the operator from radiation that would otherwise leak through or be emitted from the septum of the septum cap 562. Together with the vial shield 554 and the septum cap 562, the plunger 556 of the vial carrying system 500 shields the operator from the radiation emitted by the radiopharmaceutical and prevents unnecessary radiation exposure. Further by extending the handle 556 from the vial shield 554, the distance between the two functions to also lessen any possible radiation exposure to the operator.

Figure 5A:
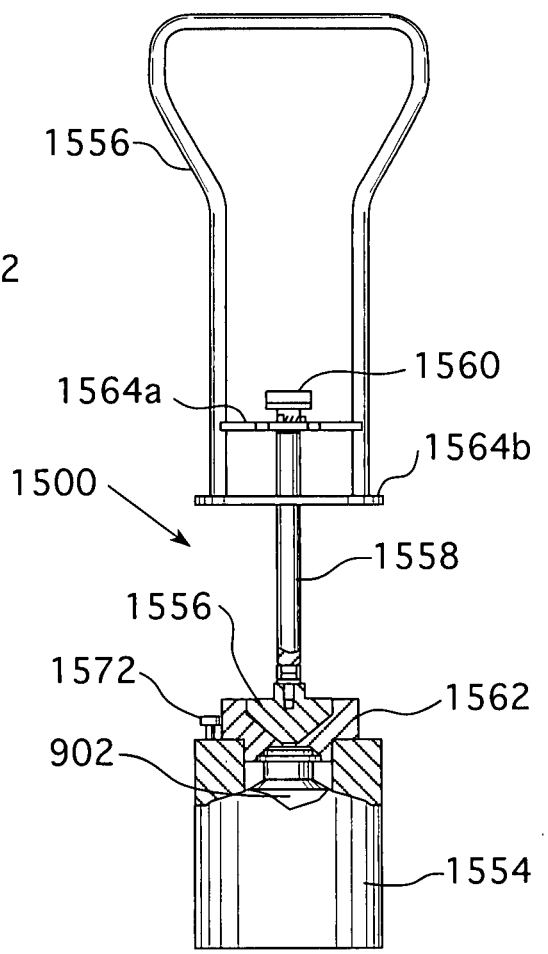
FIGS. 5A-5D are various views of an alternate embodiment of a vial shield carrying system of the present invention.

An alternate embodiment of the carrying system is shown in FIGS. 5A-5D. As with the preferred embodiment described above with respect to FIGS. 4A and 4B, the carrying system 1500 helps minimize operator exposure to radiation. Dimensions shown in FIG. 5A are for illustrative and non-restrictive purposes; here they are given in inches. As with FIGS. 4A and 4B, generally contemplated here is an integral carrying system 1500 that enables the vial shield 1554 to be carried and placed in the fluid delivery system 10 with minimal operator finger/hand radiation exposure because the design of the carrying system 1500 increases the distance from the vial 902 contained within the vial shield 1554.

Figure 5B:
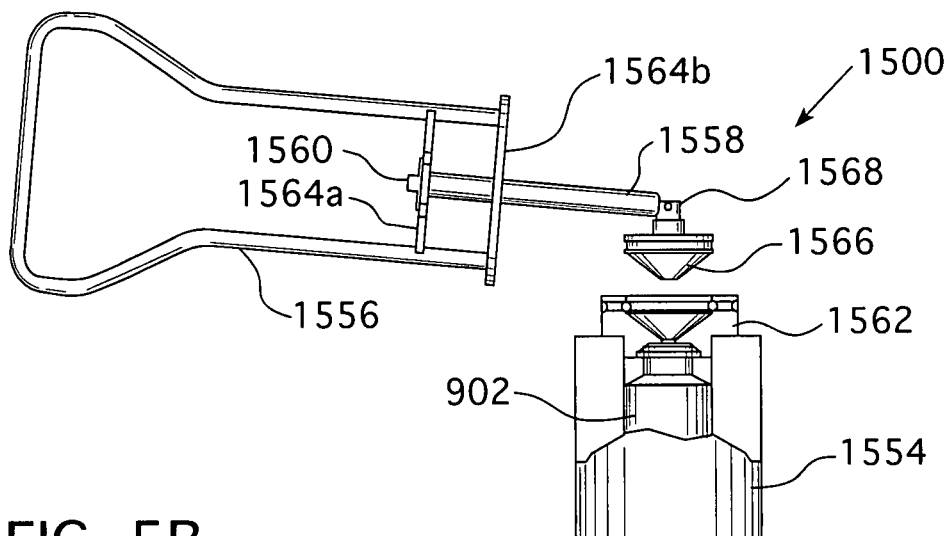
Figures 5C, 5D:
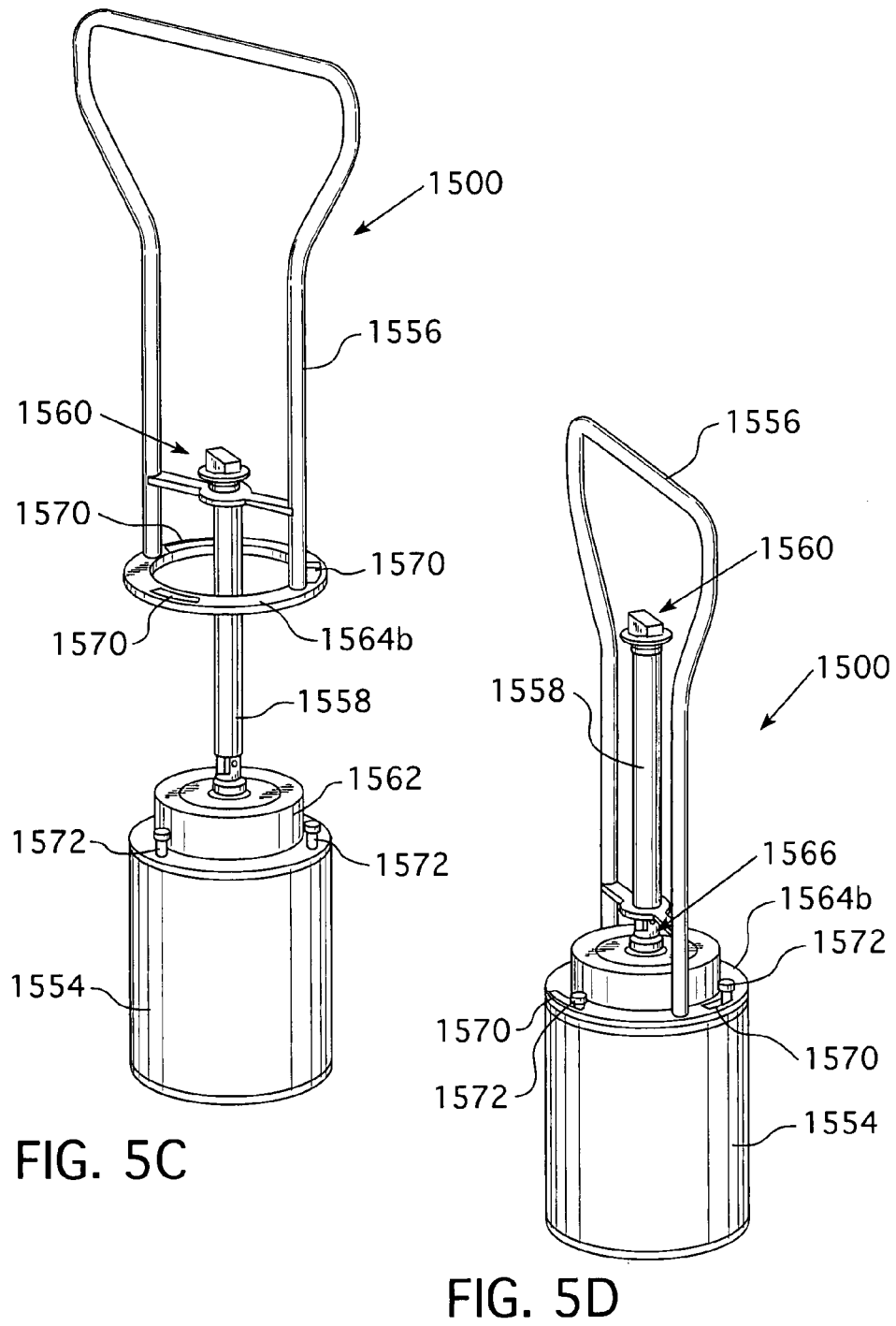

Shown in FIGS. 5A and 5C is a vial shield 1554 with a plunger 1566 of the carrying/installation handle system 1500 engaged with the septum cap 1562 of the vial shield 1544. The septum cap 1562 engages securely with the vial shield 1554 (e.g., via threading) to provide suitable radioactive shielding.

As shown in FIGS. 5A-5D, a crosspiece 1564a with a central aperture is rigidly connected to handle 1556 and is preferably configured to slidably accommodate an extension tube 1558. At a free end of extension tube 1558, the plunger 1566 is preferably disposed to engage with septum cap 1562. Though this engagement may be embodied in essentially any suitable way, here plunger 1566 has a generally frustoconical shape that engages with a generally frustoconical recess of septum cap 1562.

As further shown in FIGS. 5A and 5B (and as can be better appreciated by the perspective views in FIGS. 5C and 5D), handle 1556 preferably terminates in a ring 1564b that is configured for engaging with structural features of cap 1562 (to be described more fully below).

As shown in FIG. 5B, plunger 1566 may be hingedly or pivotably connected to extension tube 1558 via a hinge or pivot connection 1568, which provides freedom of motion to allow the plunger 1566 to mate with the septum cap 1562 without the operator having to otherwise place her hand and fingers directly above the septum cap 1562 before it is covered by the plunger 1566 (thereby reducing the possibility of radiation exposure to the operator).

While FIGS. 5A-5C show handle 1556 in a retracted position, i.e., maximally displaced away from plunger 1566, FIG. 5D shows in perspective view a different stage of the engagement of handle 1556 with vial shield 1554. As such, FIGS. 5A-5C shows handle 1556 maximally retracted from plunger 1566 (and, by extension, cap 1562), while FIG. 5D shows handle 1556 in a "fully engaged" configuration with respect to cap 1562.

Preferably, plunger 1566 will initially mate with cap 1562. Thence, handle 1556 is preferably moved towards cap 1562 (conceptually progressing from FIG. 5B to 5D) such that slots 1570 on ring 1564b fit over and capture posts 1572 (through clockwise rotation of handle 1556) on cap 1562. The handle 1556 may then be lifted to carry and deposit the vial shield 1554 in the well 111, as described above. The carrying system 1500 is disengaged from the vial shield 1554 through counter-clockwise rotation of the handle 1556 to disengage the capture posts 1572 from the slots 1570 on the ring 1564b. Of course, after the contents of the vial 902 are depleted, the carrying system 1500 can be attached to the vial shield 1554 as described above to remove the vial shield 1554 and the vial 902 from the fluid delivery system 10.

As discussed above with respect to FIGS. 4A-4B, the fluid delivery system 10 includes a vial access system 600 that is removably disposed within well 111 of fluid delivery system 10 and is adapted to hold vial shield 554, 1554 and to provide access to the contents of the vial 902 within vial shield 554, 1554.

Because vials (such as vial 902 described herein) typically come in various sizes, such as 10 ml, 15 ml, 20 ml and 30 ml, the fluid delivery system 10 of the present invention is intended to accommodate various vial sizes. To do so, the fluid delivery system 10 may include one or more vial shields and vial access systems (varying primarily in size in relation to the preferred embodiment of the vial shields 554, 1554 and vial access system 600 disclosed and described herein) that are specifically sized to accommodate known vial sizes. In a preferred embodiment, three vial shields and vial access systems 600 are provided with the fluid delivery system 10, and the well 111 is configured and designed to accept each of the vial access systems 600. However, the fluid delivery system 10 can be provided with one, four, five or any suitable number of vial shields and vial access systems depending on evolving needs or changes in the size or shape of the vials. Thus, depending on the size of the vial used at a clinical site or for a particular procedure, an operator of the fluid delivery system 10 can select the appropriate vial shield and vial access system and place it in the well 111 of the fluid delivery system to enable a fluid injection procedure.

Figure 6A:
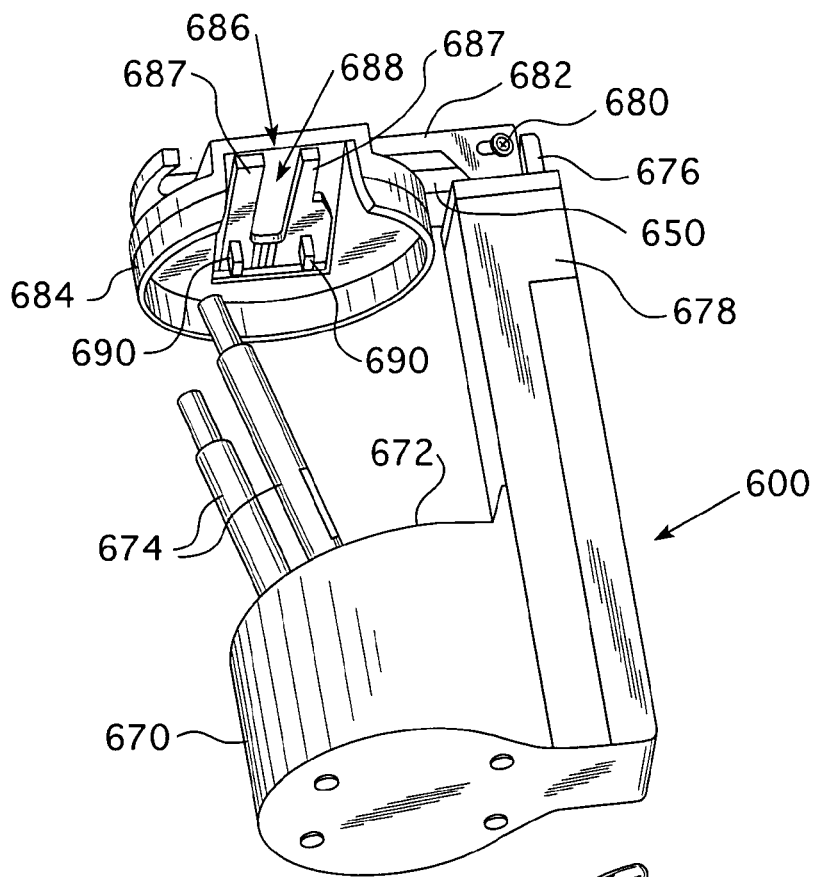
FIG. 6A is a bottom perspective view of a preferred embodiment of a vial access system of the present invention.
Figure 6B:
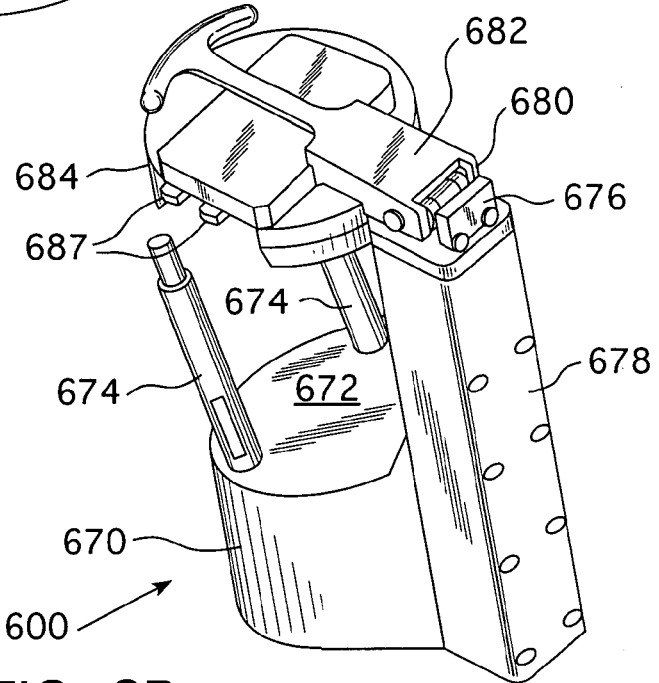
FIG. 6B is a top perspective view of the vial access system shown in FIG. 6A.

Preferred embodiments of the vial access system 600 and the vented cannula 208 of the MPDS 200 are described below in relation to FIGS. 6A-6J (and with reference to FIGS. 4A and 4B). Generally, as best shown in FIGS. 6A, 6B and 6F, the vial access system 600 includes a base portion 670 that preferably includes a sloped surface 672, the function of which will be more fully appreciated herebelow. Two (preferably removable and extendable) support members or pins 674 are provided to support and retain a vial shield 554 (i.e., enclosing a vial 902; see FIG. 4C) when it is placed on the sloped surface 672 (e.g., after being carried and disposed there using the vial shield carrying systems 500, 1500 discussed above).

As shown, the vial access system 600 further includes a vertical support arm 676 that is disposed within a housing 678. A cap member 684 and a handle member 682 are connected to an upper end of the vertical support arm 676. The vertical support arm 676 is preferably slidably and rotationally displaceable with respect to the housing 678. That is, the arm 676 may slide and rotate with respect to the housing 678 (see e.g., FIGS. 4B and 6D) to allow the vial shield 554 to be readily inserted and removed therefrom and to lower the vented cannula 208 into the vial 902 contained within the vial shield 554 (as discussed in more detail below).

The handle 682 is used by an operator or technician to insert and remove the vial access system 600 from the well 111 of the fluid delivery system 10. The handle 682 is preferably connected to the vertical support arm 676 via a suitable pivot connection (such as a hinge or bolt connection) 680 to permit movement of the handle 682 between an extended, carrying position (see FIG. 6D) for carrying the vial access system 600 and a horizontal or operating position (see FIGS. 6B and 6E) in which the handle 682 rests on top of the cap 684 (e.g., when the vial access system 600 is disposed in the well 111), thereby allowing the cover 20 of the fluid delivery system 10 to be closed.

The cap 684 is preferably rigidly connected to the vertical support arm 676 via an arm 650 (see FIGS. 6A and 6D), but it may be pivotally connected to the vertical support arm 676 via, for example, a pivot connection (not shown) or adjustably connected to the vertical support arm 676 via, for example, a slot (not shown) formed in the arm 650. As best shown in FIGS. 6E and 6F, when the cap 684 is lowered (by sliding the vertical support arm 676 within the housing 678) to insert the cannula 208 into the vial 902 within the vial shield 554, and the handle 682 is pivoted to a horizontal position atop the cap 684, the cap 684 and the handle 682 (and thus the remainder of the vial access system 600) lies below or flush with the upper surface 103 of the fluid delivery system 10, thereby allowing the cover 20 to close over the upper surface 103 of the fluid delivery system 10 and the MPDS 200 installed therein. The cap 684 preferably includes or is formed with radioactive shielding material (e.g., lead) to minimize radiation exposure to personnel from the FDG or other radioactive solution contained within the vial 902 in the vial shield 554.

Figure 6C:
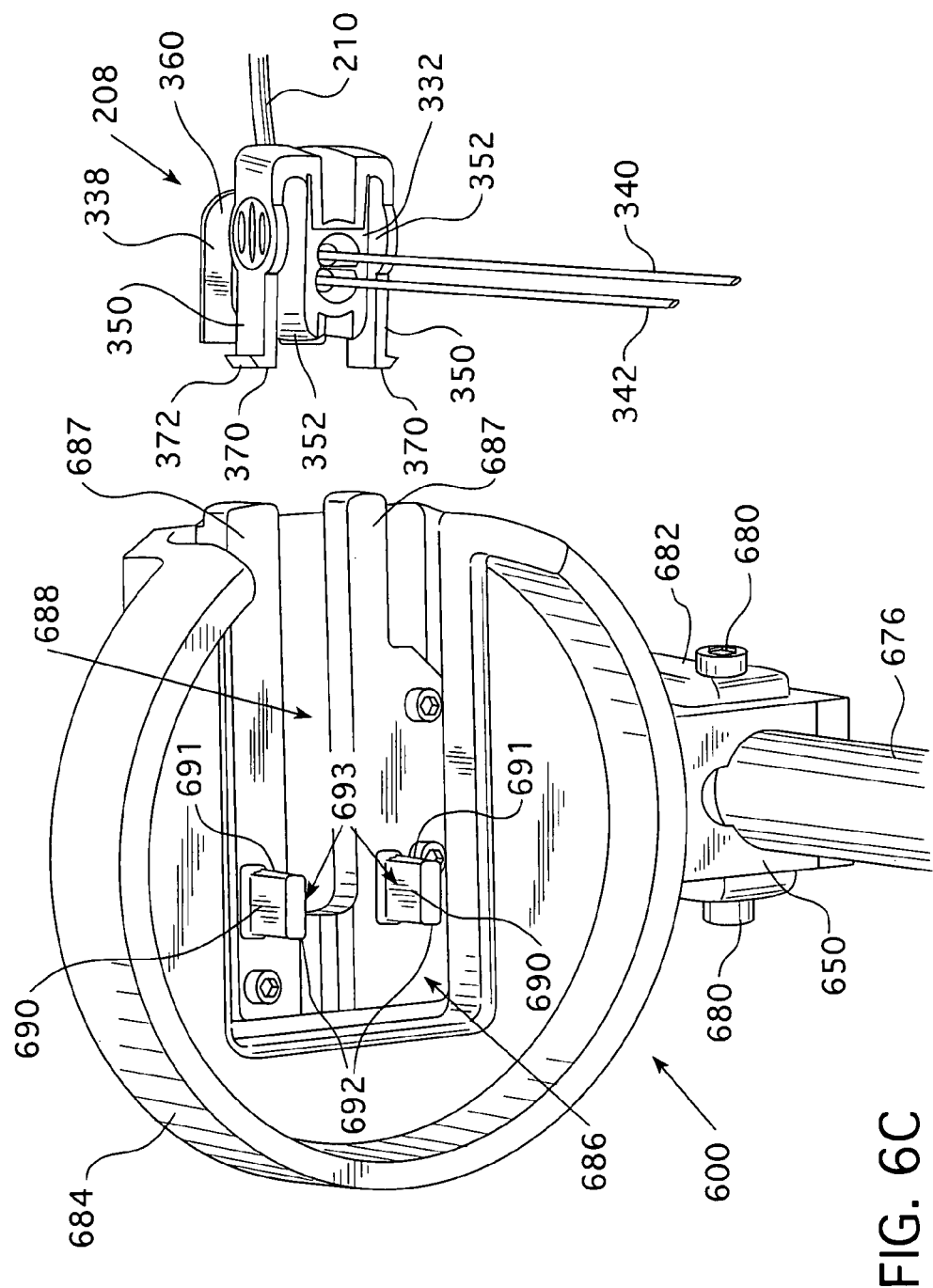
FIG. 6C is an exploded, perspective view of a preferred embodiment of the vented cannula of the multi-patient fluid path set of the present invention oriented to be connected to the cap of the vial access system shown in FIGS. 6A-6B.

As best shown in FIGS. 6A and 6C, the underside of cap 684 includes a mounting mechanism 686 for accepting the cannula 208 (or other suitable type of spike, cannula or needle) for piercing the septum of a vial 902 or other pharmaceutical container in the vial shield 554. The mounting mechanism 686 preferably includes two arms 687 that define a groove or slot 688 therebetween. Each of the arms 687 includes a tab member 690 extending downwardly therefrom.

The vented cannula 208, in accordance with a preferred embodiment of the present invention, may be employed for spiking a pharmaceutical source (such as the radiopharmaceutical vial 902 discussed above) and preferably includes a main hub 332 to which are connected (or integrally formed) two, resilient spring arms 350. The spring arms 350 and the main hub 332 cooperate to define two U-shaped channels 352 on lateral sides of the main hub 332.

As shown in FIGS. 6C and 6G-6J, each of the spring arms 350 includes a flange or hook member 370 formed thereon and extending outwardly therefrom. The hook members 370 each defines an inclined surface or edge 372 formed thereon.

The vented cannula 208 further includes a ledge or flange 338 that is connected to or integrally formed with the main hub 332 and is disposed in a horizontal plane above the two spring arms 350. The ledge 338 and the top edges of the spring arms 350 cooperate to define horizontal grooves or slots 360 therebetween for accommodating the arms 687 of the mounting mechanism 686 on the cap 684 of the vial access system 600.

To connect the cannula 208 to the mounting mechanism 686 on the cap 684, the main hub 332 of the cannula 208 is aligned with the slot 688 of the mounting mechanism 686 and the arms 687 of the mounting mechanism 686 are aligned with the grooves 360 defined between the spring arms 350 and the top ledge 338 of the main hub 332. Once the structural elements of the cannula 208 and the mounting mechanism 686 are aligned, the cannula 208 is inserted into the mounting mechanism 686 until the hook members 370 of the spring arms 350 engage the front edges 691 of the tab members 690. Upon further insertion of the cannula 208, the front edges 691 of the tab members 690 engage and ride along the inclined surfaces 372 of the hook members 370, thereby moving the spring arms 350 in an inward direction (i.e., toward the vertical axis of cannula 208). This inward movement of the hook members 370 allows them to clear the front edges 691 of the tab members 690 and ride along the inner sides 693 thereof until the hook members 370 clear the tab members 690 and move or snap back into their original position to engage the rear edges 692 of the tab members 690. At this point, the cannula 208 is fully inserted into and retained by the mounting mechanism 686. To remove the cannula 208 from the mounting mechanism 686 (e.g., when the MPDS 200 is removed from the fluid delivery system 10), the operator pinches the hook members 370 together (i.e., moves them toward the vertical axis of the cannula 208) until they clear the rear edges 692 of the tab members 690, and then slides the cannula 208 out of engagement with the mounting mechanism 686.

Referring again to FIGS. 6C and 6G-6J, the vented cannula 208 includes a longer, fluid draw needle 340 in fluid connection with the second tubing section 210 of the MPDS 200 via a fluid port 384 and a shorter, vent needle 342 in fluid connection with a vent 334. As known in the art, the vent 334 may include a suitable filter for filtering the ambient air that is drawn into the vial 902 to allow fluid to be drawn therefrom.

The description now turns to the preferred operation and use of the vial access system 600 and the vented cannula 208 of the present invention. When a vial shield 554 (holding a pharmaceutical vial 902) is to be placed in the vial access system 600, the vertical support arm 676 is raised to an extended position and rotated (see FIGS. 2B and 4A) to move the cap 684 out of its normal position above the sloped surface 672. The vial shield 554 is then inserted into the well 111 and placed on the sloped surface 672 (see FIG. 6F). The support pins 674 engage the vial shield 554 to hold it in position on the sloped surface 672.

Figure 6D:
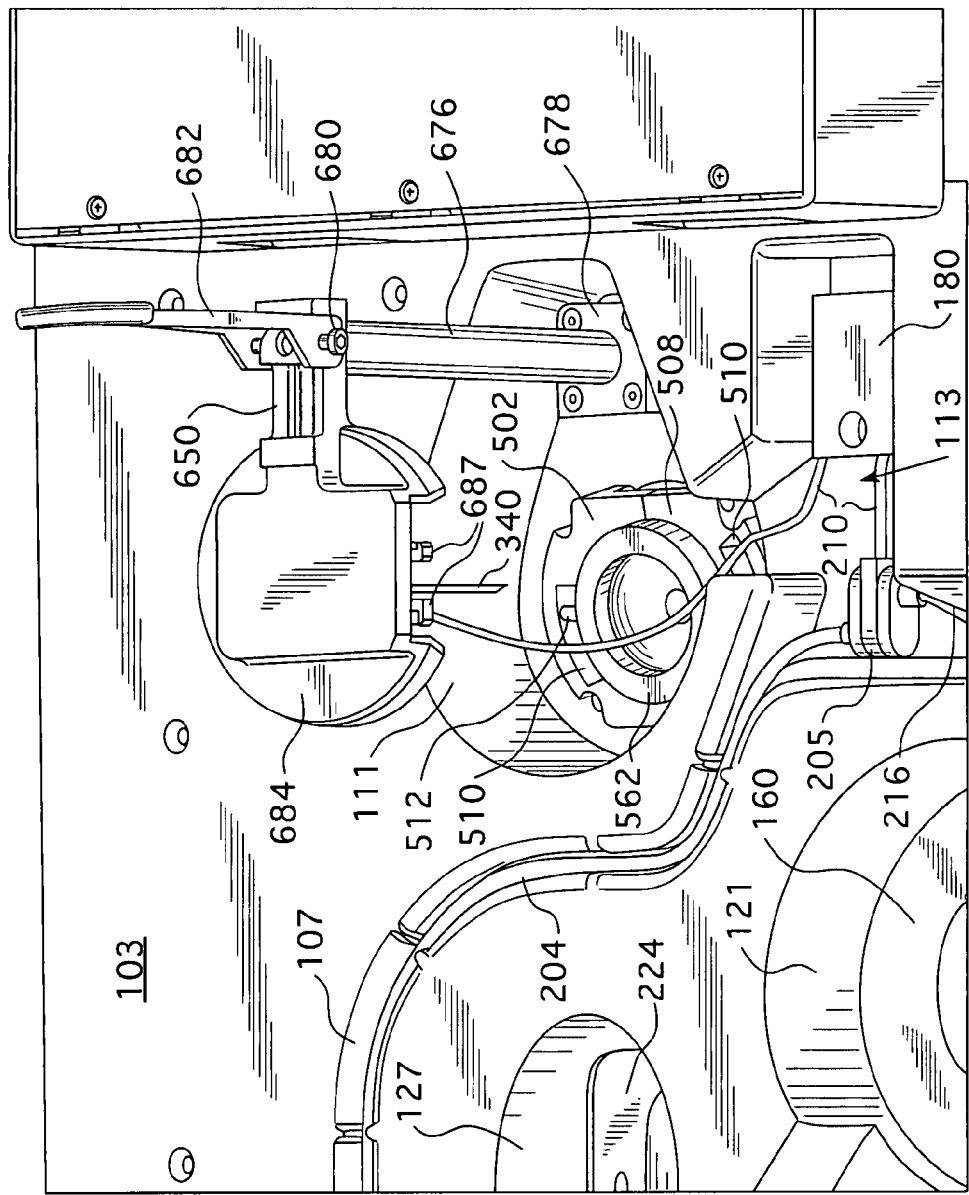
FIG. 6D is a perspective view (similar to FIG. 4B) showing the vial access system and the vial-carrying shield disposed in a well of the fluid delivery system, and the vented cannula connected to the cap of the vial access system and in position to be lowered and inserted through the septum cap of the vial shield into the radiopharmaceutical vial.
Figure 6E:
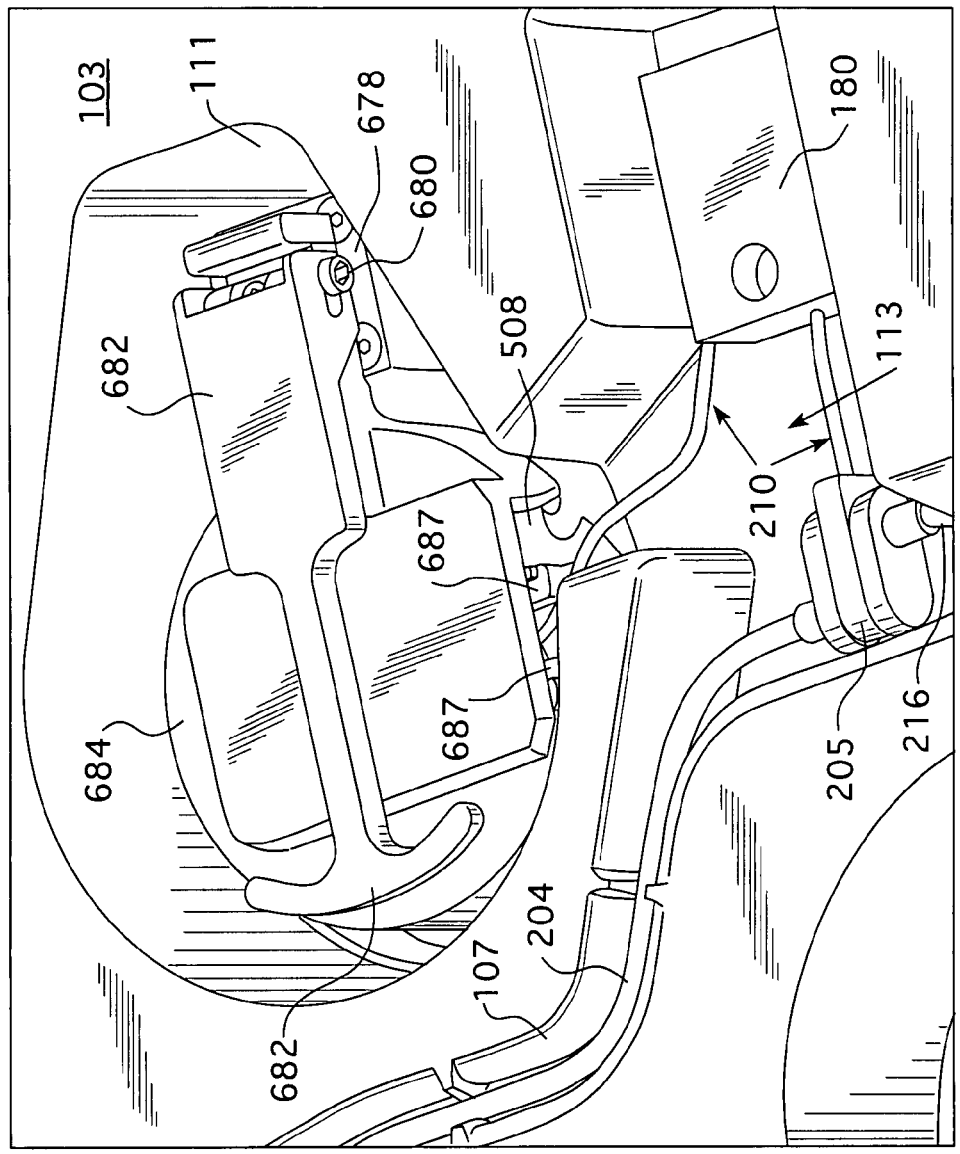
FIG. 6E is another perspective view (similar to FIG. 6D) showing the cap of the vial access system lowered into position and the vented cannula thereby inserted into the pharmaceutical vial.
Figure 6F:
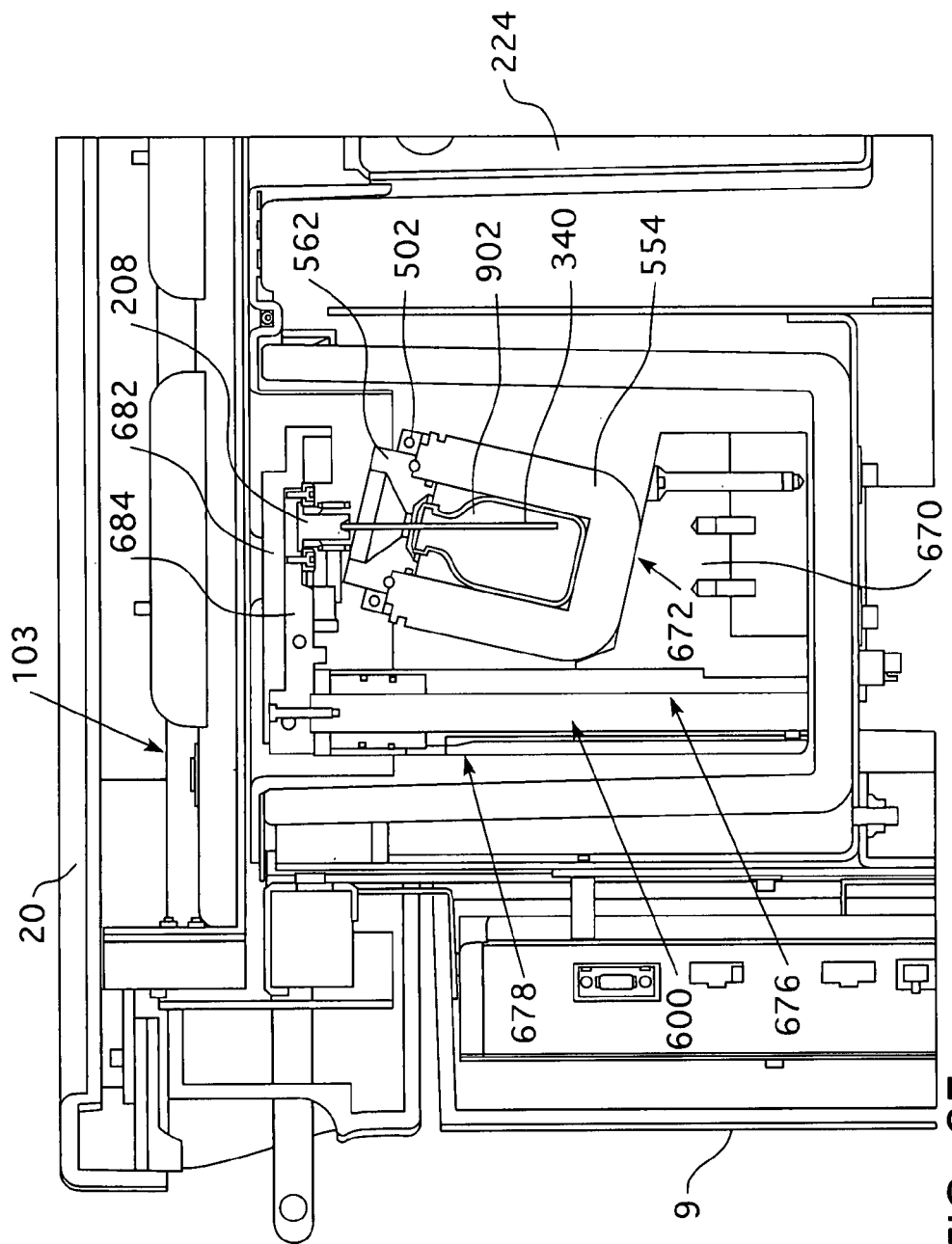
FIG. 6F is an enlarged view of FIG. 1E showing the vial access system and the vented cannula of the present invention.
Figures 6G, 6H:
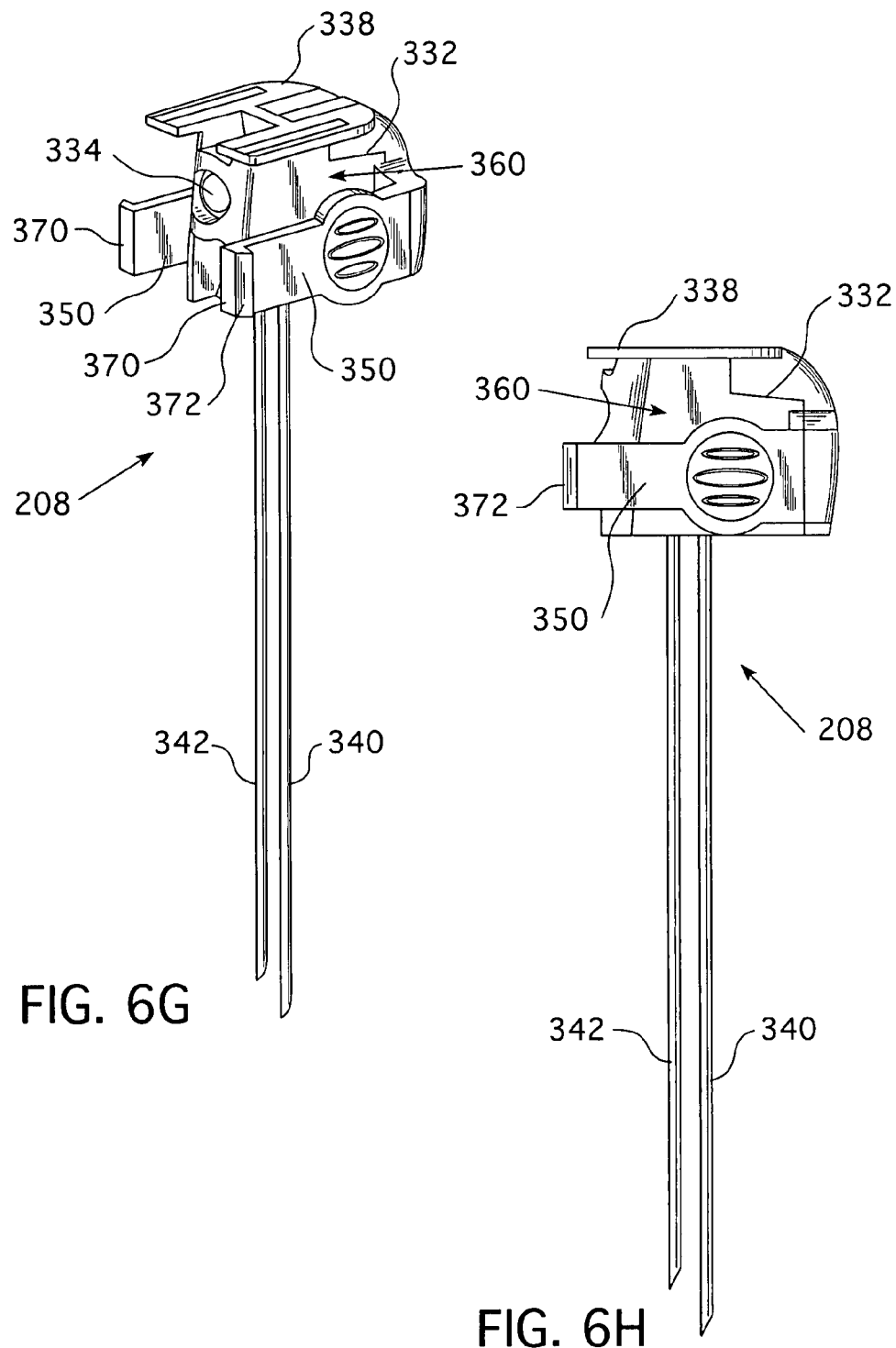
FIG. 6G is a perspective view of the vented cannula shown in FIG. 6C.
FIG. 6H is an elevational view of the vented cannula shown in FIG. 6G.
Figure 6I:
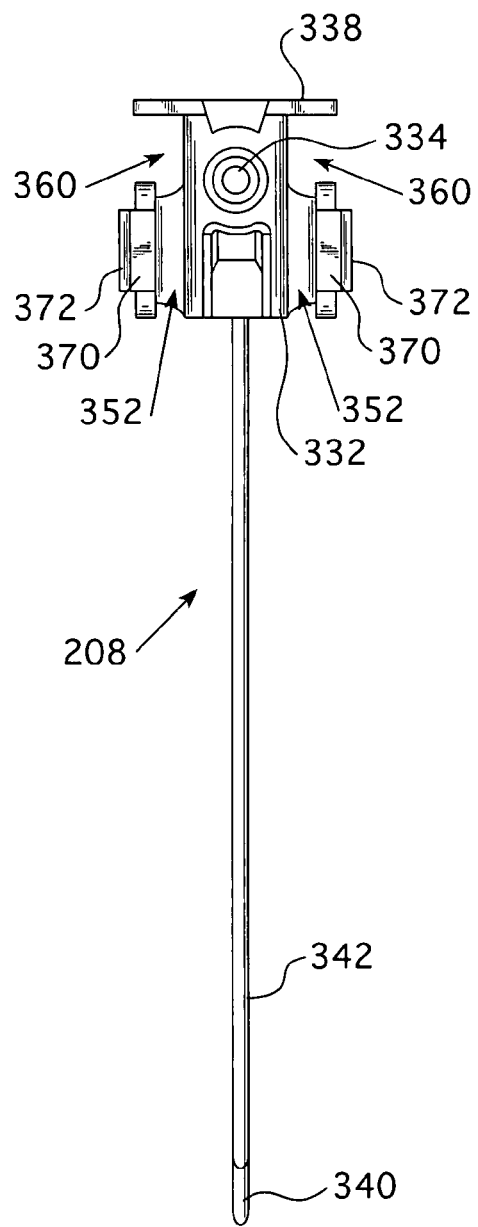
FIG. 6I is a left-side view of the vented cannula shown in FIG. 6H.
Figure 6J:
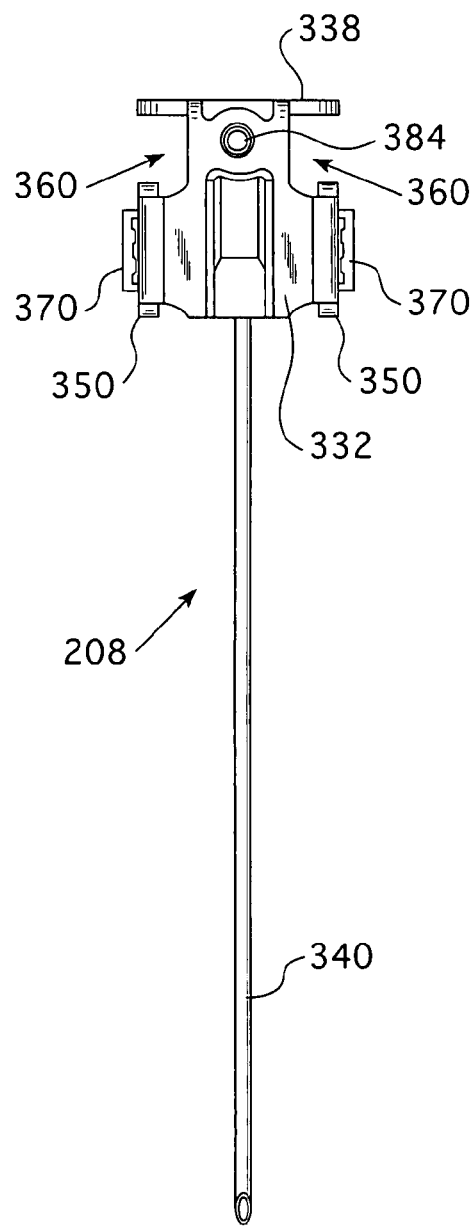
FIG. 6J is a right-side view of the vented cannula shown in FIG. 6H.

After the vial shield 554 is inserted into the vial access system 600 (see FIG. 4B), the vented cannula 208 of the MPDS 200 is inserted into the mounting mechanism 686 on the cap 684 and the cap 684 is rotated back into position (e.g., by turning the handle 682) above the septum cap 562 of the vial shield 554 (see FIG. 6D). Then the cap 684 is lowered (e.g., by using the handle 682 to urge the vertical support arm 676 into the housing 678) to insert the fluid draw needle 340 and the vent needle 342 of the cannula 208 through the septum of the septum cap 562 and into the pharmaceutical vial 902 (see FIG. 6F). The handle 682 is then rotated to lie in a substantially horizontal orientation on or above the cap 684

(see FIGS. 1C and 6E), thereby allowing the cover 20 of the fluid delivery system 10 to be closed. While the preferred method of operating the vial access system 600 and the vented cannula 208 is provided above, the method and steps can be conducted in any suitable order or arrangement to achieve the desired results.

As best shown in FIG. 6F, the support surface 672 is preferably configured such that when a vial is pierced by the fluid draw and vent needles 340, 342 of the cannula 208, the bottom end of the fluid draw needle 340 will be placed at or near the location where the cylindrical wall of the vial meets the bottom (floor) of the vial. Thus, to the extent that some vials may not have a completely flat bottom or floor (e.g., may have a rounded bump with a maximum height at the central longitudinal axis of the vial), the fluid draw needle 340 will be in a position to maximally draw fluid from the vial as it collects at the junction of the vial's bottom and cylindrical wall (i.e., to avoid waste of the pharmaceutical). Or, even in a flat-bottomed vial, such an orientation of the vial will help ensure that fluid maximally gathers and is drawn in a closely defined area.

As discussed above, the dimensions of the vial access system(s) 600 provided with the fluid delivery system 10 can preferably be chosen in accordance with dimensions of the vial shields and vials to be employed, to ensure that as much fluid from the vial is drawn as possible. By way of a nonrestrictive example, the sloped surface 672 could be sloped at an angle of about 10-13 degrees with respect to the horizontal.

Instead of being incorporated into and as part of the MPDS 200 for use with the fluid delivery system 10, the vented cannula 208 of the present invention may be used in other fluid delivery systems, including ones that use shielded syringes (see e.g., U.S. Pat. Nos. 5,927,351 and 5,514,071, the contents of which are incorporated herein by reference), for injecting pharmaceuticals or other medical fluids into patients.

Figure 47C:
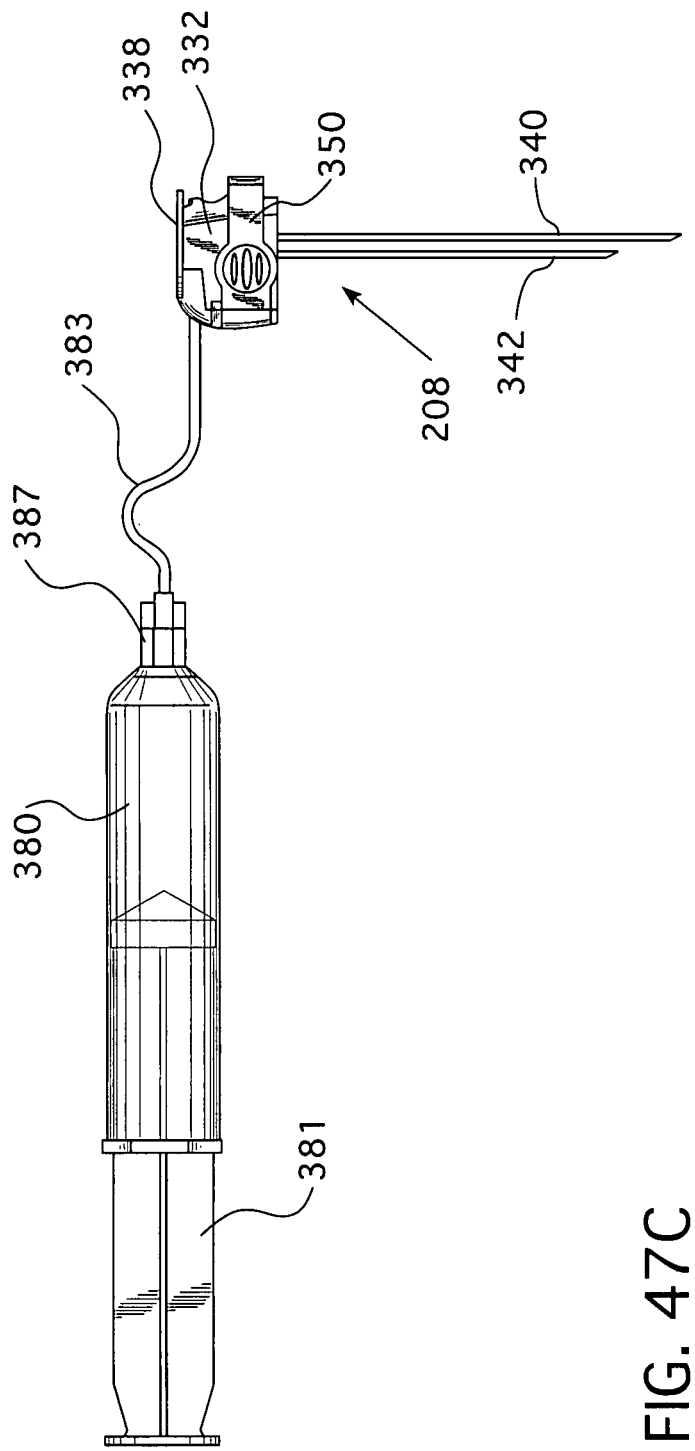
FIG. 47C is an elevational view of the first alternate fluid delivery system of FIGS. 47A and 47B.

As shown in FIGS. 47A-C, the vented cannula 208 may be used with a hand-held syringe 380 (preferably held within a conventional lead-shielded container (not shown for ease of illustration)) having a discharge outlet 386 and a plunger 381 slidably disposed therein. The fluid draw needle 340 of the cannula 208 is in fluid connection with the shielded syringe 380 by means of a tube 383 connected between the discharge outlet 386 of the syringe 380 and the fluid port 384 of the cannula 208. The tube 383 preferably includes a connector 387, such as a standard luer connector, for removably connecting the tube 383 to the shielded syringe 380. The other end of the tube 383 may be non-removably attached to the fluid port 384 of the cannula 208 by use of, for example, an adhesive. Alternately, the tube 383 may include a connector (not shown) for removable connection to the fluid port 384 or may be press fit and held by friction forces onto the fluid port 384.

The tube 383 may be fashioned in any length or diameter suitable for the application. In use, the fluid draw and vent needles 340, 342 of the cannula 208 are inserted into a vial (not shown) containing a pharmaceutical or other fluid. The plunger 381 is retracted (moved away from the discharge outlet 386 of the syringe 380) to aspirate fluid from the vial into the syringe 380. The connector 387 is disconnected from the shielded syringe 380 and the syringe 380 is then connected, generally via an intermediate tubing (not shown), to a catheter disposed in a patient. The plunger 381 is then advanced (moved toward the discharge outlet 386) to inject fluid into the patient.

Figure 48:
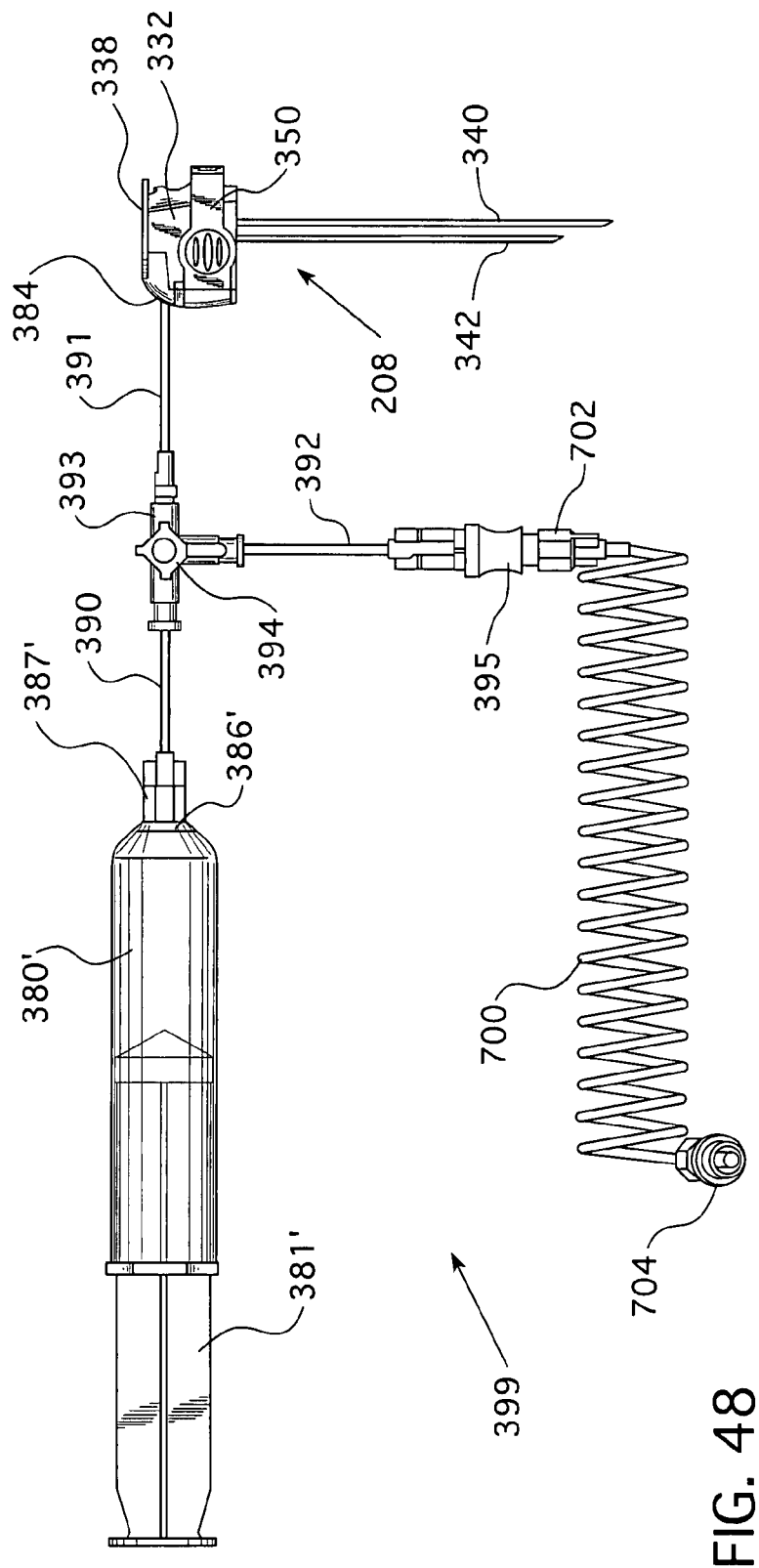
FIG. 48 is a perspective view of the vented cannula shown in FIGS. 6C and 6G-6J being utilized as part of a second alternate fluid delivery system.

As shown in FIG. 48, the vented cannula 208 may also be utilized as part of a second alternate fluid delivery system 399 including a shielded (not shown for ease of illustration), hand-held syringe 380' having a discharge outlet 386' and a plunger 381' slidably disposed therein. In addition to like elements shown in FIGS. 47A-C, the system 399 includes first, second and third tubing segments 390, 391, 392 that are connected via a T-connector 393 having an integral stopcock 394. The third tubing segment 392 also preferably includes a swabable valve 395 to which the first end 702 of the SPDS 700 described above could be connected. Instead of a swabable valve 395, it is contemplated that a conventional luer connector could be used for suitable applications.

After the vented cannula 208 is placed in a pharmaceutical source (not shown), the stopcock 394 is actuated to open the fluid path between the vented cannula 208 and the syringe 380' and to close the path to the third tubing segment 392. The plunger is then retracted to aspirate fluid into the syringe 380' from the pharmaceutical source. The stopcock 394 is then actuated to open the fluid path between the syringe 380' and the third tubing segment 392 and to close the path to the second tubing segment 391. The first end 702 of the SPDS 700 is then preferably connected to the swabable valve or luer connector 395, and the plunger 381' is advanced to pump fluid to the patient end 704 of the SPDS 700 (e.g., to purge air from the tubing and to thereby provide a wet connection between the patient end 704 of the SPDS 700 and the catheter (not shown) in a patient). The patient end 704 is then connected to the catheter and the plunger 381' is advanced again to pump or deliver fluid through the SPDS 700 to the patient.

After the fluid is delivered to the patient, the SPDS 700 is disconnected from the patient and the valve or luer connector 395 and is discarded. If another injection is to be performed, a new SPDS 700 can be connected to the valve or connector 395 and the system 399 can be primed to again provide a wet connection at the patient end 704 of the SPDS 700.

The disclosure now turns to the operation of the fluid delivery system 10 and its various components. As known in the art, in injection procedures and other fluid delivery operations in which pharmaceuticals are delivered to a patient, air is purged from the fluid path by pumping an amount of the pharmaceutical and/or a diluent, such as saline, through the fluid path to the end of a tubing set (e.g., MPDS 200 or SPDS 700) before connecting the tubing set to a catheter in the patient. Such an air purging or "priming" procedure is standard practice to prevent the occurrence of an air embolism in a patient, which can cause serious injury or death. Further, the dimensions (e.g., length and ID) of the SPDS 700 and the various tubing sections of the MPDS 200 (provided above) are necessary for accurate priming, activity measurement and delivery of the pharmaceutical to the patient because the system 10 relies on those dimensions to accurately determine and monitor the volume of pharmaceutical and saline that is required for those various operations.

Referring again to FIGS. 1C and 2A, once the MPDS 200 is installed in the fluid delivery system 10, the spike 202 is placed in fluid connection with the saline source 23 and the cannula 208 is inserted into the vial 902 and placed in fluid connection with the pharmaceutical therein, the MPDS 200 is primed to remove air therefrom.

In a preferred method of priming the MPDS 200, the pump 22 is activated to draw saline out of source 23 and to move the saline through first tubing section 204, check valve 215, T-connector 205 and into third tubing section 216. The pump 180 is then activated to draw a small amount of pharmaceutical out of vial 902 and to move the pharmaceutical through second tubing section 210, check valve 214, T-connector 205 and into third tubing section 216. The pump 23 is then activated again to draw additional saline from saline source 23 to thereby move the volume of pharmaceutical present in third tubing section 216 into the tube coil 444 of coil assembly 400 located in the dose calibrator 160.

To ensure that the second tubing section 210 is primed, the dose calibrator 160 is monitored to measure the level of radioactivity in the coil 444. If the dose calibrator measures no activity (or an activity level below a predetermined, baseline activity level), then the second tubing section 210 has not been appropriately primed and the priming process described above needs to be reinitiated by the operator. If the dose calibrator measures any activity level (or an activity level above the predetermined, baseline activity level), then the system 10 concludes that the second tubing section 210 has been correctly primed.

After the second tubing section 210 is primed, the motor 30 is activated to open the pinch valve 170 and thereby open the fluid path from the fourth tubing section 220 through the T-connector 222 and the fifth tubing section 226 to the waste receptacle 224, the motor 31 is activated to close the pinch valve 172 and thereby close the fluid path along the sixth tubing section 230, and pump 22 is activated again to move the saline and the pharmaceutical in tube coil 444 through fourth tubing section 220, T-connector 222, fifth tubing section 226 and into waste receptacle 224.

Subsequently, the first end 702 of the SPDS 700 is connected to the connector end 228 of the MPDS 200. The motor 30 is activated to close the pinch valve 170 (and thereby close the fluid path from the fourth tubing section 220 through the T-connector 222 and the fifth tubing section 226 to the waste receptacle 224), the motor 31 is activated to open the pinch valve 172 (and thereby open the fluid path along the sixth tubing section 230), and the pump 22 is activated again to move the saline through the T-connector 222 and the sixth tubing section 230 to the patient end 704 of the SPDS 700. At this point, the entire length of the MPDS 200 and the SPDS 700 is primed and the patient end 704 of the SPDS 700 can be connected to the catheter or other venous access device placed in a patient.

In an alternate embodiment, after the pharmaceutical is moved into the waste receptacle 224, the remainder of the MPDS 200 is primed prior to the SPDS 700 being connected to connector end 228 of the MPDS 200. (This alternate priming method may be accomplished if the connector end 228 of the MPDS 200 is not the preferred swabable luer valve but rather is, for example, a standard luer connector or another connector that is not biased to a closed position when disconnected from the first end 702 of the SPDS 700.) Then, the first end 702 of the SPDS 700 is connected to the connector end 228 of the MPDS 200 and the SPDS 200 is primed to provide a wet connection at the patient end 704 of the SPDS 700.

To accomplish this alternate priming method, the motor 30 is activated to close the pinch valve 170 (and thereby close the fluid path from the fourth tubing section 220 through the T-connector 222 and the fifth tubing section 226 to the waste receptacle 224), the motor 31 is activated to open the pinch valve 172 (and thereby open the fluid path along the sixth tubing section 230), and the pump 22 is activated again to move the saline through the T-connector 222 and the sixth tubing section 230 to the connector end 228 of the MPDS 200. Then, after the first end 702 of the SPDS 700 is connected to the connector end 228 of the MPDS 200, the pump 22 is activated again to move saline through the SPDS 700 to the patient end 704 thereof.

After the MPDS 200 and the SPDS 700 are primed and the patient end 704 of the SPDS 700 is connected to the patient, the system 10 is ready for an injection procedure. While preferred and alternate methods of priming the MPDS 200 and the SPDS 200 are described above, other methods or steps may be employed or the steps above may be rearranged in any suitable manner to purge air from the MPDS 200 and the SPDS 700.

In an alternate embodiment of the MPDS 200, the T-connector 205 and the check valves 214, 215 can be replaced with an automated, motor-driven stopcock. T-connector 222 also can be replaced with an automated stopcock as well.

The disclosure now turns to embodiments of the present invention, as illustrated in FIGS. 7-46, that could conceivably be employed in programming and operating a fluid delivery system as broadly contemplated herein.

Shown schematically in FIGS. 7-46 are various incarnations of a touch screen arrangement 1000 displayed on a graphical user interface, such as GUI 15, that could be employed with the fluid delivery system 10. As a non-restrictive example, such a touch screen arrangement could be utilized in conjunction with a system controller 5 and/or computer of any of a variety of fluid delivery systems as broadly contemplated herein.

In order to clearly and unambiguously communicate to an operator the current status of the system 10, a graphical user interface with easily legible symbols and icons, including exceedingly user-friendly data entry mechanisms, is broadly contemplated. An operator will thus be able to intuitively understand and undertake various tasks for operating system 10.

While a touch screen arrangement is contemplated in connection with FIGS. 7-46, it is to be understood that other types of data entry arrangements are conceivable that would achieve an equivalent purpose. For example, soft or hard key entry could be used, as well as trackball arrangements, mouse arrangements, or a cursor control touch pad (remote from the screen).

The touch screen arrangement 1000 shown in FIGS. 7-46 can preferably be employed for four categories of tasks, namely: (1) system preparation, (2) patient treatment, (3) injection history (i.e., obtaining information regarding previous treatments) and (4) system configuration. Preferably, a touch screen arrangement 1000 will be flexibly and selectably manipulable to accommodate and undertake any and all of these tasks as desired.

System Preparation

The "system preparation" category includes a number of tasks that are preferably performed in the following order to prepare the system 10 for a fluid injection or delivery procedure: (1) disposing of a used MPDS 200 and vial 902 from, for example, the previous day or previous use of the system 10 (if still present in the system 10); (2) conducting a quality control check or "daily QC" of the system 10; (3) installing a new pharmaceutical vial 902 and a new MPDS 200 in the system 10; and (4) priming the MPDS 200 to remove air therefrom. While the above order is the preferred one for preparing the system 10, the tasks may be performed in any suitable manner and order for the intended application.

Figure 7:
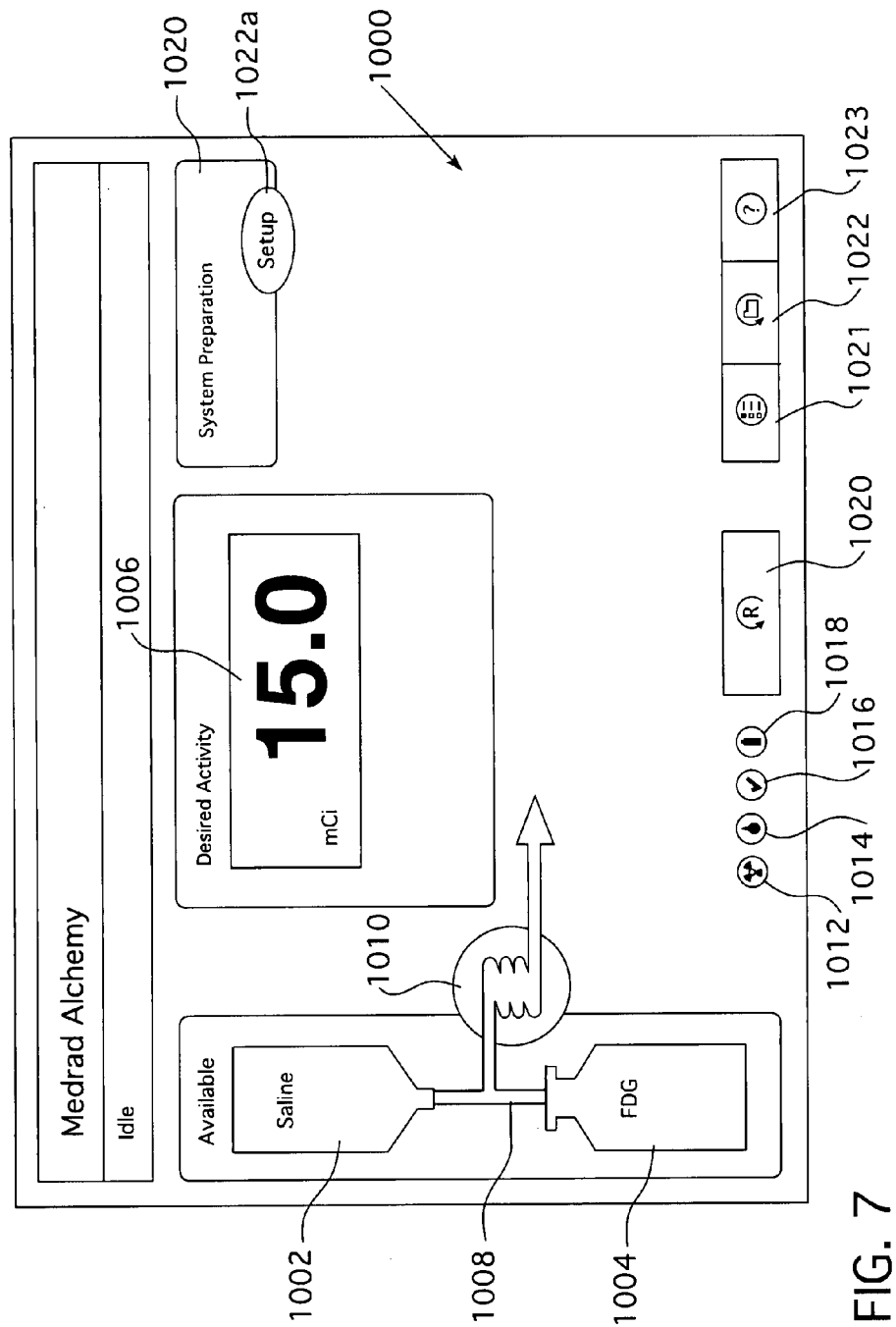
FIG. 7 shows a main screen of a graphical user interface of the present invention.

FIG. 7 conveys a "main" screen visible on touch screen arrangement 1000, which may be an initial screen presented to an operator when the system 10 is initially activated.

As such, and as shown in FIG. 7, touch screen arrangement 1000 preferably generally depicts at a very high level the fluid path (e.g., MPDS 200 and SPDS 700) of the fluid delivery system 10. It can be appreciated that touch screen 1000 can easily be "mapped" (i.e., provide a one-to-one correspondence) to major components of the MPDS 200, the SPDS 700 and other components of the system 10 such as that discussed and illustrated herein with respect to FIGS. 1A-6J, but that level of detail is generally not required for programming and use of the system 10.

As shown in FIG. 7, the touch screen shows a saline field 1002 (here in the stylized shape of an IV bag), a pharmaceutical or FDG field 1004 (here in the stylized shape of a vial) and an ionization chamber graphic 1010. A tubing graphic 1008, as shown, encompasses a three-way junction with branches leading, respectively, to saline field 1002, FDG field 1004 and ionization chamber graphic 1010. As shown, the tubing graphic 1008 is coiled inside the ionization chamber graphic 1010 to indicate the tube coil 444 described above.

Touch screen arrangement 1000 in FIG. 7 shows the system 10 as being in an "idle" state. As such, no fluid is shown as being disposed in or moving through tubing graphic 1008 and ionization chamber graphic 1010. Further, saline and FDG fields 1002, 1004 in FIG. 7 both convey an "empty" status, to indicate that the system 10 has not yet been provided with information regarding the presence and/or amount of fluid in the saline source 23 and the vial 902.

Indicated at 1006 is a touch field showing desired activity (currently displayed as 15.0 mCi) for an injection procedure to be performed. When the system 10 is activated, the desired activity field 1006 preferably displays a default activity value that can be pre-programmed into the system 10 or pre-set by the operator. Alternately, the desired activity field 1006 can default to the last activity level that was programmed into the system 10. Further, a display (read-only) system preparation field 1020 includes an associated "setup" button 1022a that, when activated, permits system preparation tasks to be performed.

Indicated at 1012, 1014, 1016 and 1018, respectively, in FIG. 7 are circular status icons that provide quick and easy reference to different aspects of system status and, as such, will highlight when an aspect of system status is "on" or "active" or provide status information on the system 10. Thus, icons 1012-1018 from left to right, respectively, convey information on the following system aspects: activity present 1012, fluid motion/injection status 1014, check for air/priming status 1016, and system battery status 1018.

The system battery (not shown) provides power to the system controller 5 and to the ionization chamber 160 (to maintain the ionization chamber at its normal operating state) in the event that the system 10 is disconnected from an AC power source. The system battery is charged while the system 10 is connected to an AC power source.

FIG. 7 also shows four rectangular touch fields 1020-1023 along the bottom thereof. Reset button 1020 is activated to reset or clear information, such as case identification information, desired activity level, etc., from the treatment screens (as described in more detail below). Configuration button 1021 is activated to access the configuration screens for the system 10 (as described in more detail below). Records or Injection History button 1022 is activated to access information regarding prior injection procedures (as described in more detail below). Help button 1023 is activated to access searchable text, FAQs or other information that might be provided about the use and operation of the system 10.

Figure 8:
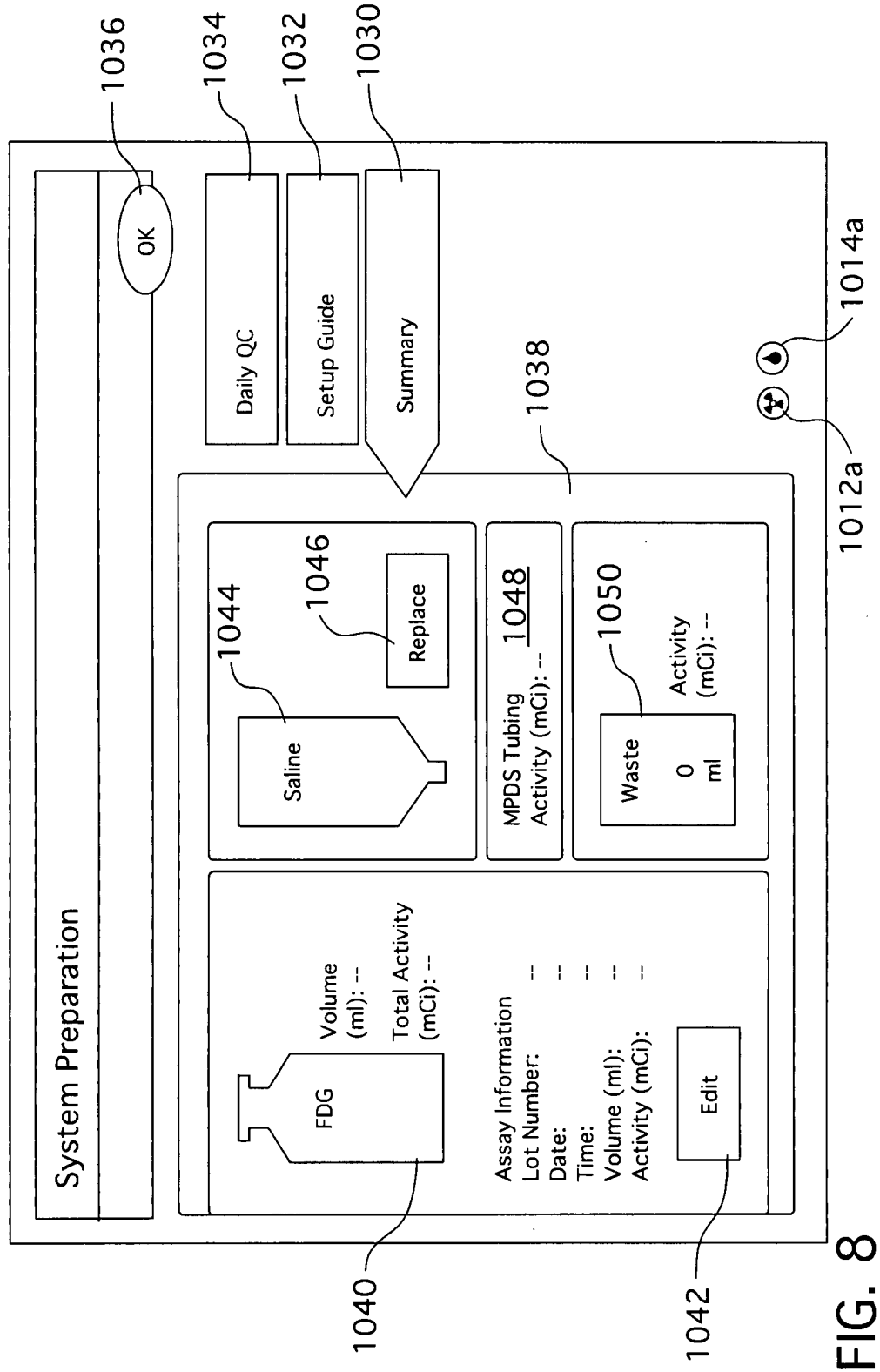

When the setup button 1022a is activated, the touch screen changes to that shown in FIG. 8. and "summary" 1030, "setup guide" 1032 and "daily QC" (quality control) 1034 touch fields preferably appear and the "summary" touch field 1030 is activated, prompting the appearance of a summary display 1038. As shown, summary display 1038 provides FDG and saline fields 1040, 1044, respectively, as well as MPDS tubing field 1048 and waste field 1050.

Figure 13:
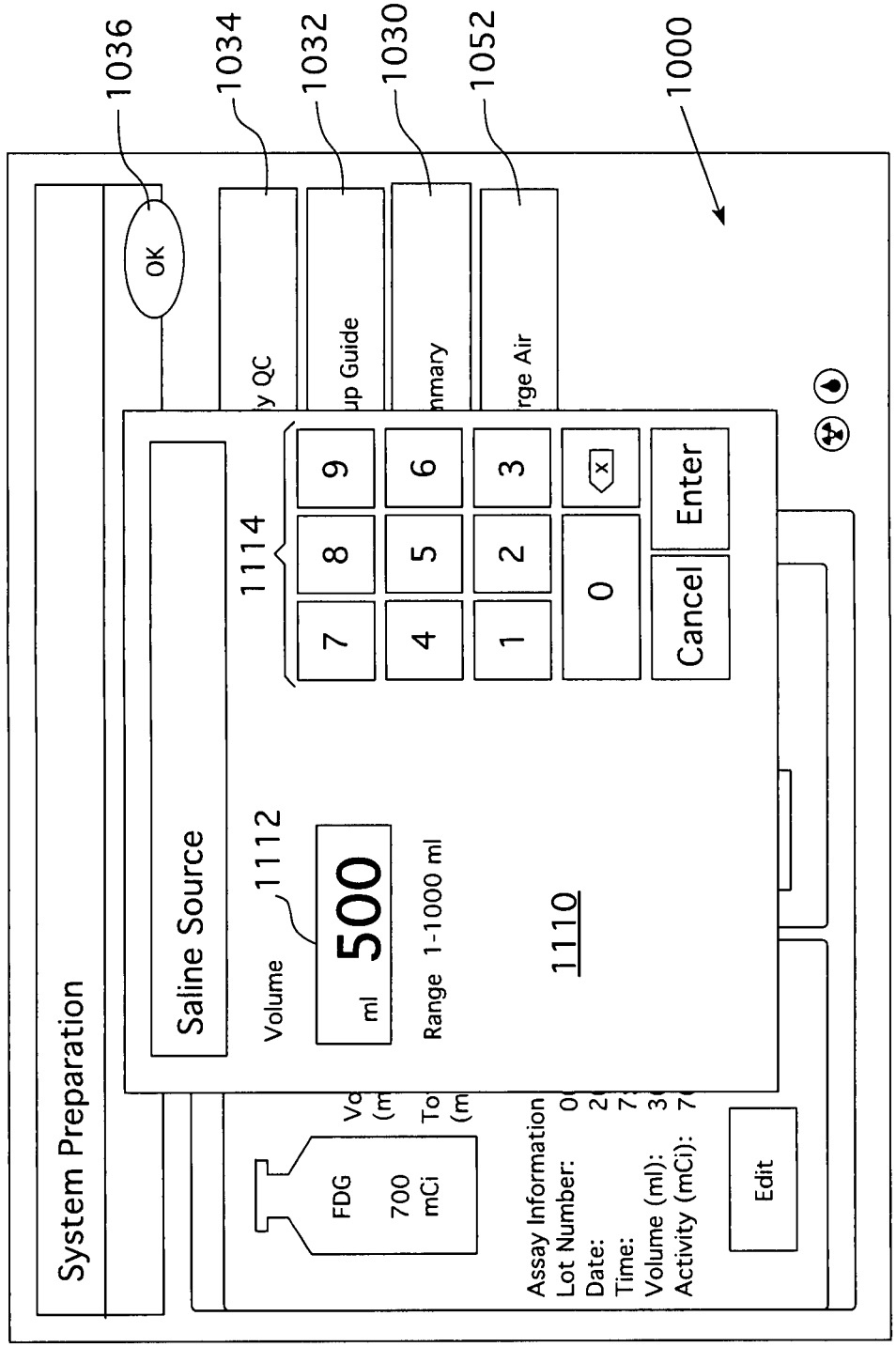

In the saline field 1044, a "replace" button 1046 can be activated by the user to inform the system 10 that the saline source 23 has been replaced and to allow the user to input the volume of the saline source into the system 10 (see FIG. 13).

Figure 11:
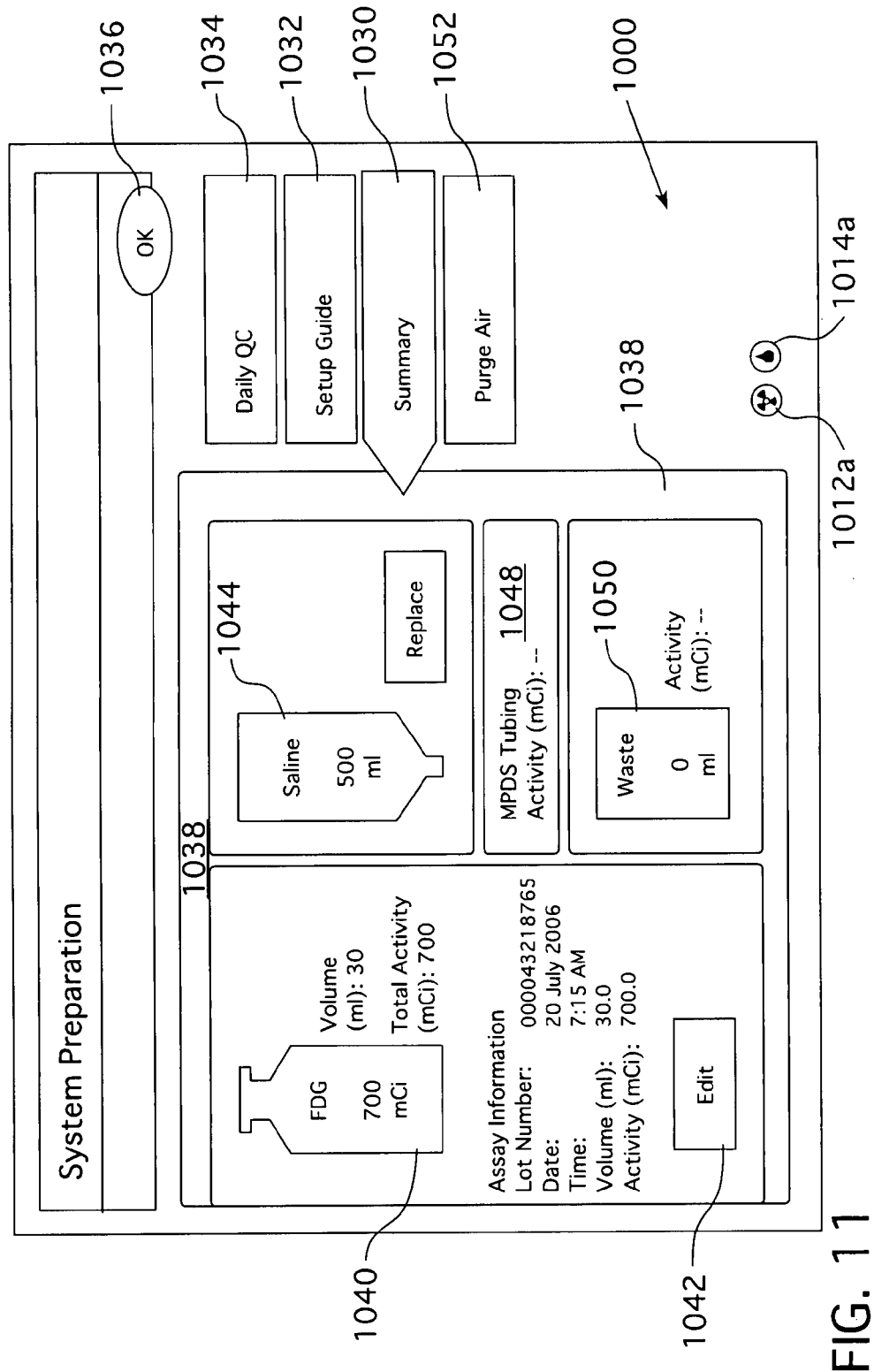

After the saline volume is input via pop-up screen 1110 including keypad 1114 in FIG. 13, the saline volume is displayed as shown in FIG. 11. In a preferred embodiment, the saline source 23 is replaced at the same time that a new vial 902 is placed into the system 10.

As part of the FDG field 1040 in FIG. 8, there are shown a number of informational displays (shown here as blank) regarding assay information that can be input by a user into the system 10. An edit button 1042 can be activated by the user to facilitate the entry of such information. When the edit button 1042 is activated, the display shown in FIG. 10 appears. The user can then input the noted assay information (typically provided on the pharmaceutical vial 902) into the system 10. Specifically, a lot number can be entered into field 1072, while the activity and volume of, for example, FDG or other radiopharmaceutical in the vial can be entered into touch fields 1080 and 1082, respectively. In a manner well known to those of ordinary skill in the art, the activation of any of these fields can prompt a numerical keypad pop-up to assist in data entry, or data can be entered in essentially any other suitable manner (e.g., directly via a physical keyboard).

Further, the assay date of the radiopharmaceutical in the vial is entered in field 1074 via a calendar button 1074a (which prompts the appearance of a pop-up calendar in known manner), or a simplified entry touch field 1074 which selectively permits the entry of a day such as "today" or "yesterday" (which is useful for radiopharmaceuticals, such as FDG, that have very short half-lives).

The assay time is entered into touch field 1076 (via a pop-up time field or keyboard/keypad entry) and an AM/PM toggle field 1076a. Other functional buttons are present, such as "clear all" 1078, "cancel" 1084 and "OK" 1086 buttons, to facilitate entry, deletion and/or acceptance of inputted values of the requested assay information. When the OK button 1086 is activated to accept the assay information shown in FIG. 10, the display shown in FIG. 11 appears.

Finally, as shown in both FIGS. 8 and 11, information regarding the amount of radioactivity present in the MPDS tubing 200 is displayed at area 1048, while a waste field 1050 is preferably provided to graphically display the quantity of fluid and the activity level in the waste receptacle 224. Further, an "OK" button 1036 is activated to notify the system 10 that the system preparation tasks have been completed.

Figure 9:
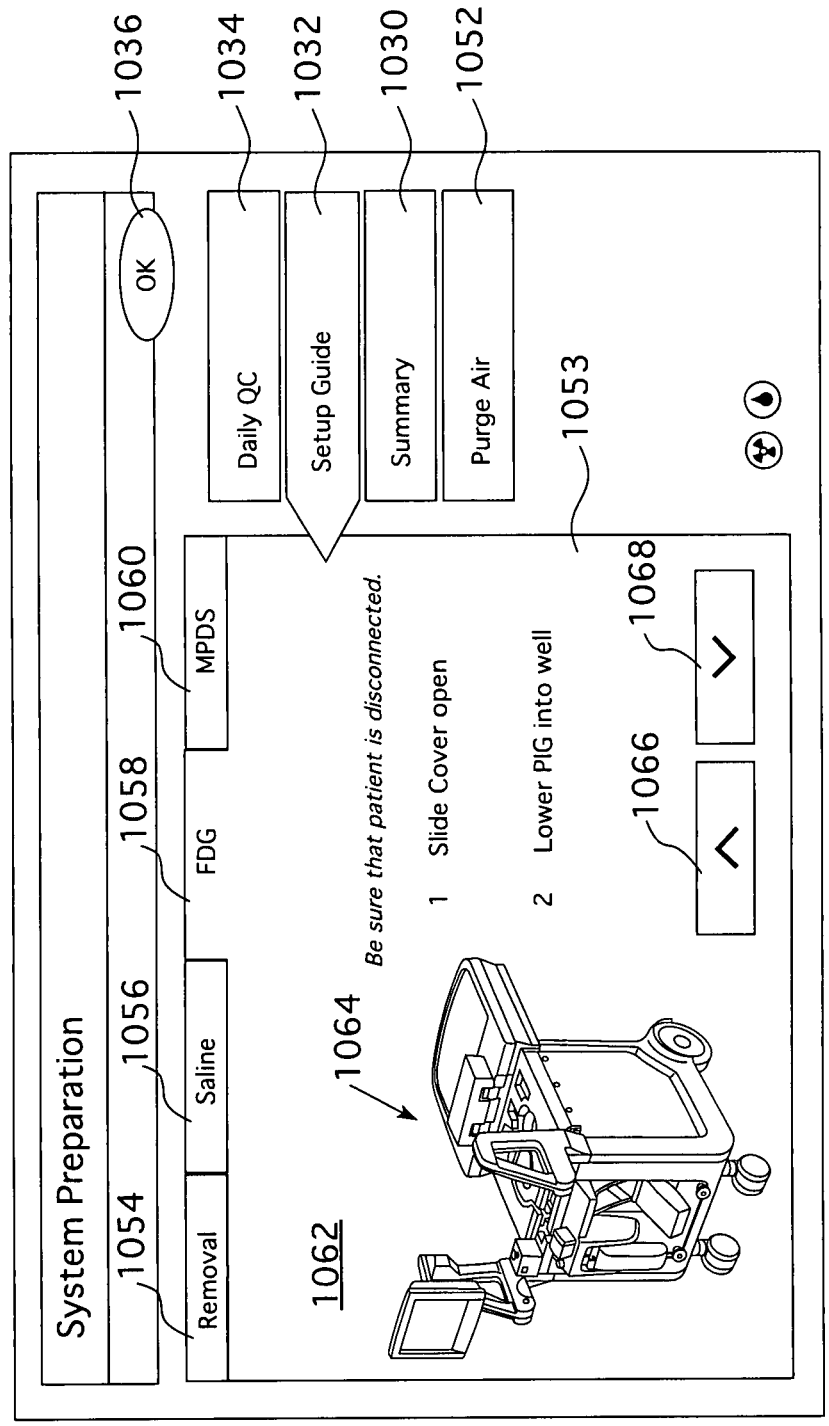

FIG. 9 illustrates the display screen that is shown when the "setup guide" touch field 1032 shown in FIG. 8 is activated. As shown, setup guide 1032 prompts the appearance of a setup screen 1053 to assist an operator in physically preparing the system 10 for a procedure. Setup screen 1053 preferably includes four tabs 1054, 1056, 1058, 1060), which each, respectively, assist an operator in a different aspect of system setup (here, FDG removal, saline source installation, FDG installation, and MPDS installation, respectively).

FIG. 9 also shows that FDG tab 1058 has been activated, prompting the appearance of display 1062. Up and down arrows 1066, 1068 preferably permit an operator to go through numbered procedure steps 1-4 as shown to install FDG vial 902 into the system 10, and a graphical image 1064 of the fluid delivery system 10 preferably graphically relates each of the numbered procedure steps. Here, for instance, "step 1" is shown graphically for the unlocking and opening of the cart. After the FDG vial 902 is installed in the system 10, status icon 1012a is highlighted (see FIG. 1) because activity is now present in the system 10.

Figure 12A:
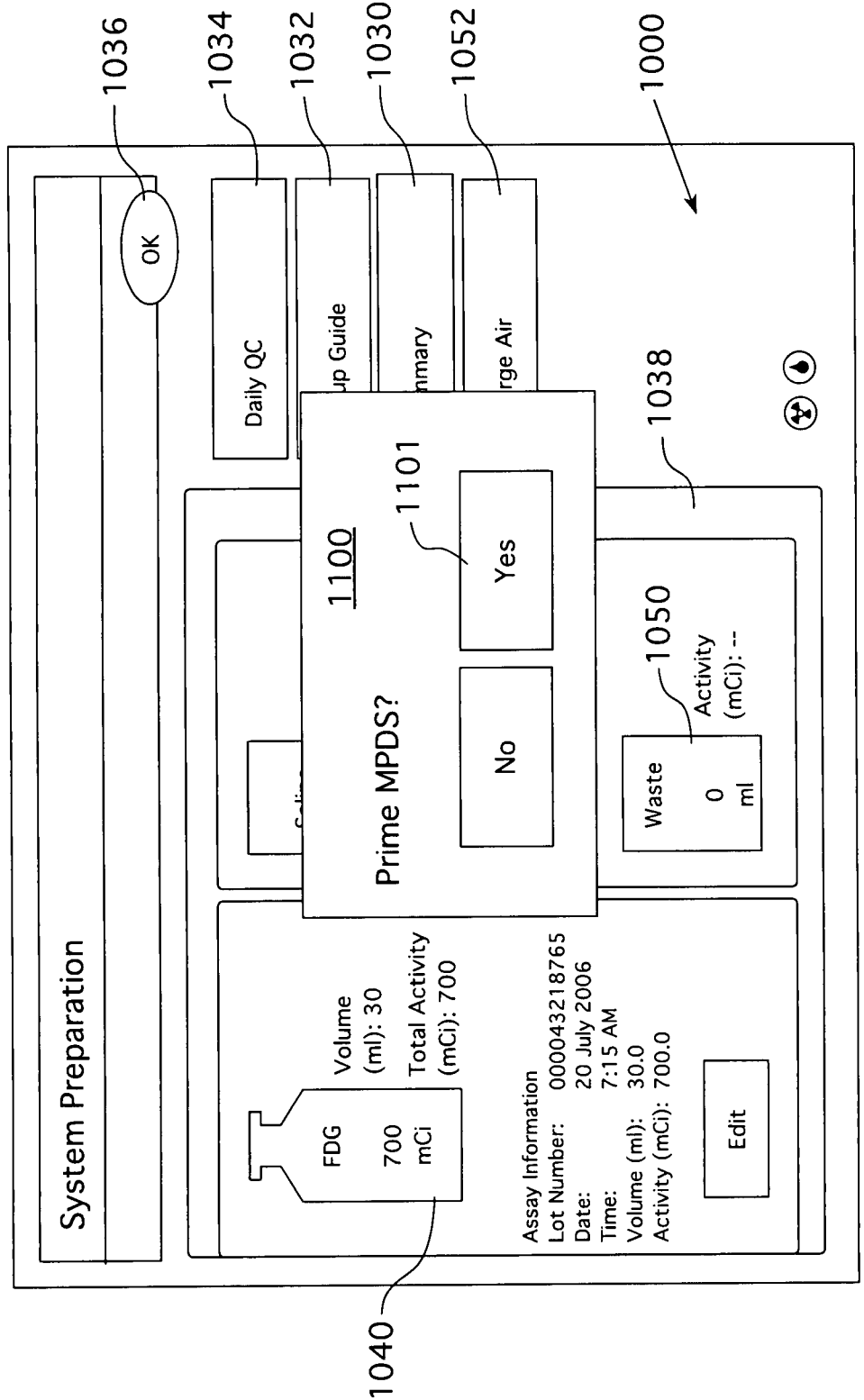
Figure 12B:
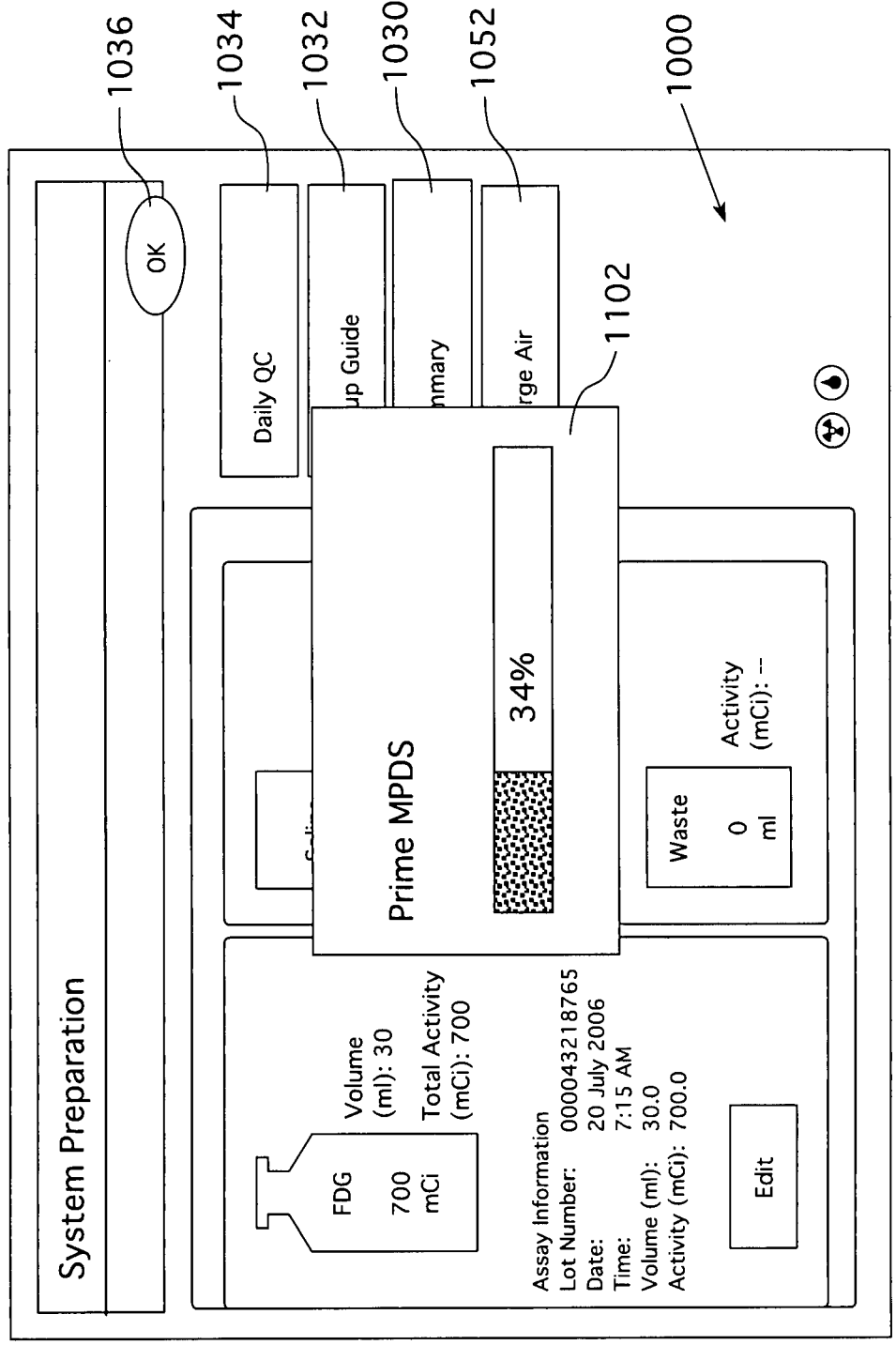

After the FDG vial 902, the saline source 23 and the MPDS 200 have been installed using, for example, the display shown in FIG. 9, and the FDG assay information and the saline volume information have been provided to the system (as shown in FIG. 11), the "purge air" button 1052 shown in FIG. 11 can be activated to prime the MPDS 200. When purge air button 1052 is activated, the "Prime MPDS" query prompt 1100 shown in FIG. 12A is displayed. When the "Yes" button 1101 in FIG. 12A is activated, the MPDS priming operation described in detail above is performed by the system 10 and a "Priming MPDS" status display 1102 is shown (see FIG. 12B) to indicate the status and completion of the MPDS priming operation to the user.

After the MPDS 200 is primed by the system 10, a volume of fluid (i.e., a mixture of saline and a pharmaceutical (e.g., FDG)) is present in the waste receptacle 224 (as described in detail above). The outcome of the MPDS priming operation and the current status of the system 10 is displayed to the user, as shown in FIG. 14.

Figure 14:
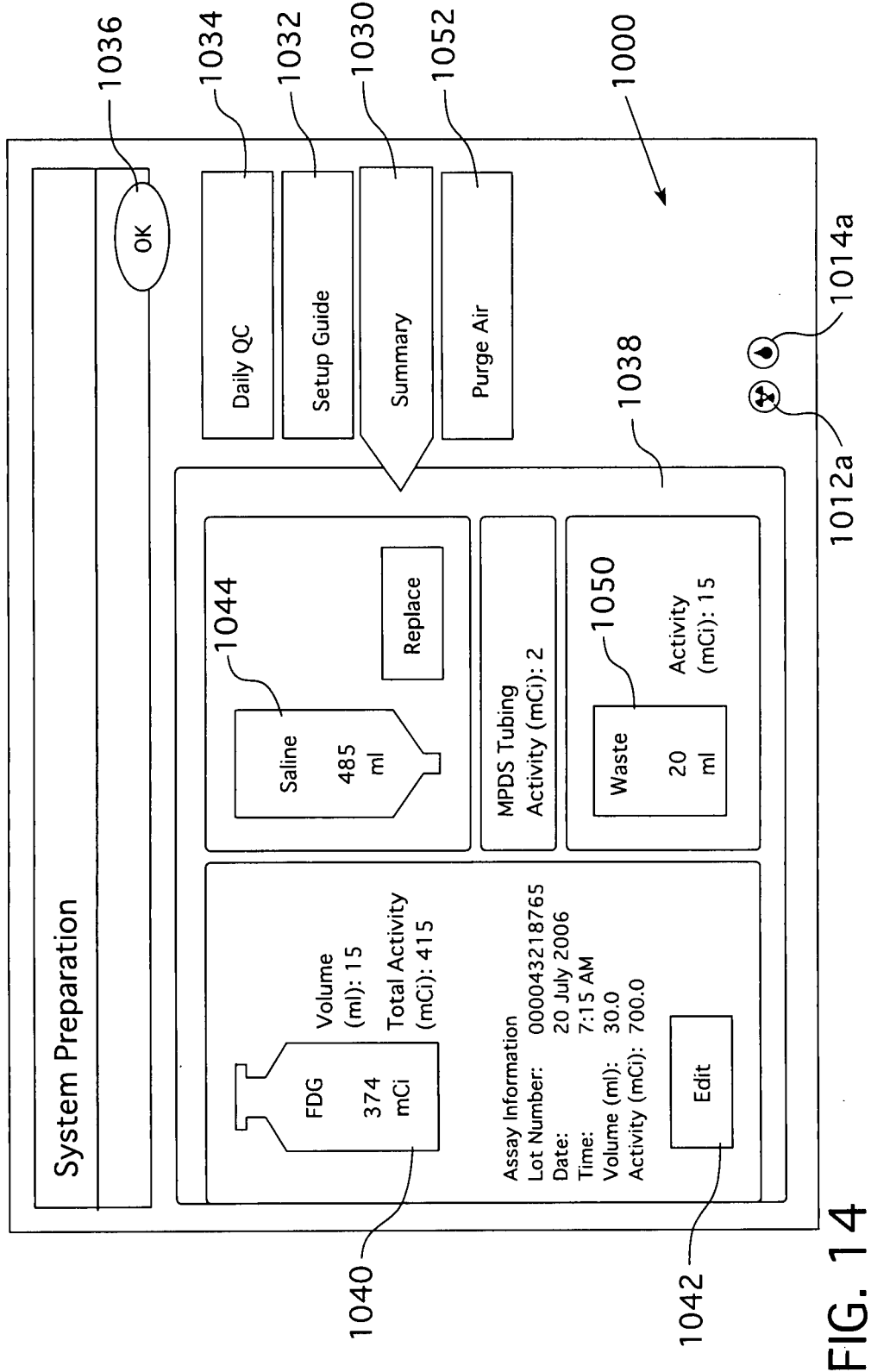

As FIG. 14 shows, and as compared to the pre-MPDS priming system status shown in FIG. 11, the waste receptacle 224 contains 20 ml of waste (i.e., saline and pharmaceutical) and has an activity level of 15 mCi, the MPDS tubing has an activity level of 2 mCi, the saline source 23 contains 485 ml of saline (compared to 500 ml in FIG. 11) and the vial 902 contains 15 ml of FDG and has an activity level of 374 mCi (compared to 30 ml and an activity level of 700 mCi in FIG. 11).

As shown in FIG. 14, the "Activity" (i.e., 700.0 mCi) listed in the Assay Information section of display 1038 is the amount of radioactivity provided by the radiopharmaceutical at the time it was assayed. The "Total Activity" (i.e., 415 mCi) shown next to the FDG display 1040 is the amount of radioactivity currently provided by the radiopharmaceutical present in the vial 902. The difference (i.e., 285 mCi) between the "Activity" and the "Total Activity" is calculated from the decay rate of the radioisotope and the elapsed time since the radiopharmaceutical was assayed. The activity level (i.e., 374 mCi) displayed within the FDG display 1040 is the 'extractable activity'; that is, the amount of activity that can be extracted from the vial 902. The "extractable activity" is less than the "total activity" because there is a small volume of radiopharmaceutical (e.g., approximately 1-2 ml) that cannot be extracted from pharmaceutical vials or containers and becomes discarded waste.

Figure 15:
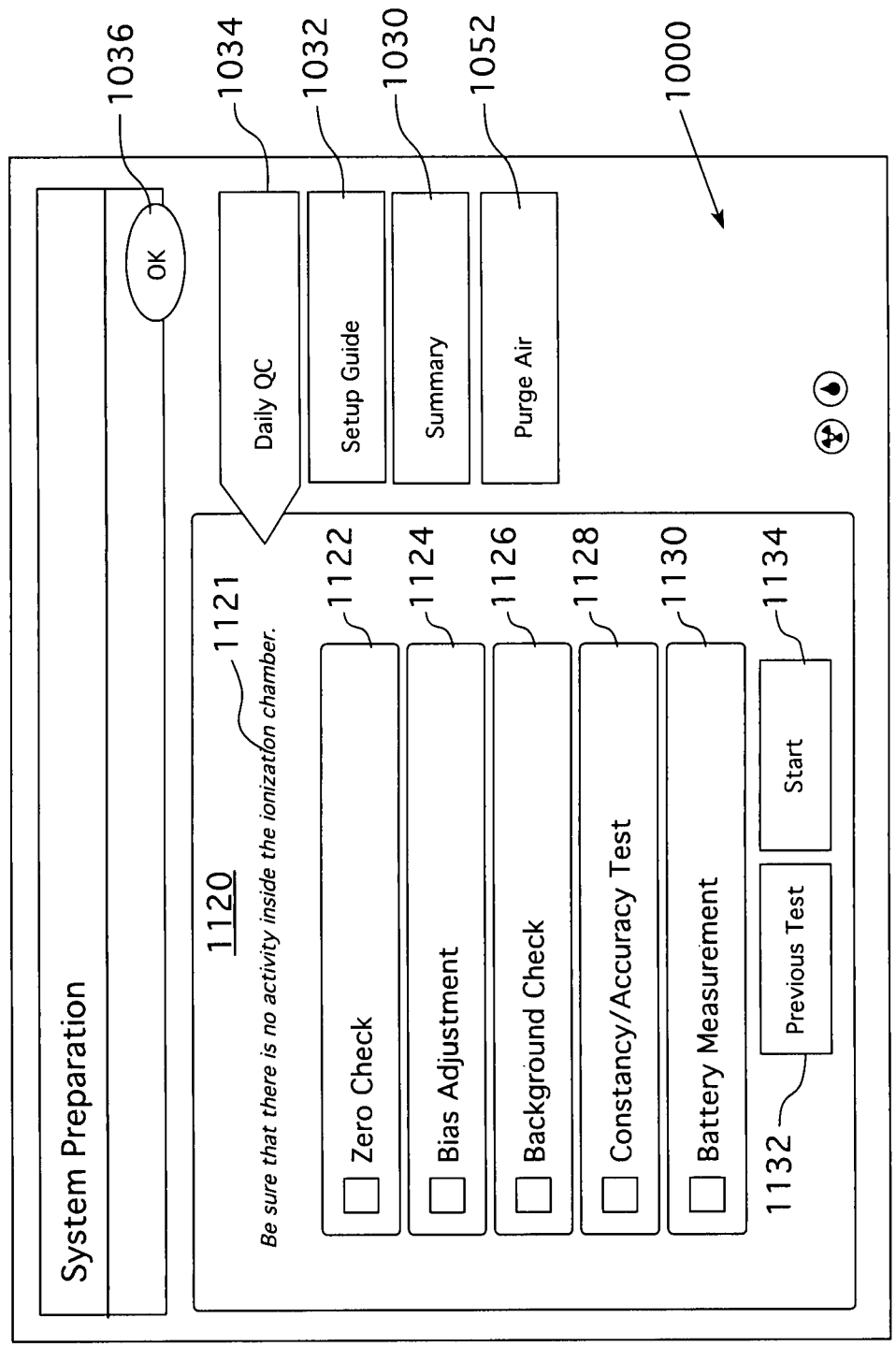

Preferably prior to installing and priming the MPDS 200, the operator or other personnel should perform a quality control check on the fluid delivery system 10. In a preferred embodiment, the quality control check is performed daily, for example at the beginning of a work day, to ensure that the fluid delivery system 10 is in good working order. The quality control check is initiated by activating the "Daily QC" field or button 1034, as shown in FIG. 15. When activated, the "daily QC" touch field 1034 prompts the appearance of a QC display 1120 to assist an operator in performing a quality control check. A menu of checks to be performed preferably appears via the following touch fields: zero check (1122), bias adjustment (1124), background check (1126), constancy/accuracy test (1128) and ionization chamber battery (i.e., high voltage) measurement check (1130). In addition, the QC display 1120 provides a warning prompt 1121 to the operator that no activity (i.e., no radiopharmaceutical) should be inside the ionization chamber 160 when the quality control check is conducted.

To the left of each touch field, preferably, is a "check box" or "pass/fail" indicator that preferably indicates one of the following four states, as appropriate: highlighted (if the corresponding touch field 1122-1130 is activated) to indicate an active test or check; not highlighted and blank to indicate an unexecuted test or check; checked with a checkmark to indicate a successful test or check; and an "X" to indicate a failed test or check.

The QC display 1120 also includes a "Previous Test" button 1132 and a "Start" button 1134. The Previous Test button 1132 is activated to display the results of the previous quality control check of the system 10. When the Start button 1134 is activated, the tests or checks displayed in the QC display 1120 are initiated. Preferably, the checks are conducted in the order presented (i.e., from top to bottom) but they may be performed in any suitable order.

Figure 16A:
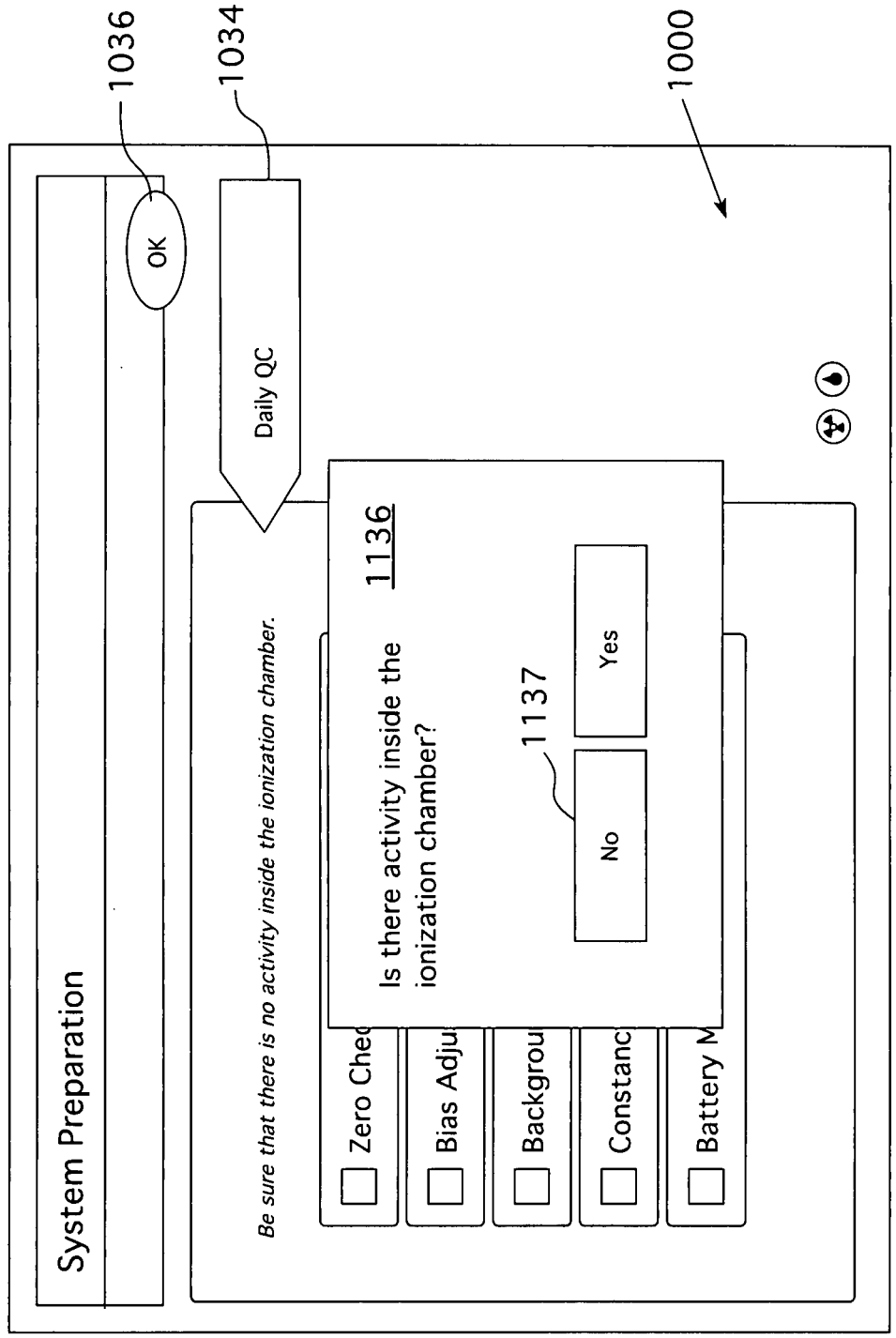
Figure 16B:
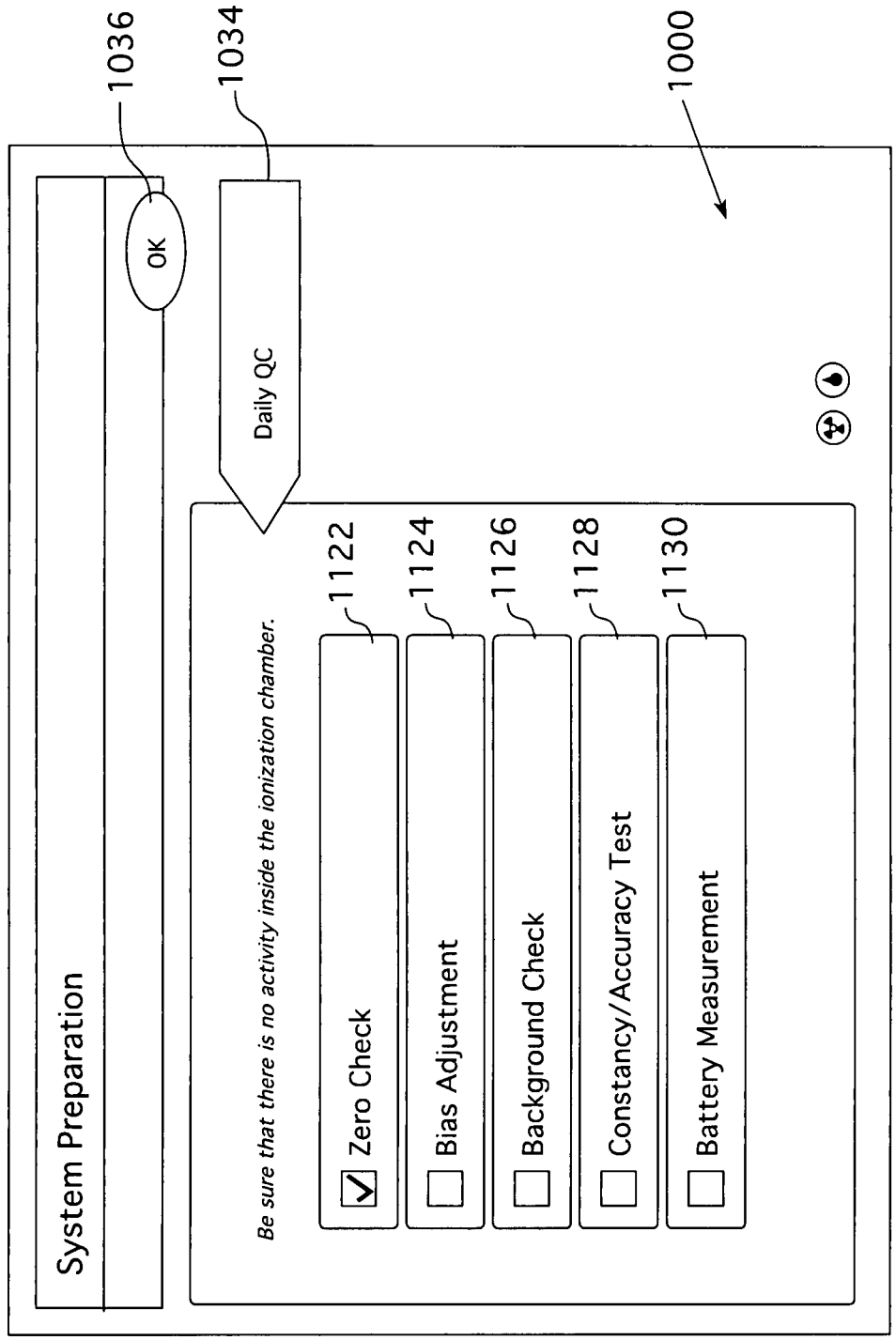

Upon activating the Start button 1134, the "Zero Check" test 1122 is initiated. As shown in FIG. 16A, when the Zero Check test is initiated, the system 10 creates a pop-up 1136 that queries the operator as to whether there is activity (i.e., a radiopharmaceutical) inside of the ionization chamber 160 of the fluid delivery system 10. If the operator activates the "No" touch button 1137 in pop-up 1136, system 10 "zeros out" the ionization chamber by automatically adjusting internal parameters so that the output from the ionization chamber indicates no activity. This check primarily accounts for environmental background radiation. When the check is completed, the system 10 displays a checkmark (see FIG. 16B) in the Zero Check display 1122.

Figure 17:
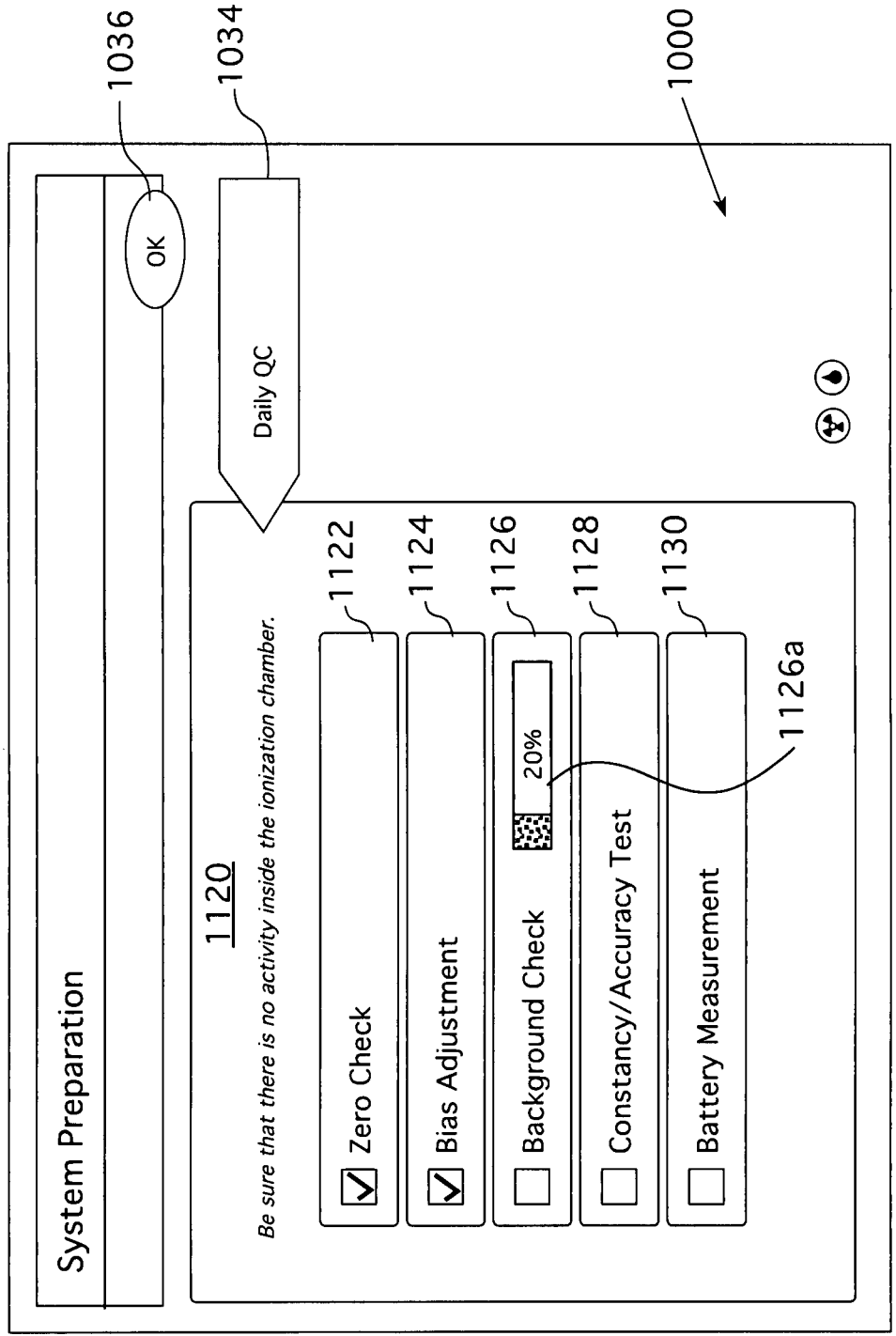
Figure 18:
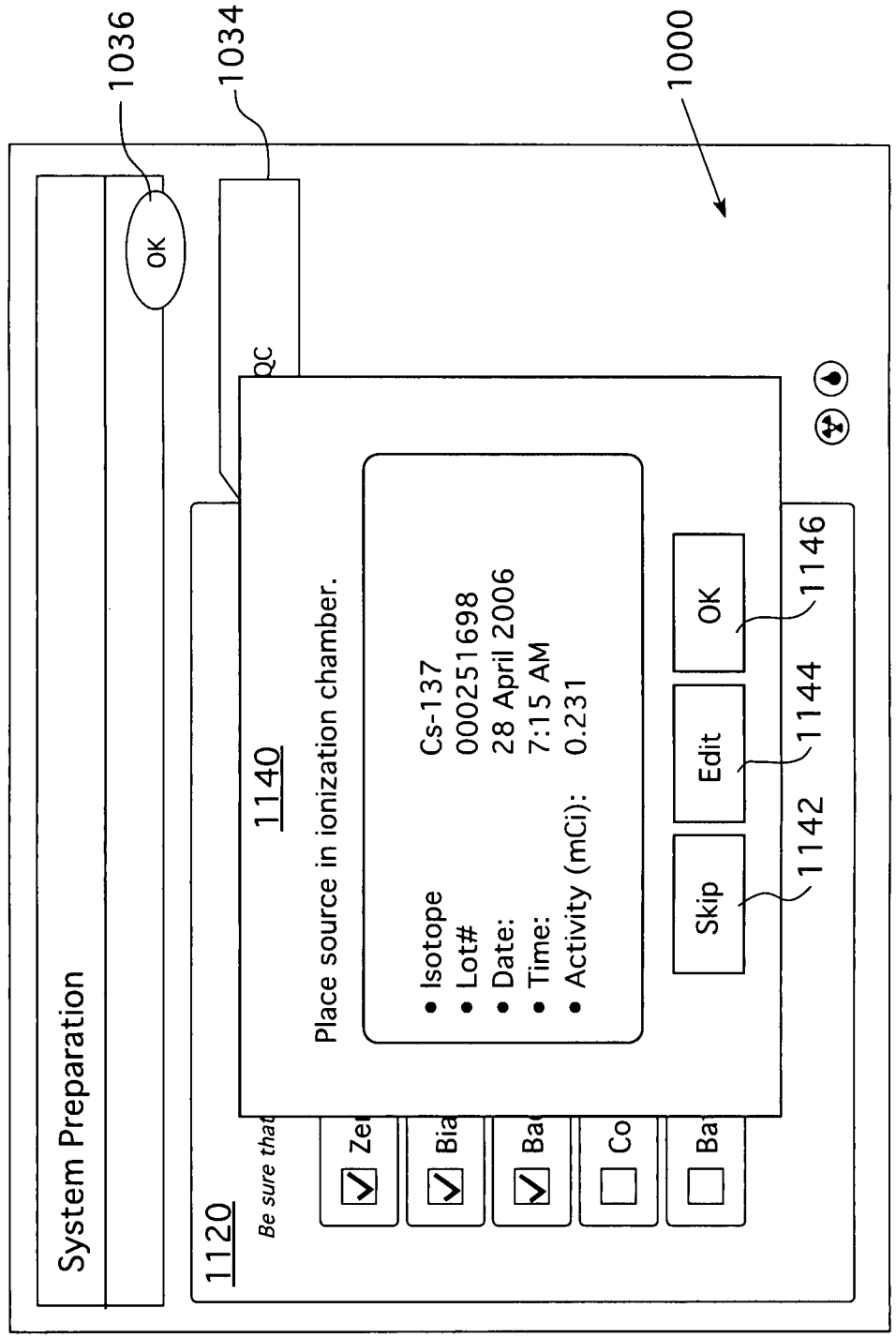
Figure 19:
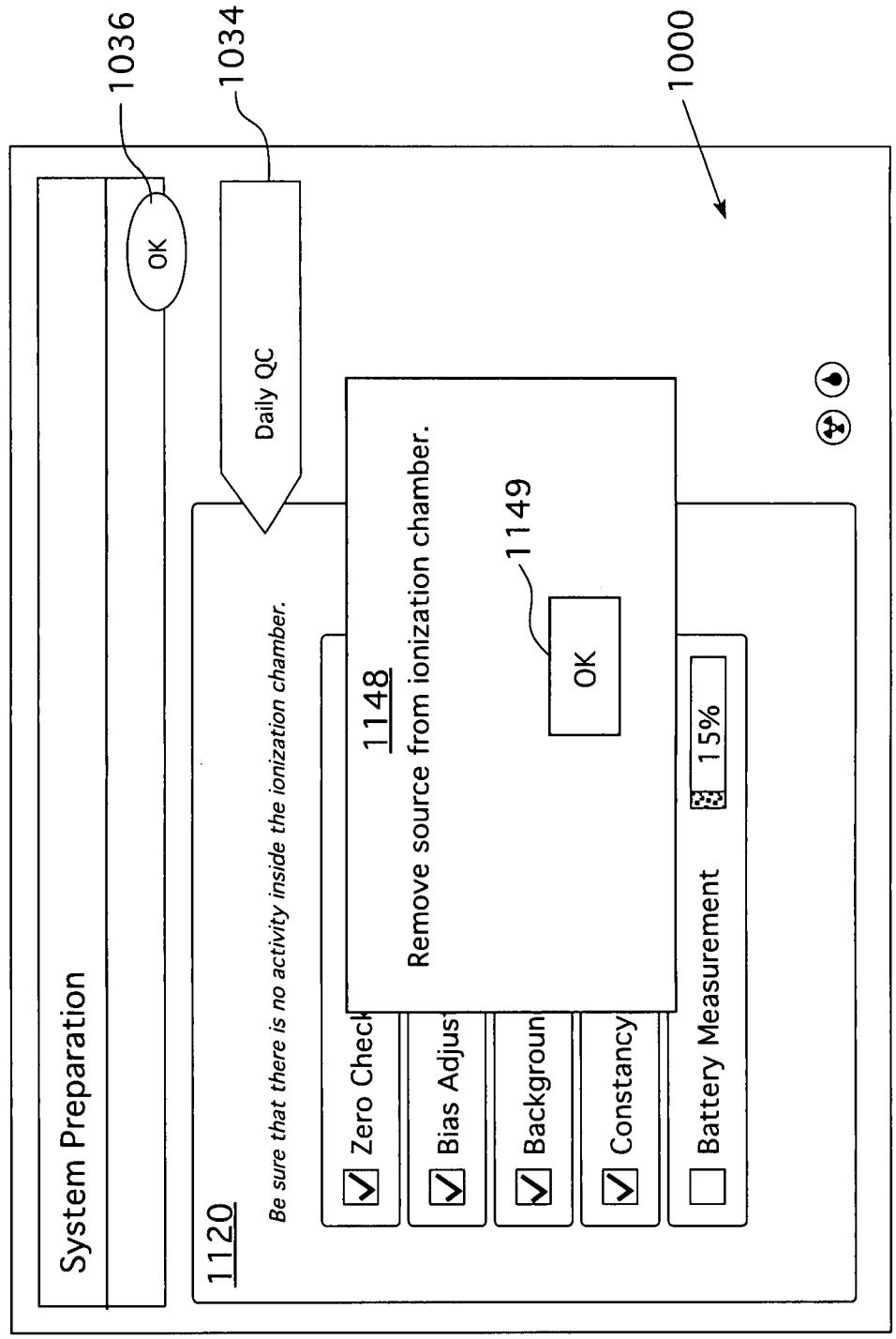

As shown in FIG. 17, the quality control check continues on to the Bias Adjustment check, which is similar to the Zero Check above but makes finer adjustments to internal biasing parameters to offset the effects of minor current fluctuations due to noise within the circuitry of the ionization chamber. The fine adjustments are made to ensure consistent activity readings from one measurement to the next. FIG. 17 shows a checkmark in the Bias Adjustment display 1124, thereby indicating that the system 10 has successfully adjusted the bias setting.

FIG. 17 further shows that the Background Check is in progress. As such, field 1126 is highlighted and a progress bar 1126a indicates the degree of progress (here, 20%). The Background Check basically completes the ionization chamber "zeroing" steps conducted during the Zero and Bias Adjustment checks. The system 10 takes several readings (e.g., 10) from the ionization chamber and captures the average of those readings for display to the user. This allows the user to determine whether the ionization chamber has been sufficiently zeroed out.

The next system check is the "Constancy/Accuracy" test, which is used to monitor the performance of the ionization chamber by measuring the same check source at intervals over a long period of time. The check source (e.g., Cs-137) is placed in the ionization chamber and the measured activity is compared to the expected activity based on the original assay information (decayed for time) of the check source. This ensures that the ionization chamber is providing accurate readings. The measured activity is also compared to previous readings of the same check source (decayed for time) by the ionization chamber. This ensures that the readings provided by the ionization chamber are consistent over time.

When the system 10 initiates the "Constancy/Accuracy" test, a pop-up 1140 is generated (see FIG. 18) to prompt the operator to place a suitable pharmaceutical (in this example, Cs-137) in the ionization chamber 160 and to input information about the radiopharmaceutical (see data fields in pop-up 1140) into the system 10. In a preferred embodiment, the pop-up 1140 automatically includes the radiopharmaceutical information from the most recent "Constancy/Accuracy" test, and the operator activates the "Edit" button 1144 to input new and accurate information when necessary. In an alternate embodiment the data fields in pop-up 1140 could be left blank for filling by the operator.

After the pharmaceutical is placed in the ionization chamber 160 and the data fields in pop-up 1140 are complete and accurate, the operator activates the "OK" button 1146 to initiate the "Constancy/Accuracy" test. The "Constancy/Accuracy" display bar 1128 preferably includes a test progress bar (not shown) similar to bar 1126a in FIG. 17 that indicates the degree of progress to the operator. If the operator wishes to bypass the Constancy/Accuracy" test, she may activate the "Skip" button 1142 to bypass the test and proceed to the "Battery Measurement" test (discussed below with respect to FIG. 20). Once the "Constancy/Accuracy" test is completed, another pop-up 1148 is generated by the system 10 (see FIG. 19) to prompt the operator to remove the pharmaceutical from the ionization chamber 160. After the operator activates the "OK" button 1149 in pop-up 1148 to inform the system 10 that the radiopharmaceutical has been removed from the ionization chamber 160, the system 10 then initiates the ionization chamber "Battery Measurement" check.

Figure 20:
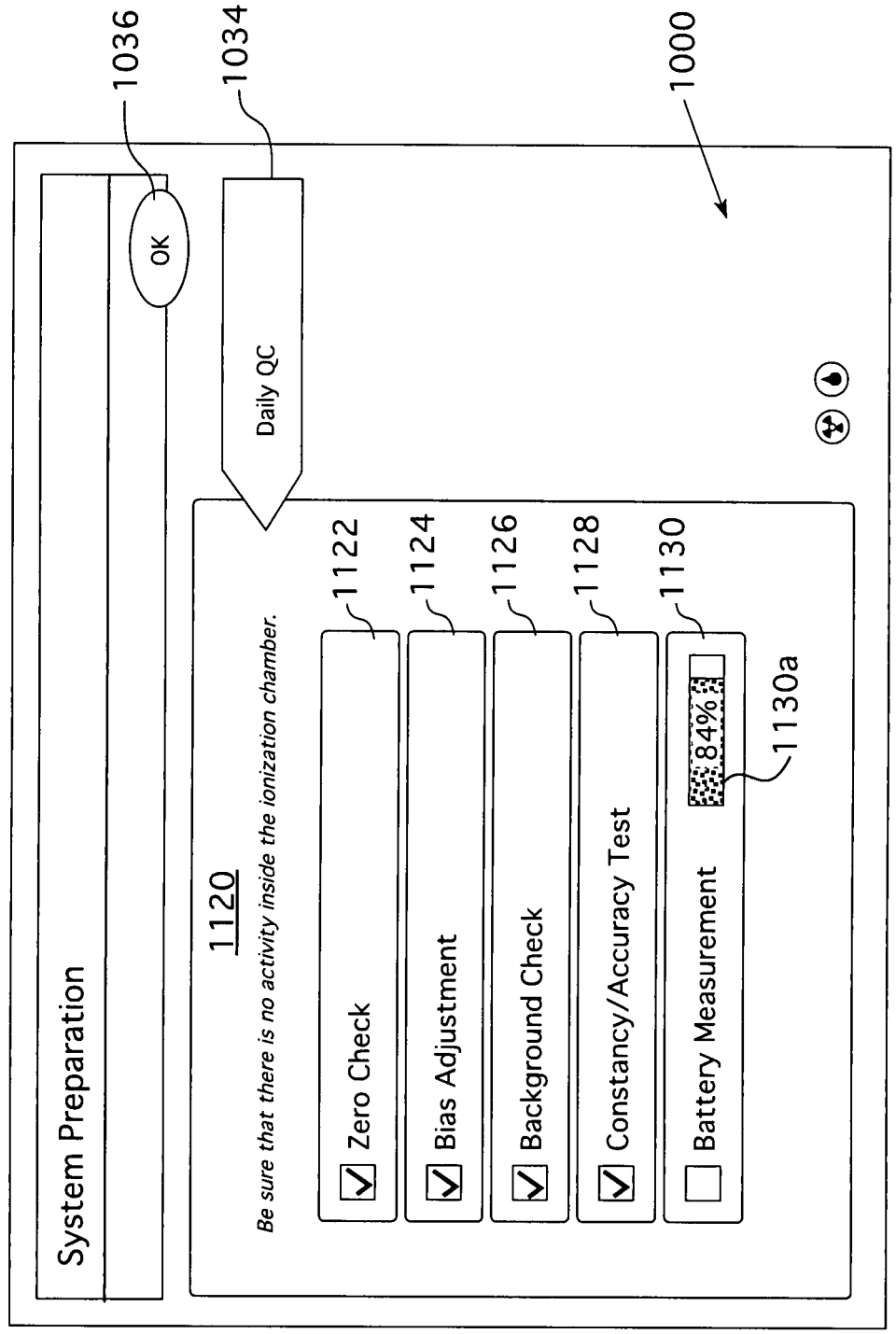

As shown in FIG. 20, the four previous system checks (see displays 1122-1128) are indicated by checkmarks as having been successfully completed. The ionization chamber "Battery Measurement" check measures the voltage output provided by a battery pack internal to the ionization chamber to ensure that the voltage output is sufficient to produce accurate readings from the ionization chamber. The ionization chamber "Battery Measurement" check is shown as being 84% completed by progress bar 1130a.

Figure 21:
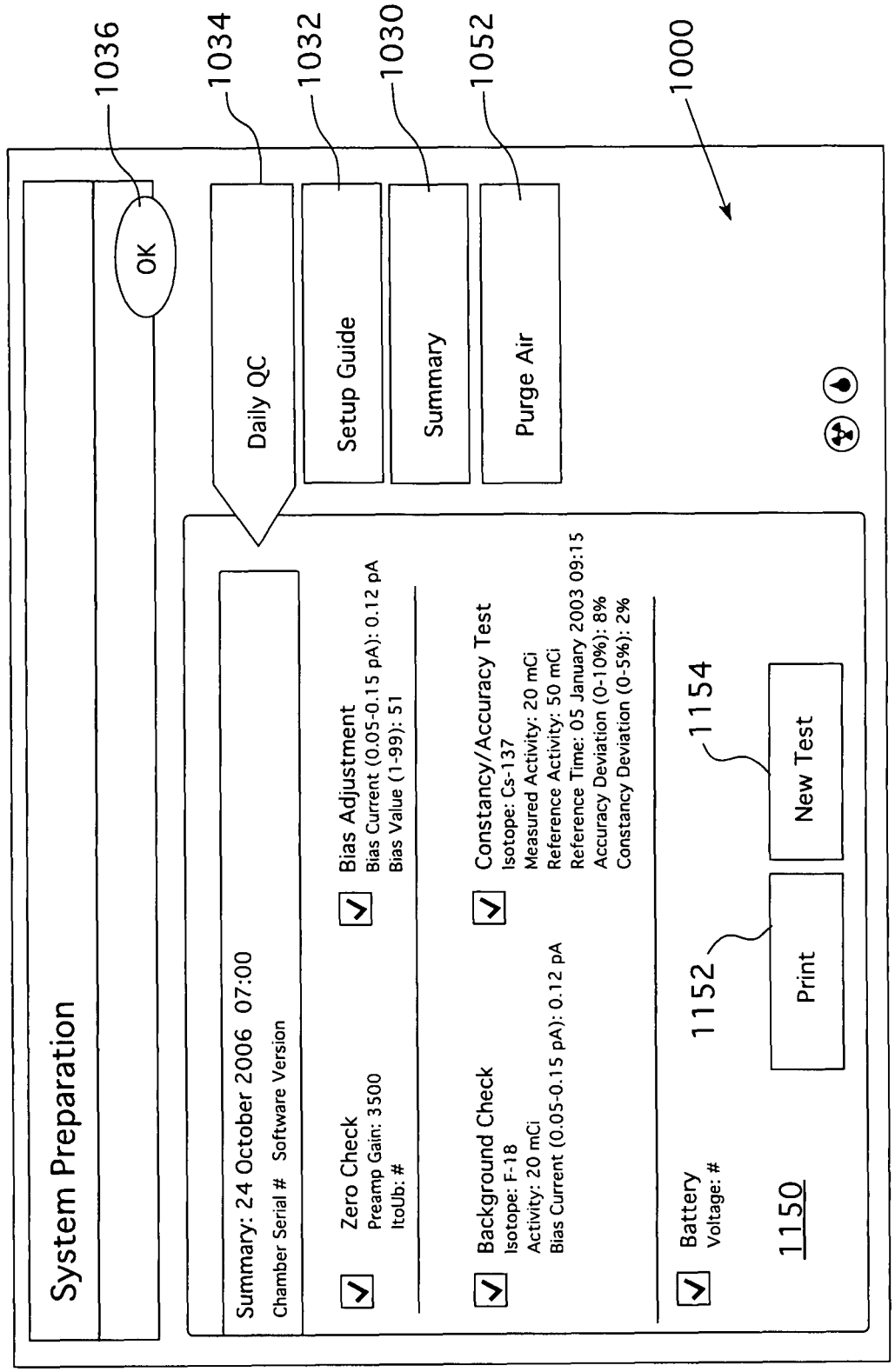
Figure 22:
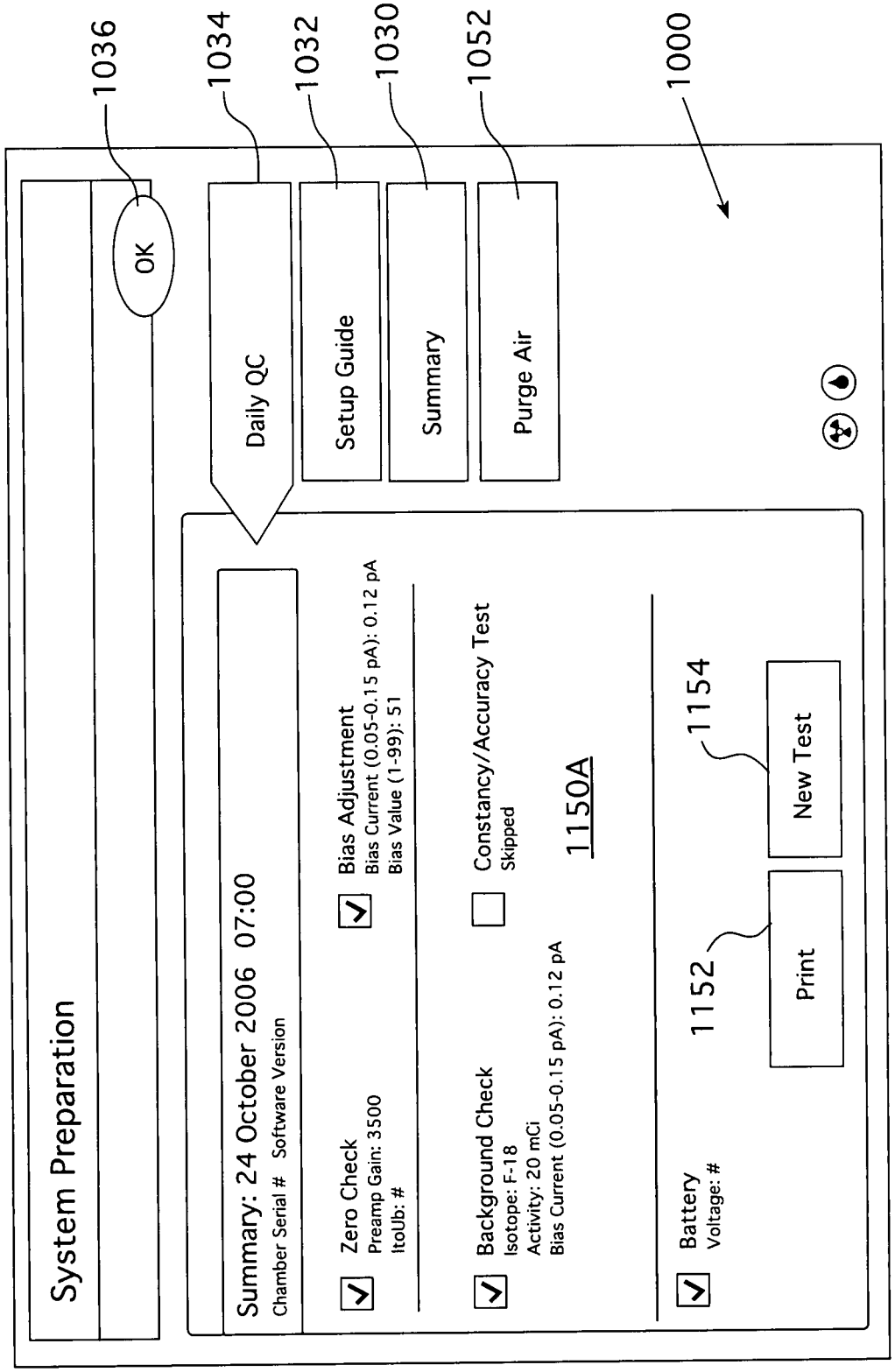

After the "Battery Measurement" check is completed, the system 10 generates a "Summary" display screen 1150, as shown in FIG. 21, with specific results for all of the checks. If the "Constancy/Accuracy" test was bypassed by the operator (by activating Skip button 1142 in FIG. 18), the system 10 generates "Summary" display 1150a shown in FIG. 22, which indicates that the "Constancy/Accuracy" test was skipped.

Screen 1150 also includes a print button 1152 that is activated to, for example, print out the test results (via printer 24 of system 10) for the system's maintenance file. In addition, the Summary display 1150 includes a New Test button 1154, which is activated by the operator to initiate a new series of quality control checks. When the New Test button is activated, the display 1120 shown in FIG. 15 is generated and the quality control check is conducted again by the system 10.

Patient Treatment

The "Patient Treatment" category of tasks is described below in relation to FIGS. 23-32B. The "Patient Treatment" category includes a number of tasks that are preferably performed in the following order to administer or inject a radiopharmaceutical into a patient: (1) setting the desired activity level to be delivered to the patient; (2) inputting patient and/or case identification information into the system 10; (3) connecting the first end 702 of the SPDS 700 to the connector end 228 of the MPDS 200; (4) priming the SPDS 700 to remove air therefrom; (5) connecting the patient end 704 of the SPDS 700 to the patient; (6) conducting a test injection to ensure the integrity of the fluid path to the patient; (7) preparing the radiopharmaceutical dose to be administered or injected into the patient; (8) measuring the activity level of the radiopharmaceutical dose in the dose calibrator 160 to ensure that it is equal or substantially equal to the desired activity level to be delivered to the patient; (9) discarding the radiopharmaceutical dose if, for example, the patient is experiencing discomfort or the measured activity level is not equal or substantially equal to the desired activity level; and (10) administering or injecting the radiopharmaceutical dose to the patient if the measured activity level is equal or substantially equal to the desired activity level. While the above order is the preferred one for the "Patient Treatment" tasks, the tasks may be performed in any suitable manlier and order for the intended application.

Figure 23:
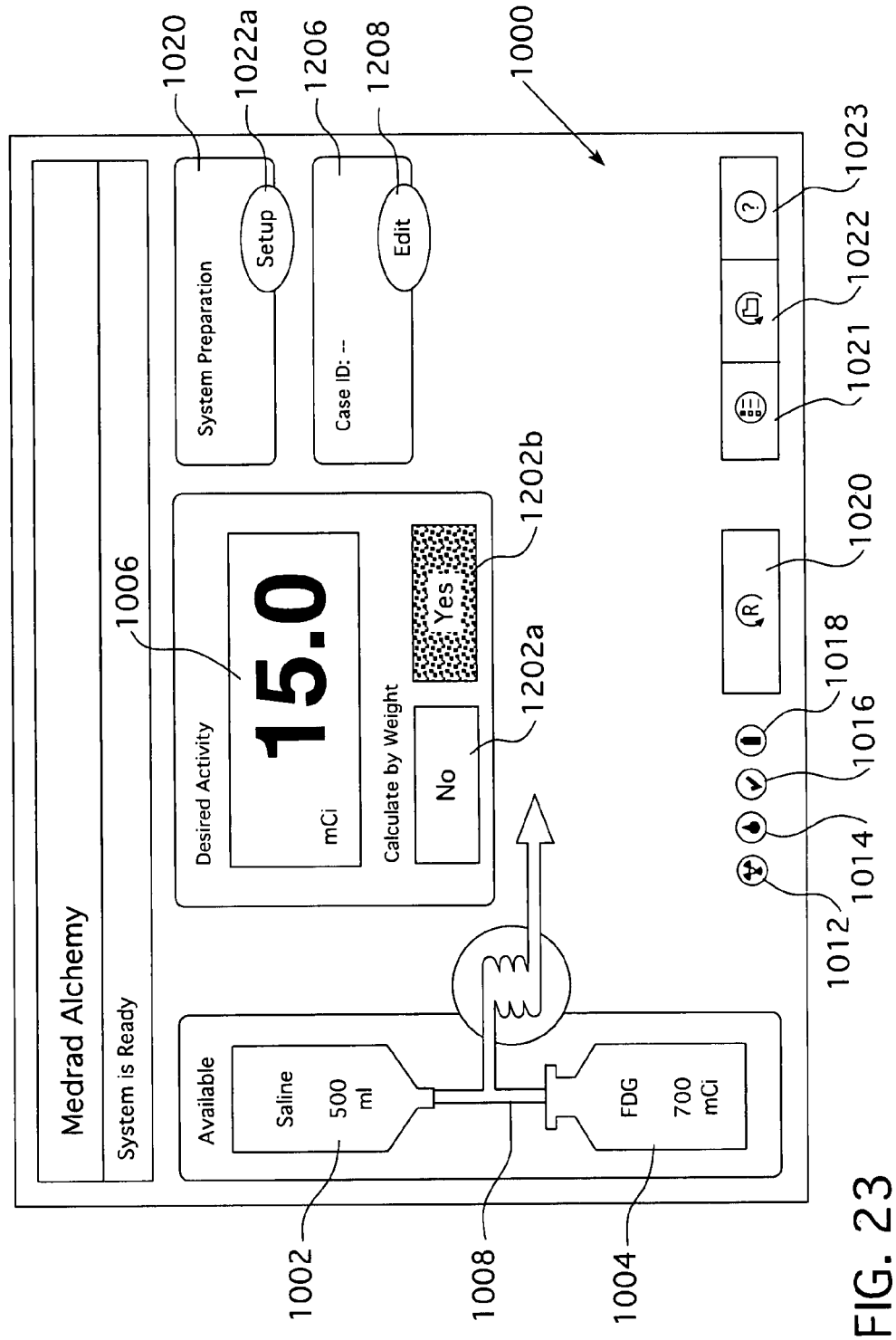
FIGS. 23, 24A-F, 25A, 25B, 26A, 26B, 27A, 27B, 28A, 28B, 29, 30A, 30B, 31, 32A and 32B are various depictions of a graphical user interface for use in patient treatment tasks.

After the operator prepares the system 10 for a fluid delivery procedure by, for example, completing the steps set forth above in the "System Preparation" tasks, the system 10 generates the display 1000 shown in FIG. 23 which indicates in the upper left hand side thereof that the "System is ready." The saline field 1002 indicates that 500 ml of saline is available and the FDG field 1004 indicates that 700 mCi of FDG are available, as shown.

As further shown in FIG. 23, the Desired Activity field 1006 indicates that 15.0 mCi is the current desired activity level. This 15.0 mCi activity level is preferably an operator-defined, default setting in the system 10, but also could be the desired activity level that was programmed for the last injection procedure.

The desired activity level is preferably set by the operator in one of two ways: (1) manual input; or (2) a calculation based on patient weight. If the operator wants to set the desired activity level by manual input rather than by patient weight, the operator activates the "No" button 1202a in display 1006. In response thereto, the system 10 generates the display and keypad 1204 shown in FIG. 24A. The operator uses the keypad 1204 to input the desired activity level.

If instead the operator wants to set the desired activity level based on patient weight, the operator activates the "Yes" button 1202b in FIG. 23. Upon activation of the "Yes" button 1202b, the system 10 generates the display 1000 and pop-up 1205 shown in FIG. 24B, which prompts the operator to "Enter patient weight" (displayed in pounds or kilograms in data field 1003) using pop-up 1205. Further, the operator can select the formula to be used in calculating the weight-based activity level by activating formula touch field 1011. When formula touch field 1011 is activated, the pop-up table 1013 shown in FIG. 24C is displayed and the operator is prompted to "Select formula." In a preferred embodiment the operator can select up to five operator-defined formulas. For example, as shown in FIG. 24C, the operator can select among three predefined formulas: (1) Standard (0.1 mCi/lb.); (2) Melanoma (0.13 mCi/lb.); and (3) Pediatric (0.07 mCi/lb.). However, the system 10 can include more than pre-set or pre-defined weight-based formulas. For example, the system 10 can also include formulas based on other patient parameters, such as glucose-level or cardiac output, or scanner parameters, such as acquisition time or crystal type.

Once the formula is selected, the desired activity level is calculated using the formula and the patient's weight. The desired activity level (e.g., 13.5 mCi), the patient's weight (e.g., 135 lb.) and the formula (e.g., 0.1 mCi/lb.) are displayed in field 1006 and the screen display 100 indicates that the "System is ready", as shown in FIG. 24D.

Figure 24A:
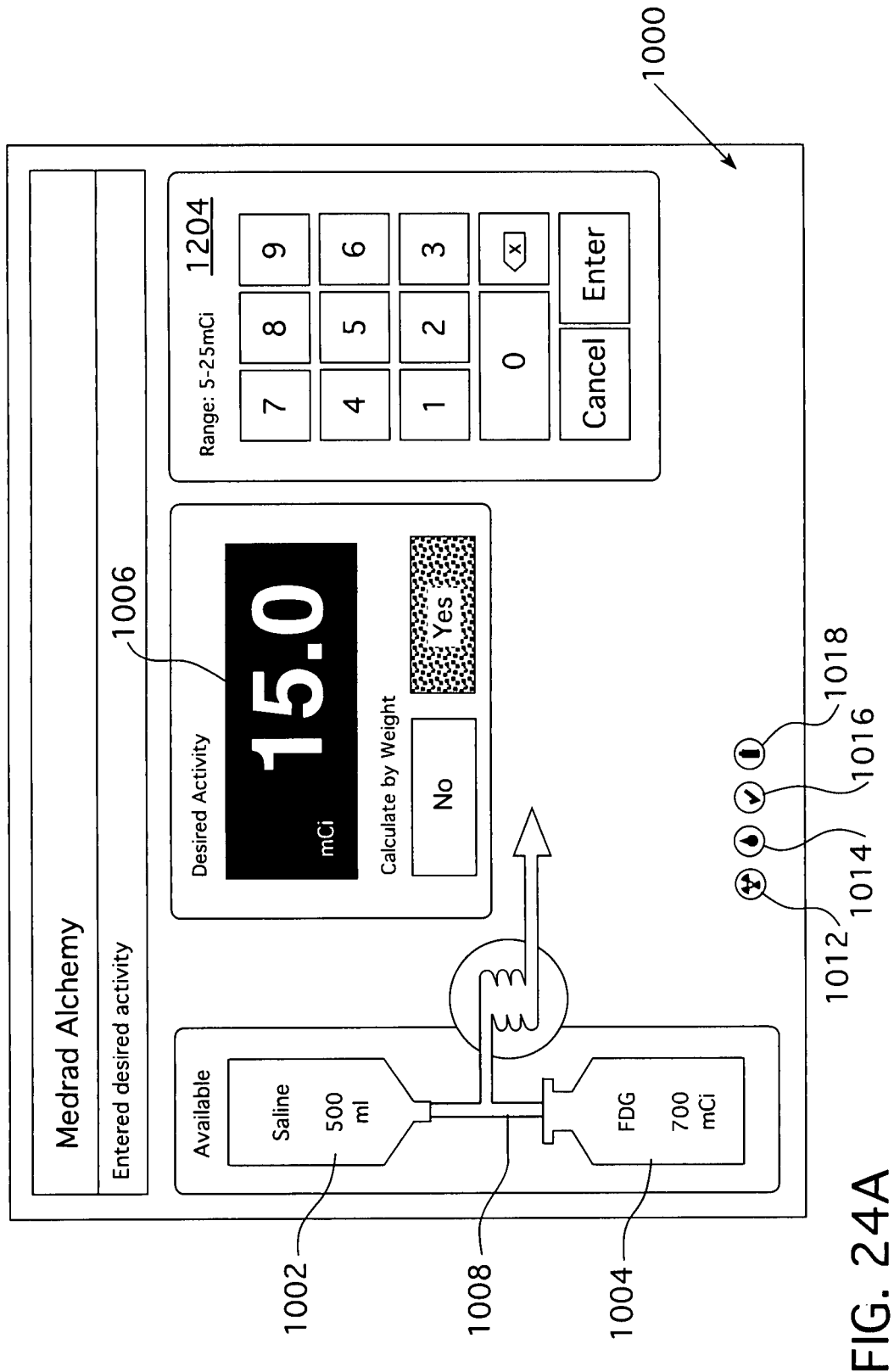
Figure 24B:
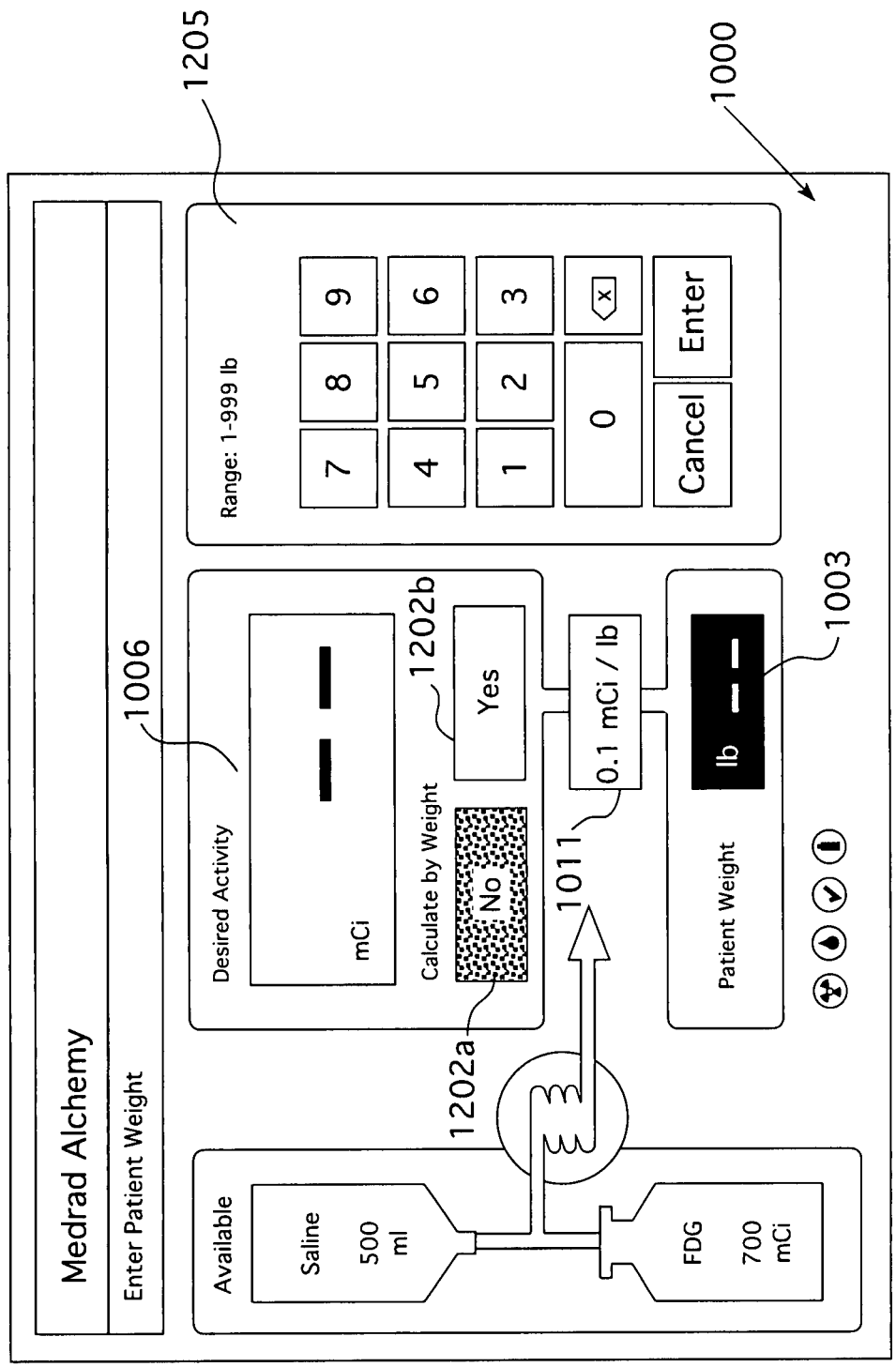
Figure 24C:
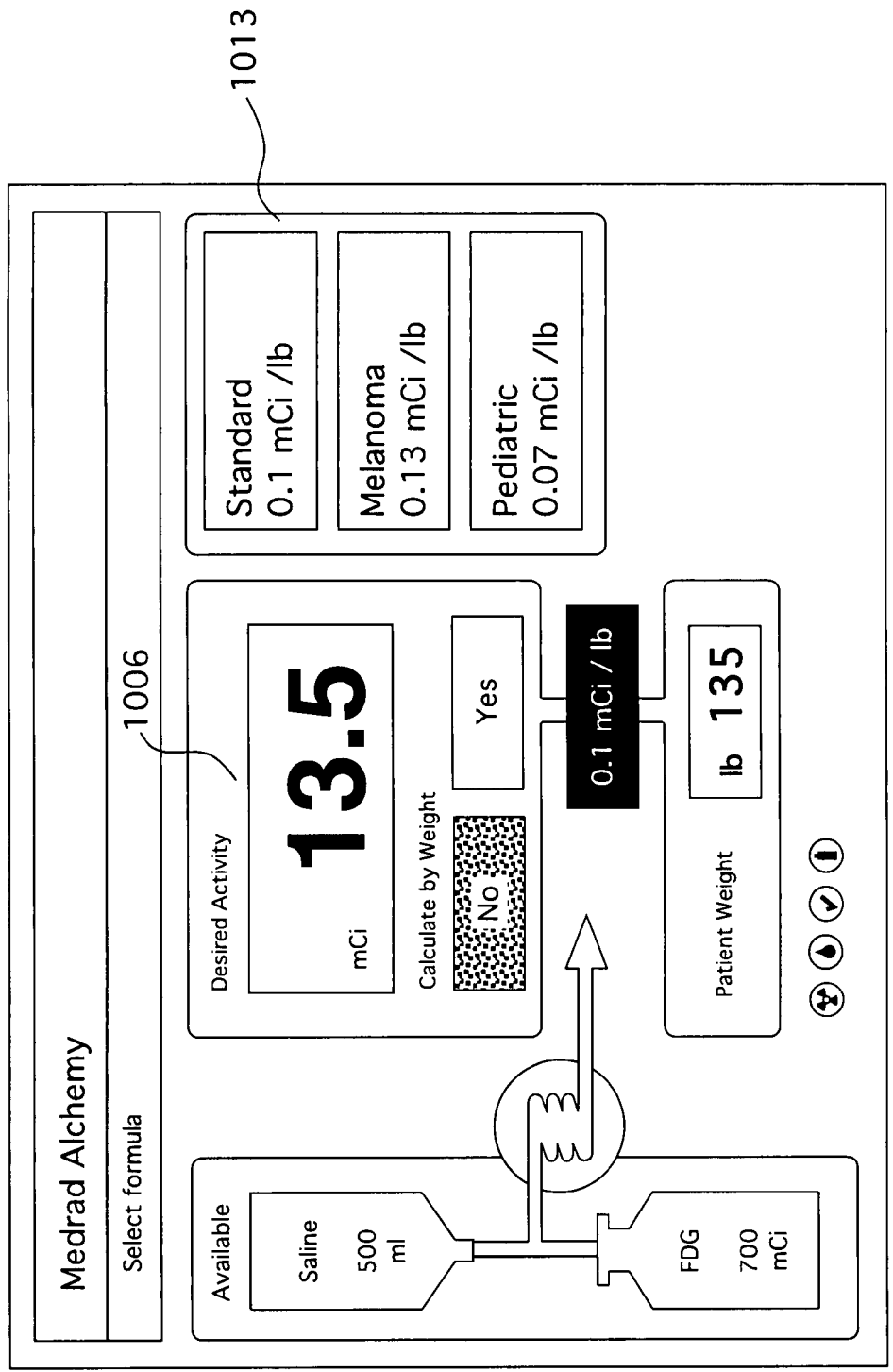
Figure 24D:
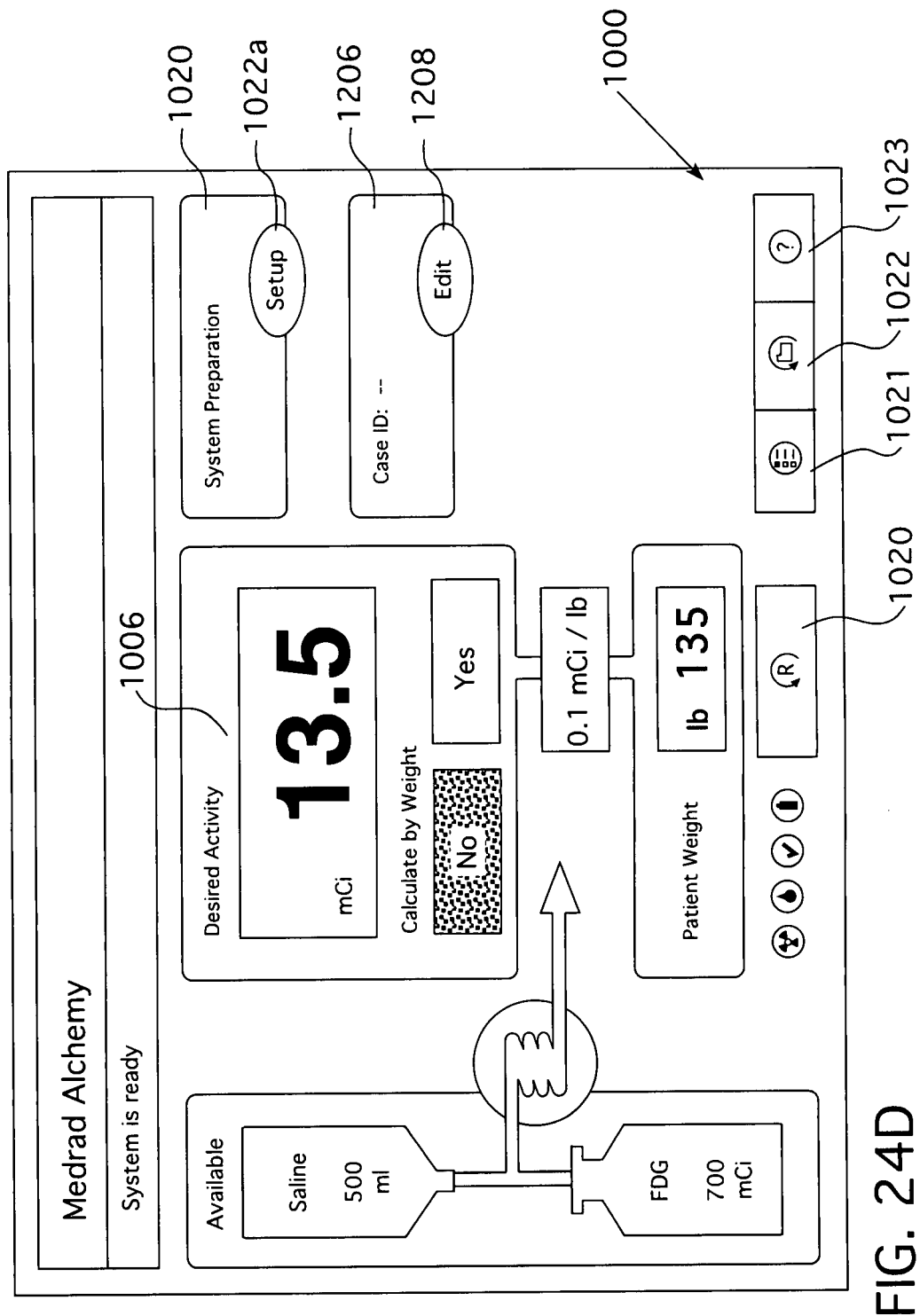

In addition, as displayed in display and keypad 1204 shown in FIG. 24A, in a preferred embodiment the system 10 includes pre-defined minimum and maximum activity levels that define the operating range (i.e., 5-25 mCi) of the system 10. The operating range of the system 10 cannot be altered by the operator, and the system 10 preferably will not accept a desired activity level (whether manually input or calculated based on patient weight or other patient or scanner parameter) that falls outside of the system's operating range. In a preferred embodiment, the system will default to the maximum or the minimum activity level (i.e., 25 mCi or 5 mCi) if the operator attempts to input or the system calculates a desired activity level that is greater than the maximum activity level or less than the minimum activity level, respectively.

Figure 24E:
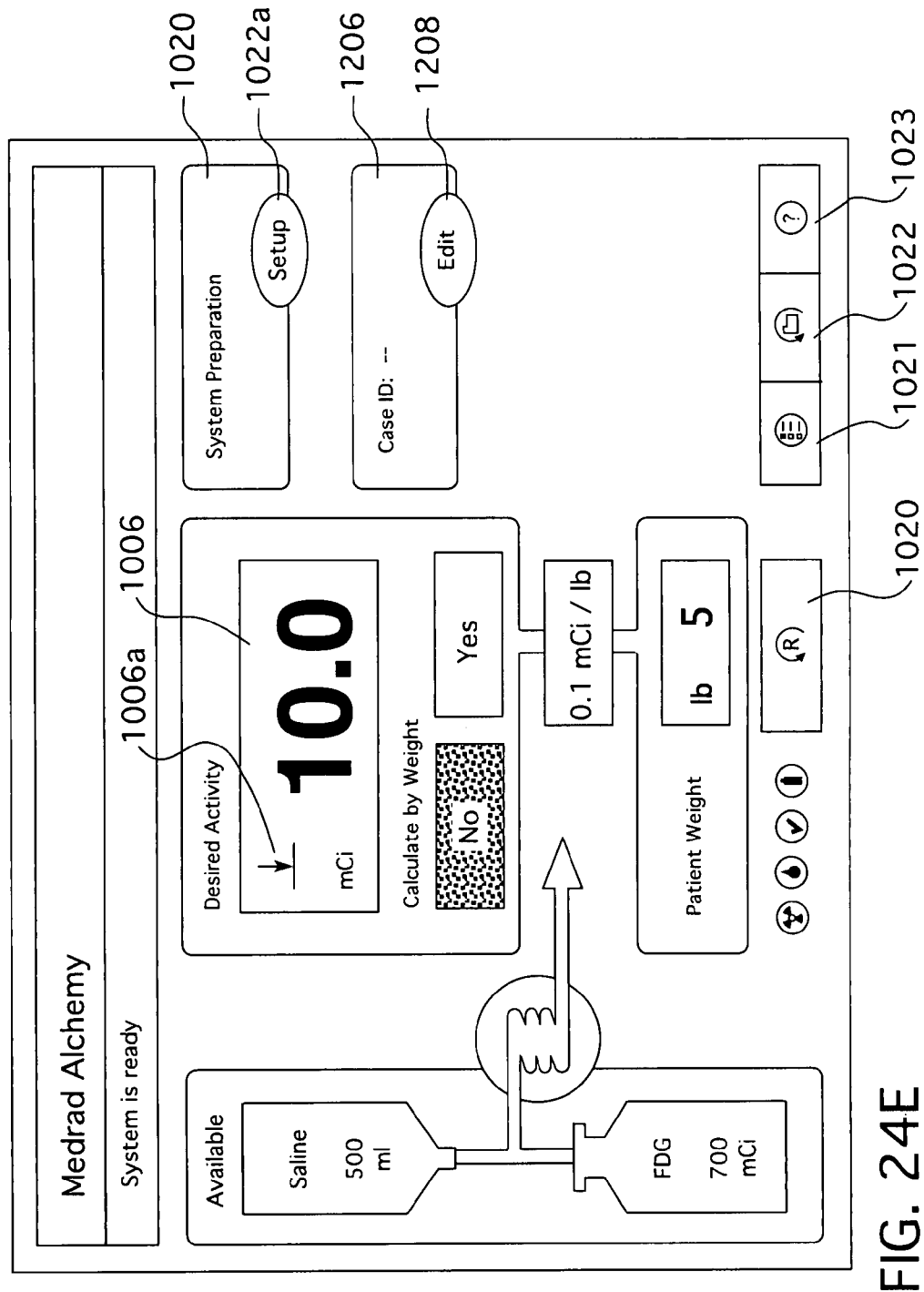

Furthermore, if desired for safety or medical practice or preference reasons, the operator preferably can define her own minimum and maximum desired activity levels for the system, as long as they fall within the operating range of the system 10. For example, the operator can define a minimum desired activity level of 10.0 mCi and a maximum desired activity level of 17.5 mCi for the system 10 because those two parameters fall within the 5-25 mCi operating range of the system 10. In such a case, as shown in FIG. 24E, even though the operator inputted a patient weight of 5 lb. and chose a formula of 0.1 mCi/lb. (which would result in a calculated desired activity level of 0.5 mCi), the system 10 sets the desired activity level to the minimum desired activity level of 10.0 mCi. When the system 10 uses the minimum desired activity level instead of a manually input activity level or a calculated weight-based activity level, the system 10 indicates that to the operator by using, for example, the downward arrow icon 1006a shown in display field 1006 of FIG. 24E.

Figure 24F:
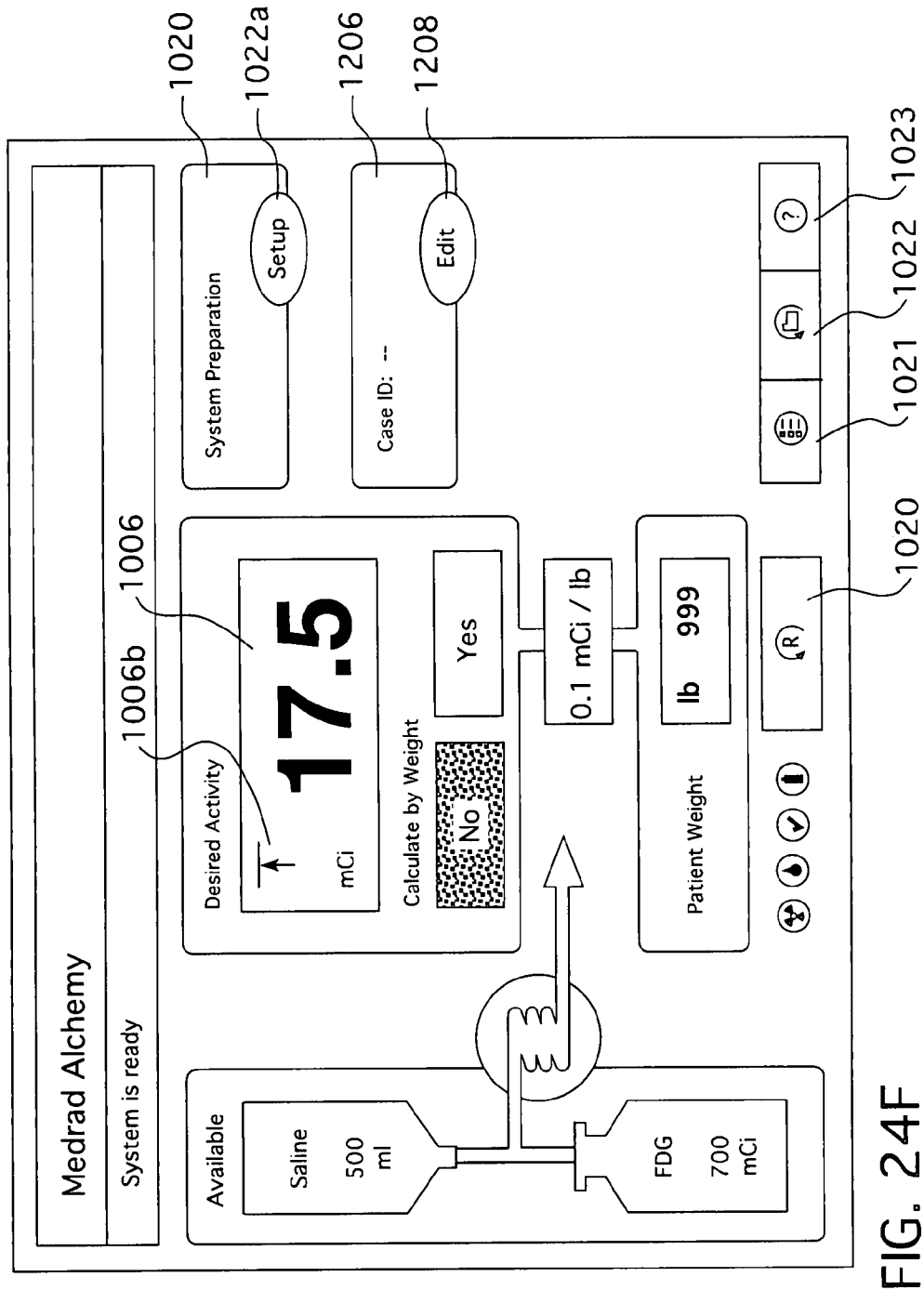

Likewise, as shown in FIG. 24F, even though the operator inputted a patient weight of 999 lb. and chose a formula of 0.1 mCi/lb. (which would result in a calculated desired activity level of 99.9 mCi), the system 10 set the desired activity level to the maximum desired activity level of 17.5 mCi. When the system 10 uses the maximum desired activity level instead of a manually input activity level or a calculated weight-based activity level, the system 10 indicates that to the operator by using, for example, the upward arrow icon 1006b shown in display field 1006 of FIG. 24F.

Figure 25A:
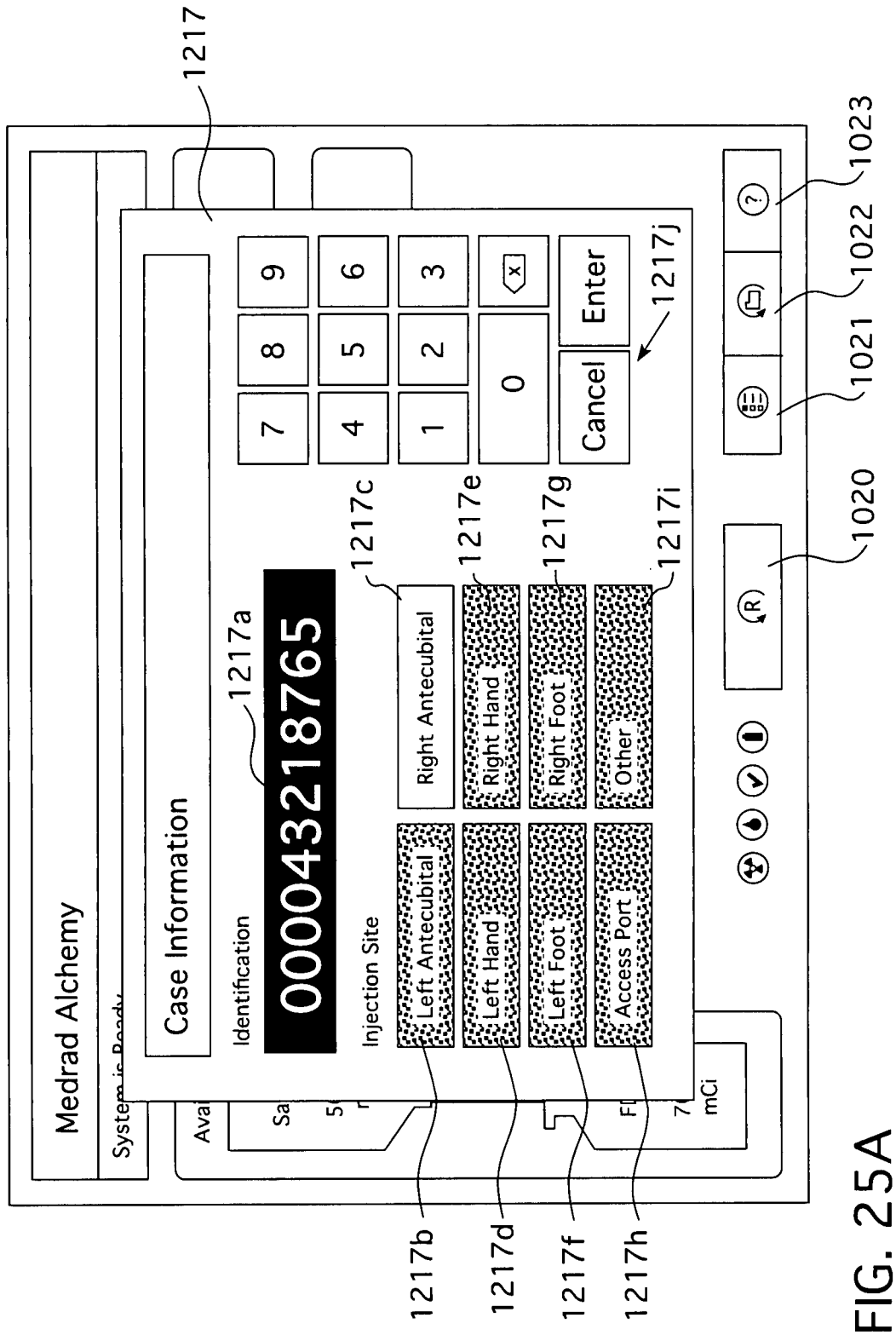
Figure 25B:
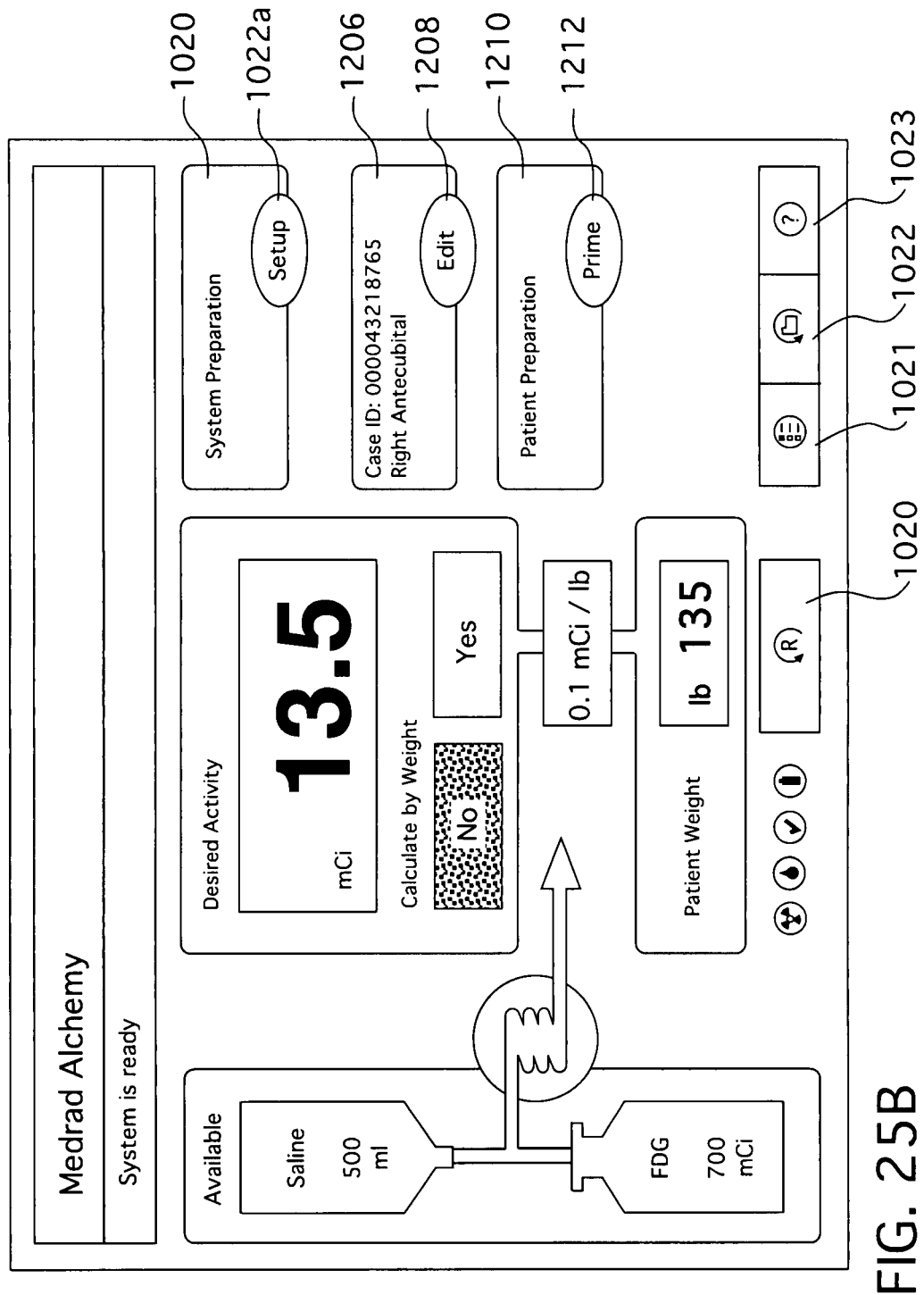

After the desired activity level is programmed or set by the system 10, preferably the operator inputs case information including patient identification and injection site information into the system 10, as shown in FIGS. 25A and 25B. When the operator activates the Edit button 1208 in the Case ID field 1206 (see e.g., FIG. 23), the "Case Information" pop-up display 1217 shown in FIG. 25A appears. The display 1217 includes an "Identification" field 1217a and a keypad 1217j for inputting a patent or other identification number in field 1217a. In addition, the display 1217 includes a number of "Injection Site" touch buttons 1217b-1217i for identifying and recording in the system 10 the site on the patient at which the radiopharmaceutical will be administered or injected, including 'Left Antecubital' 1217b, 'Right Antecubital' 1217c, 'Left Hand' 1217d, 'Right Hand' 1217e, 'Left Foot' 1217f, 'Right Foot' 1217g, 'Access Port' 1217h and 'Other' 1217i.

Once the Identification and Injection Site information is input into the system 10, the information is displayed in the Case ID field 1206, as shown in FIG. 25B. Further, as shown in FIG. 25B, after the requisite information is input into the system 10 and displayed in the Case ID field 1206, a Patient Preparation field 1210 including a Prime touch button 1212 is generated and displayed for the operator.

Before the Prime button is 1212 is activated, the first end 702 of the SPDS 700 should be attached to the connector end 228 of the MPDS 200, as discussed in detail above. When the SPDS 700 is connected to the MPDS 700, the operator can activate the prime button 1212 to cause the system 10 to prime the SPDS 700 to remove air therefrom.

Figure 26A:
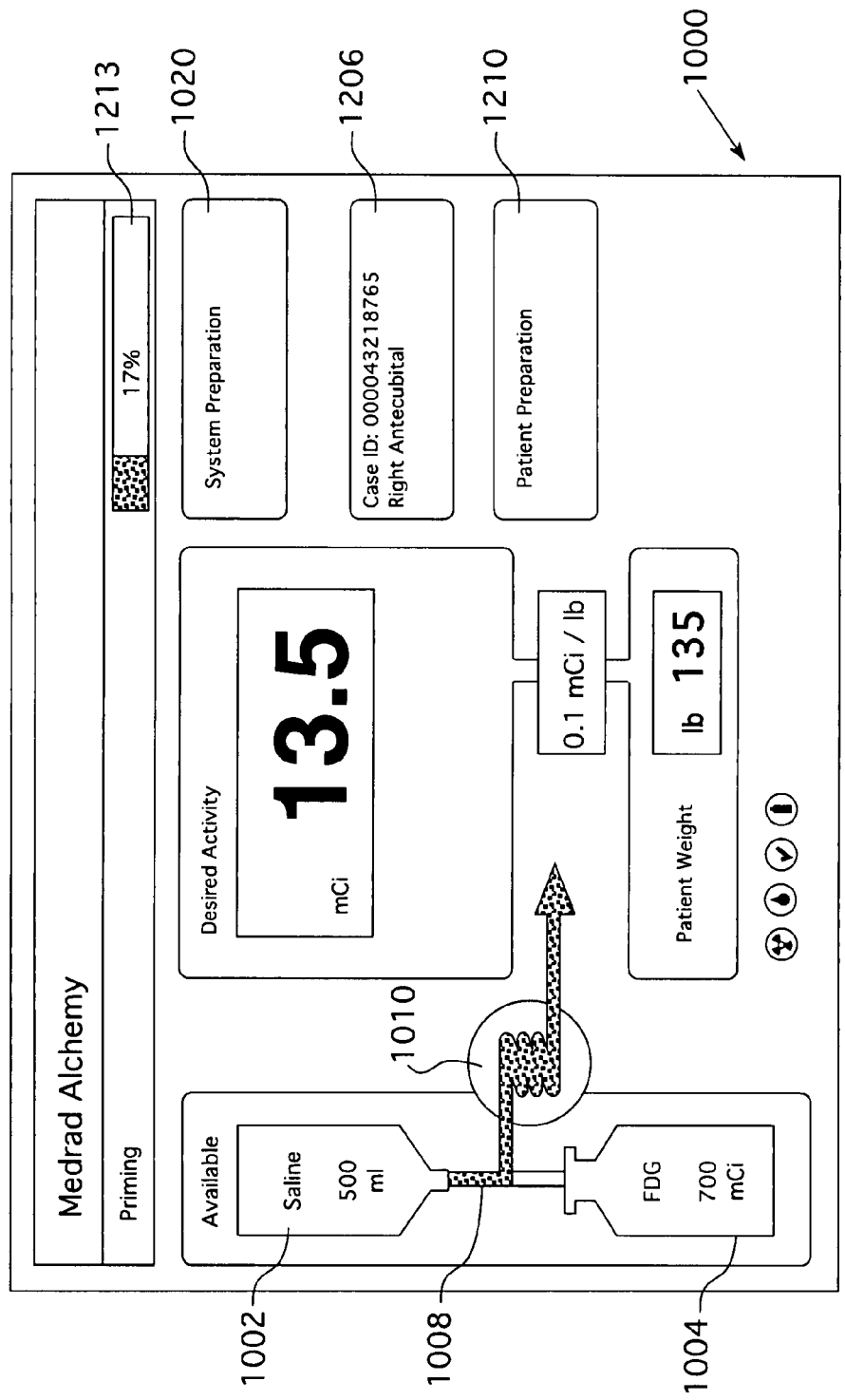
Figure 26B:
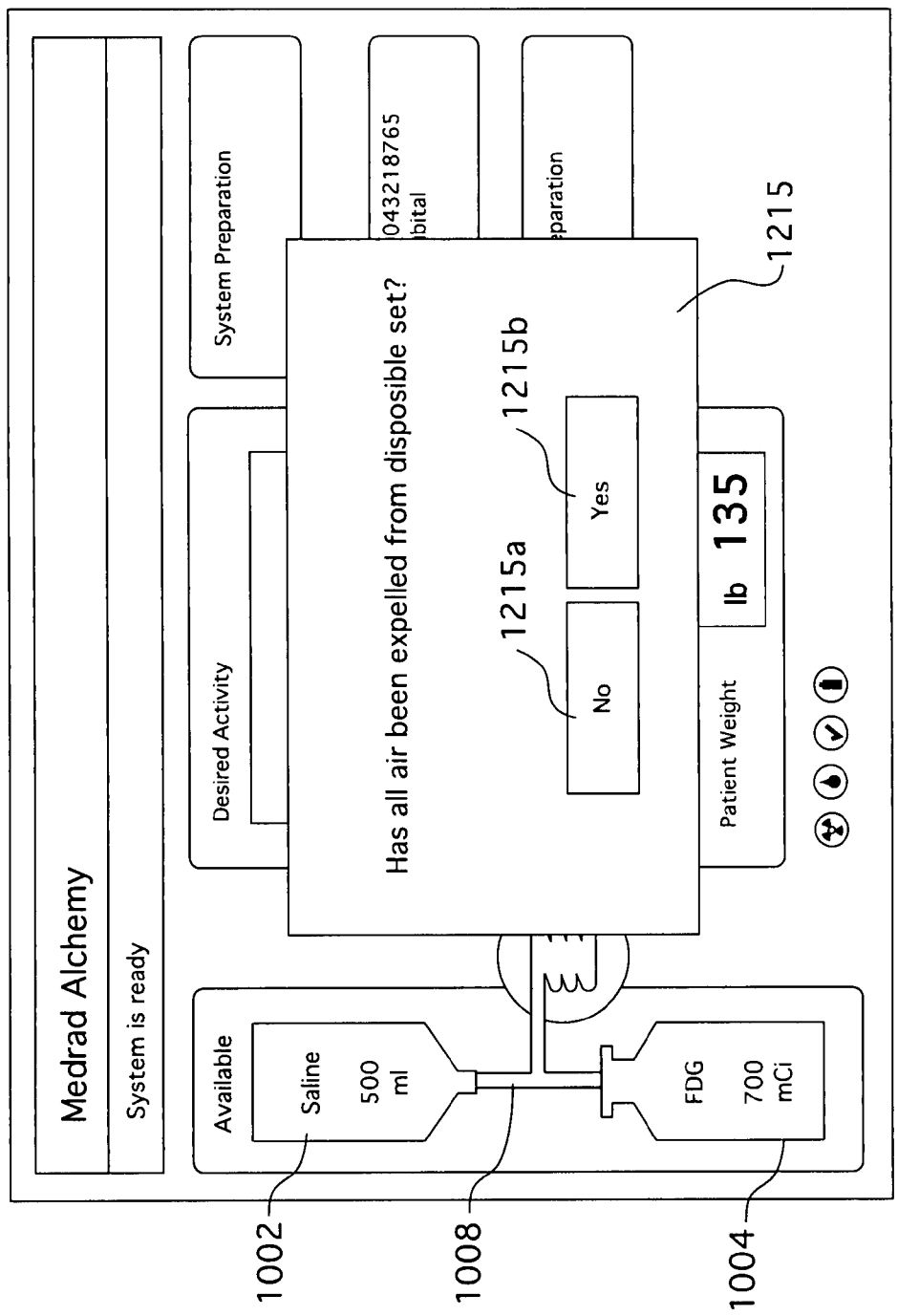
Figure 27A:
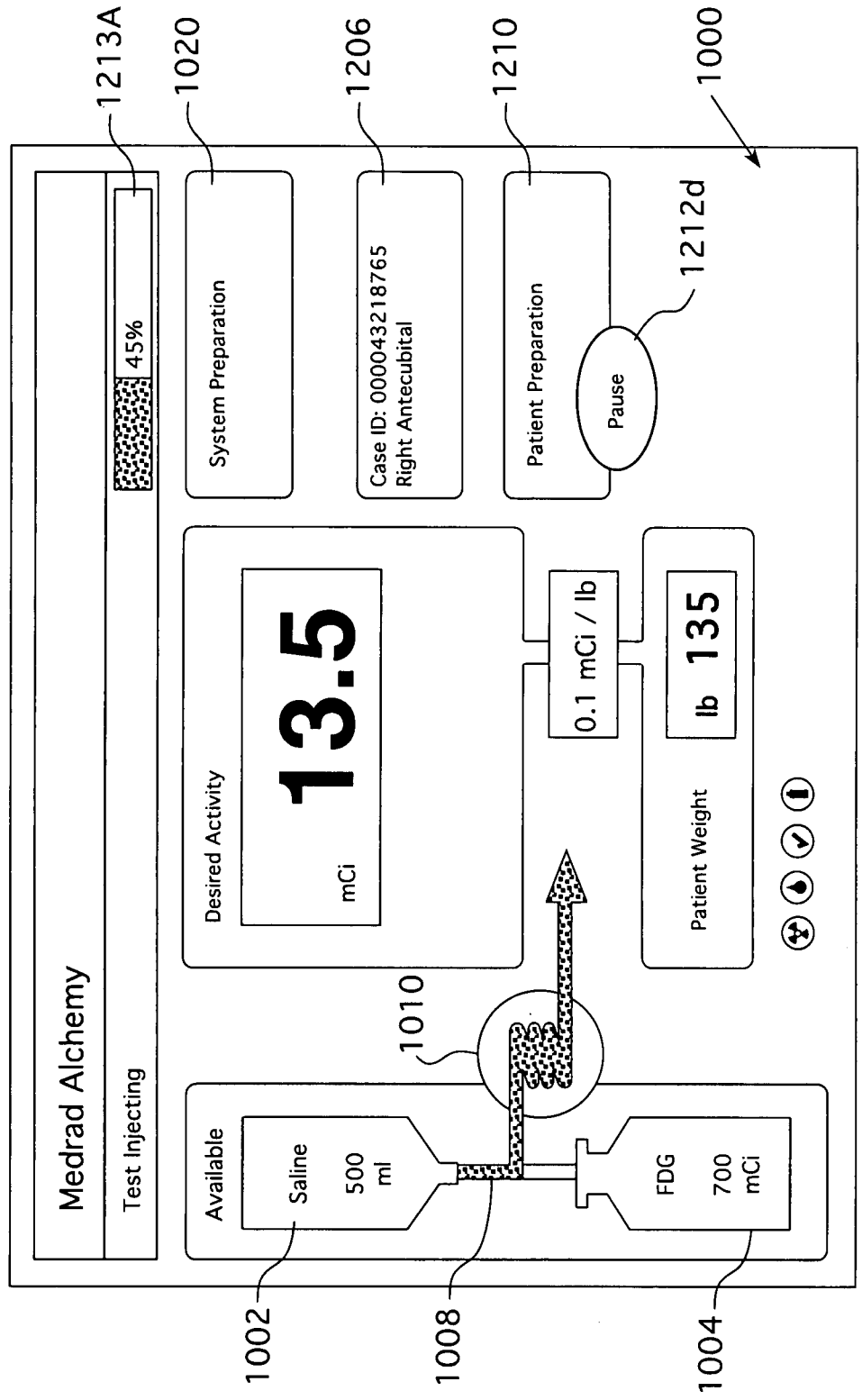
Figure 27B:
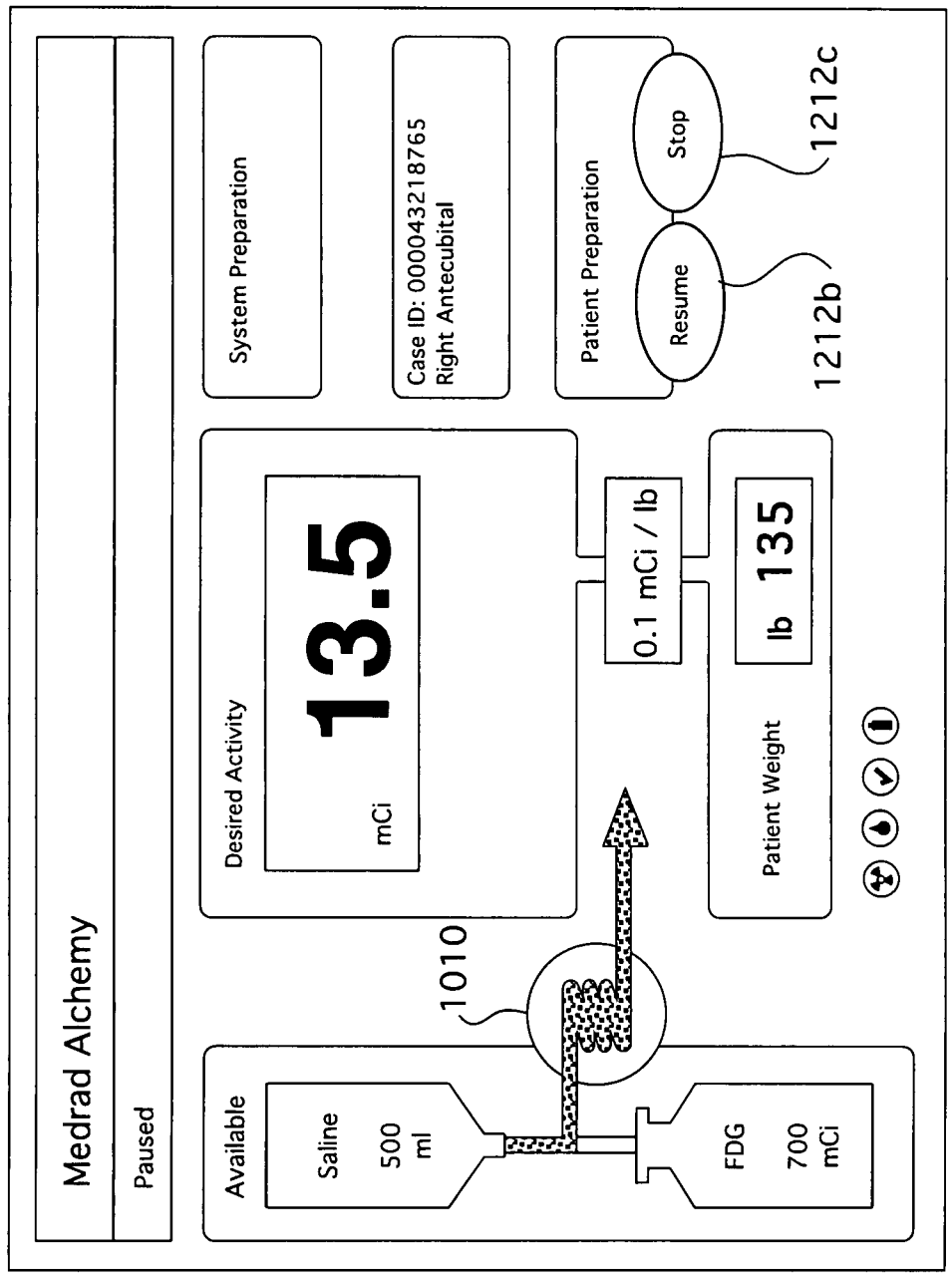

As shown in FIG. 26A, after the Prime button 1212 is activated the system 10 indicates that the system is "Priming" the SPDS 700 and generates a progress bar 1213 (which indicates in FIG. 26A that the priming operation is 17% completed). Further, the system 10 highlights the fluid path field 1008 and the coil field 1010 in display 1000 to indicate that saline is being pumped from saline source 23 (indicated by saline field 1002) through the MPDS 200 and the SPDS 700 to prime the SPDS 700. After the SPDS priming operation is completed, the system 10 generates a prompt display 1215, as shown in FIG. 26B, that queries the operator as to whether all air has been expelled or purged from the SPDS 700. If the "Yes" button 1215a is activated, the SPDS priming operation is completed and the system 10 is ready to conduct a test injection and/or to prepare the pharmaceutical dose for injection into the patient, as discussed in more detail below. If, on the other hand, the "No" button 1215b is activated, the SPDS priming operation is preferably conducted again.

Figure 28A:
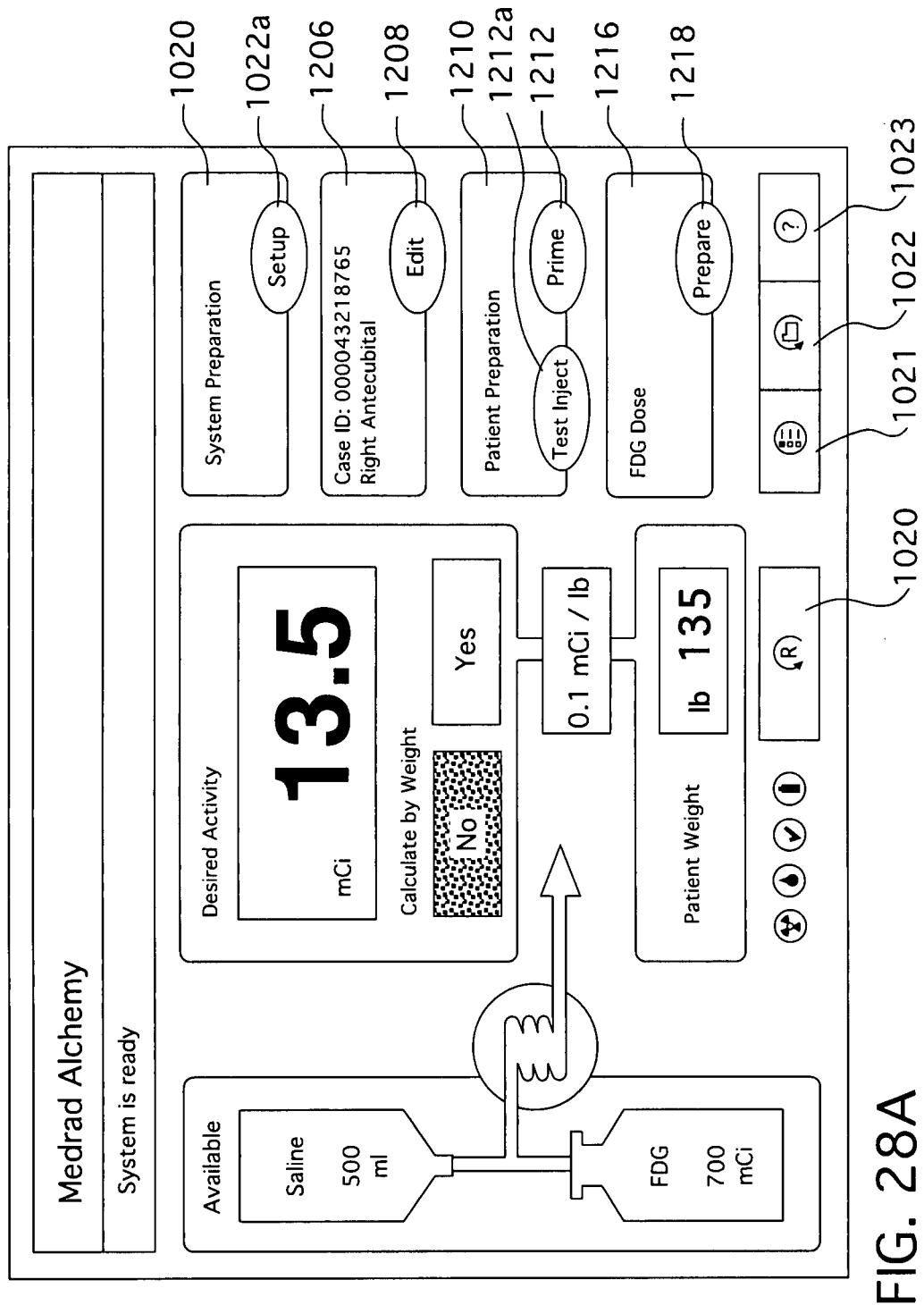

After the SPDS priming operation is completed, the patient end 704 of the SDPS 700 is connected to the patient (as described above) and the Patient Preparation display field 1210 on the touch screen 1000 includes a "Test Inject" button 1212a, as shown in FIG. 28A. If the operator desires to conduct a test injection to, for example, ensure the integrity of the fluid path along the MPDS 700, the SPDS 200 and the patient's vasculature, the operator activates the "Test Injection" button 1212a and the system 10 pumps saline from the saline source 23 through the MPDS 200 and the SPDS 700 to the patient. Concurrently, the system 10 generates the display shown in FIG. 27A to inform the operator that the system 10 is "Test Injecting" and highlights the fluid path display 1008 from the saline source icon 1002 to the ionization chamber display 1010. The display 1000 also includes a progress bar 1213a to indicate the degree of progress made (here 45%) in completing the test injection procedure.

If the operator needs to pause the test injection due to, for example, patient discomfort or incorrect positioning of the catheter in the patient, she can activate the "Pause" button 1212d in the Patient Preparation" display 1210 (see FIG. 27A) to pause the procedure. When the test injection procedure is paused, the system 10 generates the display shown in FIG. 27B, indicating that the test injection is "Paused" and providing a "Resume" button 1212b and a "Stop" button 1212c in the Patient Preparation display 1210. To resume or stop the test injection, the operator can activate the corresponding "Resume" and "Stop" buttons, 1212b, 1212c, respectively.

In addition to using the various "Pause" and "Stop" buttons provided by the GUI display 15, an operator can also depress the interrupt button 25 on the cabinet 9 of the system 10 to at any time pause or stop a procedure or operation being conducted by the system.

Figure 28B:
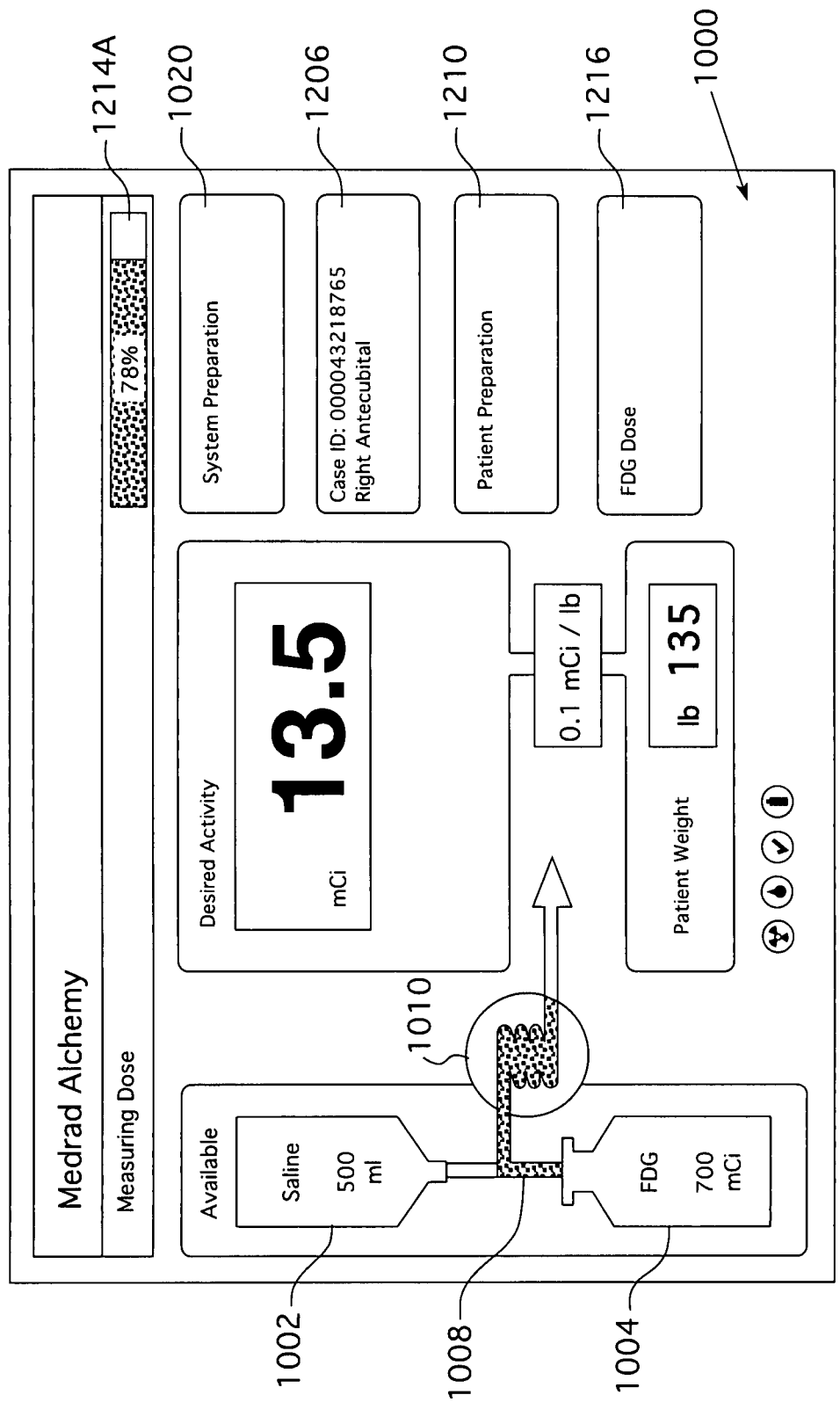

After the test injection is completed or terminated the system 10 generates the display 1000 shown in FIG. 28A, which includes an FDG Dose display 1216 and a corresponding "Prepare" button 1218. After the operator activates the "Prepare" button 1218, the system 10 generates the display shown in FIG. 28B and begins to pump a volume of FDG (or other suitable pharmaceutical or radiopharmaceutical) from the vial 902 through the MPDS 200 to the tube coil 444 thereof disposed in the ionization chamber 160. As shown in FIG. 28B, to reflect this operation the display 1000 informs the operator that the system 10 is "Measuring Dose" and highlights the fluid path display 1008 from the FDG source display 1004 to the ionization chamber display 1010. The display also includes a progress bar 1214a that shows the system's progress (here 78%) in measuring the pharmaceutical dose.

In a preferred embodiment, the system 10 prepares the pharmaceutical dose in accord with the methodology described in PCT Publication No. WO 2006/007750, in which the activity level of a first amount of a radioactive liquid is measured and used to calculate a second amount of the radioactive liquid that is required for the combined amounts to have a pre-determined level of radioactivity to be delivered to a patient. The contents of PCT Publication No. 2006/007750 are incorporated herein by reference. The dimensions of the coil assembly 400 and the core structure 446, including the height, diameter and volume of the tube coil 444, the length, number of turns, OD and ID of the tubing that forms the tube coil 444, and the dimensional location of the "linear region" of the Veenstra IK-102 ionization chamber, provided above are necessary to optimally and accurately prepare the pharmaceutical dose, whether in accord with the preferred methodology described in PCT Publication No. WO 2006/007750 or using another suitable dose preparation methodology.

The stated tube coil 444 dimensions are necessary to optimally position within the "linear region" of ionization chamber: (1) the volume(s) of pharmaceutical required to deliver the desired activity level to the patient; and (2) the volume of saline necessary to position the total volume of pharmaceutical in the tube coil. The tube coil 444 could be formed from tubing having a larger ID than that stated above (i.e., 0.156 inches), but larger IDs tend to allow the radiopharmaceutical to be diffused with the saline (which is used to 'place' or 'position' the radiopharmaceutical within the tube coil 444), which may result in the radiopharmaceutical volume or a portion thereof being positioned outside of the tube coil 444 and thus outside of the "linear region" of the ionization chamber (resulting in inaccurate activity level measurements and delivery). Likewise, the tube coil 44 could be formed from tubing having a smaller ID than 0.156 inches (which would possibly further decrease or prevent the diffusion of the radiopharmaceutical with the saline), but the dimensions of the tube coil 444 (e.g., length of tubing, coil tube height, number of turns) required to maintain a tube coil volume of 12.5 ml would result in the tube coil 444 extending beyond the "linear region" of the ionization chamber (resulting in inaccurate activity level measurements and delivery).

Further, the core structure 446 operates to maintain the desired tube coil geometry (e.g., tube coil diameter and height) and to properly position the tube coil 444 axially and vertically within the sleeve 162 so that the tube coil 444 thereby resides within the "linear region" of the ionization chamber 160 (see e.g., FIG. 3F).

With specific reference to the dose preparation methodology described in PCT Publication No. WO 2006/007750, the 12.5 ml volume of the tube coil 444 is designed to accommodate two volumes of a radiopharmaceutical from vial 902 separated by a volume of saline from source 23, regardless of whether the dose is prepared shortly after the radiopharmaceutical was assayed (when a small volume of the radiopharmaceutical is required to deliver a desired activity level) or after a significant amount of time has passed (e.g., in relation to the radioisotope's half-life) since the radiopharmaceutical was assayed (when a greater volume of the radiopharmaceutical is required to deliver the same desired activity level). As a specific example of the above, the 12.5 ml tube coil 444 is designed to accommodate: (1) two 1/16 ml volumes or "slugs" of a pharmaceutical (for a total volume of 1/8 ml) at a concentration of 40 mCi/ml (i.e., highest concentration that the system 10 is designed to handle), separated by a calculated volume of saline necessary to fill or substantially fill the remaining tube coil volume; and (2) two 1.5 ml "slugs" of a pharmaceutical (for a total volume of 3 ml) at a concentration of 1.67 mCi/ml (i.e., lowest concentration that the system 10 is designed to handle), separated by a calculated volume of saline necessary to fill or substantially fill the remaining tube coil volume.

Figure 29:
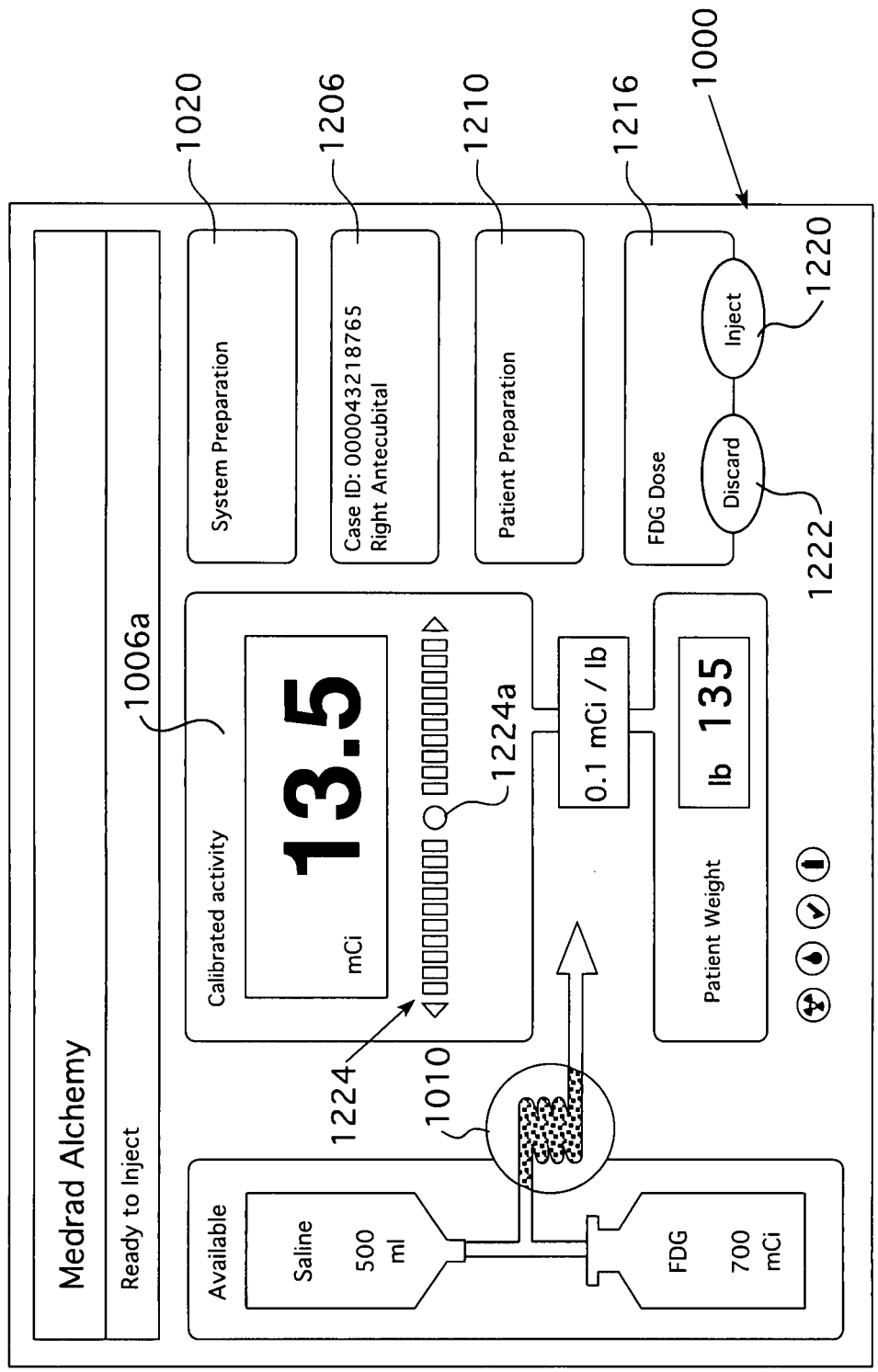

After the dose is pumped by the system 10 into the tube coil 444 disposed within the ionization chamber 160, the activity level of the dose is measured by the system 10. The measured activity level is then displayed to the operator and the ionization chamber display 1010 is highlighted, as shown in FIG. 29. A new display field 1006a is generated by the system, showing the measured "Calibrated Activity" (here 13.5 mCi) of the prepared dose. Just below field 1006a is a "plus/minus" range indicator 1224. Range indicator 1224, as shown, includes a center circle 1224a, flanked on each side by 10 rectangles. Left and right arrows are also included, respectively, at the far left and far right of indicator 1224. Preferably, as shown in FIG. 29, center circle highlights when the measured "Calibrated Activity" level is the same as the previously programmed, desired activity level (which is the case in FIG. 29). Otherwise, if the measured activity level is greater or lesser than the desired activity level, corresponding rectangles or, in some cases, arrows will highlight to the right of the center circle 1224a (for measured activity>desired activity) or to the left of the center circle 1224a (for measured activity<desired activity) to visually indicate to the operator the difference between the measured and desired activity levels.

In a preferred embodiment, each of the rectangles represents a default value of a 1% discrepancy in the desired to measured activity level, such that three rectangles to the right of the center circle 1224a would be highlighted if the measured activity level was 3% greater than the desired activity level of 13.5 mCi. If the measured activity exceeds the desired activity by more than 10%, then all the rectangles to the right of the center circle 1224a and the right arrow would highlight. Preferably, the extent of the rectangles in indicator 1224 will convey an acceptable range within which the measured activity may fall. Thus, such an acceptable range could be plus or minus ten percent or could be another range as deemed appropriate, with each rectangle representing one tenth of the positive or negative extent of that range. Alternately, however, the default value of each rectangular could be pre-set to another value (such as 0.1 mCi) or could be changed by the operator to another value more suitable for the intended application.

In addition to displaying the measured activity level, as shown in FIG. 29 the display 1000 also generates a "Discard" button 1222 and an "Inject" button 1220 in the FDG Dose display 1216. If for example the measured activity is outside of a clinically acceptable range for the intended procedure, the operator can activate the "Discard" button 1222 to have the system 10 discard the measured dose (i.e., by pumping the dose to the waste receptacle 224, as discussed in detail above) and to prepare another dose for delivery to the patient. Specifically, when the "Discard" button 1222 is activated the system generates the dialog box 1231 shown in FIG. 30A, which queries the operator to confirm that the measured dose is to be discarded. If the operator confirm that the measured dose is to be discarded by activating the "Yes" button 1231a, the system 10 generates the display shown in FIG. 30B, which indicates to the operator that the system is "Discarding" and creates a progress bar 1233 that indicates the status of the "discarding" operation (here 86% completed). The display 1000 also highlights the fluid path display 1008 from the saline source display 1002 to the ionization chamber display 1010 to indicate that the system 10 is pumping saline through the MPDS 200 to push the dose from the tube coil 444 to the waste receptacle 224 (as described above).

Figure 30A:
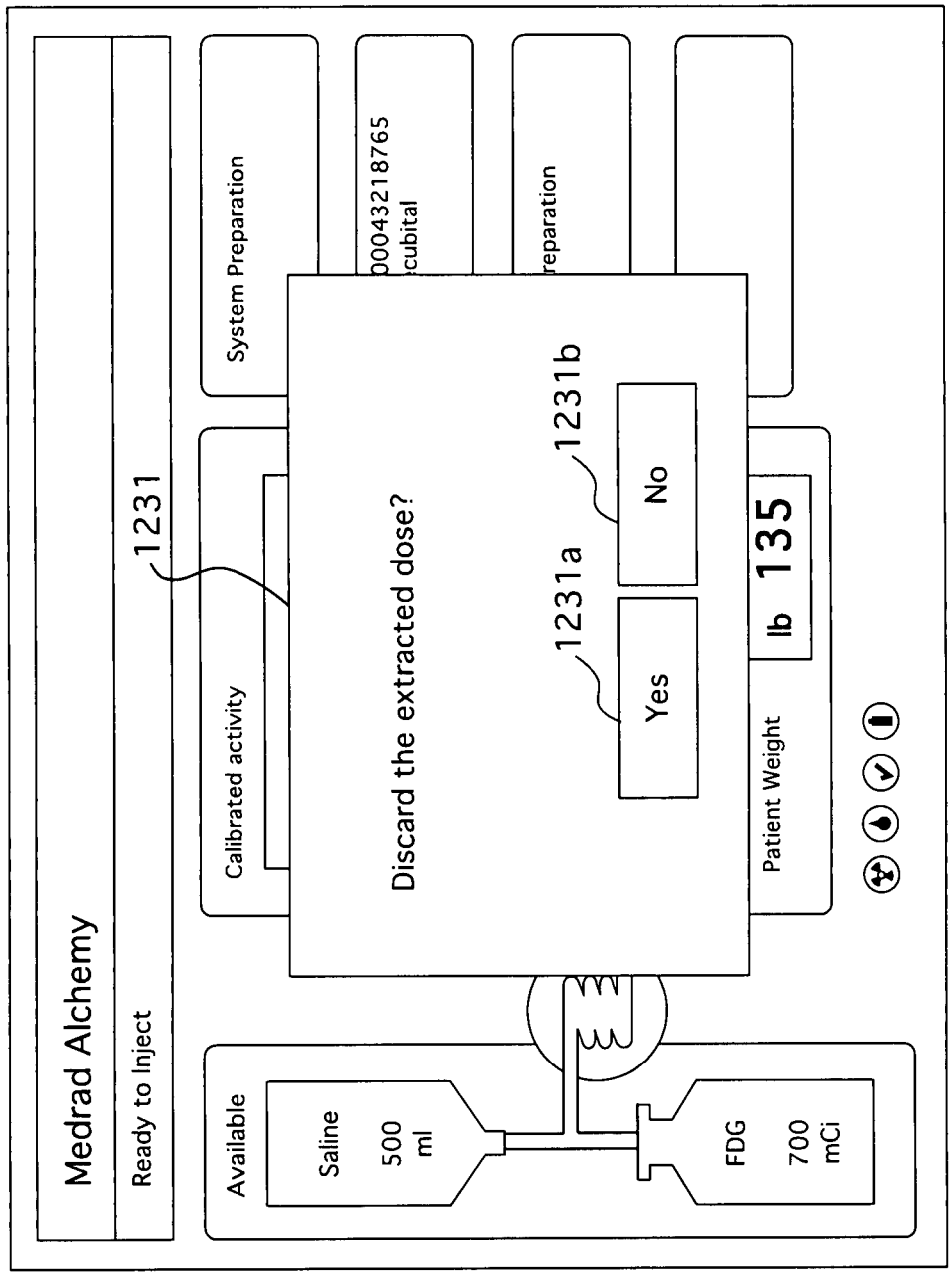
Figure 30B:
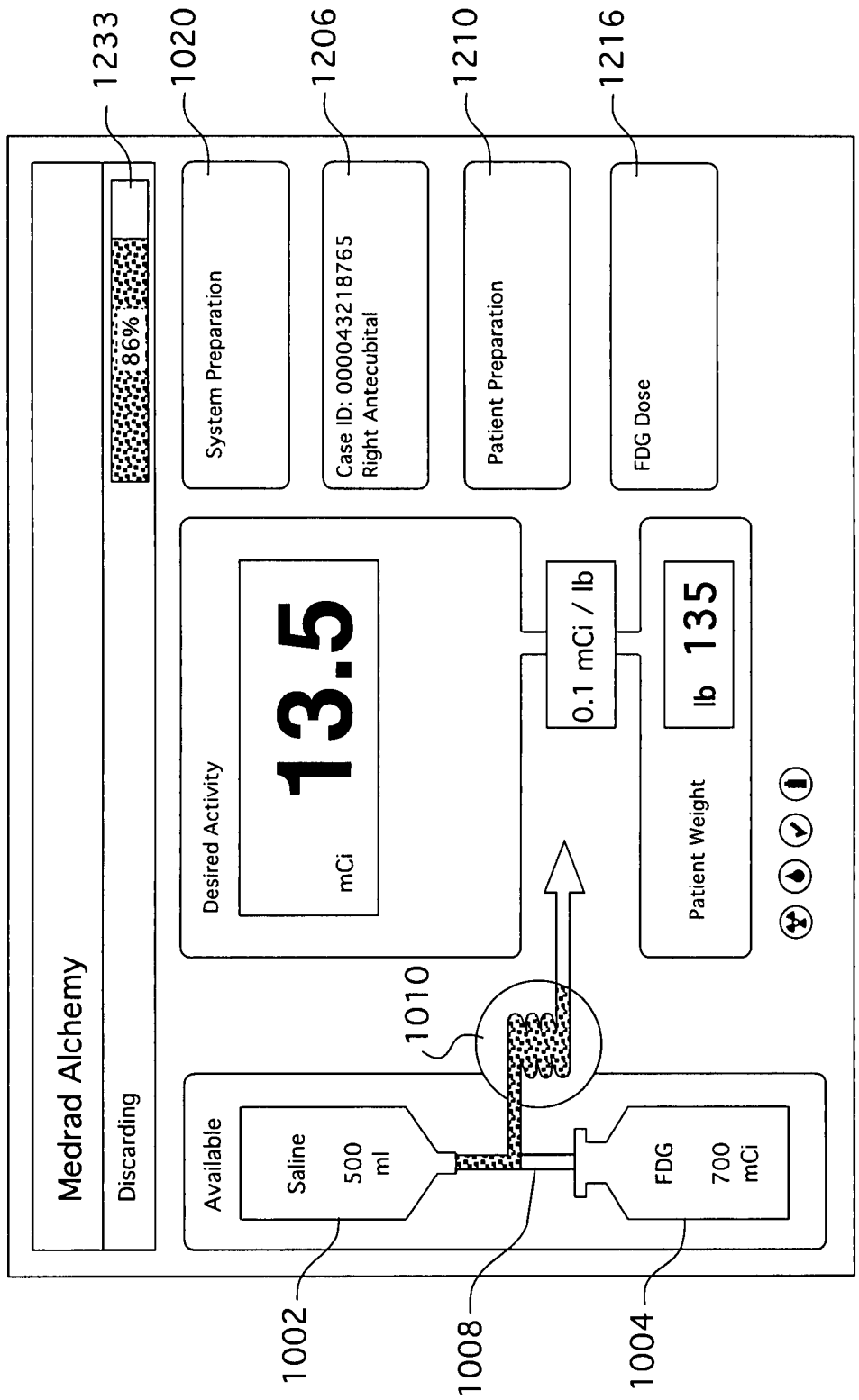

If, on the other hand, the operator activates the "No" button 1231b in FIG. 30A to inform the system 10 that she does not want to discard the measured dose, the system 10 reverts to the display shown in FIG. 29 and the "Discard" button 1222 and the "Inject" button 1220 are again made available to prompt the operator to decide whether to discard or to inject the measured pharmaceutical dose.

Figure 31:
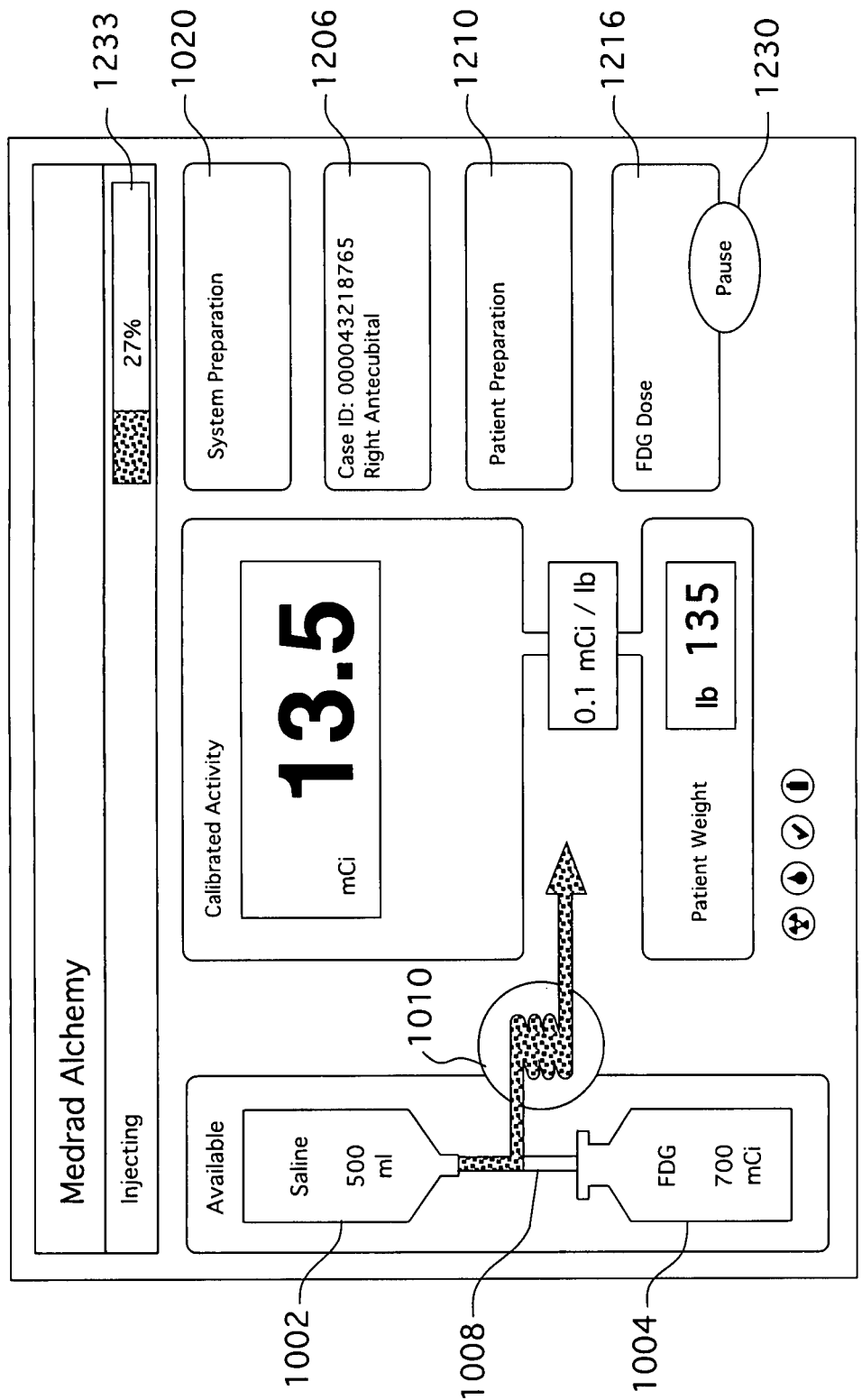

If the operator desires to inject the measured dose and thus activates the "Inject" button 1220 shown in FIG. 29, the system 10 generates the display shown in FIG. 31 which indicates to the operator that the system 10 is "Injecting" and, via progress bar 1223, that the injection operation (in FIG. 31) is 27% completed. The fluid path display 1008 between the saline source display 1002 and through the ionization chamber display 1010 to the arrow at the end of the fluid path display 1008 is highlighted to indicate that the system 10 is pumping saline from the saline source 23 to push the dose in the ionization chamber 160 through the remainder of the MPDS 200 and the SPDS 700 to the patient (as described above). Further, the system 10 generates a "Pause" button 1230 in FDG Dose display 1216. As with the test injection operation discussed above (see FIG. 27A), the operator can activate the "Pause" button 1230 or the interrupt button 25 to pause the injection procedure.

Figure 32A:
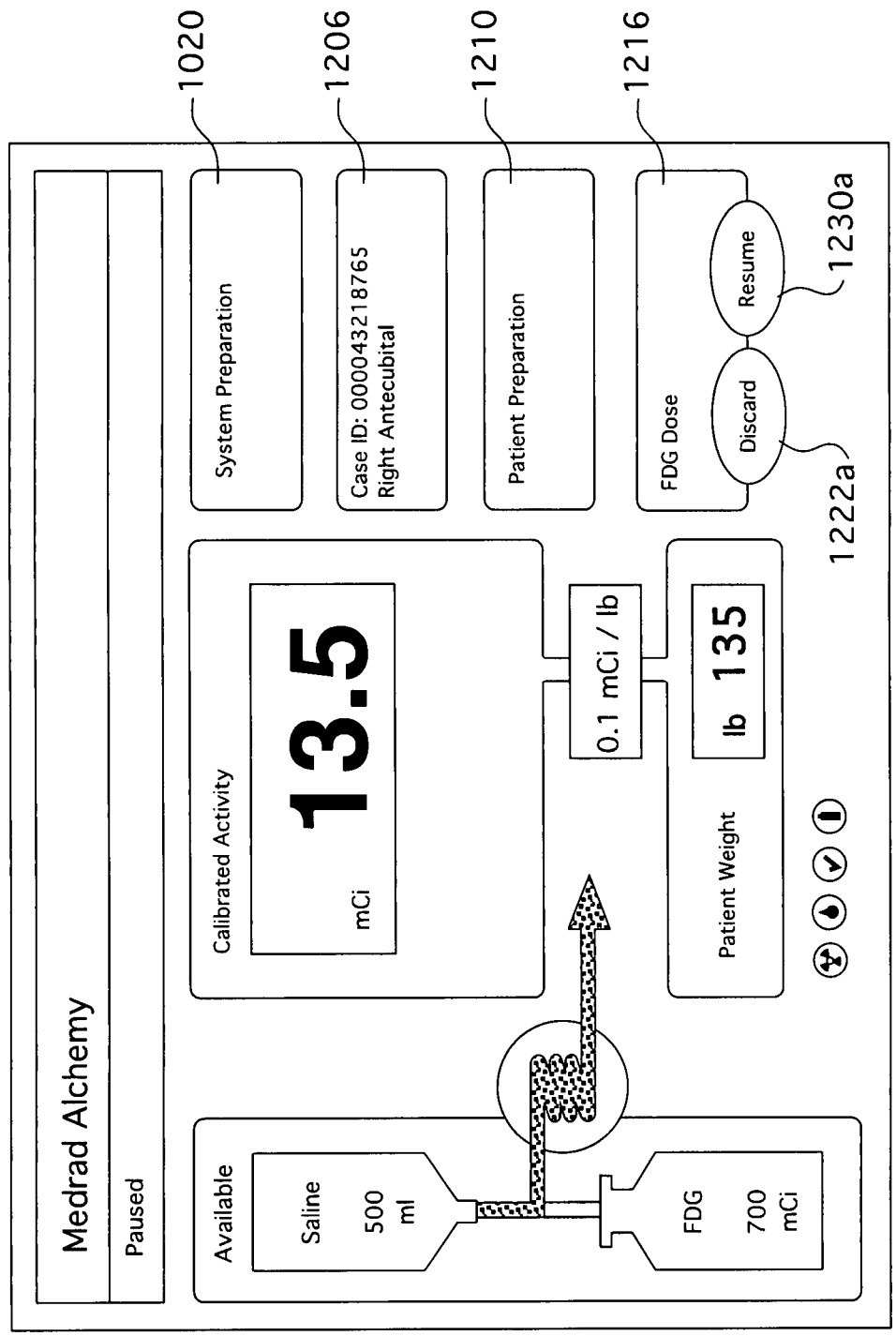

After the "Pause" button 1221 is activated, the display shown in FIG. 32A is generated and displayed to the operator. The display shown in FIG. 32A informs the operator that the system 10 is "Paused" and includes a "Discard" button 1222a and a "Resume" button 1230a in the FDG Dose display 1216.

If the injection needs to be terminated, the operator activates the "Discard" button 1222a and the system reverts to that shown and described above with respect to FIGS. 30A and 30B to discard the dose into the waste receptacle 224. However, if the procedure can be resumed, the operator activates the "Resume" button 1230a in FIG. 32A and the injection procedure continues to deliver the measured dose to the patient.

Figure 32B:
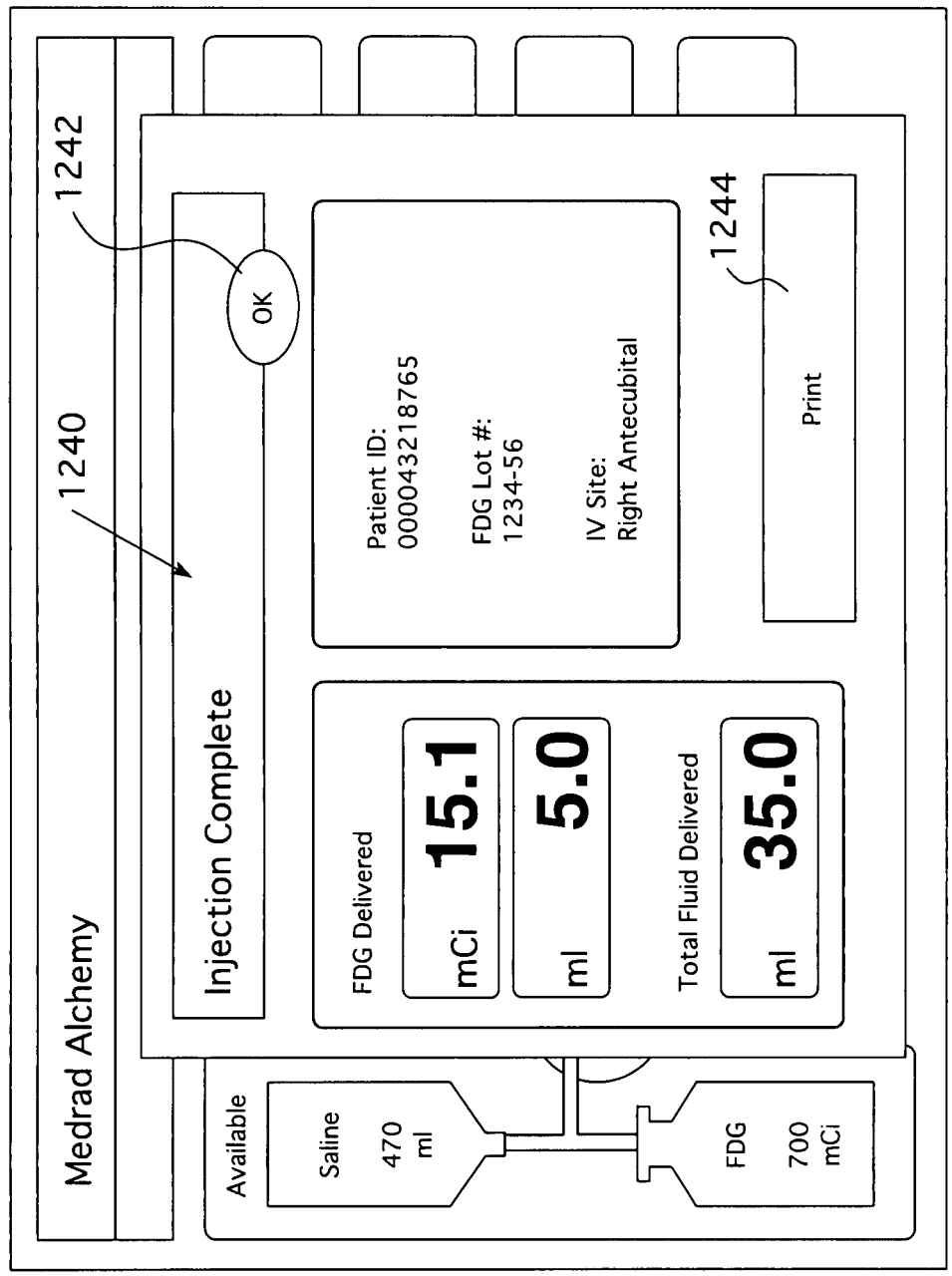

When the injection procedure is completed, a pop-up 1240 preferably appears as shown in FIG. 32B. This pop-up 1240, as shown, preferably contains information about the activity and volume of the dose (e.g., FDG) just delivered to the patient, the total fluid delivered (which would include saline) and other identifying information including, for example, the patient identification number, radiopharmaceutical lot number and patient injection site (as shown on the right of pop-up 1240). Activating the "OK" button 1242 causes pop-up 1240 to disappear and the system to revert to an "Idle" state (as shown in FIG. 7) or a "Ready" state (as shown in FIG. 23), while activating the "print" button 1244 prompts the injection information to be printed out by the printer 24 for patient, billing, inventory or other suitable records.

Other capabilities and functions not expressly discussed hereinabove or shown ill the drawings are of course conceivable in accordance with the embodiments of the present invention. For instance, if the extraction of a pharmaceutical dose (e.g., FDG) from a vial is interrupted for an unforeseeable reason and is not prompted by a desired "pause", the system could alert the operator to discard the dose (and in that connection present a button for the purpose).

Injection History

The disclosure now turns to a discussion of the injection history operations or tasks that can be performed using the display 1000, as depicted in FIGS. 33A-C, 34A and 34B.

The injection history operations or tasks may be prompted by activating the Records/Injection History button 1022, which is displayed when the system 10 is in an "Idle" state (see e.g., FIG. 7) or a "Ready" state (see e.g., FIGS. 23, 24D and 28A). Activation of Records button 1022 preferably prompts the appearance of the calendar display 1302 shown in FIG. 33A (here 'October 2006'). Highlighted touch fields within the calendar display 1302 preferably correspond to those dates of the displayed month (here 'October 2006' in field 1309) on which the system 10 was used to perform an injection procedure, while those other days of the displayed month in which the system 10 was not used are not highlighted. Arrow buttons to the left 1309a and right (not shown), respectively, of field 1309 preferably permit the operator to scroll through different months to access and retrieve injection history information.

The calendar display 1302 also includes a "Print Summary" button 1304, a "Print Days" button 1306 and a "Done" button 1308. Activation of the "Print Summary" button 1304 provides a high-level summary of the injection procedures conducted for the specified month (here 'October 2006'), similar to the injection procedure information displayed in FIG. 34A. The "Print Days" button 1306 preferably prompts the appearance of the display 1302a shown in FIG. 33B. The "Done" button 1308 can be activated once the operator has completed the necessary injection history retrieval operation or task, and the display 1000 then preferably reverts to the "Idle" state display (see e.g., FIG. 7) or the "Ready" state display (see e.g., FIGS. 23, 24D and 28A) as appropriate.

Figure 33A:
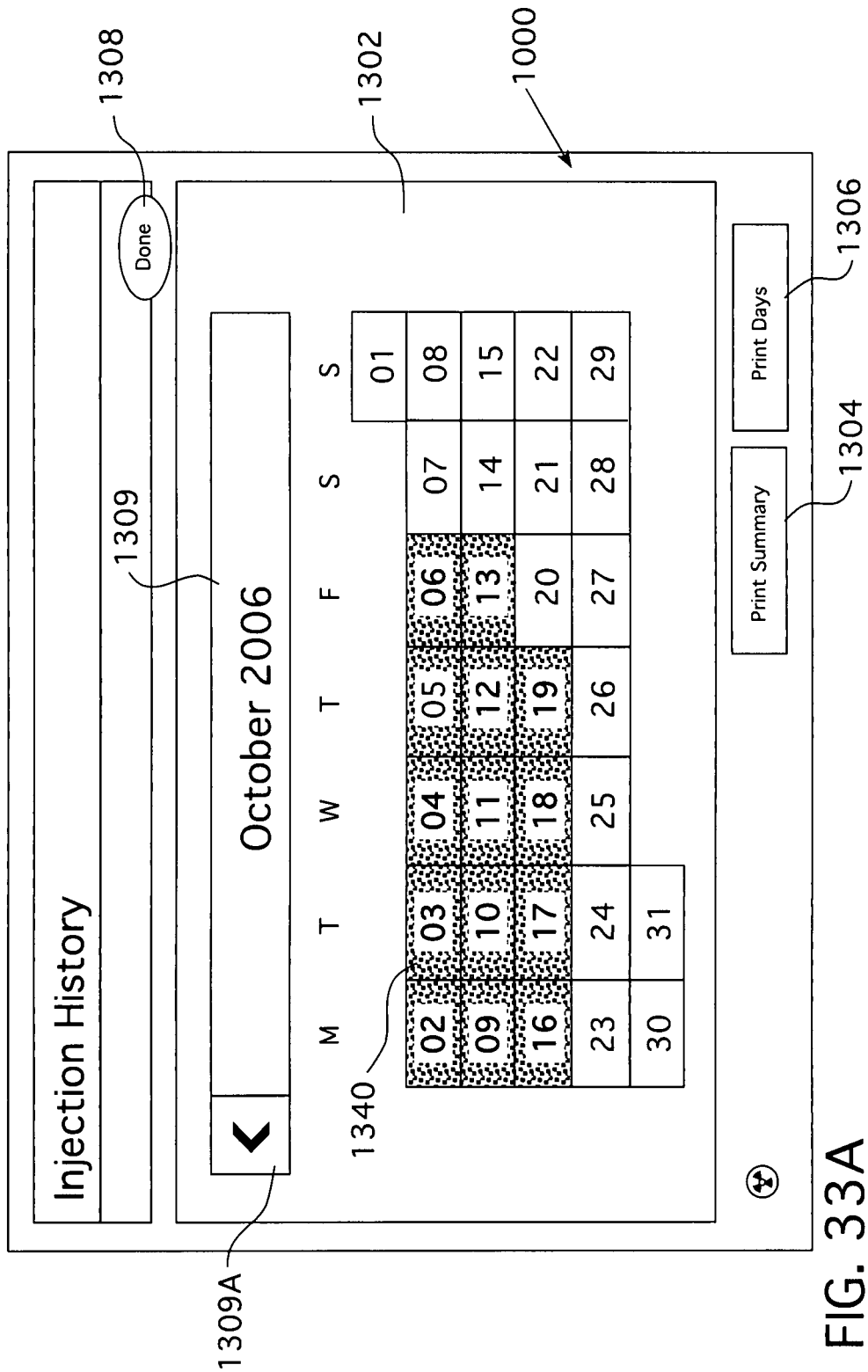
FIGS. 33A-C, 34A and 34B are various depictions of a graphical user interface for use in injection history/recall operations or tasks.
Figure 33B:
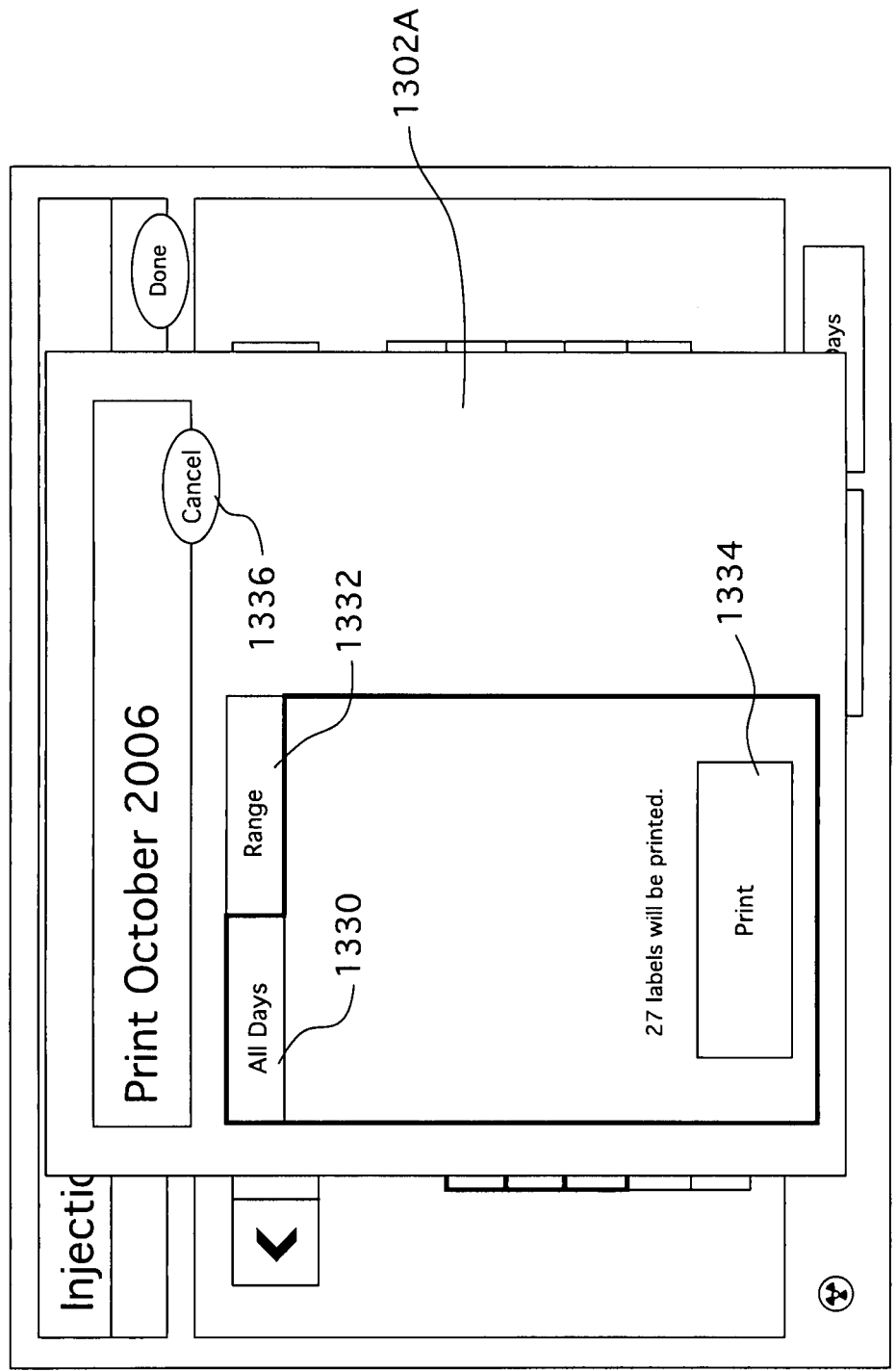

Referring now to FIG. 33B (prompted by activation of "Print Days" button 1306), the display 1302a includes an "All Days" touch field 1330 (which is activated in FIG. 33B) including a "Print" button 1334, and a "Range" touch field 1332. If the operator mistakenly activated the "Print Days" button 1309 on display 1302 (see FIG. 33A), she can activate the "Cancel" button 1336 to return to the display 1302 shown in FIG. 33A. If the operator wishes to print the injection history information for all the days in the selected month (here 'October 2006'), "Print" button 1334 can be activated and the printer 24 will print the injection history records for the days in which the system 10 performed injection procedures. If the operator instead wants to access injection history information for a range of days in the selected month, the operator can activate the "Range" touch field 1332, which prompts the appearance of the display 1302b shown in FIG. 33C.

Figure 33C:
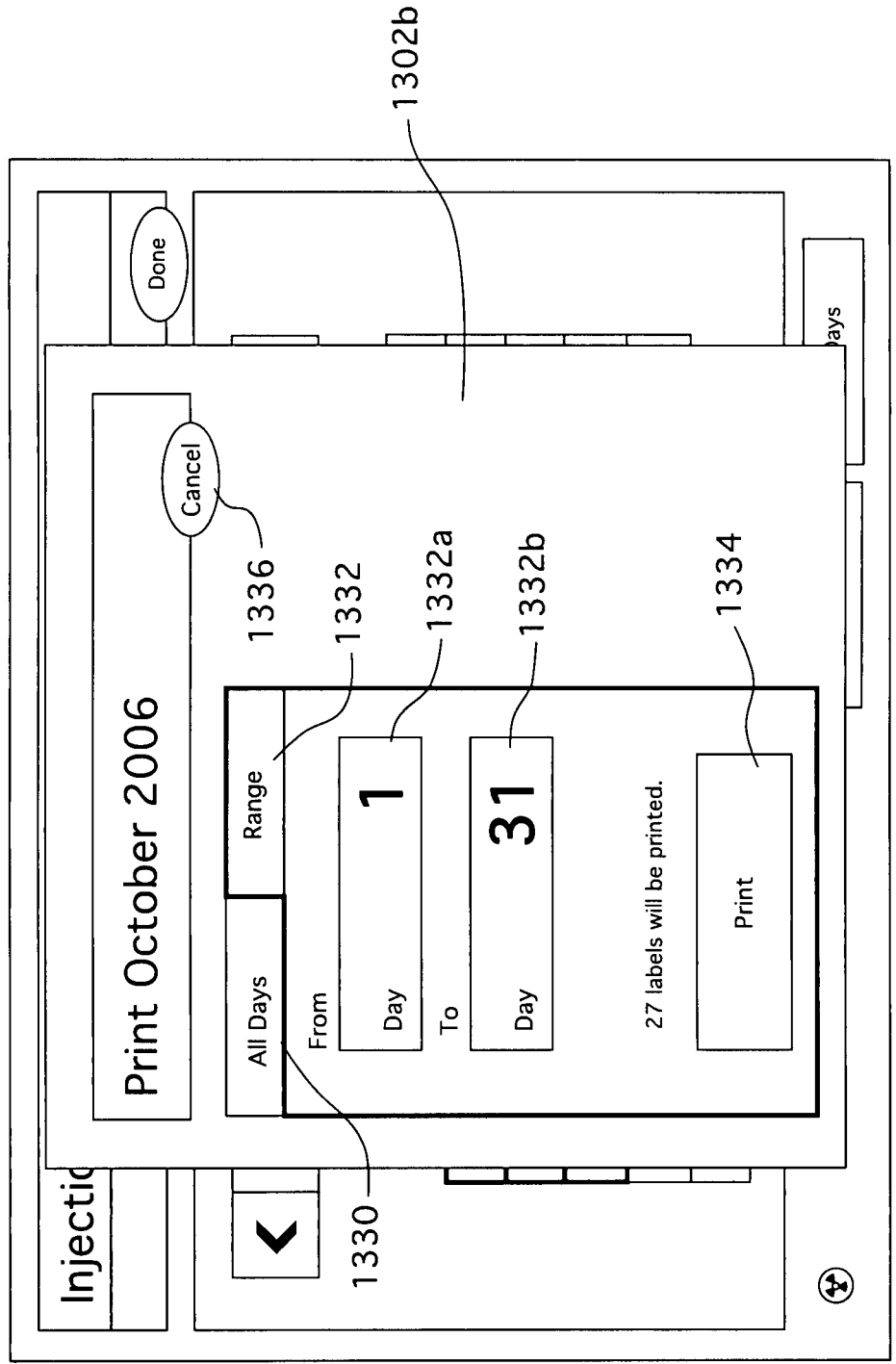

As shown in FIG. 33C, the display 1302b includes a "From" touch field 1332a and a "To" touch field 1332b which the operator activates to select the "From" and "To" dates in the selected month to establish the range of dates for which injection history information is to be accessed. Once the date range is selected, the "Print" button 1334 is activated to prompt the printer 24 to print the injection history information.

Referring back to FIG. 33A, in addition to activating the "Print Summary" button 1304 or the "Print Days" button 1306, the operator is also able to activate any of the highlighted calendar buttons to access injection history information for that day of the selected month. For example, if the operator wanted to retrieve injection history information for 10 Oct. 2006, the operator would activate the "10" button 1340 shown in FIG. 33A and the system 10 would generate the display 1310 (including selected date field 1310a) shown in FIG. 34A.

Figure 34A:
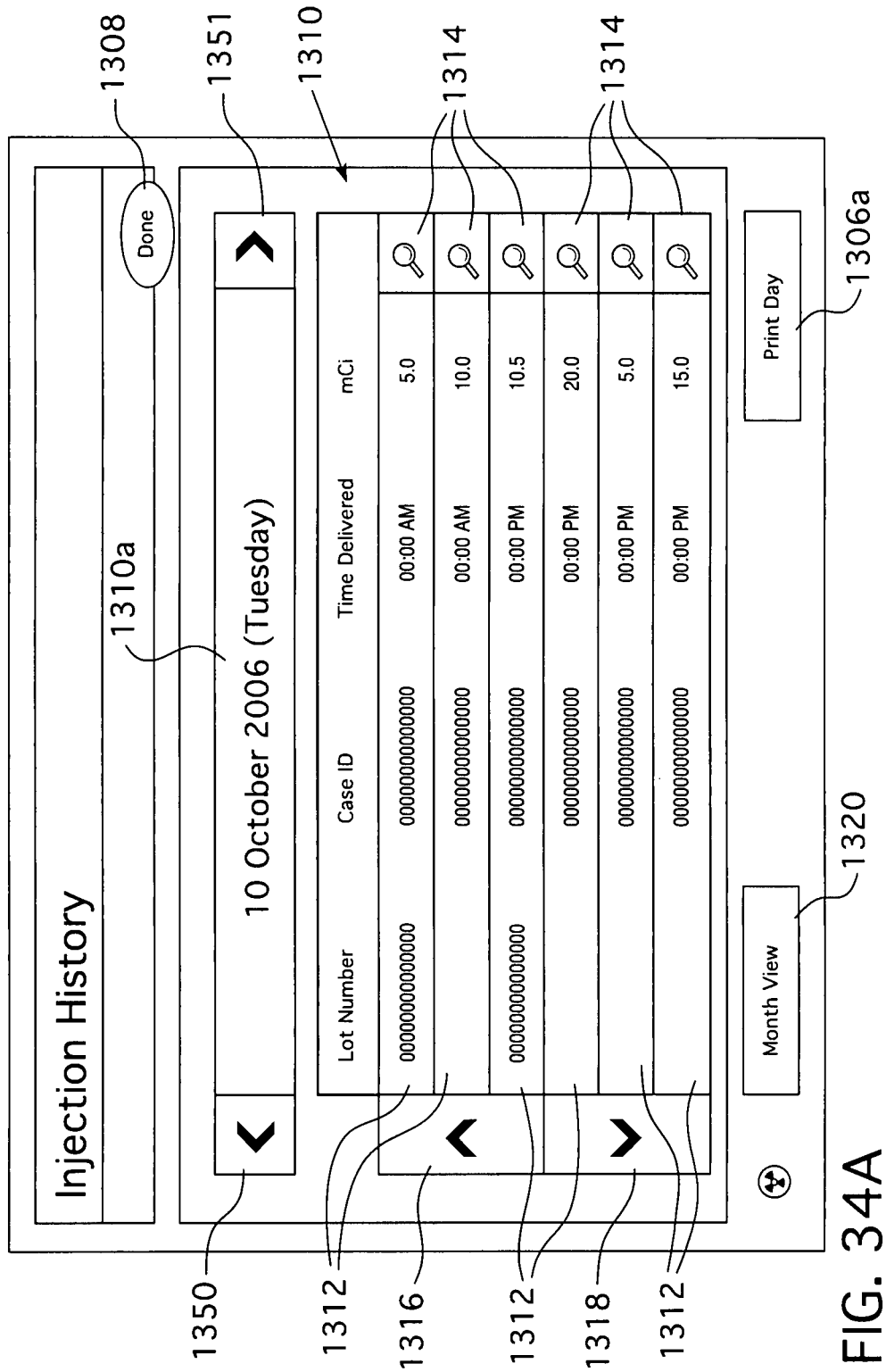

As shown in FIG. 34A, a series of display fields 1312 includes information on the lot number, case ID, delivery time and delivered activity of a given injection procedure conducted on the selected day (here '10 Oct. 2006 (Tuesday)'). Page up 1316 and page down 1318 arrow buttons are provided to allow the operator to scroll through the procedures conducted on the selected day. Page left 1350 and page right 1351 arrow buttons are also provided to allow the operator to scroll through and select dates prior to or subsequent to the selected '10 Oct. 2006' date displayed in date field 1310a. A "Month View" button 1320 can be activated to revert to a "month view" as shown in FIG. 33A, while the "Print Day" button 1306*a* can be activated to print the injection history details of all injection procedures on the day in question (i.e., the day currently being displayed). Further, "magnifying glass" touch fields 1314 are provided for each procedure and, upon activation, preferably prompts a detailed injection history display 1360 (see FIG. 34B) for the selected procedure.

Figure 34B:
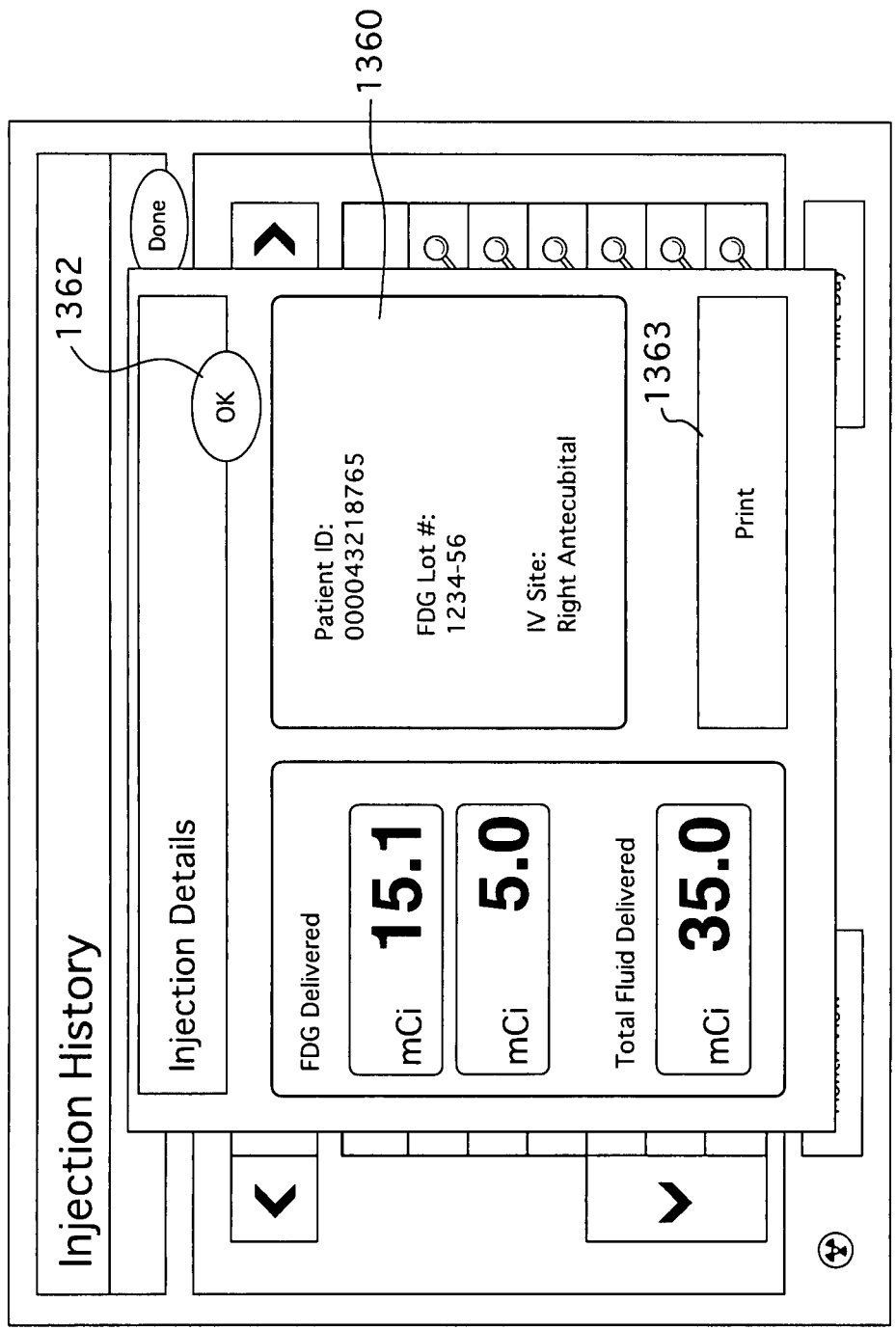

As shown in FIG. 34B, the detailed injection history display 1360 provides details on the specific pharmaceutical injected (here "FDG"), the date (10 Oct. 2006) and time (09:15) of injection and the activity level (15.1 mCi) and volume (5 ml) of the injected pharmaceutical. Further, the display 1360 indicates the total volume (35.0 ml) of injected fluid (pharmaceutical and saline), the Patient Identification number, the Lot number of the pharmaceutical and the IV Injection Site on the patient. The "Print" button 1363 is activated to print the injection details and the "OK" button 1362 is activated to revert to the display 1310 shown in FIG. 34A.

System Configuration

The disclosure now turns to a discussion of system configuration tasks, as depicted in FIGS. 35-46. The configuration tasks are undertaken to permit an operator to set various system preferences, including but not limited to preferences related to the following: (1) Language; (2) Date/Time display; (3) Units; (4) Audio; (5) FDG/Pharmaceutical dose preparation formulas; (6) Saline volumes; (7) Case Information display; (8) Printing; (9) Daily QC isotope reference information; (10) Linearity measurement tests; (11) Calibration tests; and (12) Field Service reminders.

The system configuration tasks may be prompted by activating the Configuration button 1021, which is displayed when the system 10 is in an "Idle" state (see e.g., FIG. 7) or a "Ready" state (see e.g., FIGS. 23, 24D and 28A). Activation of Configuration button 1021 preferably prompts the appearance of the "System", "Treatment" and "Maintenance" touch fields (1402, 1404 and 1406, respectively) shown in FIG. 35, each of which when activated prompts the appearance of a distinct tabbed menu display 1400*a-c* (as explained in more detail below). An "OK" button 1418 may be activated when the system configuration tasks are completed, while a "default" button" 1416 may be activated to reset the system 10 to the default configuration settings.

Figure 35:
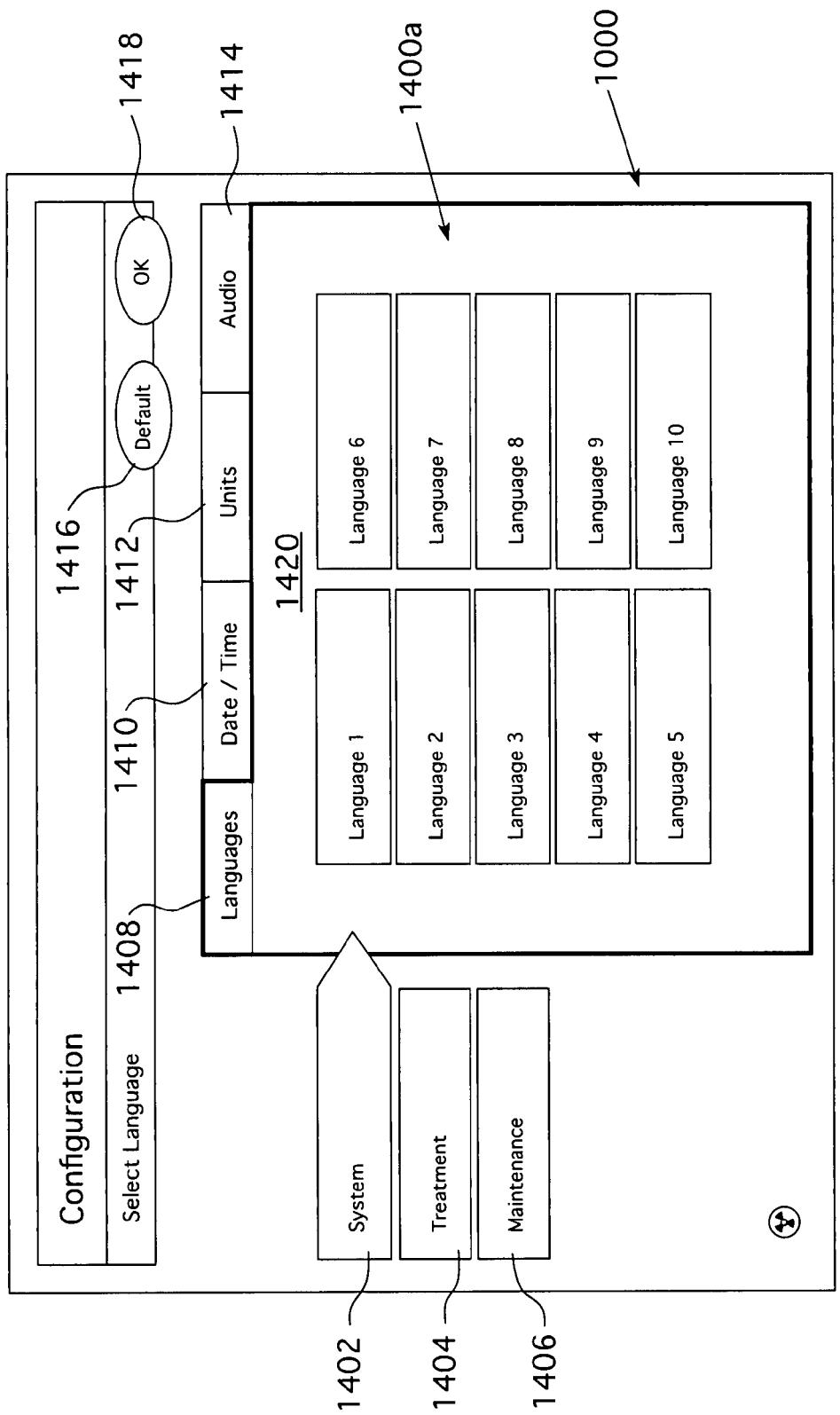
FIGS. 35, 36, 37, 38, 39A, 39B, 40, 41, 42, 43, 44A-D, 45A-D and 46 are various depictions of a graphical user interface for use in system configuration tasks.

As shown in FIG. 35, the "System" touch field 1402 is activated and the tabbed menu display 1400*a* is provided. On menu display 1400*a*, tabs for language, date/time, units and audio are provided (1408, 1410, 1412, and 1414, respectively), and language tab 1408 is activated to prompt a language menu 1420. Preferably, language menu 1420 will permit the selection of any of a number of languages to be used with the system 10 in accordance with operator or local preferences.

Figure 36:
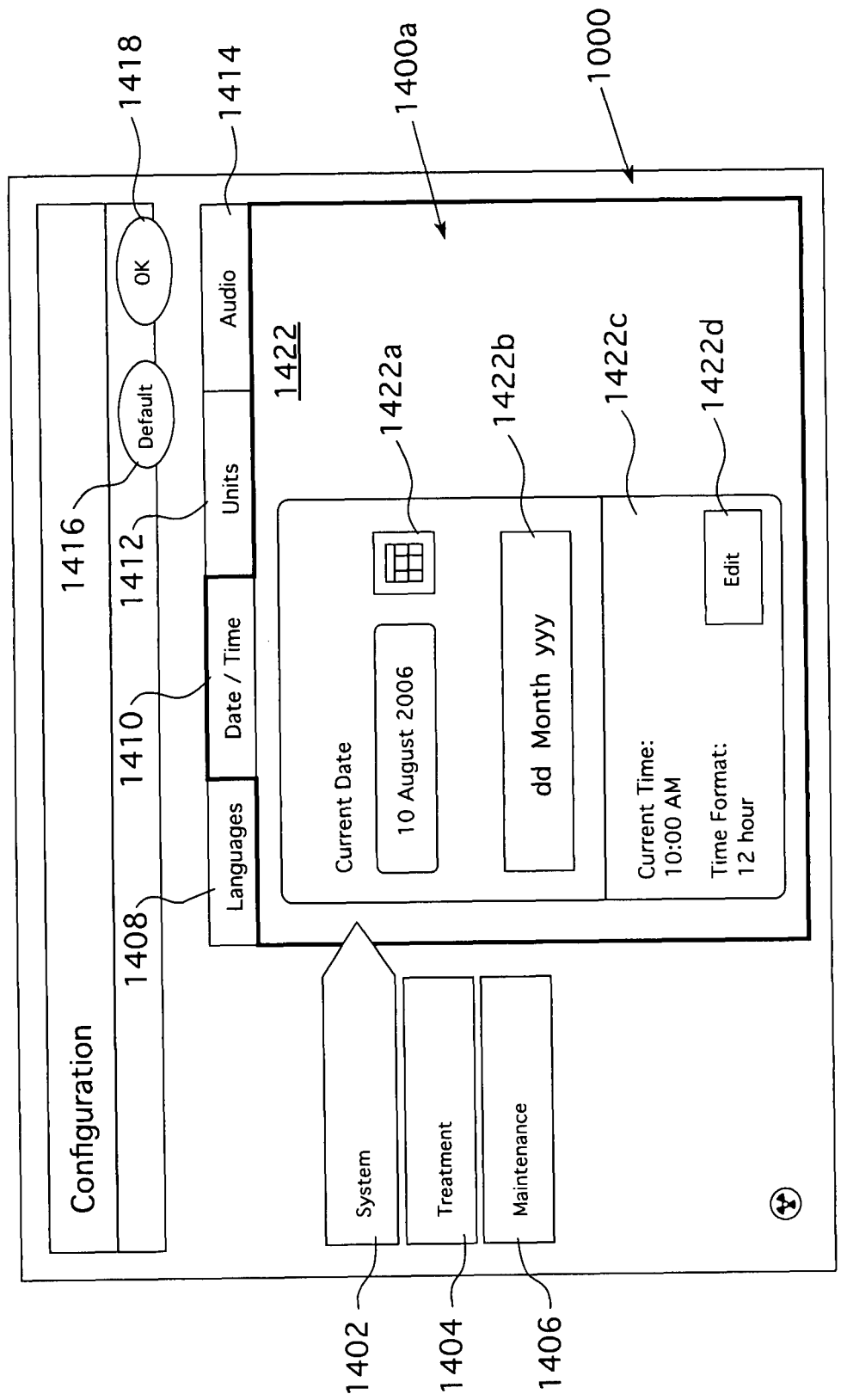

FIG. 36 shows date/time tab 1410 activated to prompt a date/time display 1422. Via a calendar button 1422*a*, a current date can be set, while date format preferences (e.g., European vs. American, etc.) can be set via touch field 1422*b*. A time display field 1422*c* preferably shows the current time and a time edit button 1422*d* may be activated to set the time as well as to select a 12- or 24-hour time format.

Figure 37:
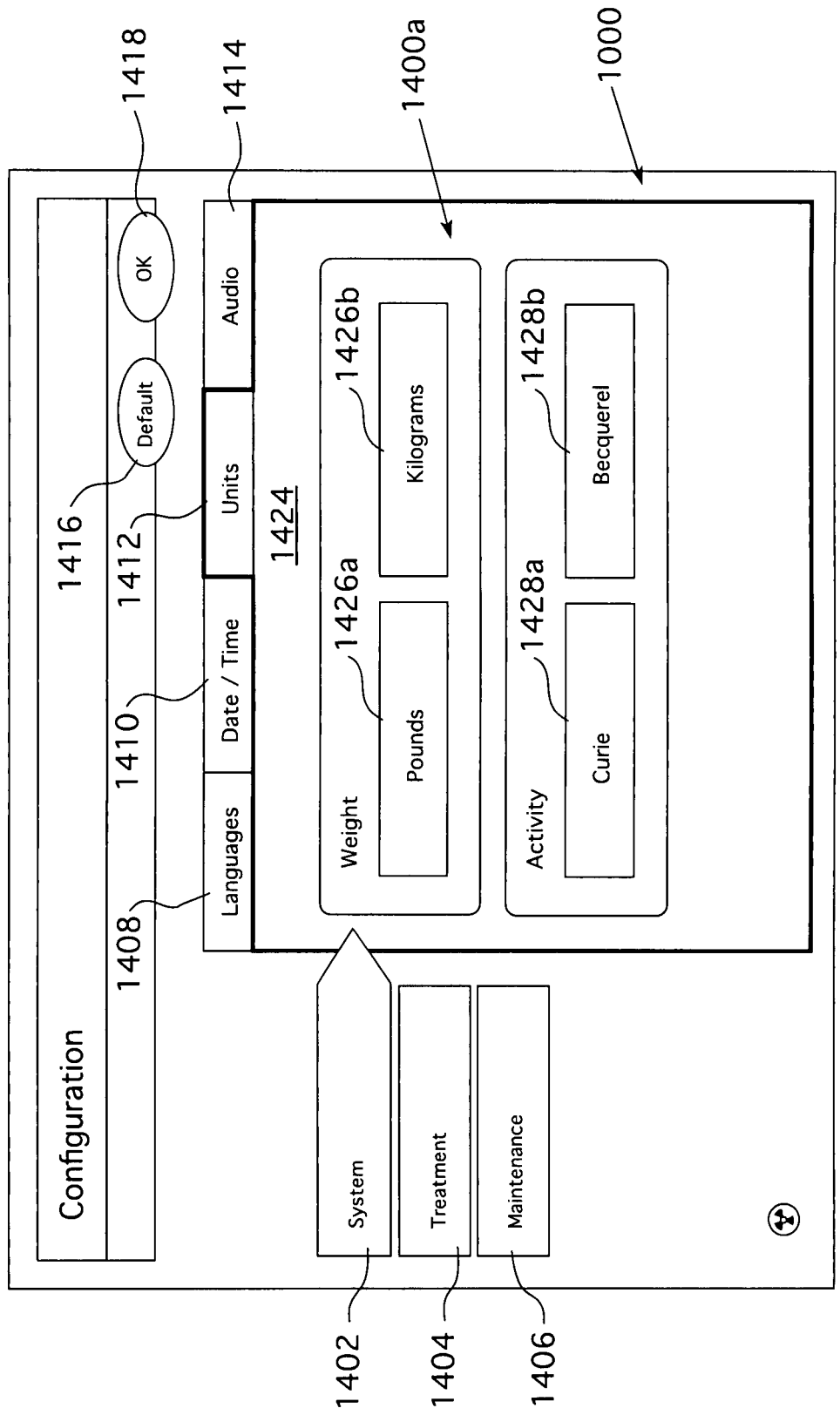

FIG. 37 shows units tab 1412 activated to prompt a display 1424. Display 1424 preferably permits, via buttons 1426*a*, 1426*b*, 1428*a*, 1428*b*, a choice of units for weight (lbs. vs. kg) and activity (Curies vs. Becquerels), respectively.

Figure 38:
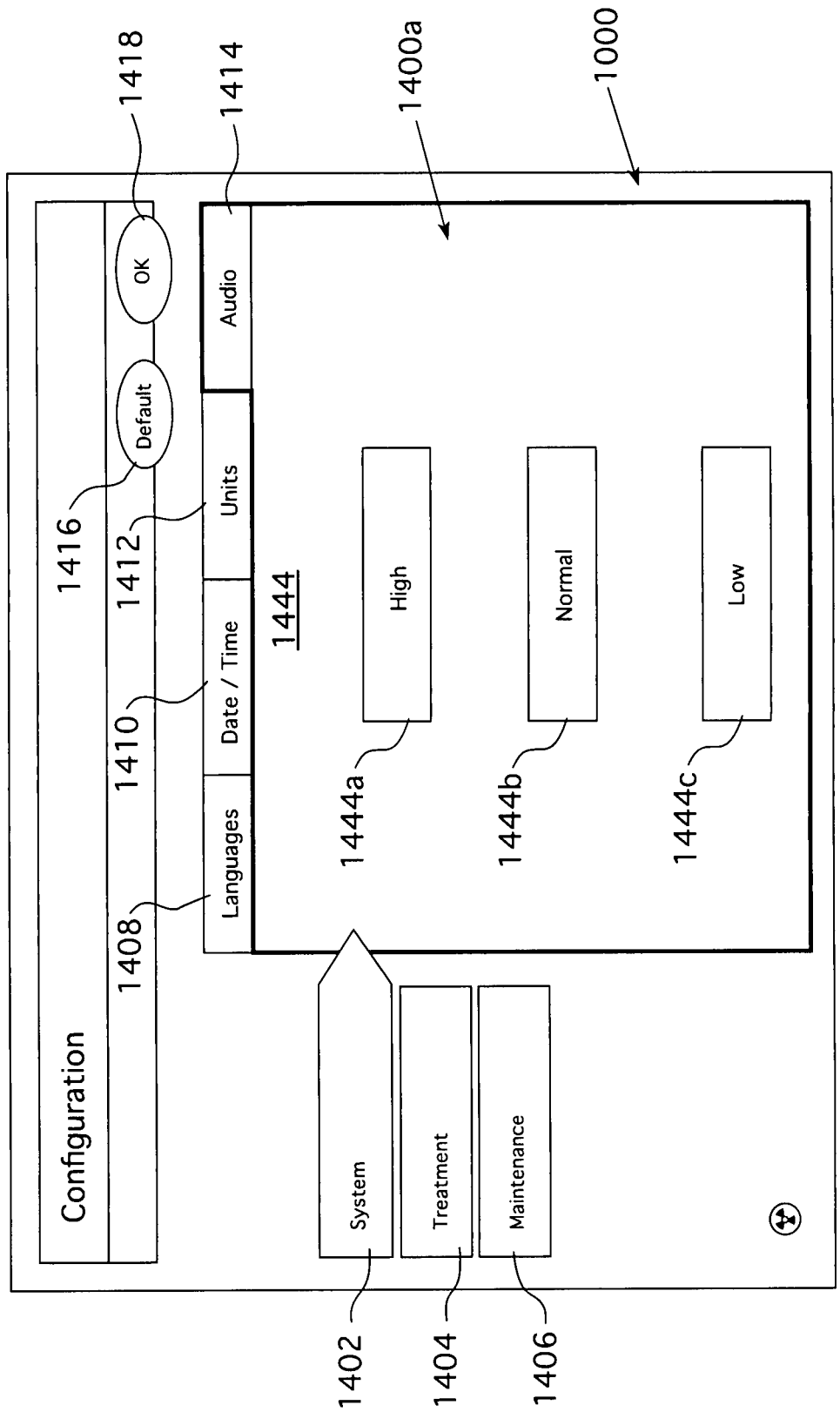

FIG. 38 shows audio tab 1414 activated to prompt a display 1444. "High", "normal" and "low" audio volumes (e.g., for prompts or alarms) can be selected via buttons 1444*a*, 1444*b* and 1444*c*, respectively.

Figure 39A:
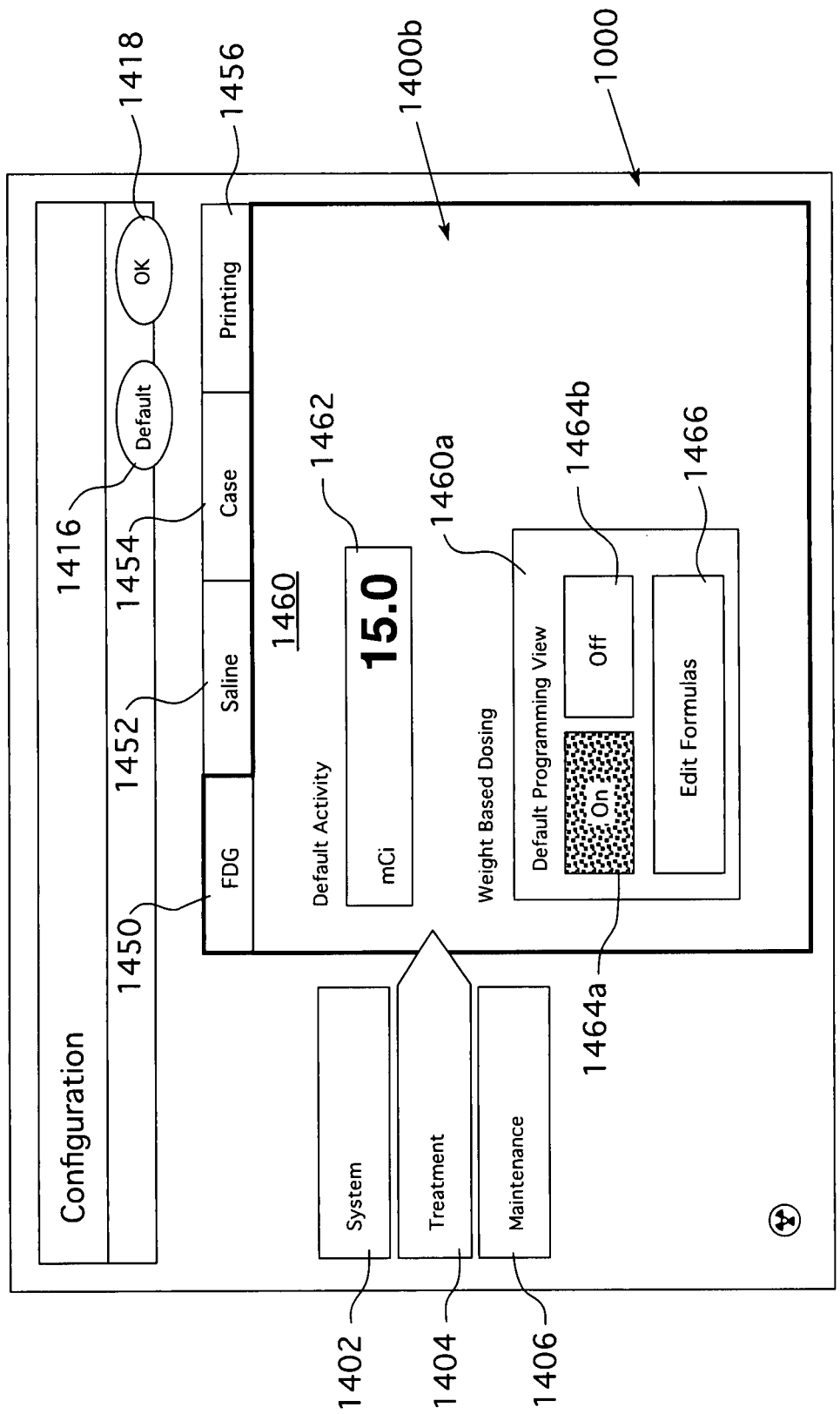

FIG. 39A shows the treatment touch field 1404 activated, which generates a second tabbed menu display 1400*b*. On menu display 1400*b*, tabs for "FDG", "saline", "case" and "printing" are provided (1450, 1452, 1454, and 1456, respectively). In FIG. 39A, FDG tab 1450 is activated to prompt a display 1460. Preferably, display 1460 includes an entry field 1462 for entering a default desired activity level (which may then automatically appear in field 1006 of FIG. 7).

The display 1460 further includes a weight-based dosing sub-menu 1460*a* that includes on/off buttons 1464*a*, 1464*b* and an "Edit Formulas" button 1466. If the operator would like the system 10 to default to a weight-based calculation for desired activity level, the operator activates the "On" button 1464*a*. If a default, weight-based calculation for desired activity level is not desired, the operator can select the "Off" button 1464*b* (as shown in FIG. 39A). Further, upon activation of the "Edit Formulas" button 1466, the system 10 generates the pop-up edit display 1470 shown in FIG. 39B to allow the operator to edit existing or add new formulas for calculating desired activity level based on, for example, patient weight.

Figure 39B:
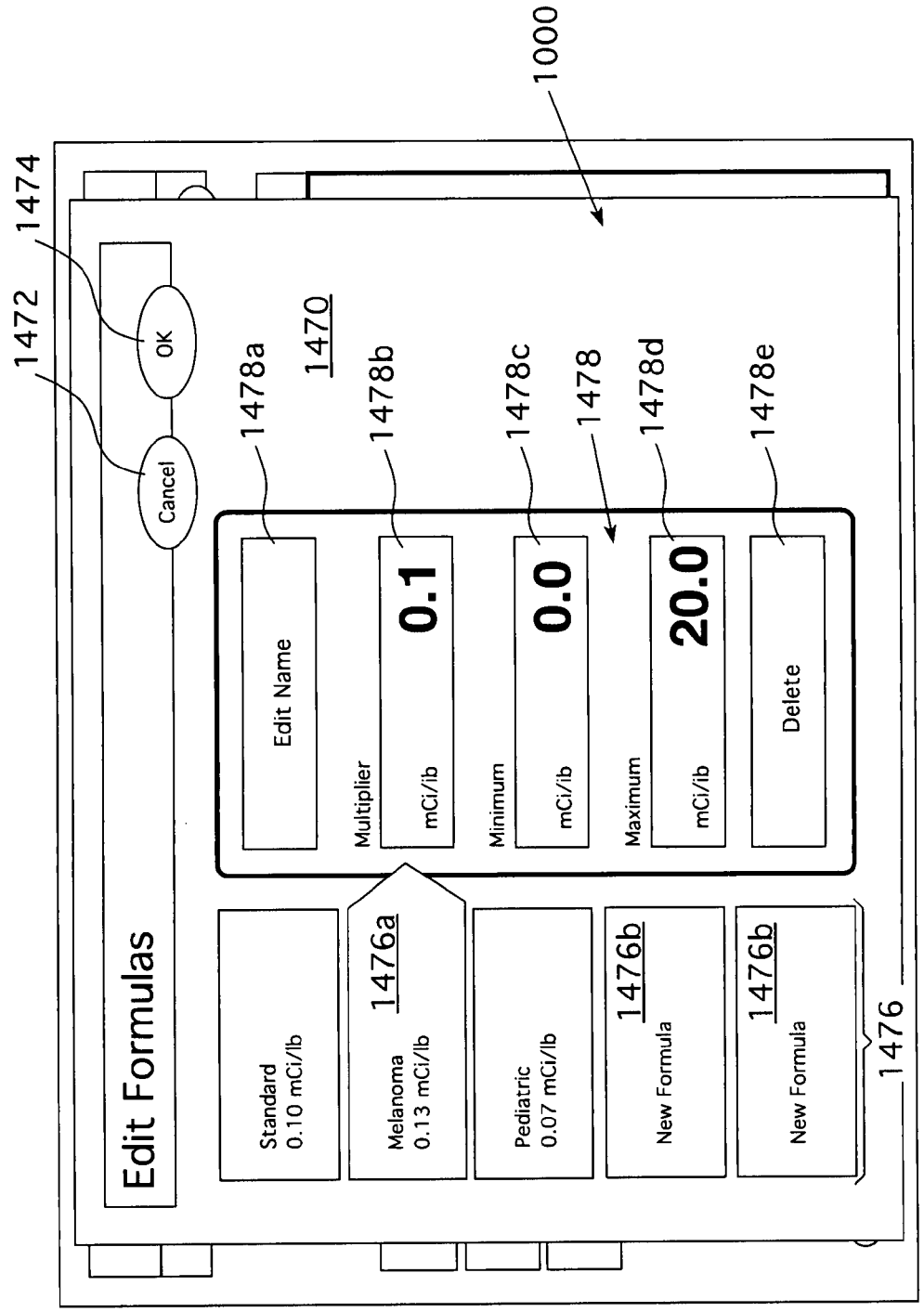

As shown in FIG. 39B, the edit display 1470 may include a column of five buttons 1476, each preferably corresponding to a predetermined formula for a procedure type that, for instance, may commonly be repeated. Here, a "Melanoma" button 1476*a* is activated to then present a sub-display 1478 which can afford an editing of any or all of the following: name of the formula (via button 1478*a*), multiplier to be used in calculating weight-based desired activity level (via touch field 1478*b*), and minimum and maximum desired activity levels (via touch fields 1478*c* and 1478*d*, respectively). Also, the entire formula can be deleted (via button 1478*e*) from the set 1476, if desired. Further, the operator may enter new formulas into the system 10 by activating the "New Formula" buttons 1476*b*

Figure 40:
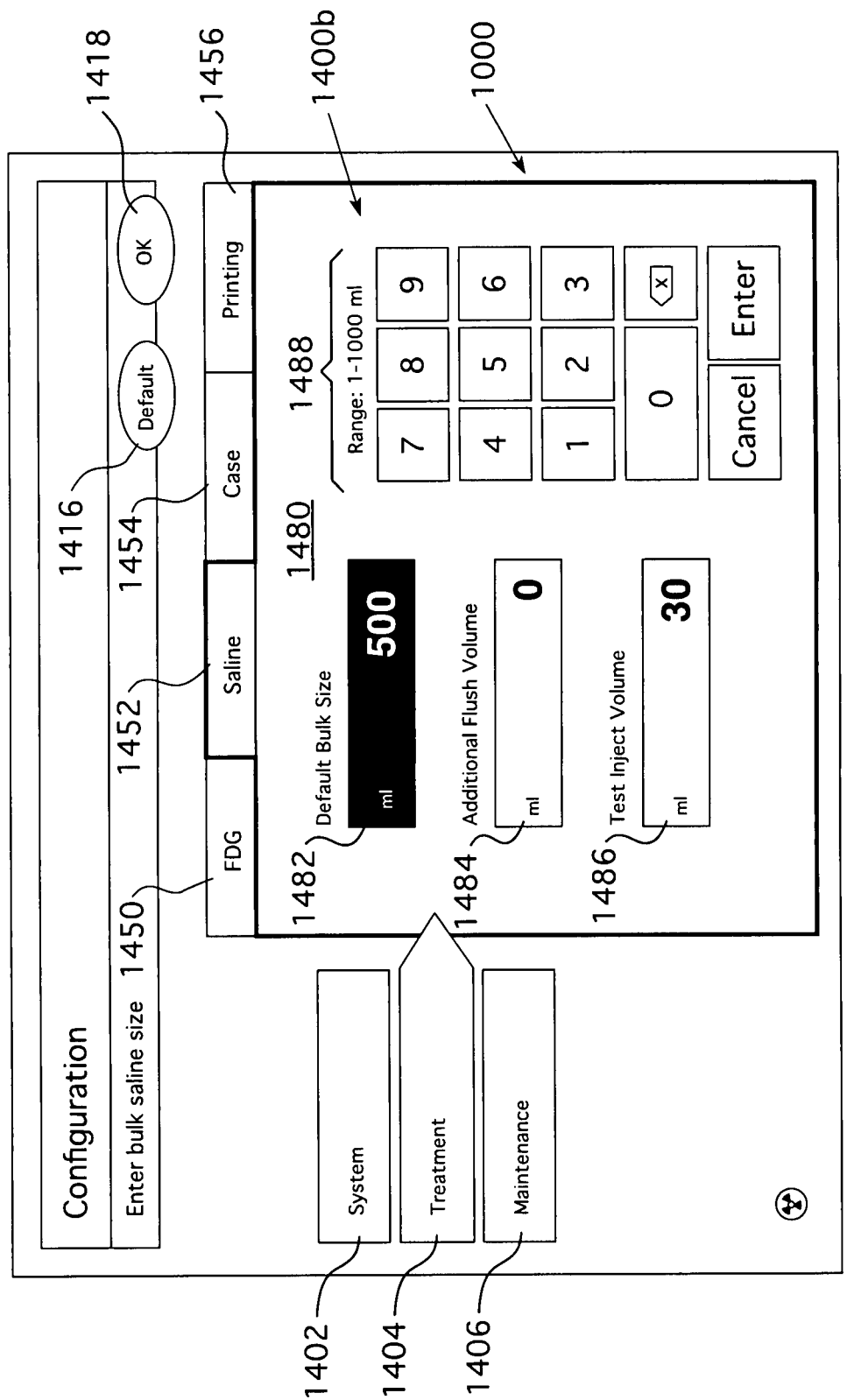

FIG. 40 shows Saline tab 1452 activated to prompt a display 1480. Display 1480 preferably contains touch fields 1482, 1484 and 1486, respectively, for pre-selecting a default saline bulk size (here 500 ml) for the saline source 23 (if, for example, the facility generally uses or will use the same bulk size of saline), an additional saline flush volume (e.g., to account for the additional tubing length if the SPDS 700 is connected to an IV instead of directly to a catheter in a patient) and a test inject volume (here 30 ml). The Default Bulk Size volume entered in 1482, for example, can be a quantity that initially appears to an operator at a time when saline is installed in the system 110, which can be changed or left alone as appropriate. Any data entry in touch fields 1482, 1484, 1486 can be accomplished, e.g., via a keypad 1488.

Figure 41:
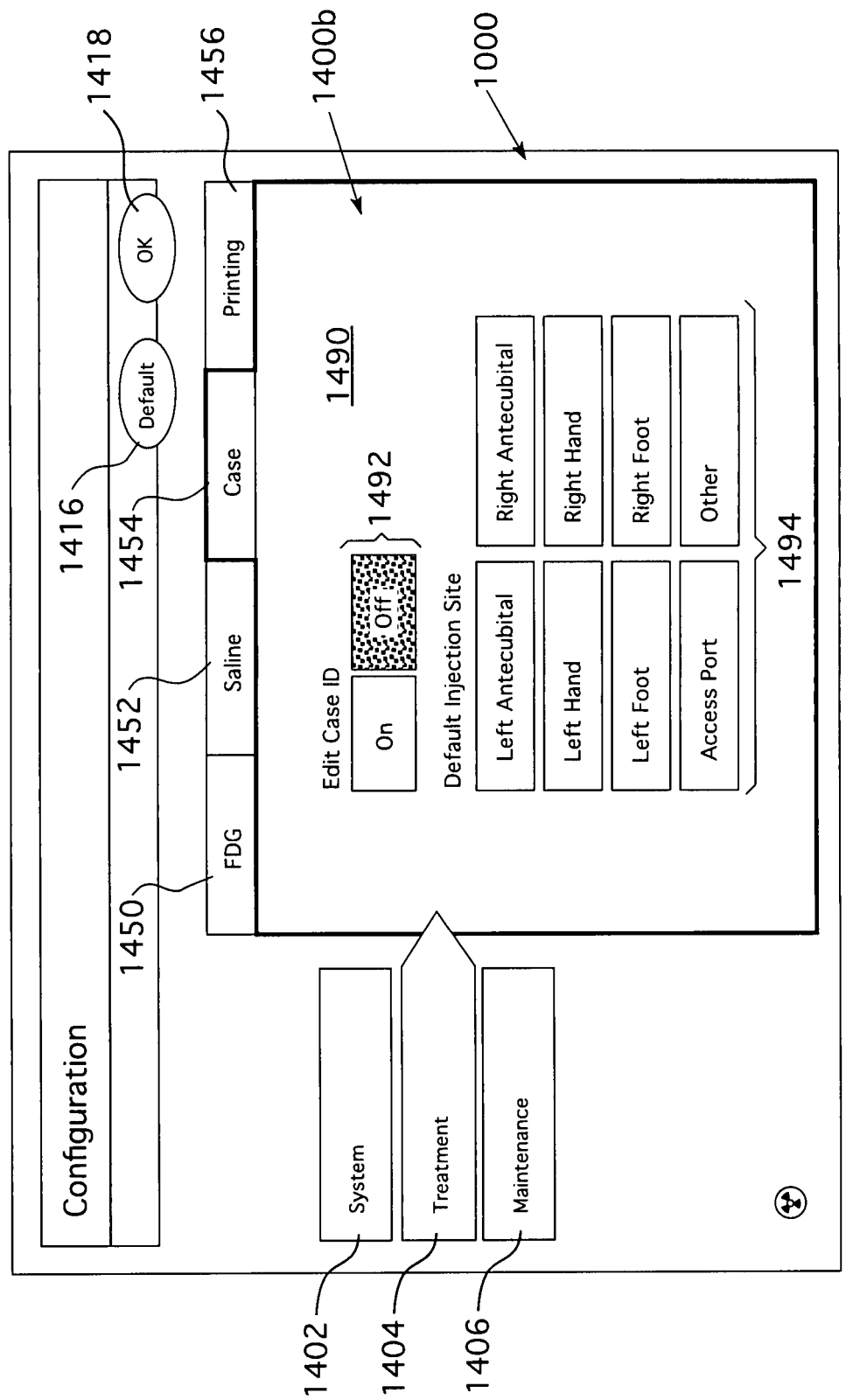

FIG. 41 shows case tab 1454 activated to prompt a display 1490. Display 1490 preferably permits the operator to set a default preference (via on/off buttons 1492) as to whether Case ID information (i.e., for a given patient) can be edited as appropriate. Further, the display 1490 allows the operator to set a default injection site for the system 10 by activating one of the injection site buttons 1494 provided in display 1490. Of course, the default injection site location can be changed by the operator during the preparation steps for the fluid delivery procedure if the actual injection site is different from the default injection site.

Figure 42:
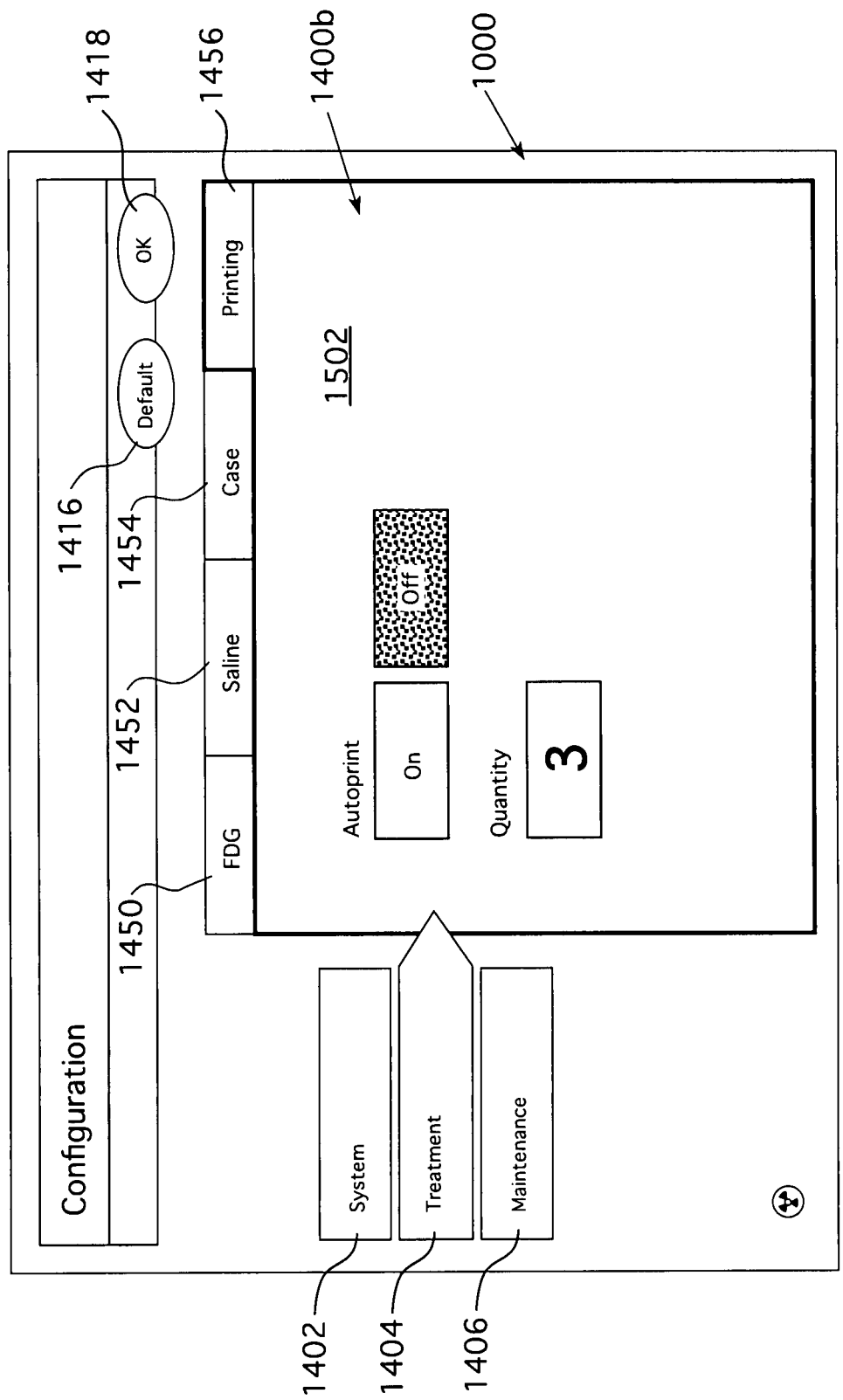

FIG. 42 shows printing tab 1456 activated to prompt a display 1502 which allows an operator to establish an automatic printing of record labels (e.g., as may be printed at the end of an injection procedure) and the quantity of record labels to be printed.

Finally, FIG. 43A shows maintenance touch field 1406 activated, which generates a third tabbed menu display 1400c. On menu display 1400c, tabs for "Daily QC", "Linearity", "Calibration" and "Field Service" (1510, 1512, 1514, 1516, respectively) are provided. The maintenance tabs relate to general maintenance and calibration of the system 10.

Figure 43:
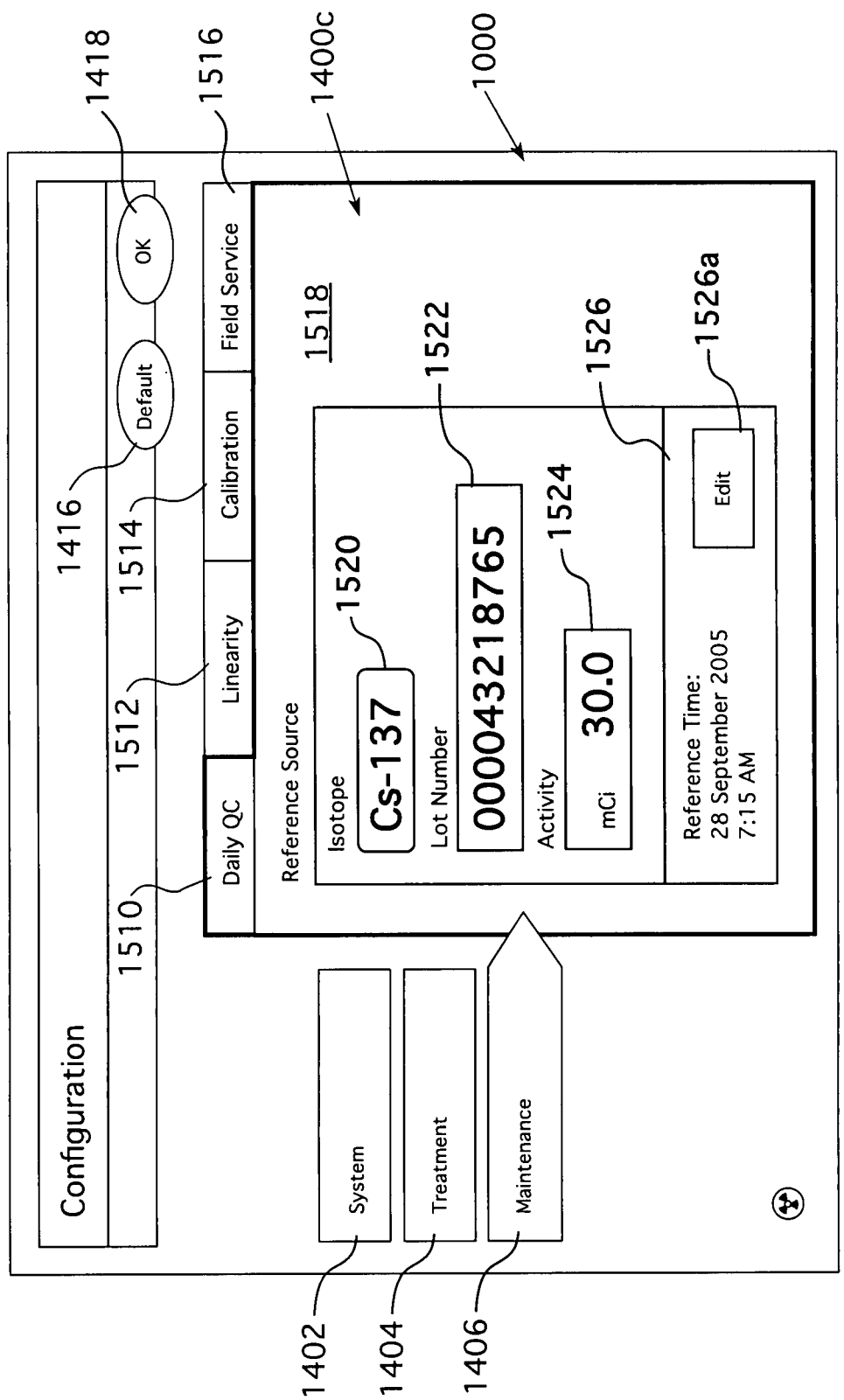

As shown in FIG. 43, Daily QC tab 1510 is activated to prompt a display 1518. Display 1518 allows the operator to input information related to the radioisotope to be used to conduct daily QC tests (described above) of the system 10. Specifically, Isotope touch field 1520 and Lot Number touch field 1522 permit the operator to input the specific radioisotope to be used (here Cs-137) and the lot number thereof, respectively. Further, the operator can input the time and date that the radioisotope was created (e.g., in a cyclotron or a reactor), as well as the activity level of the radioisotope when it was created, in the Time and Activity touch fields 1526, 1524, respectively. The Edit button 1526a can be activated to edit the previously entered time and date information.

Figure 44A:
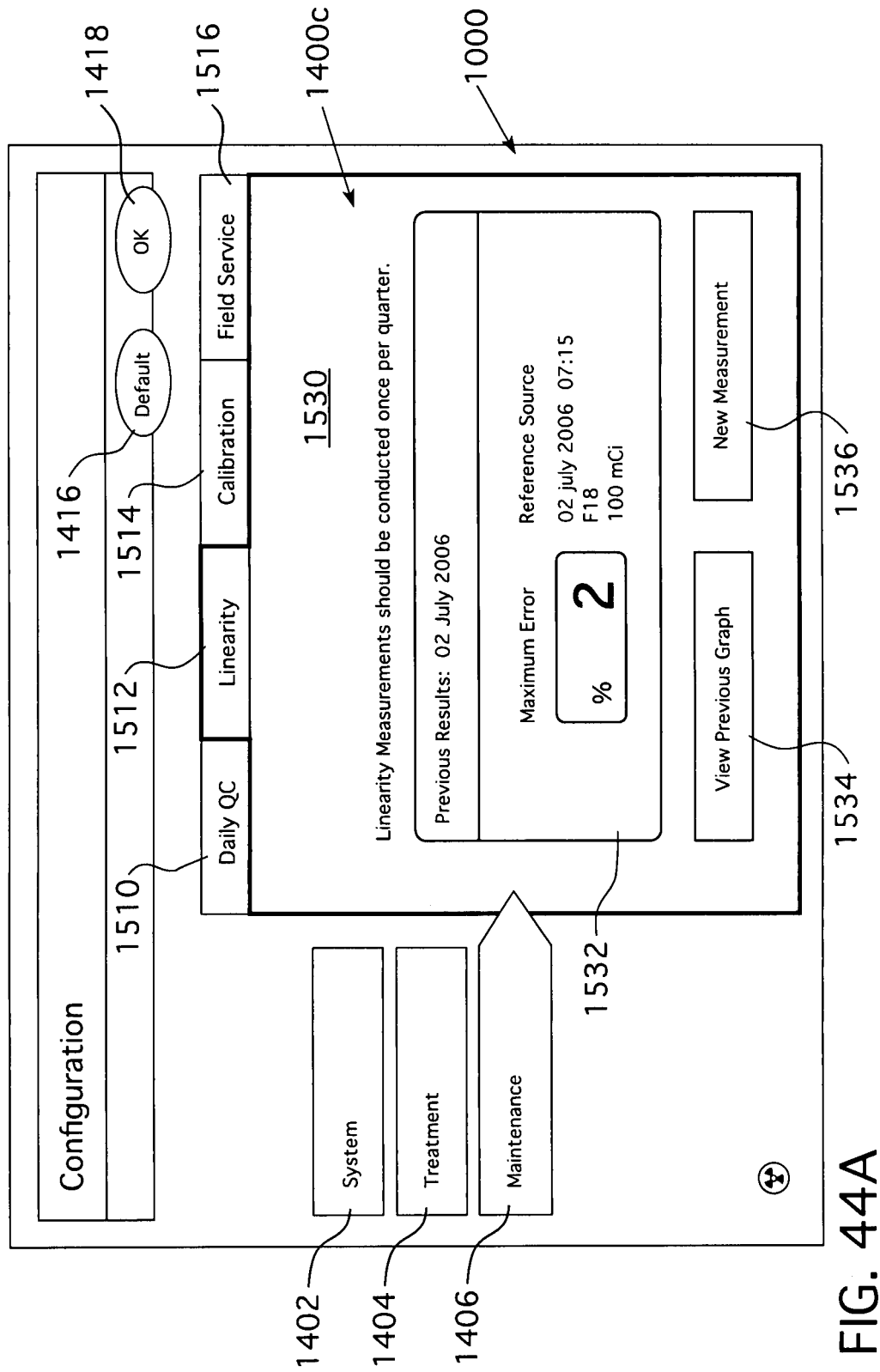

FIG. 44A shows linearity tab 1512 activated to prompt a display 1530. Display 1530 prompts the operator for information and assists in conducting a linearity measurement for the system 10, which should be conducted every quarter (as noted in display 1530). Linearity measurements are based on the known decay of radioisotopes and are conducted to ensure that the ionization chamber 160 in the system 10 is reliably measuring the activity level of a radioisotope placed therein. Specifically, during a linearity measurement the measured activity level of a radioisotope is compared to the known activity level of the radioisotope (based on its half-life decay) at selected intervals (e.g., every 15 minutes) over a period of time (e.g., 24 hours) to determine whether the measured activity level falls within an acceptable error range.

When the linearity tab 1512 is activated, details from the most recent linearity measurement are shown in sub-display 1532, while a button 1534 can be activated to prompt the appearance of a related graph (of, for example, measured vs. known activity level over the measurement period). To conduct a new linearity measurement, button 1536 is activated, which preferably generates the display 1540 shown in FIG. 44B.

Figure 44B:
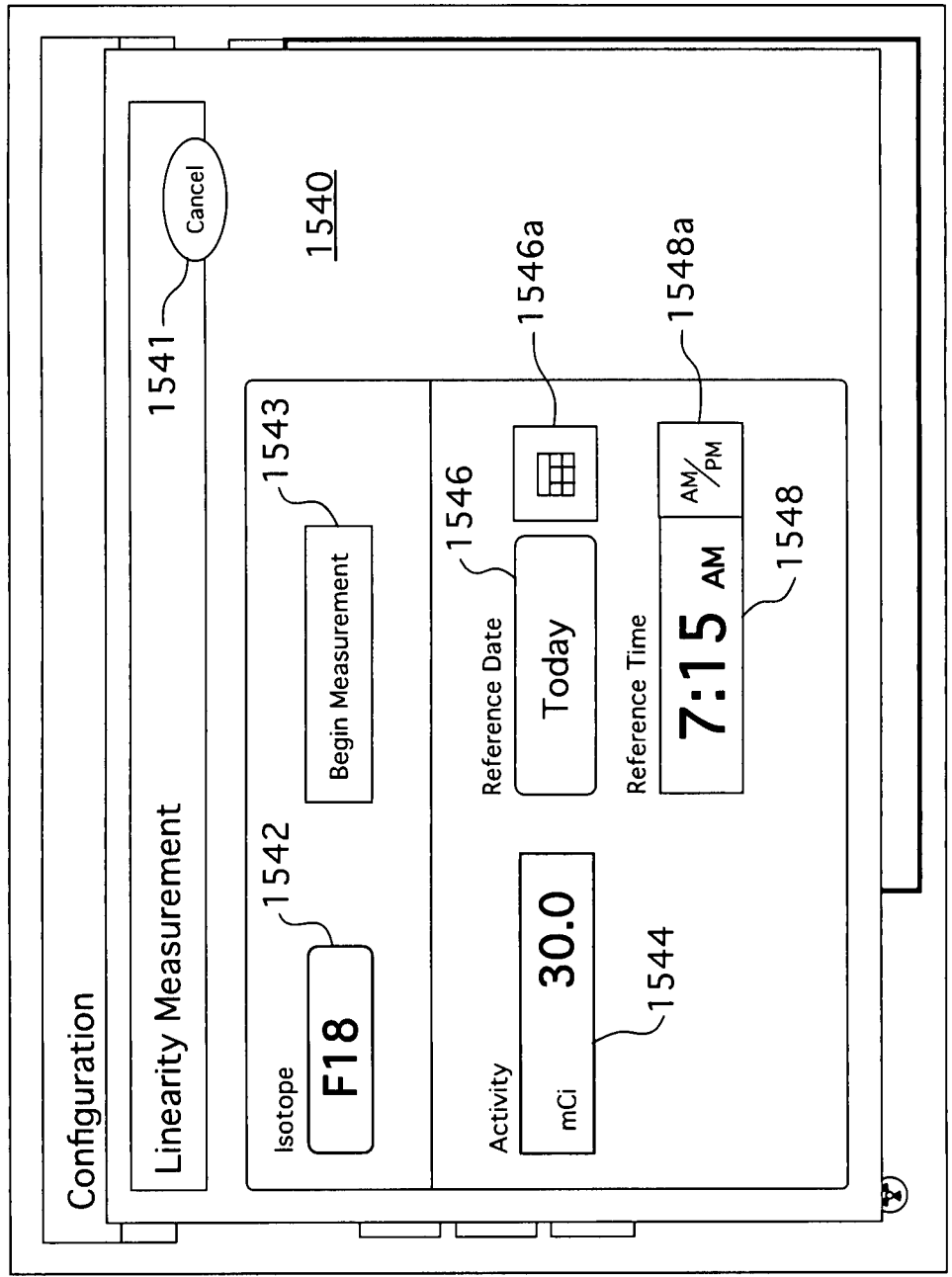

As shown in FIG. 44B, isotope field 1542 may be activated to identify the radioisotope to be used for the linearity measurement (here F-18). While isotope field 1542 preferably conveys the reference isotope, the activity level of the radioisotope (e.g., at the time it was drawn) can be input into activity level field 1544. In addition, the reference date and time for the activity level (e.g., the date and time that the radioisotope was drawn) is input into touch fields 1546 and 1548, respectively, by using, for example, a calendar button 1546a and a AM/PM time button 1548a. Once the requisite radioisotope information is inputted into display 1540, the operator can activate the "Begin Measurement" button 1543 to start the linearity measurement. Of course, the operator can activate the "Cancel" button 1541 to cancel the linearity measurement and return to the display 1530 shown in FIG. 44A.

Figure 44C:
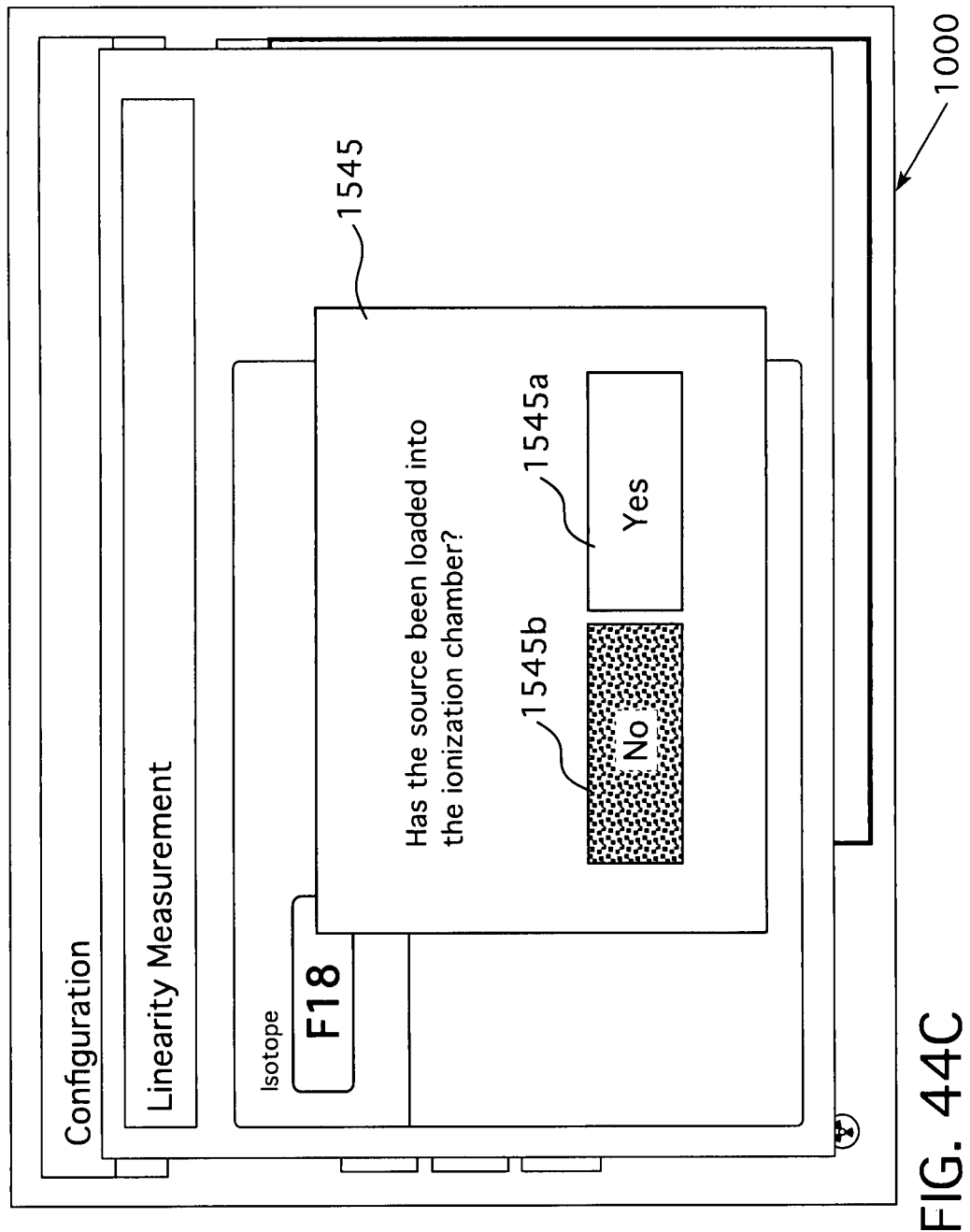

After the "Begin Measurement" button 1543 is activated, the pop-up display 1545 shown in FIG. 44C is generated to prompt the operator to confirm that the reference radioisotope has been placed in the ionization chamber 160. If the operator activates the "Yes" button 1545a (as shown in FIG. 44C) to confirm that the F-18 radioisotope has been placed in the ionization chamber 160, the system 10 will begin the linearity measurement.

If the operator activates the "No" button 1545b, the display reverts to the display 1540 shown in FIG. 44B, and the operator can then load the reference radioisotope source into the ionization chamber and once again activate the "Begin Measurement" button 1543 to start the linearity measurement.

Figure 44D:
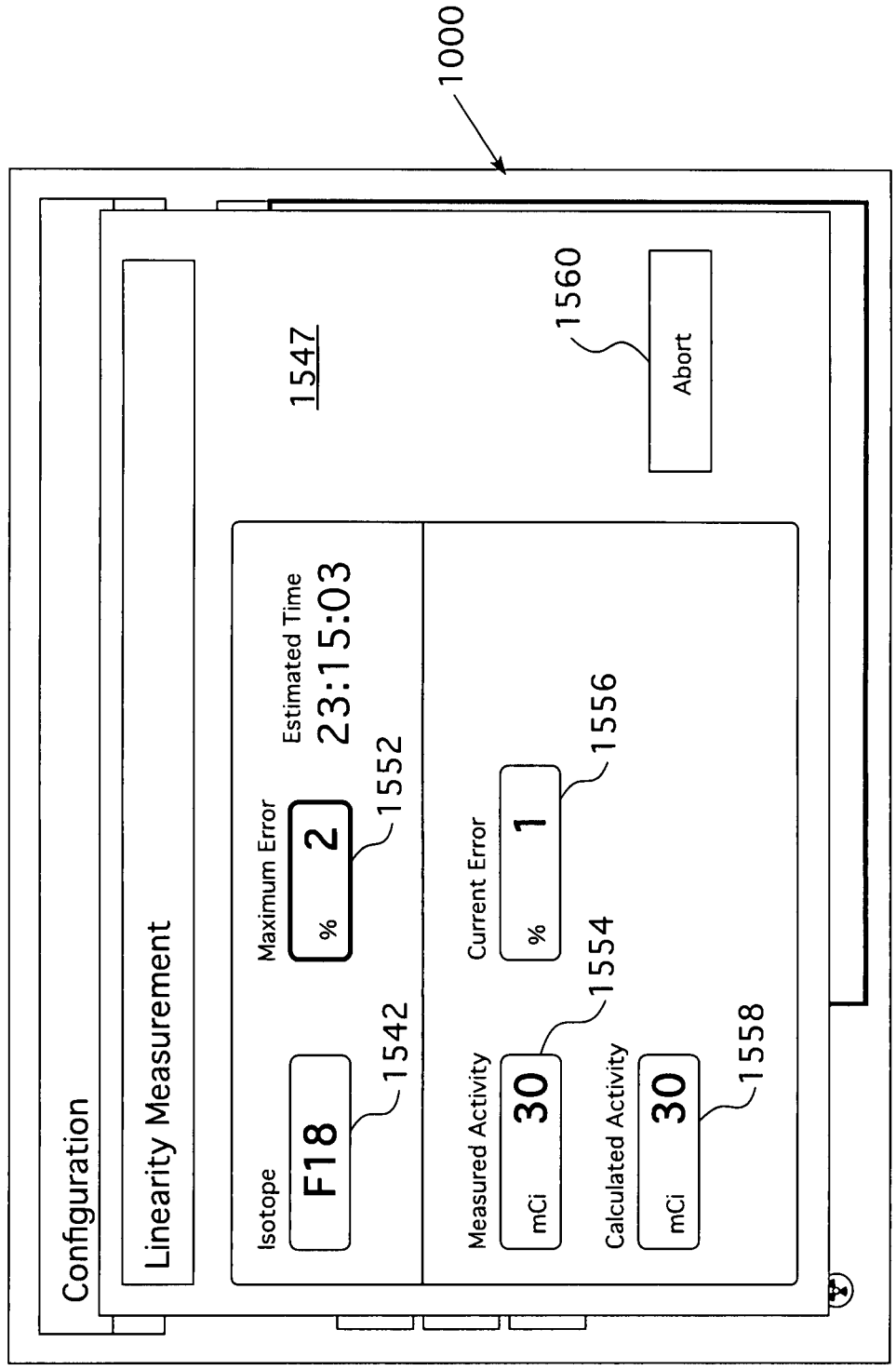

After the operator activates the "Yes" button 1545a, the display 1547 shown in FIG. 44D is generated. In addition to displaying the radioisotope in field 1542 and the maximum allowable error for the linearity measurement in field 1552, the display 1547 also shows the estimated time for completion of the linearity measurement (here "23:15:03" hours) and the measured activity (in field 1554), the calculated activity (in field 1558) and the current error (in percentage format) (in field 1556). The linearity measurement may be aborted via an "Abort" button 1560 and the results of the linearity measurement, including a graph of the results, may be printed by selecting a "Print" button (not shown).

Figure 45A:
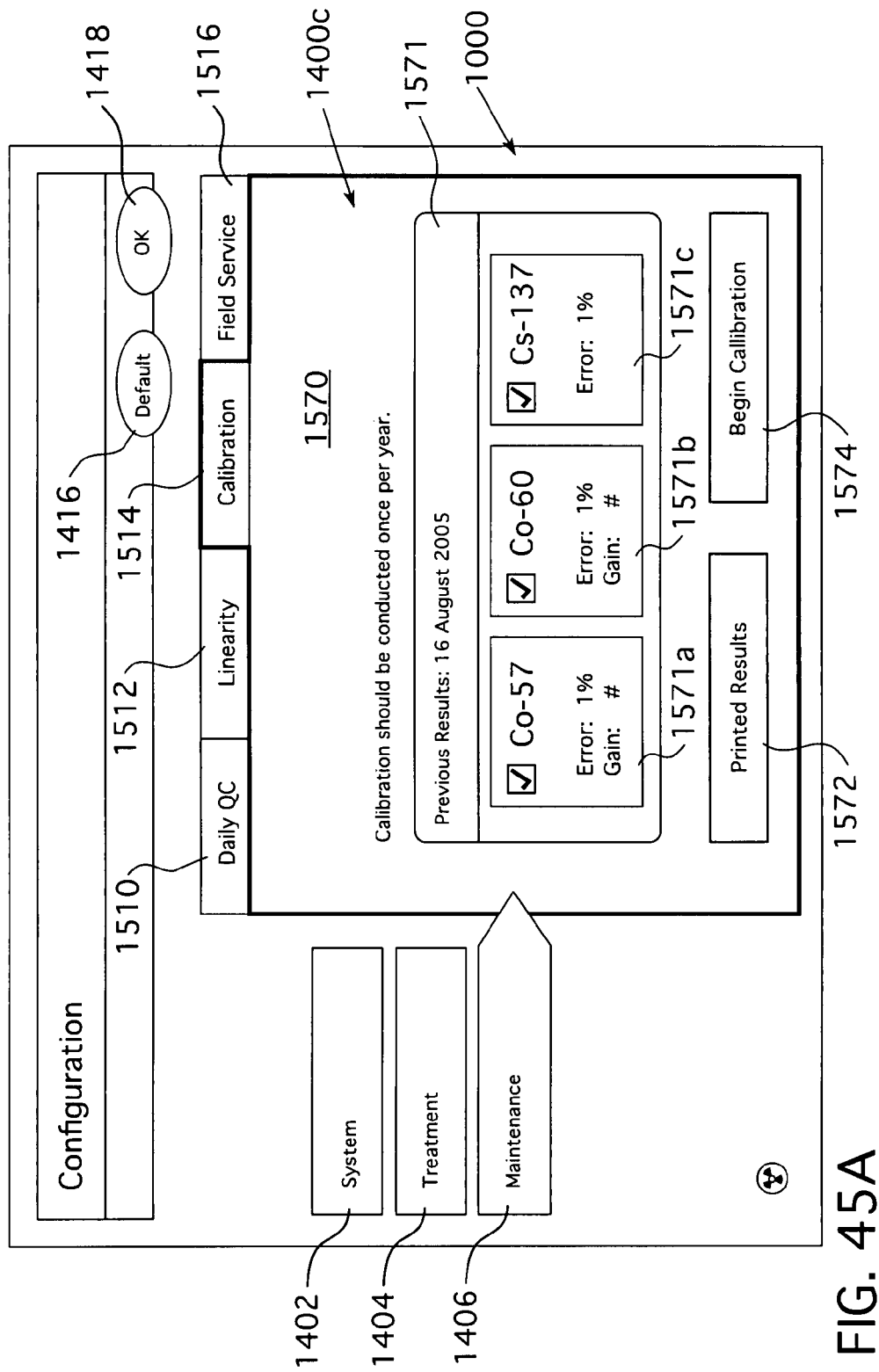

As shown in FIG. 45A, activation of calibration tab 1514 prompts the system 10 to generate a calibration display 1570, which shows the results of a previous ionization chamber calibration routine. Ionization chamber calibration routines are preferably conducted upon installation of the system 10 (at, for example, a medical facility) and approximately once a year thereafter to ensure that the ionization chamber 160 of the system 10 is properly calibrated to operate over the range of energies and activity levels of the radiopharmaceuticals for which the ionization chamber 160 is intended to be used. In a preferred calibration routine, the gain of the ionization chamber is increased or decreased to best fit or adjust the measured activity levels of two or three radioisotopes (preferably having energy levels different from (e.g., lower than and greater than) the energy levels of the radiopharmaceuticals to be used with the system 10) against their known activity levels.

By way of a specific example, the system 10 is currently intended to be used to administer FDG (which contains the radioisotope F-18) to patients. The energy level of F-18 is 511 KeV. In a first preferred embodiment, three radioisotopes are used to calibrate the ionization chamber 160: (1) Co-57 (energy level of 122 KeV; less than that of F-18); (2) Co-60 (energy level of 1333 KeV; greater than that of F-18); and (3) Cs-137 (energy level of 662 KeV; relatively close to that of F-18). In a second preferred embodiment, two radioisotopes are used for the calibration routine: (1) Co-57; and (2) Cs-137.

Returning to FIG. 45A, the calibration display 1570 includes a sub-display 1571 conveying previous calibration results for Co-57 (field 1571a), Co-60 (field 1571b) and Cs-137 (field 1571c), while a button 1574 can be activated to begin a new calibration routine. Previous results can also be printed, e.g., via a button 1572.

Figure 45B:
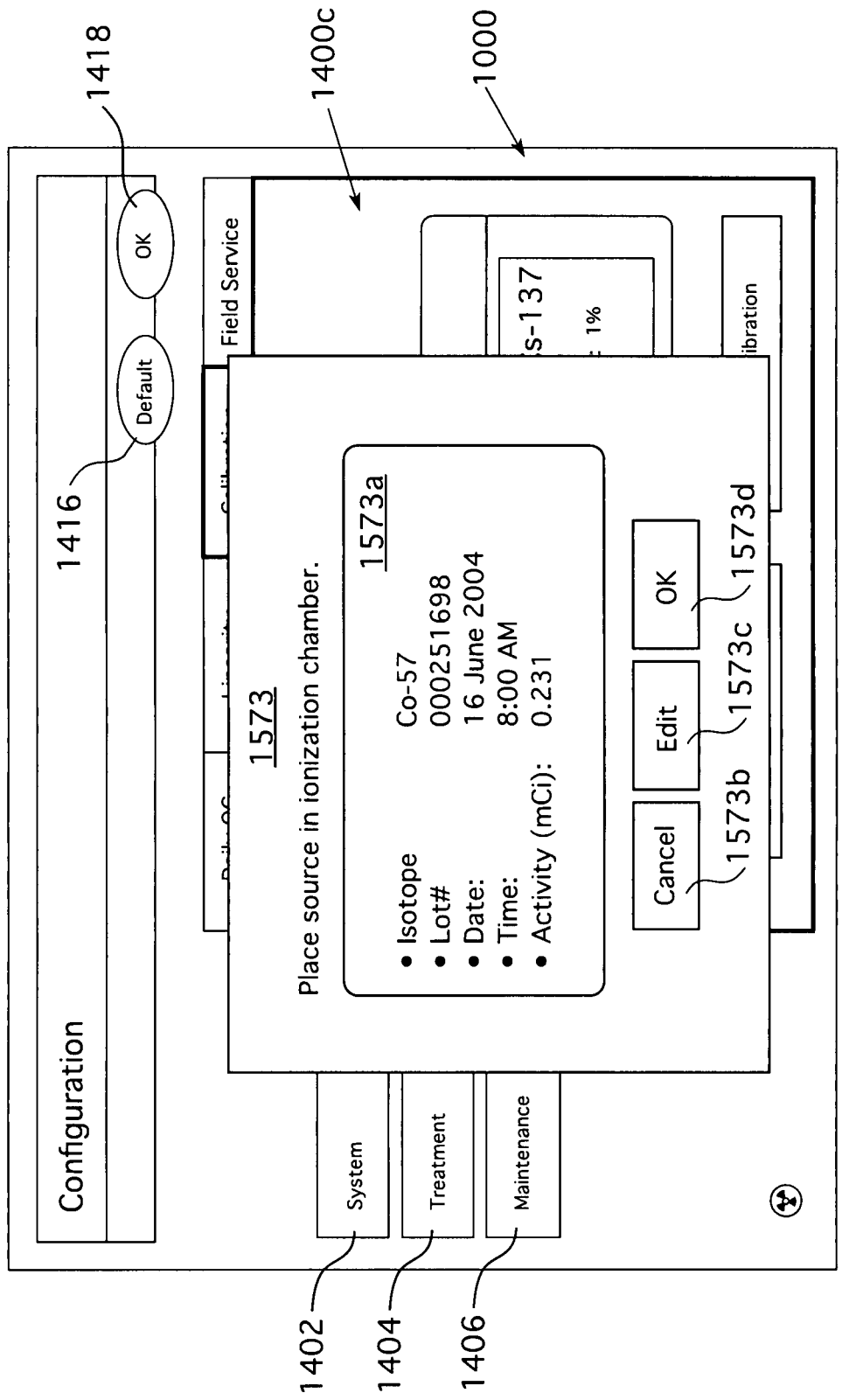

Upon activating button 1574, a display 1573 is generated (see FIG. 45B) that prompts the operator to place the radioisotope source (here Co-57) in the ionization chamber 160. The display 1573 includes a sub-display 1573a that lists various information about the isotope, including the isotope's name, the lot number, the date and time that the isotope was drawn and the activity level of the isotope when it was drawn. Further, the display 1573 includes "Cancel" button 1573b, "Edit" button 1573c and "OK" button 1573d. The cancel button 1573b is activated to cancel the calibration routine, the edit button 1573c is activated to edit the isotope information provided in sub-display 1573a and the OK button 1573d is activated (as shown in FIG. 45B) to commence the calibration routine with respect to the noted radioisotope (here Co-57), as discussed in more detail below.

Figure 45C:
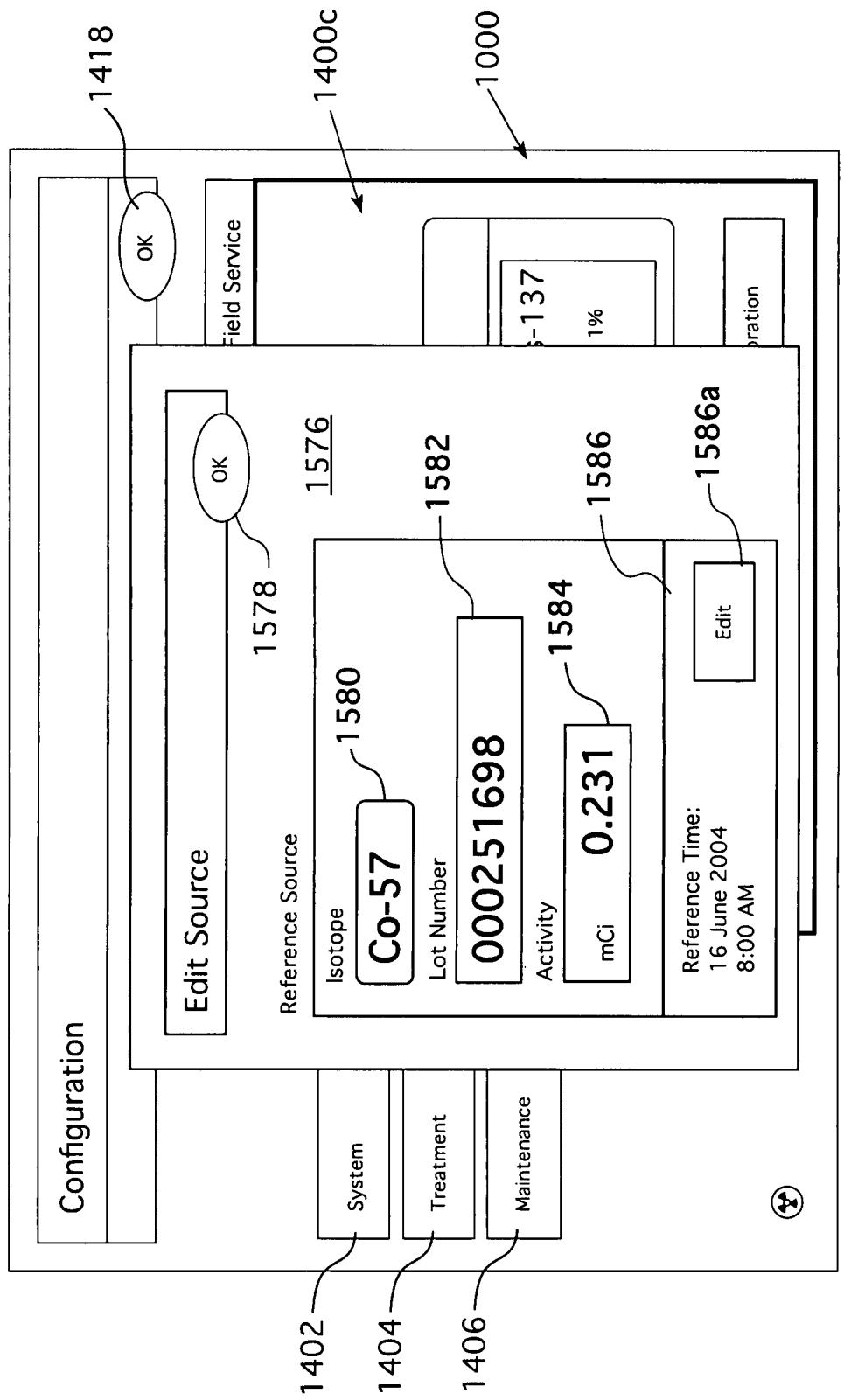

If the edit button 1573c in display 1573 is activated, the edit source display 1576 shown in FIG. 45C appears. The operator can edit the isotope information in display 1576 by entering the isotope name in field 1580, the lot number in field 1582, the activity level (at isotope creation) in field 1584 and the reference time and date (of isotope creation) in field 1586 via edit button 1586a. After the isotope information is entered, the operator activates the OK button 1578 and the display 1000 reverts to the display 1573 shown in FIG. 45B. If the isotope information is now correct, the operator can activate the OK button 1573d in display 1573 to commence the calibration routine for the noted radioisotope (here Co-57).

Figure 45D:
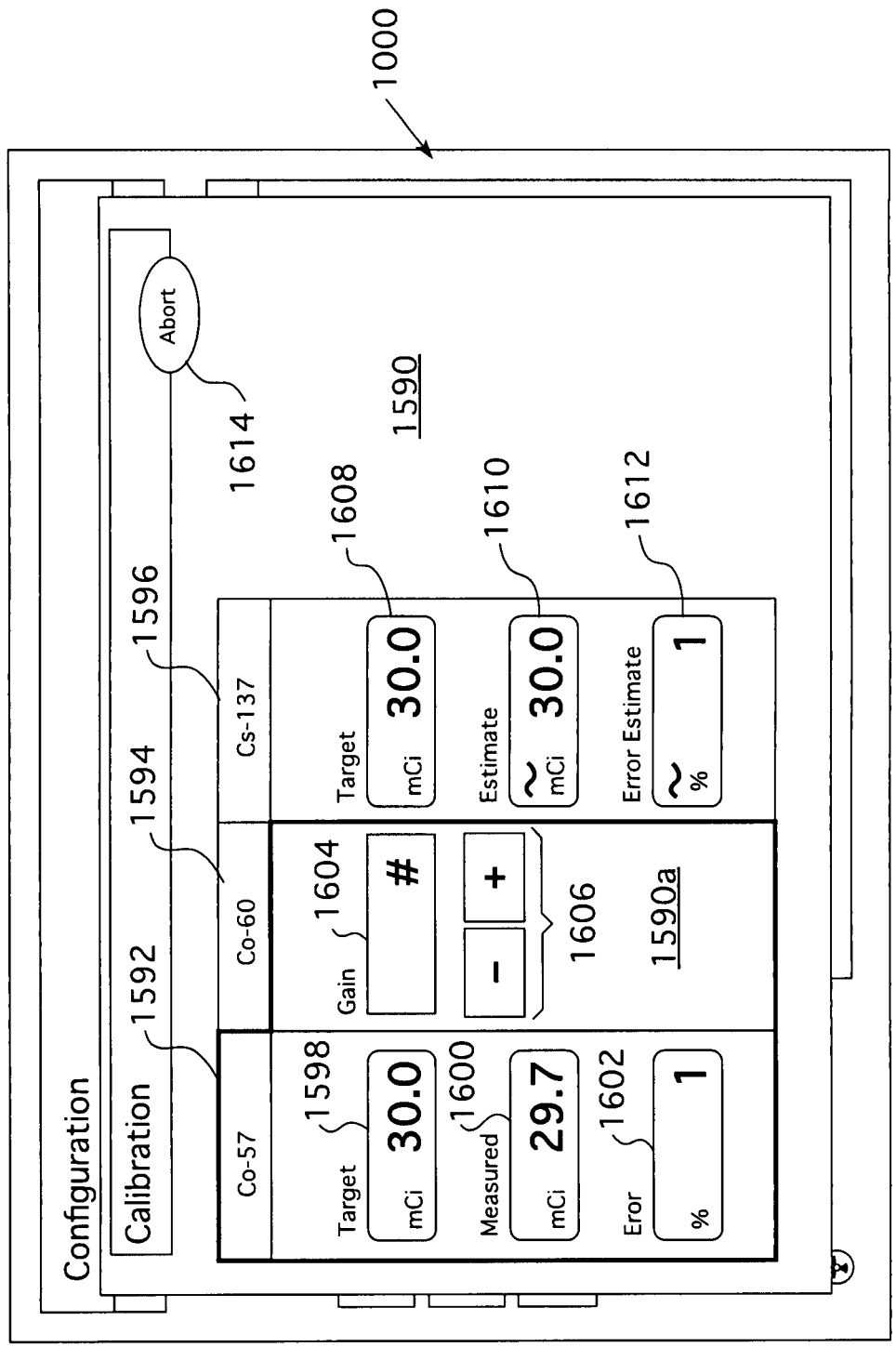

After the OK button 1573d is activated, a tabbed calibration display 1590, including touch tabs for Co-57 (tab 1592), Co-60 (tab 1594) and Cs-137 (tab 1596), appears (as shown in FIG. 45D) and shows the results of the calibration routine for the noted radioisotope (here Co-57). Specifically, the display 1590a for Co-57 tab 1592 shows the target or expected activity for Co-57 (in field 1598), the actual measured activity for the Co-57 placed in the ionization chamber 160 (in field 1600) and the error between the target and measured activity (in field 1602). To thereafter compensate for the error (here 1%), the low gain of the ionization chamber (displayed in field 1604) is adjusted by using the 'plus' and 'minus' buttons 1606, respectively. Further, as shown in FIG. 45D, based on the error for Co-57 the system 10 calculates an estimated error (here 1%) for Cs-137 and displays it in field 1612. Based on the target or expected activity for Cs-137 (entered by the operator and displayed in field 1608) and the estimated error, the estimated measured activity is calculated by the system 10 and displayed in field 1610.

The calibration routine is continued by thereafter activating the tab 1594 for the Co-60 isotope and repeating the steps described above with respect to FIGS. 45B-45D. To compensate for the error (not shown) between the expected activity and the measured activity for Co-60, the high gain of the ionization chamber is adjusted (in the same way as shown in FIG. 45D for Co-57). The system 10 then uses the error for Co-60 to revise the estimated error for Cs-137, which is then displayed in field 1612 for the operator.

The operator may continue the process above (i.e., iteratively conducting Co-57 and Co-60 activity measurements and adjusting the low and high gain of the ionization chamber) until the estimated error for Cs-137 (whose energy level of 662 KeV is relatively close to the 511 KeV energy level of F-18) is within an acceptable range (e.g., 1%). At that time, the operator activates the tab 1596 for the Cs-137 isotope and places the Cs-137 source in the ionization chamber to confirm that the difference between the expected and measured activity of the Cs-137 isotope is substantially similar to or within an acceptable range from the estimated error displayed in field 1612. At this point the calibration routine is completed, and the results may be printed and/or stored for later accessing by system maintenance personnel. As shown, an "abort" button 1614 for terminating the calibration procedure is provided for the operator.

Figure 46:
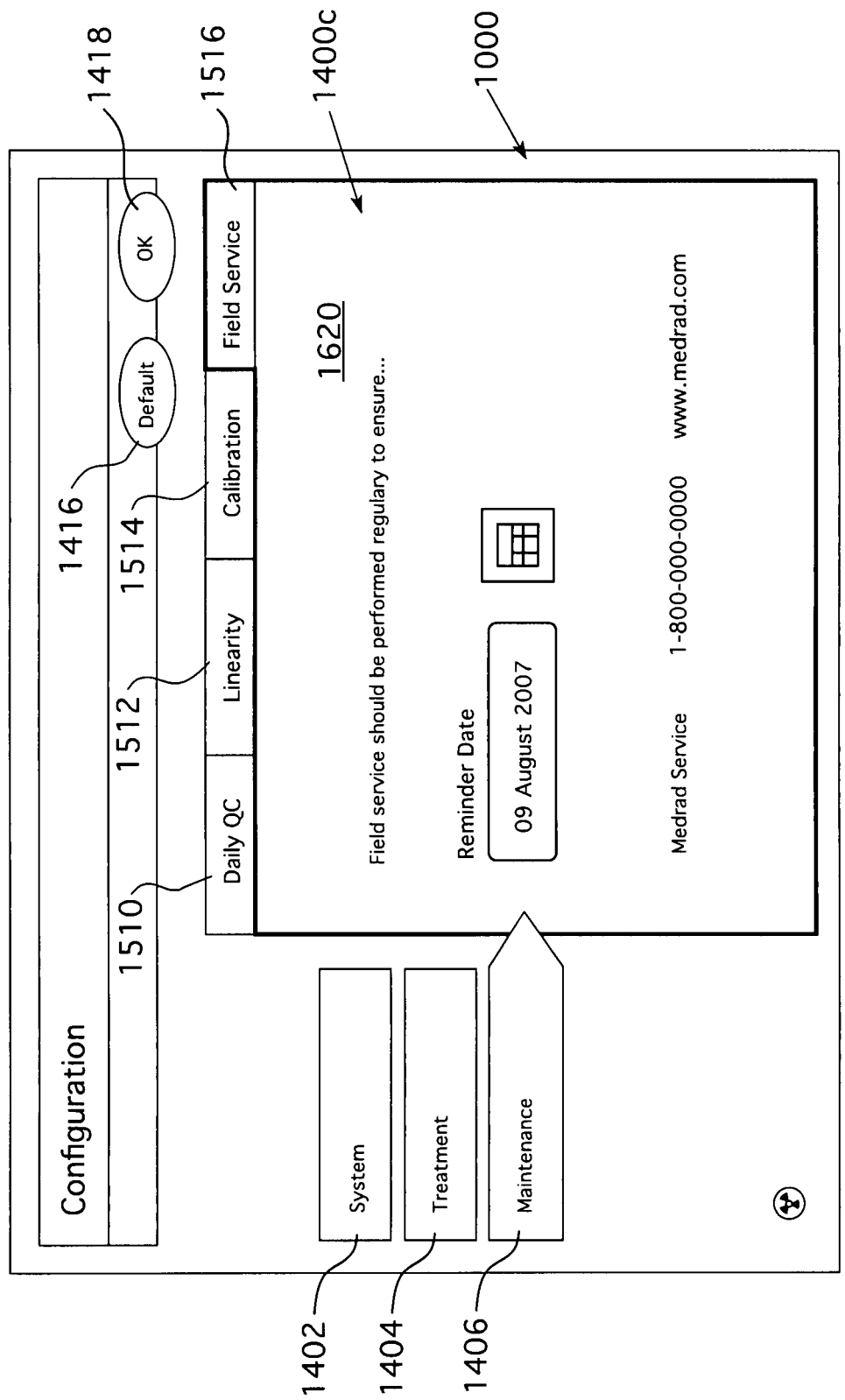

Finally, FIG. 46 shows field service tab 1516 activated to prompt a display 1620 which can be used to pre-set one or more future reminder dates to undertake preventative maintenance for the system 10.

It is to be appreciated that the systems, devices and methods of the present invention can be used in a very wide variety of drug delivery and therapeutic procedures. In general, the systems, devices and methods of the present invention are particularly suited for use in connection with any hazardous pharmaceutical or substance to be injected into a patient (human or animal). Even pharmaceuticals, such as contrast agents or thrombolytic agents, that are not considered to be especially hazardous can be beneficially administered via systems broadly contemplated herein and provide hospital personnel additional protection against adverse effects.

To the extent that systems of the present invention can be applicable to radiotherapy drugs or pharmaceuticals wherein the drug or pharmaceutical itself is radioactive, it is to be appreciated that, as clear to one skilled in the art, maintaining containment of radiotherapy pharmaceuticals promotes safety. If the drug or pharmaceutical is radioactive, the use of radiation absorbing or leaded shielding will help protect the operator and patient from unnecessary radiation. Containment of radiotherapy pharmaceutical is discussed in U.S. Patent Application Publication No. 2003-0004463, the contents of which are incorporated herein by reference.

While procedures discussed herein in accordance with embodiments of the present invention have generally been described with respect to liquid drugs, it is to be understood that they can also apply to powdered drugs with either a liquid or gaseous vehicle, or gaseous drugs that are to be delivered to a recipient.

If not otherwise stated herein, it may be assumed that all components and/or processes described heretofore may, if appropriate, be considered to be interchangeable with similar components and/or processes disclosed elsewhere in the specification, unless an express indication is made to the contrary.

If not otherwise stated herein, any and all patents, patent publications, articles and other printed publications discussed or mentioned herein are hereby incorporated by reference as if set forth in their entirety herein.

It should be appreciated that the apparatus, systems, components and methods of the present invention may be configured and conducted as appropriate for any context at hand. The embodiments described above are to be considered in all respects only as illustrative and not restrictive.

What is claimed is:

1. A fluid path set for use in a fluid delivery system, the fluid path set comprising:
   a medical fluid component comprising a first tubing section for connection to a source of a medical fluid;
   a pharmaceutical component comprising a second tubing section for connection to a source of a pharmaceutical;
   a coil assembly component comprising a tube coil having a height of approximately 1.53 inches, a diameter of approximately 1.95 inches and a volume capacity of approximately 12.5 ml; and
   a connector comprising a first port for connecting the first tubing section of the medical fluid component, a second port for connecting the second tubing section of the pharmaceutical component and a third port for connecting the tube coil of the coil assembly component.

2. The fluid path set of claim 1 wherein the tube coil comprises a coil tubing section having an outer diameter of approximately 0.218 inches, an inner diameter of approximately 0.156 inches and a length of approximately 41 inches.

3. The fluid path set of claim 2 wherein the tube coil is formed in a helical coil of approximately 7 turns of the coil tubing section.

4. The fluid path set of claim 3 wherein the coil assembly component further comprises a core structure around which the tube coil is formed, the core structure comprising an upper shoulder and a lower shoulder that define a tube channel therebetween, the upper and lower shoulders adapted to retain the tube coil therebetween within the tube channel.

5. The fluid path set of claim 4 wherein the core structure further comprises an upper surface defining an inlet for accommodating a first end of the coil tubing section and an outlet for accommodating a second end of the coil tubing section.

6. The fluid path set of claim 5 wherein the coil assembly component further comprises a third tubing section connected to the third port of the connector and the first end of the coil tubing section and a fourth tubing section connected to the second end of the coil tubing section.

7. The fluid path set of claim 6, further comprising:
a waste component comprising a fifth tubing section in connection with a waste receptacle;
a sixth tubing section having a connector end that is adapted to be connected to a single-patient tubing set; and
a second connector comprising a first port for connecting the fourth tubing section of the coil assembly component, a second port for connecting the fifth tubing section of the waste component and a third port for connecting the sixth tubing section.

8. The fluid path set of claim 7 wherein the connector end of the sixth tubing section comprises a swabable luer valve that is biased to a closed position when the single-patient tubing set is not connected thereto.

9. The fluid path set of claim 7 wherein the sixth tubing section is connected to a manifold or a stopcock each having two or more outlet ports for connection to respective single-patient tubing sets.

10. The fluid path set of claim 7 wherein the first tubing section is approximately 56.75 inches in length and has an outer diameter of approximately 0.188 inches, an inner diameter of approximately 0.062 inches and a durometer of 45, the second tubing section is approximately 8.75 inches in length and has an outer diameter of approximately 0.094 inches, an inner diameter of approximately 0.032 inches and a durometer of 45, the third tubing section is approximately 15 inches in length and has an outer diameter of approximately 0.163 inches, an inner diameter of approximately 0.062 inches and a durometer of 60, the fourth tubing section is approximately 12 inches in length and has an outer diameter of approximately 0.163 inches, an inner diameter of approximately 0.062 inches and a durometer of 60, and the fifth tubing section and the sixth tubing section are each approximately 5 inches in length and have an outer diameter of approximately 0.163 inches, an inner diameter of approximately 0.062 inches and a durometer of 60.

11. The fluid path set of claim 1 wherein the first tubing section is in fluid connection with a first check valve and a spike for connecting to the source of the medical fluid and the second tubing section is in fluid connection with a second check valve and a vented cannula for connecting to the source of the pharmaceutical.

12. The fluid path set of claim 1 wherein the second tubing section comprises a vented cannula comprising:
a main hub comprising two opposed lateral sides and defining a fluid port and a vent;
a fluid draw needle in connection with the second tubing section through the fluid port and adapted to be placed within the source of the pharmaceutical;
a vent needle in connection with the vent and adapted to be placed within the source of the pharmaceutical; and
two resilient arms connected to the opposed lateral sides of the main hub, each of the two resilient arms comprising a top edge and a hook member formed thereon and extending outwardly therefrom.

13. The fluid path set of claim 12 wherein the fluid draw needle is longer than the vent needle.

14. The fluid path set of claim 12 wherein the vent comprises a filter.

15. The fluid path set of claim 12 wherein the main hub of the vented cannula further comprises a ledge extending therefrom in a horizontal plane above the two resilient arms, the ledge and the top edges of the two resilient arms cooperating to define horizontal slots therebetween.

16. The fluid path set of claim 15 wherein the hook members extend outwardly from each of the two resilient arms in a plane substantially normal to the horizontal plane of the ledge.

17. The fluid path set of claim 12 wherein the main hub and each of the two resilient arms cooperate to define substantially U-shaped grooves extending along the lateral sides of the main hub.

* * * * *

UNITED STATES PATENT AND TRADEMARK OFFICE
CERTIFICATE OF CORRECTION

| | | |
|---|---|---|
| PATENT NO. | : 9,056,164 B2 | Page 1 of 1 |
| APPLICATION NO. | : 11/981429 | |
| DATED | : June 16, 2015 | |
| INVENTOR(S) | : Tate et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2274 days.

IN THE SPECIFICATION:
Column 5, Line 46, delete ""pigs"" and insert -- "PIGs" --, therefor.
Column 14, Line 27, delete "(Vial" and insert -- Vial --, therefor.
Column 21, Line 48, delete "SPDS 200" and insert -- SPDS 700 --, therefor.
Column 24, Line 62, delete "FIG. 1)" and insert -- FIG. 11) --, therefor.
Column 27, Line 11, delete "Constancy/" and insert -- "Constancy/ --, therefor.
Column 28, Line 5, delete "manlier" and insert -- manner --, therefor.
Column 29, Line 58, delete "MPDS 700," and insert -- MPDS 200, --, therefor.
Column 30, Line 18, delete "MPDS 700, the SPDS 200" and insert -- MPDS 200, the SPDS 700 --, therefor.
Column 30, Line 32, delete "Patient" and insert -- "Patient --, therefor.
Column 33, Line 49, delete "ill" and insert -- in --, therefor.
Column 36, Line 47, delete "110," and insert -- 10, --, therefor.

Signed and Sealed this
Second Day of February, 2016

Michelle K. Lee
*Director of the United States Patent and Trademark Office*